US010072047B2

(12) United States Patent
Guo et al.

(10) Patent No.: US 10,072,047 B2
(45) Date of Patent: Sep. 11, 2018

(54) TAGGED HEPADNAVIRUS E ANTIGEN AND ITS USE IN SCREENING ANTIVIRAL SUBSTANCES

(71) Applicants: Drexel University, Philadelphia, PA (US); Baruch S. Blumberg Institute, Doylestown, PA (US); Hoffmann-La Roche Inc., Little Falls, NJ (US)

(72) Inventors: Haitao Guo, Carmel, IN (US); Dawei Cai, Indianapolis, IN (US); Andrea Cuconati, Oreland, PA (US); Changhua Ji, Shanghai (CN)

(73) Assignees: Drexel University, Philadelphia, PA (US); Baruch S. Blumberg Institute, Doylestown, PA (US); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/309,680

(22) PCT Filed: Jun. 19, 2015

(86) PCT No.: PCT/EP2015/063838
§ 371 (c)(1),
(2) Date: Nov. 8, 2016

(87) PCT Pub. No.: WO2015/193484
PCT Pub. Date: Dec. 23, 2015

(65) Prior Publication Data
US 2017/0240600 A1 Aug. 24, 2017

Related U.S. Application Data

(60) Provisional application No. 62/014,996, filed on Jun. 20, 2014.

(51) Int. Cl.

| | |
|---|---|
| ***A01N 43/04*** | (2006.01) |
| ***A61K 31/70*** | (2006.01) |
| ***A61K 31/715*** | (2006.01) |
| ***A01N 37/18*** | (2006.01) |
| ***A61K 31/16*** | (2006.01) |
| ***C07K 14/005*** | (2006.01) |
| ***G01N 33/50*** | (2006.01) |

(52) U.S. Cl.
CPC ......... *C07K 14/005* (2013.01); *G01N 33/502* (2013.01); *C07K 2319/40* (2013.01); *C07K 2319/42* (2013.01); *C12N 2730/10122* (2013.01); *G01N 2333/02* (2013.01)

(58) Field of Classification Search
CPC ................ A61K 45/06; A61K 31/7068; A61K 31/7072; A61K 31/7076; A61K 38/21
See application file for complete search history.

(56) References Cited

FOREIGN PATENT DOCUMENTS

WO WO-2013/181584 A2 12/2013

OTHER PUBLICATIONS

Cai et al., "Identification of Disubstituted Sulfonamide Compounds as Specific Inhibitors of Hepatitis B Virus Covalently Closed Circular DNA Formation", Antimicrobial Agents and Chemotherapy, 2012, 56(8):4277-4288.*

Cal et al., "Identification of disubstituted sulfonamide compounds as specific inhibitors of hepatitis B virus covalently closed circular DNA formation," Antimicrob Agents Chemother. 56(8):4277-88 (2012).

Guo et al., "Metabolism and function of hepatitis B virus cccDNA: Implications for the development of cccDNA-targeting antiviral therapeutics," available in PMC Oct. 1, 2016, published in final edited form as: Antiviral Res. 122:91-100 (2015) (25 pages).

Yang et al., "Human hepatitis B viral e antigen interacts with cellular interleukin-1 receptor accessory protein and triggers interleukin-1 response," J Biol Chem. 281(45):34525-36 (2006) (13 pages).

International Search Report and Written Opinion for International Patent Application No. PCT/EP2015/063838, dated Sep. 28, 2015 (10 pages).

Response to Written Opinion of the International Searching Authority of Sep. 28, 2015, and Amended Claims for International Patent Application No. PCT/EP2015/063838, dated Jan. 18, 2016 (9 pages).

Written Opinion of the International Preliminary Examining Authority for International Patent Application No. PCT/EP2015/063838, dated May 18, 2016 (6 pages).

Response to Second Written Opinion of the International Preliminary Examining Authority of May 18, 2016, and Amended Claims for International Patent Application No. PCT/EP2015/063838, dated Jul. 6, 2016 (8 pages).

International Preliminary Report on Patentability for International Patent Application No. PCT/EP2015/063838, dated Aug. 31, 2016 (13 pages).

* cited by examiner

*Primary Examiner* — Barry A Chestnut
(74) *Attorney, Agent, or Firm* — Clark & Elbing LLP

(57) ABSTRACT

The present invention relates to methods and uses for screening anti-hepadnaviral substances, wherein the substances are screened for the capacity to inhibit covalently closed circular (ccc) DNA of a hepadnavirus, like hepatitis B virus. The methods and uses take advantage of cells comprising a nucleic sequence encoding a tagged hepadnavirus e antigen, like Hepatitis B virus e antigen (HBeAg). Furthermore, the present invention provides nucleic acid sequences encoding a tagged hepadnavirus e antigen and proteins encoded thereby. Also kits for use in the screening methods are provided.

20 Claims, 11 Drawing Sheets

Figure 1:
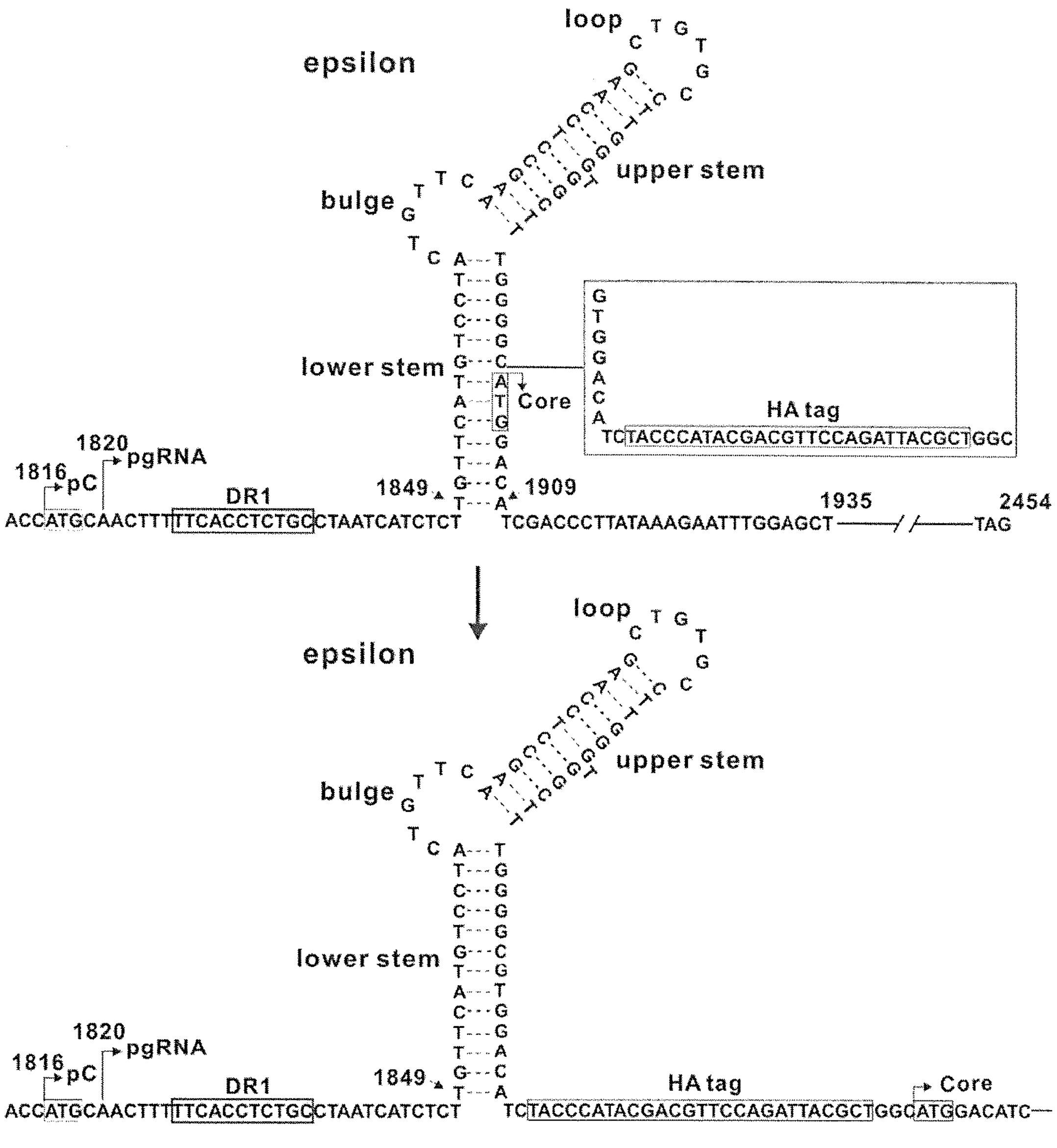

Specification includes a Sequence Listing.

SEQUENCE LISTING

<160> NUMBER OF SEQ ID NOS: 46

<210> SEQ ID NO 1
<211> LENGTH: 27
<212> TYPE: DNA
<213> ORGANISM: Hepatitis B virus

<400> SEQUENCE: 1
tacccatacg acgttccaga ttacgct 27

<210> SEQ ID NO 2
<211> LENGTH: 18
<212> TYPE: DNA
<213> ORGANISM: Hepatitis B virus

<400> SEQUENCE: 2
catcatcatc atcatcac 18

<210> SEQ ID NO 3
<211> LENGTH: 24
<212> TYPE: DNA
<213> ORGANISM: Hepatitis B virus

<400> SEQUENCE: 3
gactacaagg acgacgacga caag 24

<210> SEQ ID NO 4
<211> LENGTH: 39
<212> TYPE: DNA
<213> ORGANISM: Hepatitis B virus

<400> SEQUENCE: 4
atggcatcaa tgcagaagct gatctcagag gaggacctg 39

<210> SEQ ID NO 5
<211> LENGTH: 42
<212> TYPE: DNA
<213> ORGANISM: Hepatitis B virus

<400> SEQUENCE: 5
ggtaagccta tccctaaccc tctcctcggt ctcgattcta cg 42

<210> SEQ ID NO 6
<211> LENGTH: 27
<212> TYPE: DNA
<213> ORGANISM: Hepatitis B virus

<400> SEQUENCE: 6
actgaaacat ctcaagtagc tccagct 27

<210> SEQ ID NO 7
<211> LENGTH: 66
<212> TYPE: DNA
<213> ORGANISM: Hepatitis B virus

<400> SEQUENCE: 7
gactacaaag accacgacgg tgactacaaa gaccacgaca tcgactacaa ggacgacgac 60
gacaag 66

<210> SEQ ID NO 8
<211> LENGTH: 9
<212> TYPE: PRT
<213> ORGANISM: Hepatitis B virus

<400> SEQUENCE: 8

Tyr Pro Tyr Asp Val Pro Asp Tyr Ala
1               5

<210> SEQ ID NO 9
<211> LENGTH: 6
<212> TYPE: PRT
<213> ORGANISM: Hepatitis B virus

<400> SEQUENCE: 9

His His His His His His
1               5

<210> SEQ ID NO 10
<211> LENGTH: 8
<212> TYPE: PRT
<213> ORGANISM: Hepatitis B virus

<400> SEQUENCE: 10

Asp Tyr Lys Asp Asp Asp Asp Lys
1               5

<210> SEQ ID NO 11
<211> LENGTH: 10
<212> TYPE: PRT
<213> ORGANISM: Hepatitis B virus

<400> SEQUENCE: 11

Glu Gln Lys Leu Ile Ser Glu Glu Asp Leu
1               5                   10

<210> SEQ ID NO 12
<211> LENGTH: 14
<212> TYPE: PRT
<213> ORGANISM: Hepatitis B virus

<400> SEQUENCE: 12

Gly Lys Pro Ile Pro Asn Pro Leu Leu Gly Leu Asp Ser Thr
1               5                   10

<210> SEQ ID NO 13
<211> LENGTH: 9
<212> TYPE: PRT
<213> ORGANISM: Hepatitis B virus

<400> SEQUENCE: 13

Thr Glu Thr Ser Gln Val Ala Pro Ala
1               5

<210> SEQ ID NO 14
<211> LENGTH: 22
<212> TYPE: PRT
<213> ORGANISM: Hepatitis B virus

<400> SEQUENCE: 14

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 15
<211> LENGTH: 639
<212> TYPE: DNA

<213> ORGANISM: Hepatitis B virus

<400> SEQUENCE: 15
atgcaacttt ttcacctctg cctaatcatc tcttgttcat gtcctactgt tcaagcctcc 60
aagctgtgcc ttgggtggct ttggggcatg gacatcgacc cttataaaga atttggagct 120
actgtggagt tactctcgtt tttgccttct gacttctttc cttcagtacg agatcttcta 180
gataccgcct cagctctgta tcgggaagcc ttagagtctc ctgagcattg ttcacctcac 240
catactgcac tcaggcaagc aattctttgc tgggggggaac taatgactct agctacctgg 300
gtgggtgtta atttggaaga tccagcatct agagacctag tagtcagtta tgtcaacact 360
aatatgggcc taaagttcag gcaactcttg tggtttcaca tttcttgtct cacttttgga 420
agagaaaccg ttatagagta tttggtgtct ttcggagtgt ggattcgcac tcctccagct 480
tatagaccac caaatgcccc tatcctatca acacttccgg aaactactgt tgttagacga 540
cgaggcaggt cccctagaag aagaactccc tcgcctcgca gacgaaggtc tcaatcgccg 600
cgtcgcagaa gatctcaatc tcgggaacct caatgttag 639

<210> SEQ ID NO 16
<211> LENGTH: 477
<212> TYPE: DNA
<213> ORGANISM: Hepatitis B virus

<400> SEQUENCE: 16
tccaagctgt gccttgggtg gctttggggc atggacatcg acccttataa agaatttgga 60
gctactgtgg agttactctc gtttttgcct tctgacttct ttccttcagt acgagatctt 120
ctagataccg cctcagctct gtatcgggaa gccttagagt ctcctgagca ttgttcacct 180
caccatactg cactcaggca agcaattctt tgctgggggg aactaatgac tctagctacc 240
tgggtgggtg ttaatttgga agatccagca tctagagacc tagtagtcag ttatgtcaac 300
actaatatgg gcctaaagtt caggcaactc ttgtggtttc acatttcttg tctcactttt 360
ggaagagaaa ccgttataga gtatttggtg tctttcggag tgtggattcg cactcctcca 420
gcttatagac caccaaatgc ccctatccta tcaacacttc cggaaactac tgttgtt 477

<210> SEQ ID NO 17
<211> LENGTH: 212
<212> TYPE: PRT
<213> ORGANISM: Hepatitis B virus

<400> SEQUENCE: 17

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

```
Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Pro Gln Cys
    210
```

<210> SEQ ID NO 18
<211> LENGTH: 159
<212> TYPE: PRT
<213> ORGANISM: Hepatitis B virus

<400> SEQUENCE: 18

```
Ser Lys Leu Cys Leu Gly Trp Leu Trp Gly Met Asp Ile Asp Pro Tyr
1               5                   10                  15

Lys Glu Phe Gly Ala Thr Val Glu Leu Leu Ser Phe Leu Pro Ser Asp
            20                  25                  30

Phe Phe Pro Ser Val Arg Asp Leu Leu Asp Thr Ala Ser Ala Leu Tyr
        35                  40                  45

Arg Glu Ala Leu Glu Ser Pro Glu His Cys Ser Pro His His Thr Ala
    50                  55                  60

Leu Arg Gln Ala Ile Leu Cys Trp Gly Glu Leu Met Thr Leu Ala Thr
65                  70                  75                  80

Trp Val Gly Val Asn Leu Glu Asp Pro Ala Ser Arg Asp Leu Val Val
                85                  90                  95

Ser Tyr Val Asn Thr Asn Met Gly Leu Lys Phe Arg Gln Leu Leu Trp
            100                 105                 110

Phe His Ile Ser Cys Leu Thr Phe Gly Arg Glu Thr Val Ile Glu Tyr
        115                 120                 125

Leu Val Ser Phe Gly Val Trp Ile Arg Thr Pro Pro Ala Tyr Arg Pro
    130                 135                 140

Pro Asn Ala Pro Ile Leu Ser Thr Leu Pro Glu Thr Thr Val Val
145                 150                 155
```

<210> SEQ ID NO 19
<211> LENGTH: 678
<212> TYPE: DNA
<213> ORGANISM: Hepatitis B virus

<400> SEQUENCE: 19

```
atgcaacttt ttcacctctg cctaatcatc tcttgttcat gtcctactgt tcaagcctcc      60

aagctgtgcc ttgggtggct ttggggcgtg gacatctacc catacgacgt tccagattac     120

gctggcatgg acatcgaccc ttataaagaa tttggagcta ctgtggagtt actctcgttt     180

ttgccttctg acttctttcc ttcagtacga gatcttctag ataccgcctc agctctgtat     240

cgggaagcct tagagtctcc tgagcattgt tcacctcacc atactgcact caggcaagca     300

attctttgct ggggggaact aatgactcta gctacctggg tgggtgttaa tttggaagat     360
```

-continued

```
ccagcatcta gagacctagt agtcagttat gtcaacacta atatgggcct aaagttcagg    420

caactcttgt ggtttcacat ttcttgtctc acttttggaa gagaaaccgt tatagagtat    480

ttggtgtctt tcggagtgtg gattcgcact cctccagctt atagaccacc aaatgcccct    540

atcctatcaa cacttccgga aactactgtt gttagacgac gaggcaggtc ccctagaaga    600

agaactccct cgcctcgcag acgaaggtct caatcgccgc gtcgcagaag atctcaatct    660

cgggaacctc aatgttag                                                  678


<210> SEQ ID NO 20
<211> LENGTH: 516
<212> TYPE: DNA
<213> ORGANISM: Hepatitis B virus

<400> SEQUENCE: 20

tccaagctgt gccttgggtg gctttggggc gtggacatct acccatacga cgttccagat     60

tacgctggca tggacatcga cccttataaa gaatttggag ctactgtgga gttactctcg    120

tttttgcctt ctgacttctt tccttcagta cgagatcttc tagataccgc ctcagctctg    180

tatcgggaag ccttagagtc tcctgagcat tgttcacctc accatactgc actcaggcaa    240

gcaattcttt gctgggggga actaatgact ctagctacct gggtgggtgt taatttggaa    300

gatccagcat ctagagacct agtagtcagt tatgtcaaca ctaatatggg cctaaagttc    360

aggcaactct tgtggtttca catttcttgt ctcacttttg gaagagaaac cgttatagag    420

tatttggtgt ctttcggagt gtggattcgc actcctccag cttatagacc accaaatgcc    480

cctatcctat caacacttcc ggaaactact gttgtt                              516


<210> SEQ ID NO 21
<211> LENGTH: 225
<212> TYPE: PRT
<213> ORGANISM: Hepatitis B virus

<400> SEQUENCE: 21

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Val Asp Ile
            20                  25                  30

Tyr Pro Tyr Asp Val Pro Asp Tyr Ala Gly Met Asp Ile Asp Pro Tyr
        35                  40                  45

Lys Glu Phe Gly Ala Thr Val Glu Leu Leu Ser Phe Leu Pro Ser Asp
    50                  55                  60

Phe Phe Pro Ser Val Arg Asp Leu Leu Asp Thr Ala Ser Ala Leu Tyr
65                  70                  75                  80

Arg Glu Ala Leu Glu Ser Pro Glu His Cys Ser Pro His His Thr Ala
                85                  90                  95

Leu Arg Gln Ala Ile Leu Cys Trp Gly Glu Leu Met Thr Leu Ala Thr
            100                 105                 110

Trp Val Gly Val Asn Leu Glu Asp Pro Ala Ser Arg Asp Leu Val Val
        115                 120                 125

Ser Tyr Val Asn Thr Asn Met Gly Leu Lys Phe Arg Gln Leu Leu Trp
    130                 135                 140

Phe His Ile Ser Cys Leu Thr Phe Gly Arg Glu Thr Val Ile Glu Tyr
145                 150                 155                 160

Leu Val Ser Phe Gly Val Trp Ile Arg Thr Pro Pro Ala Tyr Arg Pro
                165                 170                 175
```

```
Pro Asn Ala Pro Ile Leu Ser Thr Leu Pro Glu Thr Thr Val Val Arg
            180                 185                 190

Arg Arg Gly Arg Ser Pro Arg Arg Arg Thr Pro Ser Pro Arg Arg Arg
        195                 200                 205

Arg Ser Gln Ser Pro Arg Arg Arg Arg Ser Gln Ser Arg Glu Pro Gln
    210                 215                 220

Cys
225


<210> SEQ ID NO 22
<211> LENGTH: 172
<212> TYPE: PRT
<213> ORGANISM: Hepatitis B virus

<400> SEQUENCE: 22

Ser Lys Leu Cys Leu Gly Trp Leu Trp Gly Val Asp Ile Tyr Pro Tyr
1               5                   10                  15

Asp Val Pro Asp Tyr Ala Gly Met Asp Ile Asp Pro Tyr Lys Glu Phe
            20                  25                  30

Gly Ala Thr Val Glu Leu Leu Ser Phe Leu Pro Ser Asp Phe Phe Pro
        35                  40                  45

Ser Val Arg Asp Leu Leu Asp Thr Ala Ser Ala Leu Tyr Arg Glu Ala
    50                  55                  60

Leu Glu Ser Pro Glu His Cys Ser Pro His His Thr Ala Leu Arg Gln
65                  70                  75                  80

Ala Ile Leu Cys Trp Gly Glu Leu Met Thr Leu Ala Thr Trp Val Gly
                85                  90                  95

Val Asn Leu Glu Asp Pro Ala Ser Arg Asp Leu Val Val Ser Tyr Val
            100                 105                 110

Asn Thr Asn Met Gly Leu Lys Phe Arg Gln Leu Leu Trp Phe His Ile
        115                 120                 125

Ser Cys Leu Thr Phe Gly Arg Glu Thr Val Ile Glu Tyr Leu Val Ser
    130                 135                 140

Phe Gly Val Trp Ile Arg Thr Pro Pro Ala Tyr Arg Pro Pro Asn Ala
145                 150                 155                 160

Pro Ile Leu Ser Thr Leu Pro Glu Thr Thr Val Val
                165                 170


<210> SEQ ID NO 23
<211> LENGTH: 552
<212> TYPE: DNA
<213> ORGANISM: Hepatitis B virus

<400> SEQUENCE: 23

atggacatcg acccttataa agaatttgga gctactgtgg agttactctc gtttttgcct      60

tctgacttct ttccttcagt acgagatctt ctagataccg cctcagctct gtatcgggaa     120

gccttagagt ctcctgagca ttgttcacct caccatactg cactcaggca agcaattctt     180

tgctgggggg aactaatgac tctagctacc tgggtgggtg ttaatttgga agatccagca     240

tctagagacc tagtagtcag ttatgtcaac actaatatgg gcctaaagtt caggcaactc     300

ttgtggtttc acatttcttg tctcactttt ggaagagaaa ccgttataga gtatttggtg     360

tctttcggag tgtggattcg cactcctcca gcttatagac caccaaatgc ccctatccta     420

tcaacacttc cggaaactac tgttgttaga cgacgaggca ggtcccctag aagaagaact     480

ccctcgcctc gcagacgaag gtctcaatcg ccgcgtcgca gaagatctca atctcgggaa     540
```

cctcaatgtt ag 552

<210> SEQ ID NO 24
<211> LENGTH: 183
<212> TYPE: PRT
<213> ORGANISM: Hepatitis B virus

<400> SEQUENCE: 24

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Pro Gln Cys
            180
```

<210> SEQ ID NO 25
<211> LENGTH: 61
<212> TYPE: DNA
<213> ORGANISM: Hepatitis B virus

<400> SEQUENCE: 25
tgttcatgtc ctactgttca agcctccaag ctgtgccttg ggtggctttg gggcatggac 60
a 61

<210> SEQ ID NO 26

<400> SEQUENCE: 26

000

<210> SEQ ID NO 27
<211> LENGTH: 3182
<212> TYPE: DNA
<213> ORGANISM: Hepatitis B virus

<400> SEQUENCE: 27
aattccacaa cctttcacca aactctgcaa gatcccagag tgagaggcct gtatttccct 60
gctggtggct ccagttcagg agcagtaaac cctgttccga ctactgcctc tcccttatcg 120
tcaatcttct cgaggattgg ggaccctgcg ctgaacatgg agaacatcac atcaggattc 180

-continued

```
ctaggacccc ttctcgtgtt acaggcgggg tttttcttgt tgacaagaat cctcacaata    240
ccgcaaagtc tagactcgtg gtggacttct ctcaattttc tagggggaac taccgtgtgt    300
cttggccaaa attcgcagtc cccaacctcc aatcactcac caacctcctg tcctccaact    360
tgtcctggtt atcgctggat gtgtctgcgg cgttttatca tcttcctctt catcctgctg    420
ctatgcctca tcttcttgtt ggttcttctg gactatcaag gtatgttgcc cgtttgtcct    480
ctaattccag gatcctcaac caccagcacg ggaccatgcc gaacctgcat gactactgct    540
caaggaacct ctatgtatcc ctcctgttgc tgtaccaaac cttcggacgg aaattgcacc    600
tgtattccca tcccatcatc ctgggctttc ggaaaattcc tatgggagtg ggcctcagcc    660
cgtttctcct ggctcagttt actagtgcca tttgttcagt ggttcgtagg gctttccccc    720
actgtttggc tttcagttat atggatgatg tggtattggg ggccaagtct gtacagcatc    780
ttgagtccct ttttaccgct gttaccaatt ttcttttgtc tttgggtata catttaaacc    840
ctaacaaaac aaagagatgg ggttactctc tgaattttat gggttatgtc attggaagtt    900
atgggtcctt gccacaagaa cacatcatac aaaaaatcaa agaatgtttt agaaaacttc    960
ctattaacag gcctattgat tggaaagtat gtcaacgaat tgtgggtctt ttgggttttg   1020
ctgccccatt tacacaatgt ggttatcctg cgttaatgcc cttgtatgca tgtattcaat   1080
ctaagcaggc tttcactttc tcgccaactt acaaggcctt tctgtgtaaa caatacctga   1140
acctttaccc cgttgcccgg caacggccag gtctgtgcca agtgtttgct gacgcaaccc   1200
ccactggctg gggcttggtc atgggccatc agcgcgtgcg tggaaccttt tcggctcctc   1260
tgccgatcca tactgcggaa ctcctagccg cttgttttgc tcgcagcagg tctggagcaa   1320
acattatcgg gactgataac tctgttgtcc tctcccgcaa atatacatcg tatccatggc   1380
tgctaggctg tgctgccaac tggatcctgc gcgggacgtc ctttgtttac gtcccgtcgg   1440
cgctgaatcc tgcggacgac ccttctcggg gtcgcttggg actctctcgt ccccttctcc   1500
gtctgccgtt ccgaccgacc acggggcgca cctctcttta cgcggactcc ccgtctgtgc   1560
cttctcatct gccggaccgt gtgcacttcg cttcacctct gcacgtcgca tggagaccac   1620
cgtgaacgcc caccgaatgt tgcccaaggt cttacataag aggactcttg gactctctgc   1680
aatgtcaacg accgaccttg aggcatactt caaagactgt ttgtttaaag actgggagga   1740
gttgggggag gagattagat taaaggtctt tgtactagga ggctgtaggc ataaattggt   1800
ctgcgcacca gcaccatgca actttttcac ctctgcctaa tcatctcttg ttcatgtcct   1860
actgttcaag cctccaagct gtgccttggg tggctttggg gcatggacat cgacccttat   1920
aaagaatttg gagctactgt ggagttactc tcgtttttgc cttctgactt ctttccttca   1980
gtacgagatc ttctagatac cgcctcagct ctgtatcggg aagccttaga gtctcctgag   2040
cattgttcac ctcaccatac tgcactcagg caagcaattc tttgctgggg ggaactaatg   2100
actctagcta cctgggtggg tgttaatttg gaagatccag catctagaga cctagtagtc   2160
agttatgtca acactaatat gggcctaaag ttcaggcaac tcttgtggtt tcacatttct   2220
tgtctcactt ttggaagaga aaccgttata gagtatttgg tgtctttcgg agtgtggatt   2280
cgcactcctc cagcttatag accaccaaat gcccctatcc tatcaacact tccggaaact   2340
actgttgtta gacgacgagg caggtcccct agaagaagaa ctccctcgcc tcgcagacga   2400
aggtctcaat cgccgcgtcg cagaagatct caatctcggg aacctcaatg ttagtattcc   2460
ttggactcat aaggtgggga actttactgg tctttattct tctactgtac ctgtctttaa   2520
tcctcattgg aaaacaccat cttttcctaa tatacattta caccaagaca ttatcaaaaa   2580
```

atgtgaacag tttgtaggcc cacttacagt taatgagaaa agaagattgc aattgattat 2640
gcctgctagg ttttatccaa aggttaccaa atatttacca ttggataagg gtattaaacc 2700
ttattatcca gaacatctag ttaatcatta cttccaaact agacactatt tacacactct 2760
atggaaggcg ggtatattat ataagagaga aacaacacat agcgcctcat tttgtgggtc 2820
accatattct tgggaacaag atctacagca tggggcagaa tctttccacc agcaatcctc 2880
tgggattctt tcccgaccac cagttggatc cagccttcag agcaaacaca gcaaatccag 2940
attgggactt caatcccaac aaggacacct ggccagacgc caacaaggta ggagctggag 3000
cattcgggct gggtttcacc ccaccgcacg gaggcctttt ggggtggagc cctcaggctc 3060
agggcatact acaaactttg ccagcaaatc cgcctcctgc ctccaccaat cgccagacag 3120
gaaggcagcc taccccgctg tctccacctt tgagaaacac tcatcctcag gccatgcagt 3180
gg 3182

<210> SEQ ID NO 28
<211> LENGTH: 3221
<212> TYPE: DNA
<213> ORGANISM: Hepatitis B virus

<400> SEQUENCE: 28
aattccactg ccttccacca agctctgcag gatcccagag tcaggggtct gtattttcct 60
gctggtggct ccagttcagg aacagtaaac cctgctccga atattgcctc tcacatctcg 120
tcaatctccg cgaggactgg ggaccctgtg gcgaacatgg agaacatcac atcaggattc 180
ctaggacccc tgctcgtgtt acaggcgggg tttttcttgt tgacaagaat cctcacaata 240
ccgcagagtc tagactcgtg gtggacttct ctcaattttc tagggggatc acccgtgtgt 300
cttggccaaa attcgcagtc cccaacctcc aatcactcac caacctcctg tcctccaatt 360
tgtcctggtt atcgctggat gtgtctgcgg cgttttatca tattcctctt catcctgctg 420
ctatgcctca tcttcttatt ggttcttctg gattatcaag gtatgttgcc cgtttgtcct 480
ctaattccag gatcaacaac aaccagtacg ggaccatgca aaacctgcac gactcctgct 540
caaggcaact ctatgtttcc ctcatgttgc tgtacaaaac ctacggatgg aaattgcacc 600
tgtattccca tcccatcgtc ctgggctttc gcaaaatacc tatgggagtg ggcctcagtc 660
cgtttctctt ggctcagttt actagtgcca tttgttcagt ggttcgtagg gctttccccc 720
actgtttggc tttcagctat atggatgatg tggtattggg ggccaagtct gtacagcatc 780
gtgagtccct ttataccgct gttaccaatt ttcttttgtc tctgggtata catttaaacc 840
ctaacaaaac aaaaagatgg ggttattccc taaacttcat gggttacata attggaagtt 900
ggggaacttt gccacaggat catattgtac aaaagatcaa acactgtttt agaaaacttc 960
ctgttaacag gcctattgat tggaaagtat gtcaaagaat tgtgggtctt ttgggctttg 1020
ctgctccatt tacacaatgt ggatatcctg ccttaatgcc tttgtatgca tgtatacaag 1080
ctaaacaggc tttcactttc tcgccaactt acaaggcctt tctaagtaaa cagtacatga 1140
acctttaccc cgttgctcgg caacggcctg gtctgtgcca agtgtttgct gacgcaaccc 1200
ccactggctg gggcttggcc ataggccatc agcgcatgcg tggaaccttt gtggctcctc 1260
tgccgatcca tactgcggaa ctcctagccg cttgttttgc tcgcagccgg tctggagcaa 1320
agctcatcgg aactgacaat tctgtcgtcc tctcgcggaa atatacatcg tttccatggc 1380
tgctaggctg tgctgccaac tggatccttc gcggaacgtc ctttgtctac gtcccgtcgg 1440

-continued

```
cgctgaatcc cgcggacgac ccctctcggg gccgcttggg actctctcgt ccccttctcc   1500

gtctgccgtt ccagccgacc acggggcgca cctctcttta cgcggtctcc ccgtctgtgc   1560

cttctcatct gccggtccgt gtgcacttcg cttcacctct gcacgttgca tggagaccac   1620

cgtgaacgcc catcagatcc tgcccaaggt cttacataag aggactcttg gactcccagc   1680

aatgtcaacg accgaccttg aggcctactt caaagactgt gtgtttaagg actgggagga   1740

gctgggggag gagattaggt taaaggtctt tgtattagga ggctgtaggc ataaattggt   1800

ctgcgcacca gcaccatgca actttttcac ctctgcctaa tcatctcttg tacatgtccc   1860

actgttcaag cctccaagct gtgccttggg tggctttggg gcatggacat tgacccttat   1920

aaagaatttg gagctactgt ggagttactc tcgtttttgc cttctgactt ctttccttcc   1980

gtcagagatc tcctagacac cgcctcagct ctgtatcgag aagccttaga gtctcctgag   2040

cattgctcac ctcaccatac tgcactcagg caagccattc tctgctgggg ggaattgatg   2100

actctagcta cctgggtggg taataatttg gaagatccag catccaggga tctagtagtc   2160

aattatgtta atactaacat gggtttaaag atcaggcaac tattgtggtt tcatatatct   2220

tgccttactt ttggaagaga gactgtactt gaatatttgg tctctttcgg agtgtggatt   2280

cgcactcctc cagcctatag accaccaaat gcccctatct tatcaacaat tccggaaact   2340

actgttgtta gacgacggga ccgaggcagg tcccctagaa gaagaactcc ctcgcctcgc   2400

agacgcagat ctcaatcgcc gcgtcgcaga agatctcaat ctcgggaatc tcaatgttag   2460

tattccttgg actcataagg tgggaaactt tacggggctt tattcctcta cagtacctat   2520

ctttaatcct gaatggcaaa ctccttcctt tcctaagatt catttacaag aggacattat   2580

taataggtgt caacaatttg tgggccctct cactgtaaat gaaaagagaa gattgaaatt   2640

aattatgcct gctagattct atcctaccca cactaaatat ttgcccttag acaaaggaat   2700

taaaccttat tatccagatc aggtagttaa tcattacttc caaaccagac attatttaca   2760

tactctttgg aaggctggta ttctatataa gagggaaacc acacgtagcg catcattttg   2820

cgggtcacca tattcttggg aacaagagct acagcatggg aggttggtca tcaaaacctc   2880

gcaaaggcat ggggacgaat ctttctgttc ccaaccctct gggattcttt cccgatcatc   2940

agttggaccc tgcattcgga gccaactcaa acaatccaga ttgggacttc aaccccatca   3000

aggaccactg gccaacagcc aaccaggtag gagtgggagc attcgggcca gggctcaccc   3060

ctccacacgg cggtattttg ggggggagcc ctcaggctca gggcatattg accacagtgt   3120

caacaattcc tcctcctgcc tccaccaatc ggcagtcagg aaggcagcct actcccatct   3180

ctccacctct aagagacagt catcctcagg ccatgcagtg g                        3221
```

```
<210> SEQ ID NO 29
<211> LENGTH: 3215
<212> TYPE: DNA
<213> ORGANISM: Hepatitis B virus

<400> SEQUENCE: 29
```

```
aactccacca cttttcacca aactcttcaa gatcccagag tccgggctct gtactttcct     60

gctggtggct ccagttcagg aacagtaagc cctgctcaga atactgtctc tgccatatcg    120

tcaatcttat cgaagactgg ggaccctgtg ccgaacatgg agaacatcgc atcaggactc    180

ctaggacccc tgctcgtgtt acaggcgggg tttttcttgt tgacaaaaat cctcacaata    240

ccacagagtc tagactcgtg gtggacttct ctcaattttc tagggggaac acccgtgtgt    300

cttggccaaa attcgcagtc ccaaatctcc agtcactcac caacctgttg tcctccaatt    360
```

-continued

```
tgtcctggtt atcgctggat gtgtctgcgg cgttttatca tcttcctctg catcctgctg    420
ctatgcctca tcttcttgtt ggttcttctg gactatcaag gtatgttgcc cgtttgtcct    480
ctaattccag gatcatcaac caccagcacg ggaccatgca agacctgcac aactcctgct    540
caaggaacct ctatgtttcc ctcatgttgc tgtacaaaac ctacggatgg aaactgcacc    600
tgtattccca tcccatcatc ttgggctttc gcaaaatacc tatgggagtg ggcctcagtc    660
cgtttctctt ggctcagttt actagtgcca tttgttcagt ggttcgtagg gctttccccc    720
actgtctggc tttcagttat atggatgatg tggtattggg ggccaagtct gtacaacatc    780
ttgagtccct ttatgccgct gttaccaatt ttcttttgtc tttgggtata catttaaacc    840
ctcacaaaac aaaaagatgg ggatattccc ttaacttcat gggatatgta attgggagtt    900
ggggcacatt gccacaggaa catattgtac aaaaaatcaa actatgtttt aggaaacttc    960
ctgtaaacag gcctattgat tggaaagtat gtcaacgaat tgtgggtctt ttggggtttg   1020
ctgcccccttt tacgcaatgt ggatatcctg ctttaatgcc tttatatgca tgtatacaag  1080
caaaacaggc ttttactttc tcgccaactt acaaggcctt tctaagtaaa cagtatctag   1140
ccctttaccc cgttgctcgg caacggcctg gtctgtgcca agtgtttgct gacgcaaccc   1200
ccactggttg gggcttggcc ataggccatc agcgcatgcg tggaaccttt gtgtctcctc   1260
tgccgatcca tactgcggaa ctcctagccg cttgttttgc tcgcagcagg tctggagcga   1320
aactcatcgg gactgacaat tctgtcgtgc tctcccgcaa gtatacatcg tttccatggc   1380
tgctaggctg tgctgccaac tggatcctgc gcgggacgtc ctttgtttac gtcccgtcgg   1440
cgctgaatcc cgcggacgac ccctcccggg gccgcttggg gctctaccgc ccgcttctcc   1500
gtctgccgta ccgaccgacc acggggcgca cctctcttta cgcggactcc ccgtctgtgc   1560
cttctcgtct gccggaccgt gtgcacttcg cttcacctct gcacgtcgca tggaaaccac   1620
cgtgaacgcc caccggaacc tgcccaaggt cttgcacaag aggactcttg gactttcagc   1680
aatgtcaacg accgaccttg aggcatactt caaagactgt gtgtttcatg agtgggagga   1740
gctgggggag gagattaggt taaaggtctt tgtactagga ggctgtaggc ataaattggt   1800
ctgttcacca gcaccatgca actttttcac ctctgcctag tcatctcttg ttcatgtcct   1860
actgttcaag cctccaagct gtgccttggg tggctttggg acatggacat tgacccttat   1920
aaagaatttg gagctactgt ggagttactc tctttttttgc cttctgactt ctttccgtcg  1980
gtacgagacc tcctagatac cgctgctgct ctgtatcggg aagccttaga atctcctgaa   2040
cattgctcac ctcaccacac agcactcagg caagctattc tgtgctgggg ggaattaatg   2100
actctagcta cctgggtggg taataattta gaagatccag cgtccaggga tctagtagtc   2160
aattatgtta acactaacat gggcctaaag atcaggcaat tattgtggtt tcacatttcc   2220
tgtcttactt ttggaagaga aactgttctt gaatatttgg tgtcttttgg agtgtggatt   2280
cgcactcctc cggcctacag accaccaaat gcccctatct tatcaacact tccggaaact   2340
actgttgtta gacgacgagg caggtcccct agaagaagaa ctccctcgcc tcgcagacga   2400
aggtctcaat caccgcgtcg cagaagatct caatctcggg aatcccaatg ttagtattcc   2460
ttggactcat aaggtgggaa actttacggg gctctattct tctacagtac ctgtctttaa   2520
tcctgaatgg caaactcctt cttttccaga cattcatttg caggaggata ttgttgatag   2580
atgtaagcaa tttgtgggac cccttacagt aaatgaaaac aggagactaa aattaataat   2640
gcctgctaga ttttatccta atgttaccaa atatttgccc ttagataaag ggatcaaacc   2700
```

```
ttattatcca gagcatgtag ttaatcatta cttccagaca agacattatt tgcatactct   2760

ttggaaggcg ggtatcttat ataagagaga gtcaacacat agcgcctcat tttgcgggtc   2820

accatattct tgggaacaag atctacagca tgggaggttg gtcttccaaa cctcgaaaag   2880

gcatggggac aaatctttct gtccccaatc ccctgggatt cttccccgat catcagttgg   2940

accctgcatt caaagccaac tcagaaaatc cagattggga cctcaaccca cacaaggaca   3000

actggccgga cgcccacaag gtgggagtgg gagcattcgg gccagggttc acccctcccc   3060

acgggggact gttggggtgg agccctcagg ctcagggcat acttacatct gtgccagcag   3120

ctcctcctcc tgcctccacc aatcggcagt caggaaggca gcctactccc ttatctccac   3180

ctctaaggga cactcatcct caggccatgc agtgg                              3215
```

<210> SEQ ID NO 30
<211> LENGTH: 3215
<212> TYPE: DNA
<213> ORGANISM: Hepatitis B virus

<400> SEQUENCE: 30

```
aactccacaa ctttccacca agctctgcta gatcccagag tgaggggcct atactttcct     60

gctggtggct ccagttccgg aacagtaaac cctgttccga ctactgcctc tcccatatcg    120

tcaatcttca cgaggactgg ggaccctgta ccgaacatgg agaacacaac atcaggattc    180

ctaggacccc tgctcgtgtt acaggcgggg tttttcttgt tgacaagaat cctcacaata    240

ccgcagagtc tagactcgtg gtggacttct ctcaattttc tagggggagc acccacgtgt    300

cctggccaaa attcgcagtc cccaacctcc aatcactcac caacctcttg tcctccaatt    360

tgtcctggct atcgctggat gtgtctgcgg cgttttatca tattcctctt catcctgctg    420

ctatgcctca tcttcttgtt ggttcttctg gactatcaag gtatgttgcc cgtttgtcct    480

ctacttccag gaacatcaac tacaagcacg ggaccatgca agacctgcac gattcctgct    540

caaggaamct ctatgtttcc ctcttgttgc tgtacaaaac cttcggacgg aaactgcact    600

tgtattccca tcccatcatc ctgggctttc gcaagattcc tatgggagtg ggcctcagtc    660

cgtttctcct ggctcagttt actagtgcca tttgttcagt ggttcgtagg gctttccccc    720

actgtttggc tttcagctat atggatgatg tggtattggg ggccaagtct gtacaacatc    780

ttgagtccct ttttacctct attaccaatt ttcttttgtc tttgggtata catttgaacc    840

ctaataaaac caagcgttgg ggctactccc ttaactttat gggatatgta attggaagtt    900

ggggtacttt accacaggaa catattgttc taaaaatcaa acaatgtttt cggaaactgc    960

ctgtaaatag acctattgat tggaaagtat gtcaacgaat tgtgggtctt ctgggctttg   1020

ctgccccttt tacacaatgt gggtatcctg ccttgatgcc tttgtatgca tgtatacaag   1080

ctaagcaggc tttcactttc tcgccaactt ataaggcctt tctgtgtaaa caatatctga   1140

acctttaccc cgttgctcgg caacggtcag gtctctgcca agtatttgct gacgcaaccc   1200

ccactggatg gggcttggca ataggccatc agcgcatgcg tggaaccttt gtggctcctc   1260

tgccgatcca tactgcggaa ctcttagcag cctgctttgc tcgcagccgg tctggagcra   1320

atcttattgg aaccgacaac tccgttgtcc tctctcggaa atacacctcc tttccatggc   1380

tgctagggtg tgctgcaaac tggatcctgc gcgggacgtc ctttgtctac gtcccgtcgg   1440

cgctgaatcc agcggacgac ccgtctcggg gccgtttggg actctaccgt ccccttcttc   1500

gtctgccgtt ccggccgacc acggggcgca cctctcttta cgcggtctcc ccgtctgtgc   1560

cttctcatct gccggaccgt gtgcacttcg cttcacctct gcacgtcgca tggagaccac   1620
```

cgtgaacgcc caccaggtct tgcccaaggt cttacataag aggactcttg gactctcggc 1680
aatgtcaacg accgaccttg aggcatactt caaagactgt gtgtttaaag actgggagga 1740
gttgggggag gagattaggt taaaggtctt tgtactagga ggctgtaggc ataaattggt 1800
ctgttcacca gcaccatgca actttttcac ctctgcctaa tcatctcatg ttcatgtcct 1860
actgttcaag cctccaagct gtgccttggg tggctttggg gcatggacat tgacccgtat 1920
aaagaatttg gagcttctgt ggagttactc tctttttgc cttctgactt ctttccttcc 1980
attcgagatc tcctcgacac cgcctctgct ctgtatcggg aggccttaga gtctccggaa 2040
cattgttcac ctcaccatac agcactcagg caagctattc tgtgttgggg tgagttgatg 2100
aatctggcca cctgggtggg aagtaatttg gaagacccag catctaggga attagtagtc 2160
agttatgtta atgttaatat gggcctaaag atcagacaac tattgtggtt tcacatttcc 2220
tgtcttactt ttggaagaga aactgttctt gagtatttgg tgtcctttgg agtgtggata 2280
cgcactcctc ccgcttacag accaccaaat gcccctatct tatcaacact tccggaaact 2340
actgttgtta gacgacgagg caggtcccct agaagaagaa ctccctcgcc tcgcagacga 2400
aggtctcaat cgccgcgtcg cagaagatct caatctcggg aatctcaatg ttagtatccc 2460
ttggactcat aaggtgggaa attttactgg gctttattct tctactgtac ctgtcttcaa 2520
tcctgagtgg caaactccct cctttcctca cattcatttg caggaggaca ttattaatag 2580
atgtcaacaa tatgtgggcc ctcttacagt taatgaaaaa aggagattaa aattaattat 2640
gcctgccagg ttttatccta accgtaccaa atatttgccc ctagataaag gcattaaacc 2700
ttattatcct gaatatacag ttaatcatta cttccaaacc aggcattatt tacatactct 2760
gtggaaggct ggcattctat ataagagaga aactacacgc agcgcctcat tttgtgggtc 2820
accatattct tgggaacaag agctacagca tgggaggttg gtcctccaaa cctcgaaagg 2880
gcatggggac gaatctttct gttcccaatc ctctgggctt ctttcccgat caccagttgg 2940
accctgcatt cggagccaac tcaaacaatc cggattggga cttcaatccc aacaaggatc 3000
actggccagc agcaaaccag gtaggagcgg gagccttcgg gccagggttc accccaccgc 3060
acggcggtct tttggggtgg agccctcagg ctcagggcgt attgacaaca gtgccagcag 3120
cgcctcctcc tgcctccacc aatcggcagt caggcagaca gcctactccc atctctccac 3180
ctctaagaga cagtcatcct caggccatgc agtgg 3215

<210> SEQ ID NO 31
<211> LENGTH: 3212
<212> TYPE: DNA
<213> ORGANISM: Hepatitis B virus

<400> SEQUENCE: 31
aattccacaa cattccacca agctctgcag gatcccagag taagaggcct gtatcttcct 60
gctggtggct ccagttccgg aacagtgaac cctgttccga ctactgcctc actcatctcg 120
tcaatcttct cgaggattgg ggaccctgca ccgaacatgg aaggcatcac atcaggattc 180
ctaggacccc tgctcgtgtt acaggcgggg tttttcttgt tgacaaaaat cctcacaata 240
ccgcagagtc tagactcgtg gtggacttct ctcaattttc tagggggagc tcccgtgtgt 300
cttggccaaa attcgcagtc cccaatctcc aatcactcac caacctcttg tcctccaatt 360
tgtcctggct atcgctggat gtgtctgcgg cgttttatca tcttcctctt catcctgctg 420
ctatgcctca tcttcttgtt ggttcttctg gactatcaag gtatgttgcc cgtttgtcct 480

-continued

```
ctaattccag gatcatcaac caccagtacg ggaccctgcc gaacctgcac gactcttgct    540
caaggaacct ctatgtttcc ctcatgttgt tgtttaaaac cttcggacgg aaattgcact    600
tgtattccca tcccatcatc atgggctttc ggaaaattcc tatgggagtg ggcctcagcc    660
cgtttctcct ggctcagttt actagtgcca tttgttcagt ggttcgccgg gctttccccc    720
actgtctggc tttcagttat atggatgatg tggtattggg ggccaagtct gtacaacatc    780
ttgagtccct ttatacctct gttaccaatt ttcttttgtc tttgggtata catttaaatc    840
ccaacaaaac aaaaagatgg ggatattccc taaatttcat gggttatgta attggtagtt    900
gggggtcatt accacaagaa cacatcagac tgaaaatcaa agactgtttt agaaagctcc    960
ctgttaacag gcctattgat tggaaagtat gtcaaagaat tgtgggtctt ttgggctttg   1020
ctgccccttt tacacaatgt ggatatcctg ctttaatgcc tctatatgcg tgtattcaat   1080
ctaagcaggc tttcactttc tcgccaactt acaaggcctt tctgtgtaaa caatatatga   1140
acctttaccc cgttgcccgg caacggccag gtctgtgcca agtgtttgct gatgcaaccc   1200
ccactggctg gggcttggcc ataggccatc agcgcatgcg tggaaccttt gtggctcctc   1260
tgccgatcca tactgcggaa ctcctagccg cttgttttgc tcgcagcagg tctggagcga   1320
aactcatagg gacagataat tctgtcgttc tctcccggaa atatacatca tttccatggc   1380
tgctaggctg tgctgccaac tggatcctgc gagggacgtc ctttgtctac gtcccgtcag   1440
cgctgaatcc tgcggacgac ccctctcggg gccgcttggg ggtctatcgt ccccttctcc   1500
gtctgccgtt ccggccgacc acggggcgca cctctcttta cgcggtctcc ccgtctgtgc   1560
cttctcatct gccggaccgt gtgcacttcg cttcacctct gcacgtcgca tggagaccac   1620
cgtgaacgcc caccagatct tgcccaaggt cttacataag aggactcttg gactctctgc   1680
aatgtcaacg accgaccttg aggcatactt caaagactgt ttgtttaaag actgggagga   1740
gttgggggag gagactagat taatgatctt tgtactagga ggctgtaggc ataaattggt   1800
ctgcgcacca gcaccatgca actttttcac ctctgcctaa tcatctcttg ttcatgtcct   1860
actgttcaag cctccaagct gtgccttggg tggctttggg acatggacat tgacccttat   1920
aaagaatttg gagctactgt ggagttactc tcgtttttgc cttctgactt ctttccttca   1980
gtaagagatc ttctagatac cgcctctgct ctgtatcggg atgccttaga atctcctgag   2040
cattgttcac ctcaccatac tgcactcagg caagccattc tttgctgggg agaattaatg   2100
actctagcta cctgggtggg tgtaaatttg gaagatccag catccaggga cctagtagtc   2160
agttatgtca atactaatat gggcctaaag ttcaggcaat tattgtggtt tcacatttct   2220
tgtctcactt ttggaagaga aaccgtcata gagtatttgg tgtcttttgg agtgtggatt   2280
cgcactcctc cagcttatag accaccaaat gcccctatct tatcaacact tccggagaat   2340
actgttgtta gacgaagagg caggtcccct agaagaagaa ctccctcgcc tcgcagacga   2400
agatctcaat cgccgcgtcg cagaagatct caatctccag cttcccaatg ttagtattcc   2460
ttggactcac aaggtgggaa attttacggg gctttattct tctactatac ctgtctttaa   2520
tcctaactgg aaaactccat cttttcctga tattcatttg caccaggaca ttattaacaa   2580
atgtgaacaa tttgtaggtc ctytaacagt aaatgaaaaa cgaagattaa acttagtcat   2640
gcctgctaga tttttttccca tctccacgaa atatttgccc ctagagaaag gtataaaacc   2700
ttattatcca gataatgtag ttaatcatta cttccaaacc agacactatt tacataccct   2760
atggaaggcg ggcatcttat ataaaagaga aactacccgt agcgcctcat tttgtgggtc   2820
accttattct tgggaacacg agctacatca tggggctttc ttggacggtc cctctcgaat   2880
```

gggggaagaa tcattccacc accaatcctc tgggattttt tcccgaccac cagttggatc 2940
cagcattcag agcaaacacc agaaatccag attgggacca caatcccaac aaagaccact 3000
ggacagaagc caacaaggta ggagtgggag catttgggcc ggggttcact cccccacacg 3060
gaggcctttt ggggtggagc cctcaggctc aaggcatgct aaaaacattg ccagcaaatc 3120
cgcctcctgc ctccaccaat cggcagtcag gaaggcagcc taccccaatc actccacctt 3180
tgagagacac tcatcctcag gccatgcagt gg 3212

<210> SEQ ID NO 32
<211> LENGTH: 3215
<212> TYPE: DNA
<213> ORGANISM: Hepatitis B virus

<400> SEQUENCE: 32
aactcaaccc agttccatca ggctctgttg gatcccaggg taagggctct gtatcttcct 60
gctggtggct ccagttcagg aacacaaaac cctgctccga ctattgcctc tctcacatcc 120
tcaatcttct cgacgactgg gggccctgct atgaacatgg acaacattac atcaggactc 180
ctaggacccc tgctcgtgtt acaggcggtg tgtttcttgt tgacaaaaat cctcacaata 240
ccacagagtc tagactcgtg gtggacttct ctcaattttc taggggggact acccgggtgt 300 cctggccaaa attcgcagtc cccaacctcc aatcacttac caacctcctg tcctccaact 360
tgtcctggct atcgttggat gtgtctgcgg cgttttatca tcttcctctt catcctgctg 420
ctatgcctca tcttcttgtt ggttcttctg gactaccagg gtatgttgcc cgtttgtcct 480
ctacttccag gatccacgac caccagcacg ggaccctgca aaacctgcac aactcttgca 540
caaggaacct ctatgtttcc ctcctgttgc tgttcaaaac cctcggacgg aaactgcact 600
tgtattccca tcccatcatc ctgggcttta ggaaaatacc tatgggagtg ggcctcagcc 660
cgtttctcat ggctcagttt actagtgcaa tttgttcagt ggtgcgtagg gctttccccc 720
actgtctggc ttttagttat attgatgatc tggtattggg ggccaaatct gtgcagcacc 780
ttgagtccct ttataccgct gttaccaatt ttctgttatc tgtgggtatc catttaaata 840
cttctaaaac taagagatgg ggttacaccc tacattttat gggttatgtc attggtagtt 900
ggggatcatt acctcaagat catattgtac acaaaatcaa agaatgtttt cggaaactgc 960
ctgtaaatcg tccaattgat tggaaagtct gtcaacgcat tgtgggtctt ttgggctttg 1020 ctgcccctttt cacacaatgt ggttatcctg ctctcatgcc tctgtatgct tgtattactg 1080
ctaaacaggc ttttgttttt tcgccaactt acaaggcctt tctctgtaaa caatacatga 1140
acctttaccc cgttgccagg caacggccgg gcctgtgcca agtgtttgct gacgcaaccc 1200
ccactggttg gggcttggcc attggccatc agcgcatgcg tggaaccttt gtggctcctc 1260
tgccgatcca tactgcggaa ctccttgcag cttgtttcgc tcgcagcagg tctggagcga 1320
ctctcatcgg cacggacaac tctgttgtcc tctctaggaa gtacacctcc ttcccatggc 1380
tgctcgggtg tgctgcaaac tggatcctgc gcgggacgtc ctttgtttac gtcccgtcgg 1440
cgctgaatcc cgcggacgac ccctcccggg gccgcttggg gctgtaccgc cctcttctcc 1500
gtctgccgtt ccagccgaca acgggtcgca cctctcttta cgcggactcc ccgtctgttc 1560
cttctcatct gccggaccgt gtgcacttcg cttcacctct gcacgtcgca tggagaccac 1620
cgtgaacgcc ccttggagtt tgccaacagt cttacataag aggactcttg gactttcagg 1680
agggtcaatg acccggattg cagaatacat caaagactgt gtatttaagg actgggagga 1740

```
gttgggggag gagactaggt taatgatctt tgtactagga ggctgtaggc ataaattggt   1800
ctgttcacca gcaccatgca actttttcac ctctgcctaa tcatcttttg ttcatgtcct   1860
actgttcaag cctccaagct gtgccttggg tggctttggg acatggacat tgacccttat   1920
aaagaatttg gcgcttctgt ggagttactc tctttttgc cttctgattt ctttccatcg   1980
gttcgggacc tactcgacac cgcttcagcc ctttaccggg atgctttaga gtcacctgaa   2040
cattgcactc cccatcacac tgccctcagg caagttattt tgtgctgggg tgagttaatg   2100
actttggctt cctgggtggg caataacttg gaagaccctg ctgccaggga tttagtagtt   2160
aactatgtta acactaacat gggcctaaaa attagacaac tactgtggtt tcacatttcc   2220
tgccttactt ttggaagaga tatagttctt gagtatttgg tgtcctttgg agtgtggatt   2280
cgcactcctc ctgcttacag accacaaaat gcccctatcc tatccacact tccggaaact   2340
actgttgtta gacgacgagg caggtcccct agaagaagaa ctccctcgcc tcgcagacga   2400
agatctcaat cgccgcgtcg ccgaagatct caatctccag cttcccaatg ttagtattcc   2460
ttggactcat aaggtgggaa attttacggg gctttactct tctactgtgc ctgcttttaa   2520
tcctgactgg ttaactcctt cttttcctaa tattcattta catcaagacc taatttctaa   2580
atgtgaacaa tttgtaggcc cactcactaa aaatgaatta aggaggttaa aattggttat   2640
gccagctaga ttttatccta aggttaccaa atattttcct atggagaaag gaatcaagcc   2700
ttattatcct gagcatgcag ttaatcatta ctttaaaaca agacattatt tgcatacttt   2760
atggaaggcg ggaattttat ataagagaga atccacacgt agcgcatcat tttgtgggtc   2820
accatattcc tgggaacaag agctacagca tgggagcacc tctctcaacg acaagaagag   2880
gcatgggaca gaatctttct gtgcccaatc ctctgggatt ctttccagac catcagctgg   2940
atccgctatt caaagcaaat tccagcagtc ccgactggga cttcaacaca aacaaggaca   3000
gttggccaat ggcaaacaag gtaggagtgg gagcatacgg tccagggttc acaccccac   3060
acggtggcct gctggggtgg agccctcagg cacaaggtat gttaacaacc ttgccagcag   3120
atccgcctcc tgcttccacc aatcggcggt ccgggagaaa gccaacccca gtctctccac   3180
ctctaagaga cactcatcca caggcaatgc agtgg                              3215
```

<210> SEQ ID NO 33
<211> LENGTH: 3248
<212> TYPE: DNA
<213> ORGANISM: Hepatitis B virus

<400> SEQUENCE: 33

```
aactctacag cattccacca agctctacaa aatcccaaag tcaggggcct gtattttcct     60
gctggtggct ccagttcagg gatagtgaac cctgttccga ctattgcctc tcacatctcg    120
tcaatcttct ccaggattgg ggaccctgca ccgaacatgg agaacatcac atcaggattc    180
ctaggacccc tgctcgtgtt acaggcgggg tttttcttgt tgacaagaat cctcacaata    240
ccgcagagtc tagactcgtg gtggacttct ctcaattttc tagggggagt gcccgtgtgt    300
cctggcctaa attcgcagtc cccaacctcc aatcactcac caatctcctg tcctccaact    360
tgtcctggct atcgctggat gtgtctgcgg cgttttatca tattcctctt catcctgctg    420
ctatgcctca tcttcttgtt ggttcttctg gactatcaag gtatgttgcc cgtttgtcct    480
ctgattccag gatcctcgac caccagtacg ggaccctgca aaacctgcac gactcctgct    540
caaggcaact ctatgtatcc ctcatgttgc tgtacaaaac cttcggacgg aaattgcacc    600
tgtattccca tcccatcatc ttgggctttc gcaaaatacc tatgggagtg ggcctcagtc    660
```

-continued cgtttctctt ggctcagttt actagtgcca tttgttcagt ggttcgtagg gctttccccc 720
actgtctggc tttcagctat atggatgatg tggtattggg ggccaaatct gtacaacatc 780
ttgagtccct ttataccgct gttaccaatt ttcttttgtc tttgggtata catctaaacc 840
ctaacaaaac aaaaagatgg ggttattcct taaattttat gggatatgta attggaagtt 900
ggggtacttt gccacaagaa cacatcacac agaaaattaa gcaatgtttt cggaaactcc 960
ctgttaacag gccaattgat tggaaagtct gtcaacgaat aactggtctg ttgggtttcg 1020
ctgctccttt tacccaatgt ggttaccctg ccttaatgcc tttatatgca tgtatacaag 1080
ctaagcaggc ttttactttc tcgccaactt ataaggcctt tctctgtaaa caatacatga 1140
acctttaccc cgttgctagg caacggcccg gtctgtgcca agtgtttgct gacgcaaccc 1200
ccactggttg gggcttggcc atcggccatc agcgcatgcg tggaaccttt gtggctcctc 1260
tgccgatcca tactgcggaa ctcctagctg cttgttttgc tcgcagccgg tctggagcaa 1320
aactcattgg gactgacaat tctgtcgtcc tttctcggaa atatacatcc tttccatggc 1380
tgctaggctg tgctgccaac tggatccttc gcgggacgtc ctttgtttac gtcccgtcag 1440
cgctgaatcc agcggacgac ccctcccggg gccgtttggg gctctgtcgc cccttctcc 1500
gtctgccgtt cctgccgacc acggggcgca cctctcttta cgcggtctcc ccgtctgtgc 1560
cttctcatct gccggaccgt gtgcacttcg cttcacctct gcacgttaca tggaaaccgc 1620
catgaacacc tctcatcatc tgccaaggca gttatataag aggactcttg gactgtttgt 1680
tatgtcaaca accggggtgg agaaatactt caaggactgt gtttttgctg agtgggaaga 1740
attaggcaat gagtccaggt taatgacctt tgtattagga ggctgtaggc ataaattggt 1800
ctgcgcacca gcaccatgta actttttcac ctctgcctaa tcatctcttg ttcatgtcct 1860
actgttcaag cctccaagct gtgccttggg tggctttagg gcatggatag aacaactttg 1920
ccatatggcc tttttggctt agacattgac ccttataaag aatttggagc tactgtggag 1980
ttgctctcgt ttttgccttc tgactttttc ccgtctgttc gtgatcttct cgacaccgct 2040
tcagctttgt accgggaatc cttagagtcc tctgatcatt gttcgcctca ccatacagca 2100
ctcaggcaag caatcctgtg ctggggtgag ttgatgactc tagctacctg ggtgggtaat 2160
aatttggaag atccagcatc cagagatttg gtggtcaatt atgttaatac taatatgggt 2220
ttaaaaatca ggcaactatt gtggtttcac atttcctgtc ttacttttgg gagagaaacc 2280
gttcttgagt atttggtgtc ttttggagtg tggattcgca ctcctcctgc ttatagacca 2340
ccaaatgccc ctatcctatc aacacttccg gagactactg ttgttagacg aagaggcagg 2400
tcccctcgaa gaagaactcc ctcgcctcgc agacgaagat ctcaatcgcc gcgtcgcaga 2460
agatctgcat ctccagcttc ccaatgttag tattccttgg actcacaagg tgggaaactt 2520
tacggggctg tattcttcta ctatacctgt ctttaatcct gattggcaaa ctccttcttt 2580
tccaaatatc catttgcatc aagacattat aactaaatgt gaacaatttg tgggccctct 2640
cacagtaaat gagaaacgaa gattaaaact agttatgcct gccagatttt tcccaaactc 2700
tactaaatat ttaccattag acaaaggtat caaaccgtat tatccagaaa atgtagttaa 2760
tcattacttc cagaccagac attatttaca taccctttgg aaggcgggta ttctatataa 2820
gagagaaacg tcccgtagcg cttcattttg tgggtcacca tatacttggg aacaagatct 2880
acagcatggg gctttcttgg acggtccctc tcgagtgggg aaagaacctt tccaccagca 2940
atcctctagg attccttccc gatcaccagt tggacccagc attcagagca aataccaaca 3000
atccagattg ggacttcaat cccaaaaagg acccttggcc agaggccaac aaagtaggag 3060
ttggagccta tggacccggg ttcacccctc cacacggagg ccttttgggg tggagccctc 3120
agtctcaggg cacactaaca actttgccag cagatccgcc tcctgcctcc accaatcgtc 3180
agtcagggag gcagcctact cccatctctc caccactaag agacagtcat cctcaggcca 3240
tgcagtgg 3248

<210> SEQ ID NO 34
<211> LENGTH: 3215
<212> TYPE: DNA
<213> ORGANISM: Hepatitis B virus

<400> SEQUENCE: 34
aactcaacac agttccacca agcactgttg gattcgagag taaggggtct gtattttcct 60
gctggtggct ccagttcaga aacacagaac cctgctccga ctattgcctc tctcacatca 120
tcaatcttct cgaagactgg ggaccctgct atgaacatgg agaacatcac atcaggactc 180
ctaggacccc ttctcgtgtt acaggcggtg tgtttcttgt tgacaaaaat cctcacaata 240
ccacagagtc tagactcgtg gtggacttct ctcaattttc taggggtacc acccgggtgt 300
cctggccaaa attcgcagtc cccaatctcc aatcacttac caacctcctg tcctccaact 360
tgtcctggct atcgttggat gtgtctgcgg cgttttatca tcttcctctt catcctgctg 420
ctatgcctca tcttcttgtt ggttcttctg gactatcaag gtatgttgcc cgtgtgtcct 480
ctacttccag gatctacaac caccagcacg ggaccctgca aaacctgcac cactcttgct 540
caaggaacct ctatgtttcc ctcctgctgc tgtaccaaac cttcggacgg aaattgcacc 600
tgtattccca tcccatcatc ttgggctttc ggaaaatacc tatgggagtg ggcctcagcc 660
cgtttctctt ggctcagttt actagtgcaa tttgctcagt ggtgcgtagg gctttccccc 720
actgtctggc ttttagttat atggatgatt tggtattggg ggccaaatct gtgcagcatc 780
ttgagtccct ttataccgct gttaccaatt ttttgttatc tgtgggcatc catttgaaca 840
cagctaaaac aaaatggtgg ggttattcct tacactttat gggttatata attgggagtt 900
gggggacctt gcctcaggaa catattgtgc ataaaatcaa agattgcttt cgcaaacttc 960
ccgtgaatag acccattgat tggaaggttt gtcaacgcat tgtgggtctt ttgggctttg 1020 cagcccettt tactcaatgt ggttatcctg ctctcatgcc cttgtatgcc tgtattaccg 1080
ctaagcaggc ttttgttttc tcgccaactt acaaggcctt tctctgtcaa caatacatga 1140
acctttaccc cgttgctcgg caacggccag gcctttgcca agtgtttgct gacgcaaccc 1200
ccactggctg gggcttggcg attggccatc agcgcatgcg cggaaccttt gtggctcctc 1260
tgccgatcca tactgcggaa ctcctagcag cctgtttcgc tcgcagcagg tctggagcgg 1320
acgttatcgg cactgacaac tccgttgtcc tttctcggaa gtacacctcc ttcccatggc 1380
tgctaggctg tgctgccaac tggatcctgc gcgggacgtc ctttgtctac gtcccgtcgg 1440
cgctgaatcc tgcggacgac ccctctcgtg gtcgcttggg gctctgccgc cctcttctcc 1500
gcctaccgtt ccggccgacg acgggtcgca cctctcttta cgcggactcc ccgcctgtgc 1560
cttctcatct gccggcccgt gtgcacttcg cttcacctct gcacgtcgca tggagaccac 1620
cgtgaacgcc ccttggaact tgccaacaac cttacataag aggactcttg gactttcgcc 1680
ccggtcaacg acctggattg aggaatacat caaagactgt gtatttaagg actgggagga 1740
gtcgggggag gagttgaggt taaaggtctt tgtattagga ggctgtaggc ataaattggt 1800
ctgttcacca gcaccatgca actttttcac ctctgcctaa tcatcttttg ttcatgtccc 1860

```
actgttcaag cctccaagct gtgccttggg tggctttggg gcatggacat tgacccttat   1920
aaagaatttg gagcttctgt ggagttactc tcatttttgc cttctgactt cttcccgtct   1980
gtccgggacc tactcgacac cgcttcagcc ctctaccgag atgccttaga atcacccgaa   2040
cattgcaccc ccaaccacac tgctctcagg caagctattt tgtgctgggg tgagttgatg   2100
accttggctt cctgggtggg caataattta gaggatcctg cagcaagaga tctagtagtt   2160
aattatgtca atactaacat gggtctaaaa attagacaat tattatggtt tcacatttcc   2220
tgccttacat ttggaagaga aactgtgctt gagtatttgg tgtcttttgg agtgtggatc   2280
cgcactccac ctgcttacag accaccaaat gcccctatcc tatcaacact tccggagact   2340
actgttgtta gacaacgagg cagggcccct agaagaagaa ctccctcgcc tcgcagacga   2400
agatctcaat caccgcgtcg cagaagatct caatctccag cttcccaatg ttagtattcc   2460
ttggactcat aaggtgggaa actttaccgg tctttactcc tctactgtac ctgttttcaa   2520
tcctgactgg ttaactcctt cttttcctga cattcacttg catcaagatc tgatacaaaa   2580
atgtgaacaa tttgtaggcc cactcactac aaatgaaagg agacgattga aactaattat   2640
gccagctagg ttttatccca aagttactaa atacttccct ttggataaag gtattaagcc   2700
ttactatcca gagaatgtgg ttaatcatta ctttaaaact agacattatt tacatacttt   2760
gtggaaggca ggaattctat ataagagaga atccacacat agcgcctcat tttgtgggtc   2820
accatattcc tgggaacaag agctacagca tgggagcacc tctctcaacg gcgagaaggg   2880
gcatgggaca gaatctttct gtgcccaatc ctctgggatt ctttccagac caccagttgg   2940
atvcactatt cagagcaaat tccagcagtc ccgattggga cttcaacaca aacaaggaca   3000
attggccaat ggcaaacaag gtaggagtgg gaggcttcgg tccagggttc acaccccccac   3060
acggtggcct tctggggtgg agccctcagg cacagggcat tctgacaacc tcgccaccag   3120
atccacctcc tgcttccacc aatcggaggt caggaagaaa gccaacccca gtctctccac   3180
ctctaaggga cacacatcca caggccatgc agtgg                              3215
```

<210> SEQ ID NO 35
<211> LENGTH: 5980
<212> TYPE: DNA
<213> ORGANISM: Hepatitis B virus

<400> SEQUENCE: 35

```
ctcgagttta ccactcccta tcagtgatag agaaaagtga aagtcgagtt taccactccc     60
tatcagtgat agagaaaagt gaaagtcgag tttaccactc cctatcagtg atagagaaaa    120
gtgaaagtcg agtttaccac tccctatcag tgatagagaa aagtgaaagt cgagtttacc    180
actccctatc agtgatagag aaaagtgaaa gtcgagttta ccactcccta tcagtgatag    240
agaaaagtga aagtcgagtt taccactccc tatcagtgat agagaaaagt gaaagtcgag    300
ctcggtaccc gggtcgaggt aggcgtgtac ggtgggaggc ctatataagc gtcgagcacc    360
agcacctgca actttttcac ctctgcctaa tcatctcttg ttcatgtcct actgttcaag    420
cctccaagct gtgccttggg tggctttggg gcgtggacat ctacccatac gacgttccag    480
attacgctgg catggacatc gacccttata aagaatttgg agctactgtg gagttactct    540
cgtttttgcc ttctgacttc tttccttcag tacgagatct tctagatacc gcctcagctc    600
tgtatcggga agccttagag tctcctgagc attgttcacc tcaccatact gcactcaggc    660
aagcaattct ttgctggggg gaactaatga ctctagctac ctgggtgggt gttaatttgg    720
```

-continued

```
aagatccagc atctagagac ctagtagtca gttatgtcaa cactaatatg ggcctaaagt    780
tcaggcaact cttgtggttt cacatttctt gtctcacttt tggaagagaa accgttatag    840
agtatttggt gtctttcgga gtgtggattc gcactcctcc agcttataga ccaccaaatg    900
cccctatcct atcaacactt ccggaaacta ctgttgttag acgacgaggc aggtccccta    960
gaagaagaac tccctcgcct cgcagacgaa ggtctcaatc gccgcgtcgc agaagatctc   1020
aatctcggga acctcaatgt tagtattcct tggactcata aggtggggaa ctttactggt   1080
ctttattctt ctactgtacc tgtctttaat cctcattgga aaacaccatc ttttcctaat   1140
atacatttac accaagacat tatcaaaaaa tgtgaacagt ttgtaggccc acttacagtt   1200
aatgagaaaa gaagattgca attgattatg cctgctaggt tttatccaaa ggttaccaaa   1260
tatttaccat tggataaggg tattaaacct tattatccag aacatctagt taatcattac   1320
ttccaaacta gacactattt acacactcta tggaaggcgg gtatattata taagagagaa   1380
acaacacata gcgcctcatt ttgtgggtca ccatattctt gggaacaaga tctacagcat   1440
ggggcagaat ctttccacca gcaatcctct gggattcttt cccgaccacc agttggatcc   1500
agccttcaga gcaaacacag caaatccaga ttgggacttc aatcccaaca aggacacctg   1560
gccagacgcc aacaaggtag gagctggagc attcgggctg ggtttcaccc caccgcacgg   1620
aggccttttg gggtggagcc ctcaggctca gggcatacta caaactttgc cagcaaatcc   1680
gcctcctgcc tccaccaatc gccagacagg aaggcagcct accccgctgt ctccaccttt   1740
gagaaacact catcctcagg ccatgcagtg gaattccaca acctttcacc aaactctgca   1800
agatcccaga gtgagaggcc tgtatttccc tgctggtggc tccagttcag gagcagtaaa   1860
ccctgttccg actactgcct ctcccttatc gtcaatcttc tcgaggattg gggaccctgc   1920
gctgaacatg gagaacatca catcaggatt cctaggaccc cttctcgtgt tacaggcggg   1980
gtttttctag tagacaagaa tcctcacaat accgcaaagt ctagactcgt ggtggacttc   2040
tctcaatttt ctagggggaa ctaccgtgtg tcttggccaa aattcgcagt ccccaacctc   2100
caatcactca ccaacctcct gtcctccaac ttgtcctggt tatcgctgga tgtgtctgcg   2160
gcgttttatc atcttcctct tcatcctgct gctatgcctc atcttcttgt tggttcttct   2220
ggactatcaa ggtatgttgc ccgtttgtcc tctaattcca ggatcctcaa ccaccagcac   2280
gggaccatgc cgaacctgca tgactactgc tcaaggaacc tctatgtatc cctcctgttg   2340
ctgtaccaaa ccttcggacg gaaattgcac ctgtattccc atcccatcat cctgggcttt   2400
cggaaaattc ctatgggagt gggcctcagc ccgtttctcc tggctcagtt tactagtgcc   2460
atttgttcag tggttcgtag ggctttcccc cactgtttgg ctttcagtta tatggatgat   2520
gtggtattgg gggccaagtc tgtacagcat cttgagtccc tttttaccgc tgttaccaat   2580
tttcttttgt ctttgggtat acatttaaac cctaacaaaa caaagagatg gggttactct   2640
ctgaatttta tgggttatgt cattggaagt tatgggtcct tgccacaaga acacatcata   2700
caaaaaatca aagaatgttt tagaaaactt cctattaaca ggcctattga ttggaaagta   2760
tgtcaacgaa ttgtgggtct tttgggtttt gctgccccat ttacacaatg tggttatcct   2820
gcgttaatgc ccttgtatgc atgtattcaa tctaagcagg ctttcacttt ctcgccaact   2880
tacaaggcct ttctgtgtaa acaatacctg aacctttacc ccgttgcccg gcaacggcca   2940
ggtctgtgcc aagtgtttgc tgacgcaacc cccactggct ggggcttggt catgggccat   3000
cagcgcgtgc gtggaacctt ttcggctcct ctgccgatcc atactgcgga actcctagcc   3060
gcttgttttg ctcgcagcag gtctggagca aacattatcg ggactgataa ctctgttgtc   3120
```

```
ctctcccgca aatatacatc gtatccatgg ctgctaggct gtgctgccaa ctggatcctg   3180
cgcgggacgt cctttgttta cgtcccgtcg gcgctgaatc ctgcggacga cccttctcgg   3240
ggtcgcttgg gactctctcg tccccttctc cgtctgccgt tccgaccgac cacggggcgc   3300
acctctcttt acgcggactc cccgtctgtg ccttctcatc tgccggaccg tgtgcacttc   3360
gcttcacctc tgcacgtcgc atggagacca ccgtgaacgc ccaccgaatg ttgcccaagg   3420
tcttacataa gaggactctt ggactctctg caatgtcaac gaccgacctt gaggcatact   3480
tcaaagactg tttgtttaaa gactgggagg agttggggga ggagattaga ttaaaggtct   3540
ttgtactagg aggctgtagg cataaattgg tctgcgcacc agcaccatgc aacttttca   3600
cctctgccta atcatctctt gttcatgtcc tactgttcaa gcctccaagc tgtgccttgg   3660
gtggctttgg ggcatggaca tcgaccctta taaagaattt ggagctactg tggagttact   3720
ctcgtttttg ccttctgact tctttccttc agtacgagat ccactagttc tagagcggcc   3780
ccaaacaatt gctcaaaccg atacaattgt actttgtccc gagcaaatat aatcctgctg   3840
acggcccatc caggcacaaa cctcctgatt ggacggcttt tccatacacc cctctctcga   3900
aagcaatata tattccacat aggctatgtg gaacttaagc ttcctcgctc actgactcgc   3960
tgcgctcggt cgttcggctg cggcgagcgg tatcagctca ctcaaaggcg gtaatacggt   4020
tatccacaga atcaggggat aacgcaggaa agaacatgtg agcaaaaggc cagcaaaagg   4080
ccaggaaccg taaaaaggcc gcgttgctgg cgtttttcca taggctccgc ccccctgacg   4140
agcatcacaa aaatcgacgc tcaagtcaga ggtggcgaaa cccgacagga ctataaagat   4200
accaggcgtt tccccctgga agctccctcg tgcgctctcc tgttccgacc ctgccgctta   4260
ccggatacct gtccgccttt ctcccttcgg gaagcgtggc gctttctcat agctcacgct   4320
gtaggtatct cagttcggtg taggtcgttc gctccaagct gggctgtgtg cacgaacccc   4380
ccgttcagcc cgaccgctgc gccttatccg gtaactatcg tcttgagtcc aacccggtaa   4440
gacacgactt atcgccactg gcagcagcca ctggtaacag gattagcaga gcgaggtatg   4500
taggcggtgc tacagagttc ttgaagtggt ggcctaacta cggctacact ataagaacag   4560
tatttggtat ctgcgctctg ctgaagccag ttaccttcgg aaaaagagtt ggtagctctt   4620
gatccggcaa acaaaccacc gctggtagcg gtggtttttt tgtttgcaag cagcagatta   4680
cgcgcagaaa aaaaggatct caagaagatc ctttgatctt ttctacgggg tctgacgctc   4740
agtggaacga aaactcacgt taagggattt tggtcatgag attatcaaaa aggatcttca   4800
cctagatcct tttaaattaa aaatgaagtt ttaaatcaat ctaaagtata tatgagtaaa   4860
cttggtctga cagttaccaa tgcttaatca gtgaggcacc tatctcagcg atctgtctat   4920
ttcgttcatc catagttgcc tgactccccg tcgtgtagat aactacgata cgggagggct   4980
taccatctgg ccccagtgct gcaatgatac cgcgagaccc acgctcaccg gctccagatt   5040
tatcagcaat aaaccagcca gccggaaggg ccgagcgcag aagtggtcct gcaactttat   5100
ccgcctccat ccagtctatt aattgttgcc gggaagctag agtaagtagt tcgccagtta   5160
atagtttgcg caacgttgtt gccattgcta caggcatcgt ggtgtcacgc tcgtcgtttg   5220
gtatggcttc attcagctcc ggttcccaac gatcaaggcg agttacatga tcccccatgt   5280
tgtgcaaaaa agcggttagc tccttcggtc ctccgatcgt tgtcagaagt aagttggccg   5340
cagtgttatc actcatggtt atggcagcac tgcataattc tcttactgtc atgccatccg   5400
taagatgctt ttctgtgact ggtgagtact caaccaagtc attctgagaa tagtgtatgc   5460
```

-continued

```
ggcgaccgag ttgctcttgc ccggcgtcaa tacgggataa taccgcgcca catagcagaa   5520

ctttaaaagt gctcatcatt ggaaaacgtt cttcggggcg aaaactctca aggatcttac   5580

cgctgttgag atccagttcg atgtaaccca ctcgtgcacc caactgatct tcagcatctt   5640

ttactttcac cagcgtttct gggtgagcaa aaacaggaag gcaaaatgcc gcaaaaaagg   5700

gaataagggc gacacggaaa tgttgaatac tcatactctt cctttttcaa tattattgaa   5760

gcatttatca gggttattgt ctcatgagcg gatacatatt tgaatgtatt tagaaaaata   5820

aacaaatagg ggttccgcgc acatttcccc gaaaagtgcc acctgacgtc taagaaacca   5880

ttattatcat gacattaacc tataaaaata ggcgtatcac gaggcccttt cgtcttcact   5940

cgaatatctg caggcgtatc acgaggccct ttcgtcttca                         5980
```

<210> SEQ ID NO 36
<211> LENGTH: 1170
<212> TYPE: DNA
<213> ORGANISM: Hepatitis B virus

<400> SEQUENCE: 36

```
atggggcaga atctttccac cagcaatcct ctgggattct ttcccgacca ccagttggat     60

ccagccttca gagcaaacac agcaaatcca gattgggact tcaatcccaa caaggacacc    120

tggccagacg ccaacaaggt aggagctgga gcattcgggc tgggtttcac cccaccgcac    180

ggaggccttt tggggtggag ccctcaggct cagggcatac tacaaacttt gccagcaaat    240

ccgcctcctg cctccaccaa tcgccagaca ggaaggcagc ctaccccgct gtctccacct    300

ttgagaaaca ctcatcctca ggccatgcag tggaattcca caacctttca ccaaactctg    360

caagatccca gagtgagagg cctgtatttc cctgctggtg gctccagttc aggagcagta    420

aaccctgttc cgactactgc ctctccctta tcgtcaatct tctcgaggat tggggaccct    480

gcgctgaaca tggagaacat cacatcagga ttcctaggac cccttctcgt gttacaggcg    540

gggtttttct tgttgacaag aatcctcaca ataccgcaaa gtctagactc gtggtggact    600

tctctcaatt ttctaggggg aactaccgtg tgtcttggcc aaaattcgca gtccccaacc    660

tccaatcact caccaacctc ctgtcctcca acttgtcctg gttatcgctg gatgtgtctg    720

cggcgtttta tcatcttcct cttcatcctg ctgctatgcc tcatcttctt gttggttctt    780

ctggactatc aaggtatgtt gcccgtttgt cctctaattc caggatcctc aaccaccagc    840

acgggaccat gccgaacctg catgactact gctcaaggaa cctctatgta tccctcctgt    900

tgctgtacca aaccttcgga cggaaattgc acctgtattc ccatcccatc atcctgggct    960

ttcggaaaat tcctatggga gtgggcctca gcccgtttct cctggctcag tttactagtg   1020

ccatttgttc agtggttcgt agggctttcc cccactgttt ggctttcagt tatatggatg   1080

atgtggtatt gggggccaag tctgtacagc atcttgagtc cctttttacc gctgttacca   1140

attttctttt gtctttgggt atacatttaa                                    1170
```

<210> SEQ ID NO 37
<211> LENGTH: 846
<212> TYPE: DNA
<213> ORGANISM: Hepatitis B virus

<400> SEQUENCE: 37

```
atgcagtgga attccacaac ctttcaccaa actctgcaag atcccagagt gagaggcctg     60

tatttccctg ctggtggctc cagttcagga gcagtaaacc ctgttccgac tactgcctct    120

cccttatcgt caatcttctc gaggattggg gaccctgcgc tgaacatgga gaacatcaca    180
```

```
tcaggattcc taggacccct tctcgtgtta caggcggggt ttttcttgtt gacaagaatc    240

ctcacaatac cgcaaagtct agactcgtgg tggacttctc tcaattttct agggggaact    300

accgtgtgtc ttggccaaaa ttcgcagtcc ccaacctcca atcactcacc aacctcctgt    360

cctccaactt gtcctggtta tcgctggatg tgtctgcggc gttttatcat cttcctcttc    420

atcctgctgc tatgcctcat cttcttgttg gttcttctgg actatcaagg tatgttgccc    480

gtttgtcctc taattccagg atcctcaacc accagcacgg gaccatgccg aacctgcatg    540

actactgctc aaggaacctc tatgtatccc tcctgttgct gtaccaaacc ttcggacgga    600

aattgcacct gtattcccat cccatcatcc tgggctttcg gaaaattcct atgggagtgg    660

gcctcagccc gtttctcctg gctcagttta ctagtgccat ttgttcagtg gttcgtaggg    720

ctttccccca ctgtttggct ttcagttata tggatgatgt ggtattgggg gccaagtctg    780

tacagcatct tgagtccctt tttaccgctg ttaccaattt tcttttgtct ttgggtatac    840

atttaa                                                               846
```

<210> SEQ ID NO 38
<211> LENGTH: 681
<212> TYPE: DNA
<213> ORGANISM: Hepatitis B virus

<400> SEQUENCE: 38

```
atggagaaca tcacatcagg attcctagga ccccttctcg tgttacaggc ggggtttttc     60

ttgttgacaa gaatcctcac aataccgcaa agtctagact cgtggtggac ttctctcaat    120

tttctagggg gaactaccgt gtgtcttggc caaaattcgc agtccccaac ctccaatcac    180

tcaccaacct cctgtcctcc aacttgtcct ggttatcgct ggatgtgtct gcggcgtttt    240

atcatcttcc tcttcatcct gctgctatgc ctcatcttct tgttggttct tctggactat    300

caaggtatgt tgcccgtttg tcctctaatt ccaggatcct caaccaccag cacgggacca    360

tgccgaacct gcatgactac tgctcaagga acctctatgt atccctcctg ttgctgtacc    420

aaaccttcgg acggaaattg cacctgtatt cccatcccat catcctgggc tttcggaaaa    480

ttcctatggg agtgggcctc agcccgtttc tcctggctca gtttactagt gccatttgtt    540

cagtggttcg tagggctttc ccccactgtt tggctttcag ttatatggat gatgtggtat    600

tgggggccaa gtctgtacag catcttgagt cccttttac cgctgttacc aattttcttt     660

tgtctttggg tatacattta a                                              681
```

<210> SEQ ID NO 39
<211> LENGTH: 6682
<212> TYPE: DNA
<213> ORGANISM: Hepatitis B virus

<400> SEQUENCE: 39

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420
```

-continued

```
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagcttggt accgagctcg gatccaccat gcaacttttt cacctctgcc taatcatctc    960
ttgttcatgt cctactgttc aagcctccaa gctgtgcctt gggtggcttt ggggcgtgga   1020
catctaccca tacgacgttc cagattacgc tggcatggac atcgaccctt ataaagaatt   1080
tggagctact gtggagttac tctcgttttt gccttctgac ttctttcctt cagtacgaga   1140
tcttctagat accgcctcag ctctgtatcg ggaagcctta gagtctcctg agcattgttc   1200
acctcaccat actgcactca ggcaagcaat tctttgctgg ggggaactaa tgactctagc   1260
tacctgggtg ggtgttaatt tggaagatcc agcatctaga gacctagtag tcagttatgt   1320
caacactaat atgggcctaa agttcaggca actcttgtgg tttcacattt cttgtctcac   1380
ttttggaaga gaaaccgtta tagagtattt ggtgtctttc ggagtgtgga ttcgcactcc   1440
tccagcttat agaccaccaa atgcccctat cctatcaaca cttccggaaa ctactgttgt   1500
tagacgacga ggcaggtccc ctagaagaag aactccctcg cctcgcagac gaaggtctca   1560
atcgccgcgt cgcagaagat ctcaatctcg ggaacctcaa tgttagtatt ccttggactc   1620
ataaggtggg gaactttact ggtctttatt cttctactgt acctgtcttt aatcctcatt   1680
ggaaaacacc atcttttcct aatatacatt tacaccaaga cattatcaaa aaatgtgaac   1740
agtttgtagg cccacttacg gaccgtgtgc acttcgcttc acctctgcac gtcgcatgga   1800
gaccaccgtg aacgcccacc gaatgttgcc caaggtctta cataagagga ctcttggact   1860
ctctgcaatg tcaacgaccg accttgaggc atacttcaaa gactgtttgt ttaaagactg   1920
ggaggagttg ggggaggaga ttagattaaa ggtctttgta ctaggaggct gtaggcataa   1980
attggtctgc gcaccagcac catgcaactt tttcacctct gcctaatcat ctcttgttca   2040
tgtcctactg ttcaagcctc caagctgtgc cttgggtggc tttggggcat ggacatcgac   2100
ccttataaag aaaagggcaa ttctgcagat atccagcaca gtggcggccg ctcgagtcta   2160
gagggcccgc ggttcgaagg taagcctatc cctaaccctc tcctcggtct cgattctacg   2220
cgtaccggtc atcatcacca tcaccattga gtttaaaccc gctgatcagc ctcgactgtg   2280
ccttctagtt gccagccatc tgttgtttgc ccctcccccg tgccttcctt gaccctggaa   2340
ggtgccactc ccactgtcct ttcctaataa aatgaggaaa ttgcatcgca ttgtctgagt   2400
aggtgtcatt ctattctggg gggtggggtg gggcaggaca gcaaggggga ggattgggaa   2460
gacaatagca ggcatgctgg ggatgcggtg ggctctatgg cttctgaggc ggaaagaacc   2520
agctggggct ctagggggta tccccacgcg ccctgtagcg gcgcattaag cgcggcgggt   2580
gtggtggtta cgcgcagcgt gaccgctaca cttgccagcg ccctagcgcc cgctcctttc   2640
gctttcttcc cttcctttct cgccacgttc gccggctttc cccgtcaagc tctaaatcgg   2700
ggcatccctt tagggttccg atttagtgct ttacggcacc tcgaccccaa aaaacttgat   2760
tagggtgatg gttcacgtag tgggccatcg ccctgataga cggtttttcg ccctttgacg   2820
```

ttggagtcca cgttctttaa tagtggactc ttgttccaaa ctggaacaac actcaaccct 2880
atctcggtct attcttttga tttataaggg attttgggga tttcggccta ttggttaaaa 2940
aatgagctga tttaacaaaa atttaacgcg aattaattct gtggaatgtg tgtcagttag 3000
ggtgtggaaa gtccccaggc tccccaggca ggcagaagta tgcaaagcat gcatctcaat 3060
tagtcagcaa ccaggtgtgg aaagtcccca ggctccccag caggcagaag tatgcaaagc 3120
atgcatctca attagtcagc aaccatagtc ccgcccctaa ctccgcccat cccgccccta 3180
actccgccca gttccgccca ttctccgccc catggctgac taattttttt tatttatgca 3240
gaggccgagg ccgcctctgc ctctgagcta ttccagaagt agtgaggagg cttttttgga 3300
ggcctaggct tttgcaaaaa gctcccggga gcttgtatat ccattttcgg atctgatcaa 3360
gagacaggat gaggatcgtt tcgcatgatt gaacaagatg gattgcacgc aggttctccg 3420
gccgcttggg tggagaggct attcggctat gactgggcac aacagacaat cggctgctct 3480
gatgccgccg tgttccggct gtcagcgcag gggcgcccgg ttctttttgt caagaccgac 3540
ctgtccggtg ccctgaatga actgcaggac gaggcagcgc ggctatcgtg gctggccacg 3600
acgggcgttc cttgcgcagc tgtgctcgac gttgtcactg aagcgggaag ggactggctg 3660
ctattgggcg aagtgccggg gcaggatctc ctgtcatctc accttgctcc tgccgagaaa 3720
gtatccatca tggctgatgc aatgcggcgg ctgcatacgc ttgatccggc tacctgccca 3780
ttcgaccacc aagcgaaaca tcgcatcgag cgagcacgta ctcggatgga agccggtctt 3840
gtcgatcagg atgatctgga cgaagagcat caggggctcg cgccagccga actgttcgcc 3900
aggctcaagg cgcgcatgcc cgacggcgag gatctcgtcg tgacccatgg cgatgcctgc 3960
ttgccgaata tcatggtgga aaatggccgc ttttctggat tcatcgactg tggccggctg 4020
ggtgtggcgg accgctatca ggacatagcg ttggctaccc gtgatattgc tgaagagctt 4080
ggcggcgaat gggctgaccg cttcctcgtg ctttacggta tcgccgctcc cgattcgcag 4140
cgcatcgcct tctatcgcct tcttgacgag ttcttctgag cgggactctg gggttcgcga 4200
aatgaccgac caagcgacgc ccaacctgcc atcacgagat ttcgattcca ccgccgcctt 4260
ctatgaaagg ttgggcttcg gaatcgtttt ccgggacgcc ggctggatga tcctccagcg 4320
cggggatctc atgctggagt tcttcgccca ccccaacttg tttattgcag cttataatgg 4380
ttacaaataa agcaatagca tcacaaattt cacaaataaa gcattttttt cactgcattc 4440
tagttgtggt ttgtccaaac tcatcaatgt atcttatcat gtctgtatac cgtcgacctc 4500
tagctagagc ttggcgtaat catggtcata gctgtttcct gtgtgaaatt gttatccgct 4560
cacaattcca cacaacatac gagccggaag cataaagtgt aaagcctggg gtgcctaatg 4620
agtgagctaa ctcacattaa ttgcgttgcg ctcactgccc gctttccagt cgggaaacct 4680
gtcgtgccag ctgcattaat gaatcggcca acgcgcgggg agaggcggtt tgcgtattgg 4740
gcgctcttcc gcttcctcgc tcactgactc gctgcgctcg gtcgttcggc tgcggcgagc 4800
ggtatcagct cactcaaagg cggtaatacg gttatccaca gaatcagggg ataacgcagg 4860
aaagaacatg tgagcaaaag gccagcaaaa ggccaggaac cgtaaaaagg ccgcgttgct 4920
ggcgtttttc cataggctcc gcccccctga cgagcatcac aaaaatcgac gctcaagtca 4980
gaggtggcga aacccgacag gactataaag ataccaggcg tttccccctg gaagctccct 5040
cgtgcgctct cctgttccga ccctgccgct taccggatac ctgtccgcct ttctcccttc 5100
gggaagcgtg gcgctttctc aatgctcacg ctgtaggtat ctcagttcgg tgtaggtcgt 5160

-continued

```
tcgctccaag ctgggctgtg tgcacgaacc ccccgttcag cccgaccgct gcgccttatc   5220

cggtaactat cgtcttgagt ccaacccggt aagacacgac ttatcgccac tggcagcagc   5280

cactggtaac aggattagca gagcgaggta tgtaggcggt gctacagagt tcttgaagtg   5340

gtggcctaac tacggctaca ctagaaggac agtatttggt atctgcgctc tgctgaagcc   5400

agttaccttc ggaaaaagag ttggtagctc ttgatccggc aaacaaacca ccgctggtag   5460

cggtggtttt tttgtttgca agcagcagat tacgcgcaga aaaaaaggat ctcaagaaga   5520

tcctttgatc ttttctacgg ggtctgacgc tcagtggaac gaaaactcac gttaagggat   5580

tttggtcatg agattatcaa aaaggatctt cacctagatc cttttaaatt aaaaatgaag   5640

ttttaaatca atctaaagta tatatgagta aacttggtct gacagttacc aatgcttaat   5700

cagtgaggca cctatctcag cgatctgtct atttcgttca tccatagttg cctgactccc   5760

cgtcgtgtag ataactacga tacgggaggg cttaccatct ggccccagtg ctgcaatgat   5820

accgcgagac ccacgctcac cggctccaga tttatcagca ataaaccagc cagccggaag   5880

ggccgagcgc agaagtggtc ctgcaacttt atccgcctcc atccagtcta ttaattgttg   5940

ccgggaagct agagtaagta gttcgccagt taatagtttg cgcaacgttg ttgccattgc   6000

tacaggcatc gtggtgtcac gctcgtcgtt tggtatggct tcattcagct ccggttccca   6060

acgatcaagg cgagttacat gatcccccat gttgtgcaaa aaagcggtta gctccttcgg   6120

tcctccgatc gttgtcagaa gtaagttggc cgcagtgtta tcactcatgg ttatggcagc   6180

actgcataat tctcttactg tcatgccatc cgtaagatgc ttttctgtga ctggtgagta   6240

ctcaaccaag tcattctgag aatagtgtat gcggcgaccg agttgctctt gcccggcgtc   6300

aatacgggat aataccgcgc cacatagcag aactttaaaa gtgctcatca ttggaaaacg   6360

ttcttcgggg cgaaaactct caaggatctt accgctgttg agatccagtt cgatgtaacc   6420

cactcgtgca cccaactgat cttcagcatc ttttactttc accagcgttt ctgggtgagc   6480

aaaaacagga aggcaaaatg ccgcaaaaaa gggaataagg gcgacacgga aatgttgaat   6540

actcatactc ttcctttttc aatattattg aagcatttat cagggttatt gtctcatgag   6600

cggatacata tttgaatgta tttagaaaaa taaacaaata ggggttccgc gcacatttcc   6660

ccgaaaagtg ccacctgacg tc                                            6682
```

<210> SEQ ID NO 40

<400> SEQUENCE: 40

000

<210> SEQ ID NO 41
<211> LENGTH: 39
<212> TYPE: DNA
<213> ORGANISM: Hepatitis B virus

<400> SEQUENCE: 41

```
gtggacatct acccatacga cgttccagat tacgctggc                            39
```

<210> SEQ ID NO 42
<211> LENGTH: 13
<212> TYPE: PRT
<213> ORGANISM: Hepatitis B virus

<400> SEQUENCE: 42

```
Val Asp Ile Tyr Pro Tyr Asp Val Pro Asp Tyr Ala Gly
1               5                   10
```

-continued

```
<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43

attggatcca ccatgcaact ttttcacctc tgc                                  33


<210> SEQ ID NO 44
<211> LENGTH: 34
<212> TYPE: DNA
<213> ORGANISM: Artificial Sequence
<220> FEATURE:
<223> OTHER INFORMATION: primer

<400> SEQUENCE: 44

acagtagttt ccggaagtgt tgataggata gggg                                 34


<210> SEQ ID NO 45
<211> LENGTH: 123
<212> TYPE: DNA
<213> ORGANISM: Hepatitis B virus

<400> SEQUENCE: 45

accatgcaac tttttcacct ctgcctaatc atctcttgtt catgtcctac tgttcaagcc     60

tccaagctgt gccttgggtg gctttggggc atggacatcg acccttataa agaatttgga    120

gct                                                                  123


<210> SEQ ID NO 46
<211> LENGTH: 138
<212> TYPE: DNA
<213> ORGANISM: Hepatitis B virus

<400> SEQUENCE: 46

accatgcaac tttttcacct ctgcctaatc atctcttgtt catgtcctac tgttcaagcc     60

tccaagctgt gccttgggtg gctttggggc gtggacatct acccatacga cgttccagat    120

tacgctggca tggacatc                                                  138
```

TAGGED HEPADNAVIRUS E ANTIGEN AND ITS USE IN SCREENING ANTIVIRAL SUBSTANCES

This invention was made with government support under Contract No. R01AI094474 awarded by the National Institutes of Health. The government has certain rights in the invention.

The present invention relates to methods and uses for screening anti-hepadnaviral substances, wherein the substances are inhibitors of hepatitis B e antigen (HBeAg) which is predominantly covalently closed circular (ccc) DNA-dependent in cell lines described in this invention and might serve as a surrogate marker for cccDNA screened for the capacity to inhibit ccc DNA of a hepadnavirus, like Hepatitis B virus (HBV). The methods and uses take advantage of cells comprising a nucleic sequence encoding a tagged hepadnavirus e antigen, like Hepatitis B virus e antigen (HBeAg). Furthermore, the present invention provides nucleic acid sequences encoding a tagged hepadnavirus e antigen and proteins encoded thereby. Also kits for use in the screening methods are provided.

Chronic hepatitis B is currently a substantial public health burden affecting approximately 350 million individuals worldwide and at least 1.2 million in the United States. These patients have an elevated risk of liver cirrhosis, hepatocellular carcinoma (HCC), and other severe clinical sequelae (1, 2, 12, 14). Annually, there are about 1 million deaths due to HBV-related liver disease all over the world. It is therefore a global health priority to cure chronic HBV infection and prevent its dire consequences.

Hepatitis B virus (HBV) is a noncytopathic, liver tropic DNA virus belonging to Hepadnaviridae family. Hepadnaviruses are a family of enveloped, double-stranded viruses which can cause liver infections in humans and animals. Hepadnaviruses share the similar genome organisation. They have small genomes of partially double-stranded circular DNA. The genome consists of two strands of DNA, one having negative-sense orientation, the other strand having a positive-sense orientation. Replication involves reverse transcription of an RNA intermediate called pregenomic RNA (15, 19). Three main open reading frames (ORFs) are encoded and the virus has five known mRNAs (18, 19).

Upon infection, the viral genomic relaxed circular (rc) DNA is transported into the cell nucleus and converted to episomal covalently closed circular (ccc) DNA, which serves as the transcription template for all the viral mRNAs, specifically 3.5-3.6 kb precore mRNA encoding precore protein which is the precursor for HBeAg; 3.5 kb pregenomic (pg) RNA encoding core protein and viral polymerase; 2.4 kb/2.1 kb surface mRNAs encoding viral envelope proteins (large (L), middle (M), and small (S) antigens); and 0.7 kb X mRNA for X protein (18, 19). HBeAg is generated by two proteolytic events removing the N-terminal signal peptide and the C-terminal arginine-rich sequence of the precore protein (Wang (1991) J Virol 65(9), 5080 (10, 21). After transcription and nuclear exportation, cytoplasmic viral pgRNA is assembled with HBV polymerase and capsid proteins to form the nucleocapsid, inside of which polymerase-catalyzed reverse transcription yields minus-strand DNA, which is subsequently copied into plus-strand DNA to form the progeny rcDNA genome. The newly synthesized mature nucleocapsids will either be packaged with viral envelope proteins and egress as virion particles, or shuttled back to the nucleus to amplify the cccDNA reservoir through intracellular cccDNA amplification pathway (19). Therefore, the molecular basis for chronic hepatitis B is the persistence of viral cccDNA in the nuclei of infected hepatocytes.

There is no definitive cure for chronic hepatitis B. Currently approved drugs for HBV treatment are interferon-α (IFN-α) and 5 nucleos(t)ide analogues (lamivudine, adefovir, entecavir, telbivudine, and tenofovir). Xu (2010) J Virol (84) 9332-9340 discloses the treatment of mouse hepatocytes with mouse interferon. IFN-α only achieves sustained virological response in a minor group of patients after 48 weeks of standard treatment, and with significant adverse effects (9). The five nucleos(t)ide analogues (NAs) all act as viral polymerase inhibitors, but rarely cure HBV infection (6), and emergence of resistance dramatically limits their long-term efficacy (16, 24). It is now well acknowledged that the major limitation of current treatment is the failure to eliminate the preexisting cccDNA pool, and/or prevent cccDNA formation from trace-level wild-type or drug-resistant virus. Thus there is an urgent unmet need for the development of novel therapeutic agents that directly target cccDNA formation and maintenance.

Cai (2013) Methods in Mol Biol 1030 (151-161) disclose a southern blot assay for detection of HBV ccc (covalently closed circular) DNA from cell cultures. Yet, to date, screens for anti-cccDNA agents have been limited due to the lack of efficient in vitro HBV infection models, and a practical approach for measuring cccDNA in high to mid-throughput format was unavailable. Alternatively, cccDNA formation can be achieved through the intracellular amplification pathway in stably-transfected HBV cell cultures that constitutively or conditionally replicate HBV genome, as represented by HepG2.2.15 and HepAD38 cells (7, 11, 20).

However, the direct cccDNA detection from HBV cell lines by either Southern blot hybridization or real-time PCR assay would not be amenable to screening due to the sensitivity and specificity issues, respectively. On the other hand, there is no suitable surrogate marker for cccDNA in HepG2.2.15 cells since the most majority of viral products are derived from integrated viral transgene, which are indistinguishable from cccDNA contributions. It has been previously reported that the production of secreted HBeAg was predominantly cccDNA-dependent in HepAD38 cells and might serve as a surrogate marker for cccDNA (11, 23). Recently, Cai, et al. applied an upgraded version of a solely cccDNA-dependent HBeAg producing cell line, named HepDE19 cells (7), into 96-well format assay for screening of cccDNA inhibitors and identified two small molecule compounds that inhibit cccDNA formation (3). Such work thus provided a solid "proof-of-concept" demonstration that cccDNA biosynthesis can be directly targeted by chemical molecules, and cccDNA inhibitors could be identified from high throughput screening campaign. However, certain disadvantages of the existing HepDE19 assay system render a screen of larger libraries impractical. For instance, the traditional ELISA assay currently used for HBeAg requires multiple manipulations, exhibits a certain extent of cross reaction with viral core protein due to amino acid sequence homology, and are not suitable for larger format cell-based assay.

Thus, the technical problem underlying the present invention is the provision of means and methods to reliably screen inhibitors of hepadnaviral cccDNA.

The technical problem is solved by provision of the embodiments characterized in the claims.

Accordingly, the present invention relates to a method for assessing the capacity of a candidate molecule to inhibit ccc (covalently closed circular) DNA of a hepadnavirus comprising the steps of (a) contacting a cell comprising a nucleic acid molecule comprising a nucleic acid sequence encoding a tagged hepadnavirus e antigen with said candidate molecule;
(b) assessing the level of the tagged hepadnavirus e antigen; and
(c) selecting a candidate molecule when the level of tagged hepadnavirus e antigen is decreased compared to a control.

The methods are generally applicable to other mammalian and avian hepadnaviruses, such as the representative woodchuck hepatitis virus (WHV) and duck hepatitis B virus (DHBV) which share a similar gene organization and replication strategy with Hepatitis B virus (HBV). The herein provided explanations and experiments with regard to Hepatitis B virus apply therefore likewise to other hepadnaviruses. However, the teachings provided herein relate in preferred embodiment to "Hepatitis B virus"/HBV. The terms "hepadnavirus", "Hepatitis B virus", "duck hepatitis B virus", "woodchuck hepatitis virus (WHV)" are well known in the art and used accordingly herein. The abbreviations "HBV", "DHBV" or "WHV" are used interchangeably herein with the full terms "Hepatitis B virus", "duck hepatitis B virus" and "woodchuck hepatitis virus", respectively.

The herein preferred hepadnavirus is preferably Hepatitis B virus (HBV). Hepatitis B virus (HBV) is a noncytopathic, liver tropic DNA virus belonging to Hepadnaviridae family, i.e. HBV is a hepadnavirus. Examplary nucleic acid sequences of HBV genomes are shown in SEQ ID NO: 27, 28, 29, 30, 31, 32, 33 or 34.

The herein preferred hepadnavirus e antigen is Hepatitis B virus e antigen (HBeAg). The terms "Hepatitis B virus e antigen" and "HBeAg" are used interchangeably herein. An examplary nucleic acid sequence and amino acid sequence of HBeAg is shown in SEQ ID NO: 16 and 18, respectively. As used herein "hepadnavirus e antigen" (and likewise "Hepatitis B virus e antigen") refers primarily to a protein/polypeptide e.g. a protein/polypeptide having an amino acid sequences as shown in SEQ ID NO: 18.

HBeAg can be produced upon infection as follows: upon infection, the HBV virus genomic relaxed circular (rc) DNA is transported into the cell nucleus and converted to episomal cccDNA, which serves as the transcription template for all the viral mRNAs, including a 3.5-3.6 kb precore mRNA encoding precore protein which is the precursor for HBeAg. The terms "ccc DNA" and "covalently closed circular DNA" are used interchangeably herein.

Exemplary nucleic acid sequences and amino acid sequences of a HBV precore protein are shown in SEQ ID NO: 15 and 17, respectively. The HBV precore protein has an N-terminal 19-amino acid signal peptide, a 10-amino acid linker, a central amino acid stretch and a C-terminal 34-amino acid arginine-rich domain.

Exemplary nucleic acid sequences and amino acid sequences of a HBV core protein are shown in SEQ ID NO: 23 and 24, respectively. The core protein corresponds to the precore protein (see SEQ ID NO: 17) in that it comprises the C-terminal arginine-rich sequence of the precore protein; however, the core protein does not comprise the N-terminal signal peptide and the 10-amino acid linker sequence of the precore protein.

HBeAg is generated by two proteolytic events removing the N-terminal signal peptide and the C-terminal arginine-rich sequence of the precore protein (Wang (1991) J Virol 65(9), 5080 (21). Thus, Hepatitis B virus e antigen (HBeAg) corresponds to the precore protein (see SEQ ID NO: 17) in that it comprises the N-terminal 10-aa linker peptide of the precore protein; however, HBeAg does not comprise the C-terminal arginine-rich sequence of the precore protein.

The molecular basis for chronic hepatitis B is the persistence of viral cccDNA in the nuclei of infected hepatocytes.

The terms "covalently closed circular DNA" and "cccDNA" are used interchangeably herein. The term "covalently closed circular DNA"/"cccDNA" is well known in the art and used accordingly herein. Generally, "covalently closed circular DNA"/"cccDNA" as used herein refers to a DNA that serves as the authentic episomal transcription template for the hepadnaviral mRNAs.

Hepatitis B virus e antigen (HBeAg) is an accepted surrogate marker for cccDNA of HBV hepadnaviruses that in turn reflects chronic hepadnavirus infection. Yet, the known cell based assays employing HBeAg suffer from disadvantages, like cross reaction with viral core protein.

In order to improve the specificity and sensitivity of cccDNA reporter detection, herein cell lines were established that support the cccDNA-dependent production of recombinant HBeAg with a tag (like an N-terminal embedded hemagglutinin (HA) epitope tag). Moreover, chemiluminescence ELISA (CLIA) and AlphaLISA assays for the detection of (HA-)tagged HBeAg were developed. The assay system is adaptable to high throughput screening formats and full automation.

The herein provided methods take advantage of the use of established tags (like HA-tag, or His-tag, Flag-tag, c-myc-tag, V5-tag or C9-tag that can be used in the place of an HA-tag or in addition thereto). These tags can be used in the purification and detection of tagged hepadnavirus e antigen. By using antibodies specifically binding to the tag (e.g. via ELISA assays, like chemiluminescence ELISA (CLIA) and AlphaLISA), the level of tagged hepadnavirus e antigen can be reliably and rapidly assessed and cross-reactions with core protein can be avoided.

The methods provided herein employ cells comprising a nucleic acid molecule comprising a nucleic acid sequence encoding a tagged hepadnavirus e antigen. The nucleic acid molecule can comprise a sequence encoding a hepadnavirus precore protein or even a hepadnavirus genome to reflect and enable cccDNA formation of hepadnaviruses. In the art it is known that HBV genome has a highly compact gene organization which exhibits overlapped ORFs and multiple cis elements. Therefore, it was believed that gene insertion/deletion or sequence replacement would very likely affect viral DNA replication (13, 22). (Liu, et al, J Virol. 2004; 78(2):642-9.)(Wang, et al. PLoS One. 2013 2; 8(4):e60306) Previous works have replaced HBV sequence, such as pol/envelope coding region in most cases, by GFP to make recombinant HBV genome, but trans-complement of viral proteins was needed to support viral replication and virion assembly (17)(Protzer, et al, PNAS (1999), 96: 10818-23.). Moreover, this reported recombinant HBV genome can only make first round cccDNA synthesis if used to infect permissive cells, intracellular amplification of cccDNA is blocked due to the defective viral DNA replication.

The 5' stem-loop structure (epsilon) in hepadnarvius pgRNA, preferably HBV pgRNA, is an essential cis element for viral replication. It serves as the pgRNA packaging signal and DNA priming site. The epsilon overlaps with the 5' portion of precore ORF and contains the start codon of capsid (core) protein ORF. To insert a nucleic acid sequence encoding a tag downstream of the N-terminal signal peptide sequence in precore ORF without altering the integrity of epsilon structure encoded by the HBV genome, a three-amino-acid linker sequence was introduced herein (GTG GAC ATC) at the 5' end of the (HA-)tag to replace the original viral sequence (ATG GAC ATC) of the right arm at the bottom of the epsilon as encoded by the HBV genome. Thereby the base pairing of the epsilon as encoded by the HBV genome was maintained and the start codon of core ORF was moved to a position downstream of epsilon as encoded by the HBV genome. In addition, the original GGC sequence was placed between the HA-tag sequence and core AUG in order to keep the authentic Kozak motif of core start codon (FIG. 1). FIG. 1 shows part of the HBV genome encoding an epsilon structure, wherein a nucleic acid sequence encoding a tag is inserted in accordance with the present invention.

It was envisioned herein that the above modifications cause minimal effects on HBV pgRNA-dependent core expression and pgRNA encapsidation, since the epsilon and the core expression cassette were preserved, although the translation initiation site of core protein was moved 39-nt further downstream in the pgRNA template. Indeed, the recombinant HBV genome supported near wildtype level of viral DNA replication, and the HA-tagged HBeAg was successfully produced upon the reconstitution of precore ORF in cccDNA molecule.

The insertion of an oligo encoding a tag did not affect viral DNA application, so that the herein provided method allows for production of cccDNA and consequently the assessment of the capacity of substances/candidate molecules to inhibit cccDNA formation by determining the amount of the surrogate marker “tagged hepadnavirus e antigen”. The herein provided means and methods are primarily useful to screen and identify candidate molecules that can be used in the therapy of chronic diseases associated with hepadnaviruses, like (chronic) hepatitis and in particular chronic hepatitis B infection.

Figure 2:
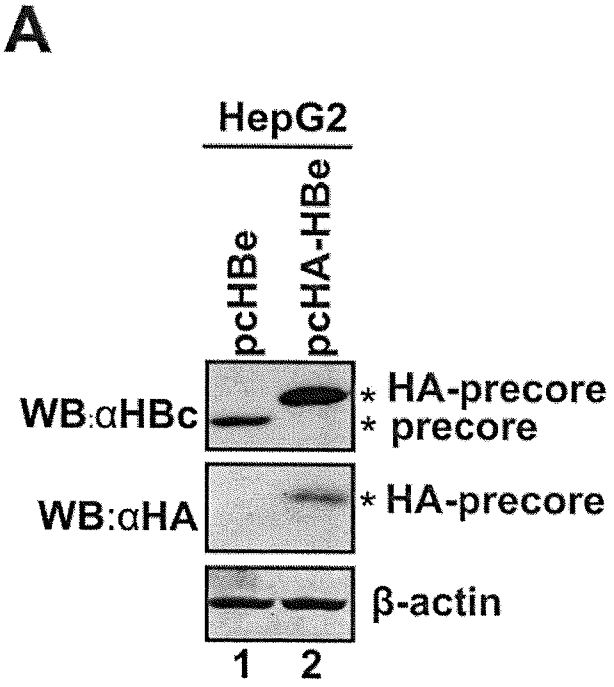
Figure 2:
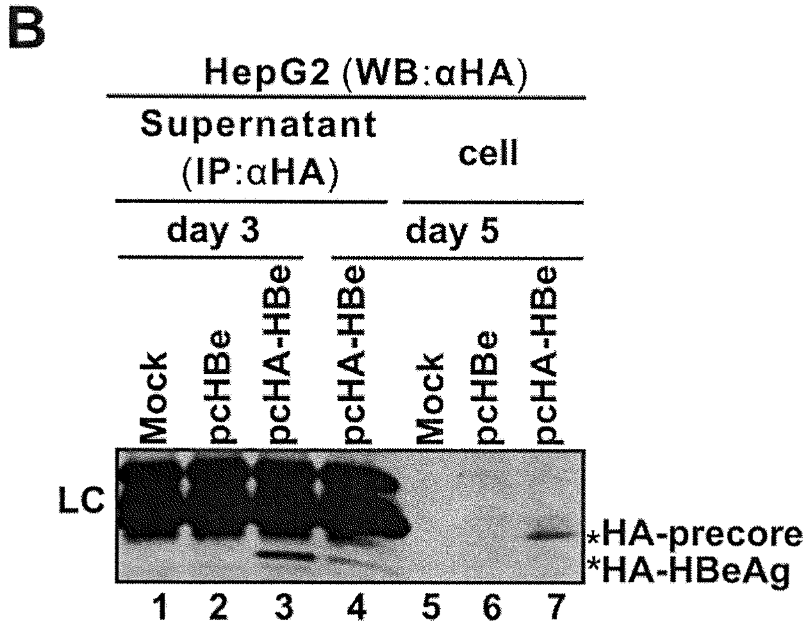

The insertion of a nucleic acid sequence encoding a tag (like an HA-tag) into the hepadnavirus (like HBV) precore ORF leads to hepadnavirus (like HBV) cccDNA-dependent production of tagged hepadnavirus e antigen (like HBeAg) which is useful for improved antigen detection specificity. In support of the present invention, it was confirmed herein that the (HA-)tag insertion does not affect the expression of precore protein and its subsequent posttranslational processing (N-terminal signal peptide cleavage and C-terminal domain cleavage) and mature HBeAg secretion (FIG. 2). More importantly, it was shown herein that such a modification in the hepadnavirus (like HBV) genome does not hamper viral pgRNA encapsidation and reverse transcription, which are the prerequisites for cccDNA formation through intracellular amplification pathway (FIGS. 4, 6-8, 12).

The present invention relates to screen and assessment of pharmacological agents for their activities against hepadnaviruses. In particular, this invention describes the design and construction of recombinant hepatitis B virus (HBV) genome and novel cell lines for inducible expression of HBV cccDNA-dependent epitope (e.g. Human influenza hemagglutinin (HA) tag)-tagged HBV e antigen (HBeAg). The tagged HBeAg secreted into the culture fluid can be quantitatively measured for example by chemiluminescence enzyme immunoassay (CLIA) and/or AlphaLISA. This invention provides an effective cell-based HBV reporter system to screen compounds for anti-hepadnaviral activity, especially those inhibiting cccDNA formation, maintenance, and/or its transcriptional activity.

Figure 10:
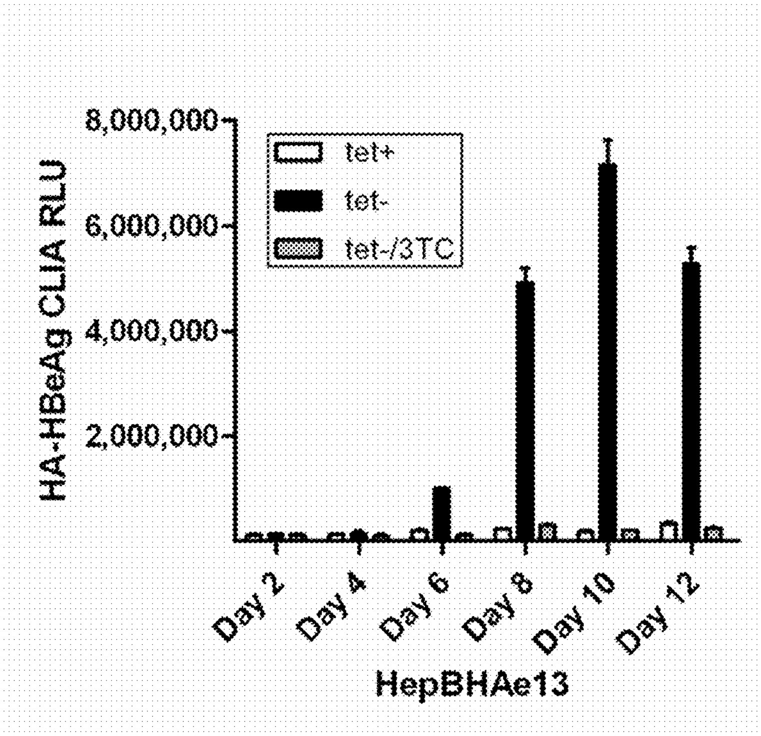

The present invention is further illustrated by FIG. 10. Here, it was shown that 3TC treatment abolished the HA-HBeAg signal in HepBHAe13 cells, although this was an extreme condition wherein 3TC blocked the viral DNA replication and thus there was no cccDNA synthesized. Further, as a proof of principle, two cccDNA formation inhibitors (CCC-0975 and CCC-0346) were tested in HepBHAe13 cells. Both compounds dose dependently reduced the HA-HBeAg level; see FIG. 11.

For example, the following non-limiting anti-hepadnaviral assays can be performed in accordance with the present invention:

1. Screen of compounds/candidate molecules regulating cccDNA stability and/or transcriptional activity using HepBHAe cell lines.

According to the present invention, the in vitro assay method can be used to screen/evaluate the efficacy of compounds/candidate molecules to regulate cccDNA stability or transcriptional activity in the nucleus. The compounds/candidate molecules thereby alter the level of tagged hepadnavirus e antigen (like HA-HBeAg) in culture supernatant. To perform the assay, cells can be first seeded in culture plates in the presence of tetracycline, and after cells reach confluent, the medium will be replaced with tetracycline-free medium to induce hapadnavirus (like HBV) DNA replication and cccDNA formation, which normally takes 6-8 days. After that, tetracycline can be added back to shut down the de novo viral DNA replication from integrated HBV genome, together with the addition of 3TC (or other HBV polymerase inhibitors) to block the intracellular amplification pathway of cccDNA. At the same time, test compounds can be added into culture medium for a certain period of time. Culture medium can then be used for ELISA measurement of tagged hepadnavirus e antigen (like HA-HBeAg). Media from wells that do not contain test compound can be used as control. Effective compounds that reduce tagged hepadnavirus e antigen (like HA-HBeAg) level in culture medium may have the activity to promote cccDNA turnover or silence cccDNA transcription. The phrase “effective or effectively” can be used herein to indicate that a compound, at certain testing concentration, is sufficient to prevent, and preferably reduce by at least 50%, most preferably by at least 90%, the production of tagged hepadnavirus e antigen (like HA-HBeAg) in a cell based assay system of the present invention. Direct measurement of the steady state levels of cccDNA and precore mRNA by qPCR or hybridization can be used to distinguish whether the test compound/candidate compound/candidate molecule reduces cccDNA stability or transcription, respectively.

2. Screen of compounds/candidate molecules that inhibit hepadnavirus (like HBV) cccDNA formation using HepBHAe cell lines.

According to another aspect of the present invention, the in vitro assay method can be used to evaluate compounds/candidate molecules that suppress cccDNA formation. Briefly, cells can be seeded into culture wells and tetracycline can be omitted at the day when cell monolayer becomes confluent. Simultaneously, test compound can be added and tagged hepadnavirus e antigen (like HA-HBeAg) in the medium can be measured by ELISA at the end of treatment (approximately 6 days). Any compound resulting in the reduction of tagged hepadnavirus e antigen (like HA-HBeAg) indicates that it may effectively block the formation of cccDNA. As an expanding aspect of this in vitro assay method, it is worth to note that the reduction of tagged hepadnavirus e antigen (like HA-HBeAg) in this assay may also indicate that the compound has the potential to inhibit hepadnavirus (like HBV) DNA replication. Such possibility can be investigated through direct measurement of viral core DNA by Southern blot and/or qPCR. The "hits" emerging from the assay described above may also include compounds that affect cccDNA stability and/or transcription. During the induction time period, the stability and/or transcription activity of the early made cccDNA may be targeted by testing compounds.

3. HepHA-HBe cell lines serve as counter-screen system.

Theoretically, compound "hits" from the aforementioned assays may directly inhibit HA-tagged precore protein translation, or posttranslational processing, or tagged hepadnavirus e antigen (like HA-HBeAg) secretion. To rule out such non-cccDNA inhibitors, "hits" can becounter-screened in HepHA-HBe cells, which produce tagged hepadnavirus e antigen (like HA-tagged HBeAg) using transgene as template. On the other hand, HepHA-HBe cells could also be used to screen HBeAg inhibitors.

The term "inhibit covalently closed circular DNA" and grammatical versions thereof can refer to an inhibition of the stability of covalently closed circular DNA (i.e. to a reduced stability of covalently closed circular DNA), to an inhibition of transcriptional activity of covalently closed circular DNA (i.e. to a reduced transcription of hepadnaviral mRNAs using covalently closed circular DNA as a transcription template) or to an inhibition of the formation of covalently closed circular DNA (i.e. no or less cccDNA is formed).

These exemplary explanations and definitions of the term "inhibit covalently closed circular DNA" are not mutually exclusive. For example, an inhibited formation of covalently closed circular DNA can lead to/be associated with a reduced transcription of hepadnaviral mRNAs using covalently closed circular DNA as a transcription template (i.e. an inhibition of transcriptional activity of covalently closed circular DNA). An inhibited stability of covalently closed circular DNA can lead to/be associated with a reduced transcription of hepadnaviral mRNAs using covalently closed circular DNA as a transcription template.

A tagged hepadnavirus e antigen can be used herein as surrogate marker for any such inhibition of cccDNA of a hepadnavirus.

In accordance with the above, the herein provided method can be (used) for assessing the capacity of a candidate molecule to inhibit the formation of cccDNA of a hepadnavirus. In this context, the cell can be contacted with the candidate molecule before cccDNA has formed.

The herein provided method can be (used) for assessing the capacity of a candidate molecule to decrease stability of cccDNA (e.g. the amount or number of cccDNA) of a hepadnavirus. Here, the cell can be contacted with the candidate molecule after cccDNA has formed.

The herein provided method can be (used) for assessing the capacity of a candidate molecule to decrease the transcription (activity) of cccDNA of a hepadnavirus. Here, the cell can be contacted with the candidate molecule after cccDNA has formed.

The tagged hepadnavirus e antigen, the level of which is to be assessed in accordance with the present invention, can contain one or more tags. As shown herein, a reliable assessment of the tagged hepadnavirus e antigen can be achieved by using only one tag, e.g. by using an antibody specifically binding to the tag. Accordingly, it is envisaged and preferred herein that the tagged hepadnavirus e antigen contains only one tag.

The following relates to the one or more tag to be used herein.

The term "tag" as used herein refers to any chemical structure useful as a marker. Primarily, the term "tag" refers to a "protein tag". The terms "tag" and "protein tag" are known in the art; see, inter alia, Fritze C E, Anderson T R. "Epitope tagging: general method for tracking recombinant proteins". Methods Enzymol. 2000; 327: 3-16; Brizzard B, Chubet R. Epitope tagging of recombinant proteins. Curr Protoc Neurosci. 2001 May; Chapter 5: Unit 5.8; and/or Terpe K. Overview of tag protein fusions: from molecular and biochemical fundamentals to commercial systems. Appl Microbiol Biotechnol. 2003 January; 60(5):523-33.

Typically, the tag to be used herein is a protein tag that is fused to the hepadnavirus e antigen. For example, a nucleic acid encoding the tag can be fused to a nucleic acid encoding a hepadnavirus e antigen, so that a fusion protein comprising both the tag and the hepadnavirus e antigen is expressed. The tag(s) can be fused to the 5'-end of the nucleic acid encoding a hepadnavirus e antigen, inserted within the nucleic acid encoding a hepadnavirus e antigen and/or fused to the 3'-end of the nucleic acid encoding a hepadnavirus e antigen. Thus, the resulting fusion protein can comprise (a) tag(s) at the N-terminus, internally (i.e. within the hepadnvirus e antigen/as internal epitope), and/or at the C-terminus As shown herein, an internal epitope tag can be used for reliable assessment of the level of a tagged hepadnavirus e antigen and is therefore preferred.

Various tags are known in the art and can be used in accordance with the present invention. Usually, a tag to be used herein has a low molecular weight of about 1-3 kDa, preferably of about 1 kDa. Exemplary, non-limiting low molecular weight tags are HA-tag, His-tag, Flag-tag, c-myc-tag, V5-tag or C9-tag. The use of HA-tag is preferred herein. The Flag-tag to be used herein can be 1×Flag-tag or 3×Flag-tag.

The low molecular weight is reflected in the length of the tag, i.e. the number of amino acid residues of which the tag consists. For example, His-tag (6 amino acids), HA-tag (9 amino acids), FLAG-tag (8 amino acids), or 3×FLAG-tag (22 amino acids) can be used herein. These exemplary tags support near wt-level HBV DNA replication and are therefore useful for performing the present invention.

Accordingly, a tag to be used herein can consist of 6 to 22 amino acids, e.g. 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, or 22 amino acids.

Exemplary nucleic acid sequences encoding a tag to be used herein is a nucleic acid sequence encoding the HA tag as shown in SEQ ID NO: 1, a nucleic acid sequence encoding the His-tag as shown in SEQ ID NO: 2; a nucleic acid sequence encoding the c-myc-tag as shown in SEQ ID NO: 4, a nucleic acid sequence encoding the V5-tag as shown in SEQ ID NO: 5, or a nucleic acid sequence encoding the C9-tag as shown in SEQ ID NO: 6. Herein the use of an HA tag encoded by SEQ ID NO: 1 or consisting of an amino acid sequence as shown in SEQ ID NO: 8 is preferred.

An exemplary nucleic acid sequence encoding a Flag-tag to be used herein is a nucleic acid sequence encoding a 1×Flag-tag as shown in SEQ ID NO: 3, or a nucleic acid sequence encoding a 3×Flag-tag as shown in SEQ ID NO: 7.

Exemplary amino acid sequences of a tag to be used herein is an amino acid sequence of an HA tag as shown in SEQ ID NO: 8, an amino acid sequence of the His-tag as shown in SEQ ID NO: 9, an amino acid sequence of the c-myc-tag as shown in SEQ ID NO: 11, an amino acid sequence of the V5-tag as shown in SEQ ID NO: 12, or an amino acid sequence of the C9-tag as shown in SEQ ID NO: 13.

An exemplary amino acid sequence of a Flag-tag to be used herein is an amino acid sequence of the 1×Flag-tag as shown in SEQ ID NO: 10 or an amino acid sequence of the 3×Flag-tag as shown in SEQ ID NO: 14.

The use of epitope tags is primarily envisaged herein, such as a hemagglutinin (HA) tag, His-tag, Flag-tag, c-myc-tag, V5-tag and/or C9-tag. Epitope tags are short peptide sequences which are chosen because high-affinity antibodies can be reliably produced in many different species. These tags are often derived from viral genes, which explain their high immunoreactivity. These tags are particularly useful for western blotting, immunofluorescence, immunohistochemistry, immunoaffinity chromatography and immunoprecipitation experiments. They are also used in antibody purification. Such epitope tags are particularly useful, because known and commercially available antibodies specifically binding to these tags can be used in accordance with the present invention.

Affinity tags are appended to proteins so that they can be purified from their crude biological source using an affinity technique. These include chitin binding protein (CBP), maltose binding protein (MBP), and glutathione-S-transferase (GST). The poly (His) tag is a widely used protein tag; it binds to metal matrices.

Chromatography tags are used to alter chromatographic properties of the protein to afford different resolution across a particular separation technique. Often, these consist of polyanionic amino acids, such as FLAG-tag.

Essentially any tag can be used herein. The nucleic acid encoding the tag as comprised in the nucleic acid molecule to be used herein should be able to support hepadnavirus DNA replication, cccDNA formation, and cccDNA-dependent tagged hepadnavirus antigen e production and secretion. This capacity can easily be validated using the assays provided herein e.g. the assays provided in the experiments. For example, it has been demonstrated herein that HA-tag insertion led to the wild-type level HBV DNA replication and the production of HA-tagged HBeAg from cccDNA in stable cell lines. These capacities can readily be confirmed and tested for other tags. His-tag and Flag-tag insertion do, for example, not affect viral DNA replication in transient transfection assays.

Further tags can be used without deferring from the gist of the present invention.

For example, reporter proteins can be used as tags herein, like luciferase (e.g. Firefly Luciferase, Renilla Luciferase, Gaussia Luciferase, etc), green fluorescent protein (GFP) and the like. These reporter proteins allow for an easy assessment of the level of the tagged hepadnavirus, e.g. by visual inspection, fluorescence measurements etc. Fluorescence tags are used to give visual readout on a protein. GFP and its variants are the most commonly used fluorescence tags.

Exemplary reporter proteins that can be used in the screening methods of the invention are, inter alia, luciferase, (green/red) fluorescent protein and variants thereof, EGFP (enhanced green fluorescent protein), RFP (red fluorescent protein, like DsRed or DsRed2), CFP (cyan fluorescent protein), BFP (blue green fluorescent protein), YFP (yellow fluorescent protein), β-galactosidase or chloramphenicol acetyltransferase.

Luciferase is a well known reporter; see, for example, Jeffrey (1987) Mol. Cell. Biol. 7(2), 725-737. A person skilled in the art can easily deduce further luciferase nucleic and amino acid sequences to be used in context of the present invention from corresponding databases and standard text books/review.

The reporter protein may allow the detection/assessment of a candidate molecule to inhibit cccDNA by inducing a change in the signal strength of a detectable signal. Said detectable signal can be a fluorescence resonance energy transfer (FRET) signal, a fluorescence polarization (FP) signal or a scintillation proximity (SP) signal. The detectable signal may be associated with a reporter protein as defined herein above. For example, GFP can be derived from *Aequorea victoria* (U.S. Pat. No. 5,491,084). A plasmid encoding the GFP of *Aequorea victoria* is available from the ATCC Accession No. 87451. Other mutated forms of this GFP including, but not limited to, pRSGFP, EGFP, RFP/DsRed, DSRed2, and EYFP, BFP, YFP, among others, are commercially available from, inter alia, Clontech Laboratories, Inc. (Palo Alto, Calif.).

The cultured cells/tissues comprising nucleic acid molecules comprising a nucleic acid sequence encoding a hepadnavirus e antigen fused to a reporter gene (like luciferase, GFP etc.) can be monitored for evidence of transcription of the reporter gene as a function of the concentration of test compound/candidate molecule in the culture medium. The variation in transcription levels of the reporter gene as a function of the concentration of test compound indicates the capacity of test compound/candidate molecule to inhibit cccDNA.

Reporter proteins are usually larger than the herein above described tags of low molecular weight, like epitope tags. Due to the longer insertion of, for example, a nucleic acid molecule comprising a nucleic acid sequence encoding luciferase compared to a nucleic acid sequence encoding smaller (epitope) tags (like an HA-tag), the expression of downstream viral core and pol from the recombinant pregenomic RNA can be reduced, so that transcomplement of core/pol may be required to restore the viral replication. For example, cell(s)/cell line(s) that constitutively express hepadnaviral core protein and hepadnaviral polymerase (core/pol) can be used in accordance with the present invention in particular in this context.

The use of a tagged hepadnavirus e antigen containing two or more tags is envisaged herein. The use of two or more tags can allow an even more reliable, and hence advantageous, assessment of the tagged hepadnavirus e antigen. For example, if the two or more tags are different tags (e.g. one tag is an HA-tag, the second tag is a His-tag), antibodies specifically binding to both tags can be employed. Such an assay can accordingly use e.g two epitope antibodies for example for ELISA detection to further increase the assay specificity.

It was found herein that the insertion of a 22 amino acid 3×FLAG tag insertion supports efficient HBV replication. Accordingly, it is believed that the use of e.g. tandem chimeric epitope tags, such as HA-linker-FLAG, can also be employed herein.

In accordance with the above, one tag may consist of 6 to 22 amino acids, when two or more tags are used (e.g. two or more different tags). It is particularly envisaged herein that the overall length of the tags (i.e. the sum of the amino acid residues of the two or more tages) to be used herein does not exceed a maximum of about 22 amino acids, because the expression of downstream viral core and pol from the recombinant pregenomic RNA might be reduced, as described in context of reporter proteins (like luciferase) above. If such a reduced expression of downstream viral core and pol occurs, e.g. when the overall length of the two or more tags exceeds about 22 amino acids, transcomplement of core/pol may be required to restore the viral replication. For example, cell(s)/cell line(s) that constitutively express hepadnaviral core protein and hepadnaviral polymerase (core/pol) can be used in accordance with the present invention in particular in this context.

Like a nucleic acid encoding only one tag, a nucleic acid encoding two or more tags can be fused to the 5'-end of the nucleic acid encoding a hepadnavirus e antigen, inserted within the nucleic acid encoding a hepadnavirus e antigen and/or fused to the 3'-end of the nucleic acid encoding a hepadnavirus e antigen. The tags can be separated by a linker: tag-linker-tag if two tags are used, tag-linker-tag-linker-tag, if three tags are used and so on.

Thus, the resulting fusion protein can comprise two or more tags at the N-terminus, internally (i.e. within the hepadnavirus e antigen/as internal epitope), and/or at the C-terminus. As shown herein, an internal epitope tag can be used for reliable assessment of the level of a tagged hepadnavirus e antigen and is therefore preferred. The use of resulting fusion protein with one tag e.g. at the N-terminus and e.g. a second internal tag and/or e.g a third at the C-terminus is envisaged herein. Further combinations are readily apparent and encompassed without deferring from the gist of this invention.

The two or more tags can be two or more of a hemagglutinin (HA)-tag, His-tag, Flag-tag, c-myc-tag, V5-tag and/or C9-tag. The Flag-tag can be 1×Flag-tag or 3×Flag-tag.

In the following, the nucleic acid molecule to be used in accordance with the present invention is described in more detail.

The nucleic acid molecule can comprise a nucleic acid sequence encoding a hepadnavirus precore protein, like a HBV precore protein. An exemplary nucleic acid sequence encoding a hepadnavirus precore protein is shown in SEQ ID NO: 15 and an exemplary amino acid sequence of a hepadnavirus precore protein is shown in SEQ ID NO: 17.

The nucleic acid molecule can comprise a nucleic acid sequence encoding the one or more tag as defined and explained herein above. The sequence encoding the one or more tag can be (inserted) 3' downstream of the nucleic acid sequence encoding the N-terminal signal peptide and the linker of the hepadnavirus precore protein.

In relation to Hepatitis B virus the N-terminal signal peptide and the linker constitute the N-terminal 29 amino acids of the precore protein as shown, for example, in SEQ ID NO. 17. Accordingly, the nucleic acid sequence encoding the one or more tag can be (inserted) 3' downstream of the nucleic acid sequence encoding the N-terminal 29 amino acids of a hepatitis B virus precore protein. In other words, the nucleic acid sequence encoding the one or more tag can be (inserted) 3' downstream of the nucleic acid sequence constituting the 87 nucleic acid residues from the 5' end of the nucleic acid encoding the HBV precore protein (the nucleic acid encoding the HBV precore protein being shown, for example, in SEQ ID NO. 15). On the protein level, the one or more tag can be inserted C-terminal of the amino acid residue corresponding to position 29 of a hepatitis B virus precore protein (the amino acid of a precore protein being shown, for example, in SEQ ID NO. 17).

In relation to HBeAg the linker constitutes the N-terminal 10 amino acids of the HBeAg as shown, for example, in SEQ ID NO. 18. With regard to HBeAg, the nucleic acid sequence encoding the one or more tag can be (inserted) 3' downstream of the nucleic acid sequence encoding the N-terminal 10 amino acids of HBeAg. In other words, the nucleic acid sequence encoding the one or more tag can be (inserted) 3' downstream of the nucleic acid sequence constituting the 30 nucleic acid residues from the 5' end of the nucleic acid encoding the HBV HBeAg (the nucleic acid encoding the HBeAg being shown, for example, in SEQ ID NO. 16). On the protein level, the one or more tag can be inserted C-terminal of the amino acid residue corresponding to position 10 of HBeAg (the amino acid of an HBeAg being shown, for example, in SEQ ID NO. 18).

More precisely, the nucleic acid sequence encoding the one or more tag can be (inserted) between nucleotides corresponding to positions 87 and 88 of a nucleic acid sequence encoding a HBV precore protein (the nucleic acid sequence encoding a HBV precore protein being shown e.g. in SEQ ID NO. 15). These positions delimit in the epsilon structure of pgRNA of a hepadnavirus or in the epsilon as encoded by a hepadnavirus genome the coding sequence of a linker and the ORF start codon of a nucleic acid sequence encoding the hepadnavirus core protein. In relation to HBV, position 87 is the last 3' nucleotide of a sequence encoding a linker and position 88 is the first nucleotide of a sequence encoding the core protein. On the protein level, the one or more tag can be inserted between amino acid residues corresponding to positions 29 and 30 of a hepatitis B virus precore protein (the amino acid of a precore protein being shown, for example, in SEQ ID NO. 17).

Likewise, the nucleic acid sequence encoding the one or more tag can be (inserted) between nucleotides corresponding to positions 30 and 31 of a nucleic acid sequence encoding HBeAg (the nucleic acid sequence encoding HBeAg being shown e.g. in SEQ ID NO. 16). On the protein level, the one or more tag can be inserted between amino acid residues corresponding to positions 10 and 11 of an HBeAg (the amino acid of HBeAg being shown, for example, in SEQ ID NO. 18).

The nucleic acid encoding the one or more tag can be (inserted) 5' upstream of a nucleic acid encoding a hepadnavirus core protein, such as a HBV core protein. An exemplary nucleic acid encoding a HBV core protein is shown in SEQ ID NO: 23. An exemplary amino acid sequence of a HBV core protein is shown in SEQ ID NO: 24.

The above defined insertion site of the nucleic acid sequence encoding one or more tags can also be defined by positions of nucleotides in a hepadnavirus genome. In relation to a HBV genome the nucleic acid molecule comprising a sequence encoding the one or more tag can, in accordance with the above, be inserted between nucleotides corresponding to position C1902 and position A1903 of the HBV genome. These positions can be determined according to nomenclature, as described, for example, in Galibert, F., et al (1979), Nature 281:646-650. It is evident that the nucleotide (positions) “C1902” and “A1903” as employed herein refer to the last nucleotide of precore region coding sequence and the first nucleotide of the core AUG, respectively. They are conserved among the different HBV genotype (A-H) sequences (as also provided herein and shown in SEQ ID NOs: 27-34). Accordingly, exemplary, non-limiting nucleic acid sequences of HBV genomes to be used herein are shown in SEQ ID NO: 27, 28, 29, 30, 31, 32, 33 or 34.

Yet, nucleotide "C", but not the "A" in the core AUG, or their positions may be different in sequences from some rare (clinical) isolates. Such sequences are also comprised in this invention.

In accordance with the present invention, the nucleic acid sequence encoding one or more tags can be inserted between nucleotides corresponding to position C1902 and position A1903 of a hepadnavirus genome other than the HBV genome. These corresponding positions in hepadnavirus genomes (i.e. the positions in a hepadnavirus genome that correspond to position C1902 and position A1903 of the HBV genome) can be determined readily. In other words, the nucleic acid sequence encoding the one or more tag can be inserted between an epsilon structure of a hepadnavirus pgRNA, preferably of HBV pgRNA, or an epsilon encoded by a a hepadnavirus genome (preferably, an HBV genome) and an ORF start codon of a nucleic acid sequence encoding the hepadnavirus core protein.

For example, if the nucleic acid molecule comprises a nucleic acid sequence encoding a hepadnavirus precore protein, the sequence encoding the one or more tag can be (inserted) 3' downstream of the nucleic acid sequence encoding the N-terminal signal peptide and the linker of the hepadnavirus precore protein. The nucleic acid sequence encoding the N-terminal signal peptide and the linker of the hepadnavirus precore protein can readily be determined. The sequence starts at (and hence includes) an ORF start codon of the nucleic acid sequence encoding the hepadnavirus precore protein and ends prior to an ORF start codon of the nucleic acid sequence encoding the hepadnavirus core protein (i.e. the coding sequence of the core protein is excluded). On the protein level, the one or more tag can be inserted C-terminal of the amino acid residue corresponding to the C-terminal final amino acid of the linker (the linker following the N-terminal signal peptide).

Accordingly, the nucleic acid sequence encoding the one or more tag can be (inserted) 3' downstream of the nucleic acid sequence encoding the N-terminal amino acids of a hepadnavirus e antigen. These N-terminal amino acids constitute the "linker" in a hepadnavirus precore protein. On the protein level, the one or more tag can be inserted C-terminal of the final C-terminal amino acid residue of the linker.

More precisely, the nucleic acid sequence encoding the one or more tag can be (inserted) between nucleotides corresponding to positions 87 and 88 of a nucleic acid sequence encoding a HBV precore protein (the nucleic acid sequence encoding a HBV precore protein being shown e.g. in SEQ ID NO. 15). On the protein level, the one or more tag can be inserted between amino acid residues corresponding to positions 29 and 30 of a hepatitis B virus precore protein (the amino acid of a precore protein being shown, for example, in SEQ ID NO. 17). These positions delimit in the epsilon structure of a hepadnavirus pgRNA, preferably HBV pgRNA, or in the epsilon structure as encoded by a hepadnavirus genome, preferably HBV genome, the coding sequence of a linker and the ORF start codon of a nucleic acid sequence encoding the hepadnavirus core protein. In relation to HBV, position 87 is the last 3' nucleotide of a sequence encoding a linker and position 88 is the first nucleotide of a sequence encoding the core protein. The corresponding positions in hepadnavirus HBV precore protein (i.e. the positions in a hepadnavirus genome that correspond to positions 87 and 88 of a nucleic acid sequence encoding a HBV precore protein) can be readily determined.

Likewise, the nucleic acid sequence encoding the one or more tag can be (inserted) between a nucleic acid sequence encoding the N-terminal signal peptide and linker of a hepadnavirus precore protein and a nucleic acid sequence encoding a hapadnavirus core protein.

For example, the nucleic acid sequence can be (inserted) between nucleotides corresponding to positions 30 and 31 of a nucleic acid sequence encoding HBeAg (the nucleic acid sequence encoding HBeAg being shown e.g. in SEQ ID NO. 16). On the protein level, the one or more tag can be inserted between amino acid residues corresponding to positions 10 and 11 of an HBeAg (the amino acid of HBeAg being shown, for example, in SEQ ID NO. 18). These positions delimit the coding sequence of the N-terminal hepadnavirus linker in the precore protein (or the coding sequence of the N-terminal hepadnavirus linker in a hepadnavirus e antigen) and the ORF start codon of a nucleic acid sequence encoding the hepadnavirus core protein. In relation to HBV, position 30 is the last 3' nucleotide of a sequence encoding a linker in a nucleic acid sequence encoding HBeAg. Position 31 is the first nucleotide of a sequence encoding the core protein. The corresponding positions in a nucleic acid sequence encoding hepadnavirus e antigen (i.e. the positions in a hepadnavirus e antigen that correspond to position 30 and 31 of a nucleic acid sequence encoding HBeAg) can be readily determined.

The nucleic acid encoding the one or more tag can be (inserted) 5' upstream of a nucleic acid encoding a hepadnavirus core protein, preferably a HBV core protein. An exemplary nucleic acid encoding a HBV core protein is shown in SEQ ID NO: 23. An exemplary amino acid sequence of a HBV core protein is shown in SEQ ID NO: 24. In other words, the nucleic acid encoding the one or more tag can be inserted between an epsilon structure of a hepadnavirus pgRNA, preferably HBV pgRNA, or between an epsilon structure as encoded by a hepadnavirus genome, (preferably a HBV genome) and an ORF start codon of nucleic acid sequence encoding the hepadnavirus core protein, preferably a HBV core protein.

As mentioned above, the nucleic acid molecule to be used/provided herein can comprise a sequence encoding the one or more tag wherein said sequence is inserted into the epsilon structure of a hepadnavirus pgRNA, preferably HBV pgRNA, or into an epsilon structure as encoded by a hepadnavirus genome, preferably an HBV genome. An exemplary epsilon structure encoded by the HBV genome is shown in FIG. 1. In relation to HBV, the epsilon structure as encoded by the HBV genome starts at (and includes) position T1849 and ends at (and includes) position A1909 of a HBV genome. An exemplary nucleic acid sequence of an epsilon structure encoded by a HBV genome is shown in SEQ ID NO: 25.

As described herein above, the nucleic acid molecule comprising a sequence encoding the one or more tag can be inserted into the lower stem of the epsilon structure of a hepadnavirus pgRNA, preferably HBV pgRNA, or as encoded by a hepadnavirus genome, preferably a HBV genome. An exemplary lower stem of an epsilon structure as encoded by a HBV genome is shown in FIG. 1. For example the nucleic acid sequence encoding the one or more tag can be inserted between nucleotides corresponding to positions 87 and 88 of a nucleic acid sequence encoding a HBV precore protein (the nucleic acid sequence encoding a HBV precore protein being shown e.g. in SEQ ID NO. 15), or between nucleotides corresponding to positions 30 and 31 of a nucleic acid sequence encoding HBeAg (the nucleic acid sequence encoding HBeAg being shown e.g. in SEQ ID NO. 16), or between nucleotides corresponding to position C1902 and position A1903 of a HBV genome. All these positions are in the lower stem of an epsilon structure of a hepadnavirus pgRNA, preferably HBV pgRNA, or in the lower stem of an epsilon structure as encoded by a hepadnavirus genome, preferably a HBV genome.

It is envisaged and preferred herein that the nucleic acid molecule comprises 5' of the sequence encoding the one or more tag a sequence that is capable of forming base pairs with the lower stem of the epsilon structure of a hepadnavirus pgRNA, preferably HBV pgRNA, or the lower stem of an epsilon structure as encoded by a hepadnavirus genome, preferably a HBV genome. It is believed that the experiments and teaching described and provided herein in relation to hepatitis B virus/tagged hepatits B virus e antigen is generally applicable to hepadnaviruses/tagged hepadnavirus e antigen. The only modification to the insertion sequence used for HBV can relate to the modification of the 5' flanking sequence of the nucleic acid sequence encoding the (epitope) tag to maintain the base pairing of epsilon of a hepadnavirus pgRNA, preferably HBV pgRNA, or epsilon as encoded by a hepadnavirus genome, preferably a HBV genome, for each specific hepadnavirus, preferably HBV. Based on the teaching of the present invention, a person skilled in the art is readily capable of designing and preparing a nucleic acid sequence 5' of the nucleic acid sequence encoding the tag to maintain the base pairing with epsilon structure of a hepadnavirus pgRNA, preferably HBV pgRNA, or an epsilon structure as encoded by a hepadnavirus genome, preferably a HBV genome. In particular in terms of duck hepatitis B virus (DHBV),since the start codon of its core ORF is located downstream of epsilon it thus not even be necessary to introduce a 5' flanking sequence of the nucleic acid sequence encoding the (epitope) tag to maintain the base pairing of epsilon for DHBV.

As shown in FIG. 1 a nucleic acid sequence was inserted between nucleotides corresponding to position C1902 and A1903 of the HBV genome, wherein said nucleic acid sequence contained a 5'-flanking region of 9 nucleotides (i.e. 5' of the nucleic acid sequence encoding the one or more tag) that formed base pairs with the lower stem of the epsilon structure of a hepadnavirus pgRNA, preferably HBV pgRNA, or of an epsilon structure as encoded by a hepadnavirus genome, preferably a HBV genome, for example with nucleotides corresponding to positions T1849 to T1855 of the HBV genome.

It is an important and preferred aspect of the present invention that the nucleic acid sequence encoding the one or more tag as defined herein and/or to be inserted as described herein above further comprises a nucleic acid sequence that is capable of forming base pairs with the epsilon structure of a hepadnavirus pgRNA, preferably HBV pgRNA, or of an epsilon structure as encoded by a hepadnavirus genome, preferably a HBV genome, particularly the lower stem of the epsilon structure of a hepadnavirus pgRNA, preferably HBV pgRNA, or of an epsilon structure as encoded by a hepadnavirus genome, preferably a HBV genome. By using a nucleic acid sequence that are capable of forming base pairs with the epsilon structure, it is aimed to preserve the epsilon structure of a hepadnavirus pgRNA, preferably HBV pgRNA, or of an epsilon structure as encoded by a hepadnavirus genome, preferably a HBV genome. The epsilon structure is, in turn thought to be important for replication, production of cccDNA and expression/production of (tagged) hepadnavirus e antigen, preferably HBV e antigen.

Preferably, the sequence that is capable of forming base pairs with the lower stem of the epsilon structure of a hepadnavirus pgRNA, preferably HBV pgRNA, or of an epsilon structure as encoded by a hepadnavirus genome, preferably a HBV genome, is capable of forming base pairs with nucleotides corresponding preferably to positions T1849 to A 1854 or, optionally, corresponding to positions T1849 to T1855 of the HBV genome. Typically, the formation of base pairs in pgRNA occurs between matching ribonucleotides, like A-U, G-C, and wobble base pair G-U. If the epsilon structure is maintained, replication, production of cccDNA and/or expression/production of (tagged) hepadnavirus e antigen is/are not hampered in the nucleic acid molecules to be used/provided herein.

It should be noted that the left arm of the epsilon structure is part of the nucleic acid sequence encoding the signal peptide of hepadnavirus e antigen (like HBeAg) and, thus, should be kept unchanged. The designed insertion at the right arm of the epsilon as described should not alter the base pairing of the lower stem. In the exemplified insertion shown in FIG. 1, the only nucleotide change related to A1903G (i.e. A was replaced by G at position 1903 of the HBV genome). The point mutation at position 1903 moves the core ORF out of the epsilon of hepadnavirus pgRNA, preferably HBV pgRNA, or of an epsilon as encoded by a hepadnavirus genome, preferably a HBV genome, allowing the maintenance of epsilon structure and the insertion of a tag in front of core AUG. The core protein is translated from pregenomic RNA which is transcribed after the start codon of precore ORF, so that the tag will not be incorporated into core protein.

The 5' flanking sequence of the epitope tag that is capable of forming base pairs with the (lower stem of the) epsilon structure of a hepadnavirus pgRNA, preferably HBV pgRNA, or of an epsilon structure as encoded by a hepadnavirus genome, preferably a HBV genome, of a hepadnavirus genome consists of up to 3, 6 or 9 nucleotides, typically of 9 nucleotides.

An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome consists of the sequence shown in SEQ ID No. 26. An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome encodes a polypeptide as shown in SEQ ID NO. 40.

The nucleic acid molecule to be used/provided herein can further comprise 3' of the sequence encoding the one or more tag a nucleic acid sequence encoding a linker. The linker can consist of one or more amino acid residues. Preferably, the linker consists of only one amino acid residue, such as a glycine residue.

For example, the nucleic acid sequence encoding the linker consists of the sequence GGC; or the nucleic acid sequence encodes a glycine residue. The GGC is copied from the original 3 nucleotides in front of the AUG of core ORF, which, together with the AUG, assemble a typical Kozak motif for optimal translation initiation. Thus, the linker that can be used/inserted is preferably and suitably selected so as to keep the authentic Kozak motif of the core start codon.

For example, the nucleic acid molecule comprising a nucleic acid sequence encoding a tagged hepadnavirus e antigen can comprise a nucleic acid sequence as shown in SEQ ID NO. 41. For example, the nucleic acid molecule comprising a nucleic acid sequence encoding a tagged hepadnavirus e antigen can comprise a nucleic acid sequence encoding an amino acid sequence as shown in SEQ ID NO. 42. The exemplary nucleic acid sequence as shown in SEQ ID NO. 41 consists of a nucleic acid sequence capable of forming base pairs with the (lower stem) of the epsilon structure (GTGGACATC; particularly the nucleotides GTGGACAT form base pairs with nucleotides corresponding to positions T1849 to T1855 of the HBV genome), a nucleic acid sequence encoding a HA-tag and a nucleic acid sequence encoding a glycine residue as linker (the latter nucleic acid sequence is primarily useful to keep the authentic Kozak motif of core start codon).

It is envisaged herein that the one or more tag is fused in frame into the hepadnavirus e antigen, preferably the Hepatitis B virus e antigen (HBeAg). Likewise it is envisaged herein that the nucleic acid sequence encoding the one or more tag (with a potential 5' flanking nucleic acid sequence capable of forming base pairs with the (lower stem of the) epsilon structure and/or with a potential 3' nucleic acid sequence keeping the authentic Kozak motif of core start condon or encoding a linker) is fused in frame to the nucleic acid sequence encoding the hepadnavirus e antigen, preferably the Hepatitis B virus e antigen (HBeAg).

The nucleic acid molecule to be used and provided in the present invention can comprise a hepadnavirus genome, preferably a Hepatitis B virus (HBV) genome. For example, the HBV genome is the genome of HBV genotype A, B, C, D, E, F, G or H. Exemplary, non-limiting nucleic acid sequences of HBV genomes to be used herein are shown in SEQ ID NO: 27, 28, 29, 30, 31, 32, 33 or 34. The HBV genome can be the genome of HBV genotype D, particularly a genome of HBV subgenotype ayw (like the HBV genome shown in SEQ ID NO: 27).

In accordance with the present invention only those nucleic acid molecules, such as hepadnavirus genomes, are to be used that allow (substantial) expression/production of (tagged) hepadnavirus e antigen. For example, some clinical HBV variants are known that to do not allow substantial expression/production of hepadnavirus e antigen. In some clinical HBV variants, the HBeAg negativity is due to either basal core promoter (BCP) double mutation (A1764T/G1766A in genotype D) or a precore (pC) mutation (G1898A in genotype D). While the BCP mutations reduce HBeAg through downregulation of precore mRNA transcription, the pC mutation introduces a premature stop codon to stall precore translation. Such hepadnavirus variants are less suitable for the herein provided methods.

In a preferred embodiment of the present invention, tagged HBeAg comprises or consists of an amino acid sequence as shown in SEQ ID NO: 22. The corresponding nucleic acid sequence encoding the tagged HBeAg is shown in SEQ ID NO: 20. These sequences are particularly useful in context of this invention but are merely examples of preferred embodiments.

A nucleic acid sequence encoding a HA-tagged precore protein, i.e. a precursor of the tagged HBeAg, is shown in SEQ ID NO: 19. Because this nucleic acid sequence encodes a precursor of the tagged HBeAg, it may be considered as a nucleic acid sequence encoding tagged HBeAg. The corresponding amino acid sequence is shown in SEQ ID NO: 21.

The following relates in more detail to the production of tagged hepadnavirus e antigen and the use thereof in the assessment of the capacity of a candidate molecule to inhibit cccDNA of a hepadnavirus.

The nucleic acid to be used/provided herein can be transcriptable into pregenomic (pg) hepadnavirus RNA, in particular pregenomic (pg) HBV RNA.

It is envisaged herein that the said nucleic acid can be designed to prevent the translation of the tagged hepadnavirus e antigen. For example, the nucleic acid does not contain a start codon ATG 5' upstream of the nucleic acid encoding a tagged hepadnavirus e antigen. In relation to HBV, the start codon of the nucleic acid encoding the precore protein can be deleted or mutated. For example, such a start codon (that is to be deleted/mutated) can correspond to nucleotides at (and including) position 1816 to (and including) position 1818 of a HBV genome; see for example FIG. 1.

Figure 5:
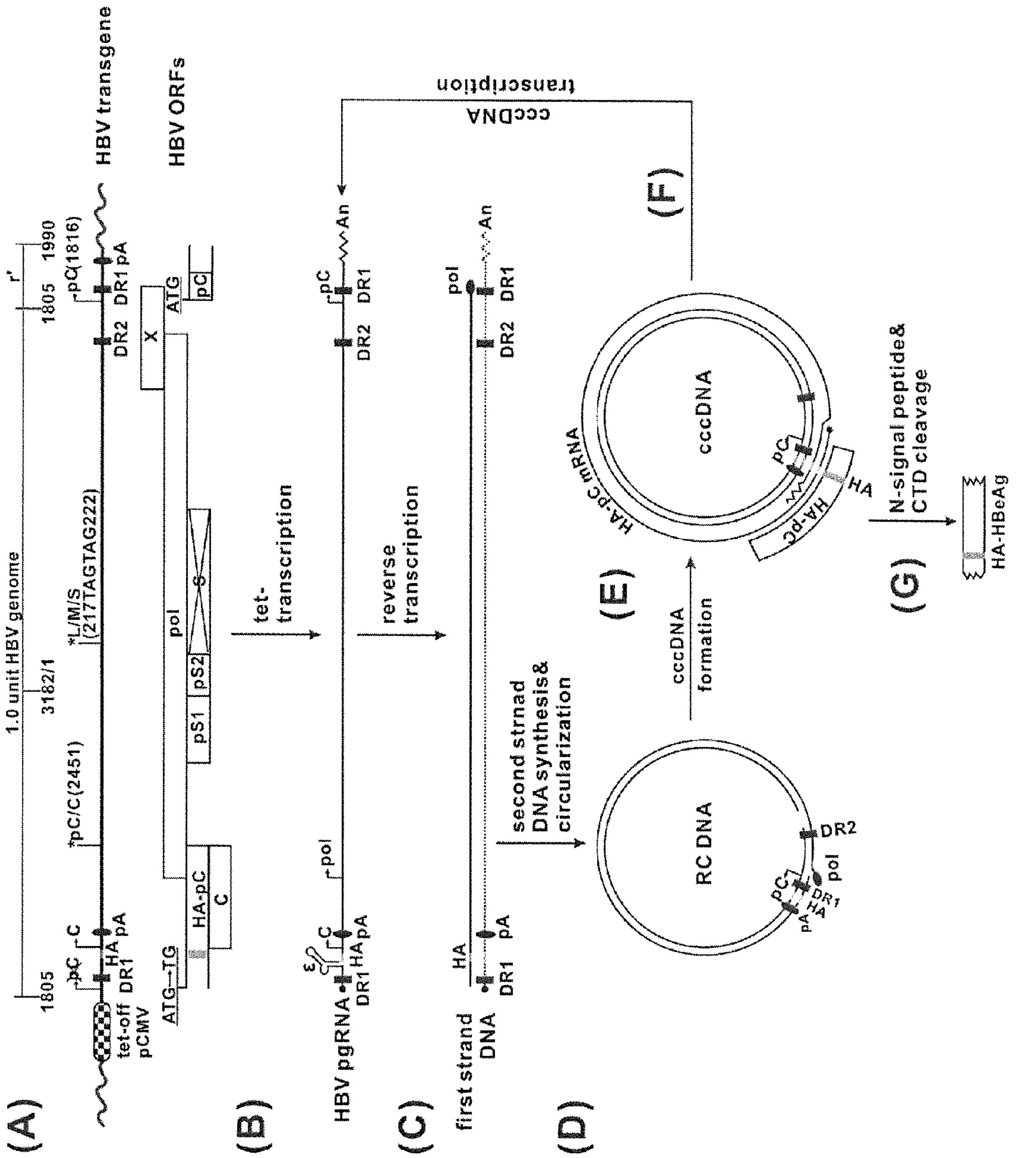

Avoiding the translation of the tagged hepadnavirus e antigen can be advantageous, to avoid production/expression thereof at the start of the assay. It is the aim of the present invention that tagged hepadnavirus e antigen is used as a surrogate marker for cccDNA. If tagged hepadnavirus e antigen is produced all the time, its expression/production does not necessarily correlate with the production of cccDNA. As shown in FIG. 5, the start codon can be restored at a later stage of the assay, when/after cccDNA is formed, so that the expression/production (i.e. the level) of tagged hepadnavirus e antigen truly reflects the production/level of cccDNA of a hepadnavirus. Thus, for an even more reliable assessment of the capacity of a candidate molecule to inhibit cccDNA, it is advantageous that production/expression of the tagged hepadnavirus e antigen is inhibited at the start of the assay e.g. by removing/mutating the start codon of the corresponding nucleic acid encoding same and that the production/expression of the tagged hepadnavirus e antigen is allowed later in order to reflect the production/level of cccDNA of a hepadnavirus.

For example, a start codon ATG 5' upstream of the nucleic acid encoding a tagged hepadnavirus e antigen as defined and described herein above can be replaced by the nucleic acids TG. Accordingly, the nucleic molecule to be used and provided herein can be modified e.g. by point mutation in order to prevent the translation of a tagged hepadnavirus e antigen.

Step (a) of the method to be used in accordance with the present invention, can further comprises a step (aa) that comprises culturing a cell comprising a nucleic acid molecule comprising a nucleic acid sequence encoding a tagged hepadnavirus e antigen in conditions allowing (i) the synthesis of hepadnavirus pregenomic (pg) RNA;
(ii) the reverse transcription of said synthesized pgRNA into a minus strand DNA;
(iii) the synthesis of a second plus strand DNA so that said minus strand DNA and said plus strand DNA form a double stranded relaxed circular DNA;
(iv) formation of cccDNA from said relaxed circular double stranded DNA;
(v) restoration of conditions allowing the translation of the tagged hepadnavirus e antigen;
(vi) transcription of an mRNA encoding a tagged hepadnavirus e antigen;
(vii) translation of a tagged hepadnavirus e antigen;

The restoration of conditions allowing the translation of the tagged hepadnavirus e antigen can relate to or be the restoration of the start codon as defined and explained above.

The nucleic acid molecule comprising a nucleic acid sequence encoding the tagged hepadnavirus e antigen can be comprised in a vector, in particular an expression vector.

The vector can, for example, comprise a sequence as shown in SEQ ID NO: 35.

The nucleic acid molecule comprising a nucleic acid sequence encoding the tagged hepadnavirus e antigen, preferably Hepatitis B virus e antigen (HBeAg), can be under control of an inducible promoter. (An) exemplary, non-limiting inducible promoter(s) to be used herein (is) are (a) tetracycline-inducible promoter(s), (a) doxycline-inducible promoter(s), (an) antibiotic-inducible promoter(s), (a) copper-inducible promoter(s), (an) alcohol-inducible promoter(s), (a) steroid-inducible promoter(s), or (a) herbicide-inducible promoter(s). The tetracycline inducible promoter (commercially available from e.g. Clontech) used in the herein provided experiments works in a tet-off manner. It is believed that a tetracycline inducible promoter working in a tet-on manner can likewise be used herein. tet-on/off system are, for example, available from Clontech and Invitrogen, either in plasmid or viral (retro-, adeno) backbones. Besides tetracycline/doxycline inducible promoter, as described above other inducible promoters that respond e.g. to antibiotics, copper, alcohol, steroids, or herbicides, among other compounds, are also suitable. For example, the inducible promoter is a CMV promoter. The inducible promoter can be a tet-EF-1 alpha promoter.

Further, one or more stop codons can be introduced into the coding region of one or more hepadnavirus envelope proteins, like one or more hepadnavirus envelope proteins is/are one or more HBV envelope proteins. The one or more hepadnavirus (HBV) envelope protein can be one or more of large surface protein (L), middle surface protein (M) and small surface protein (S). In one embodiment, the HBV envelope protein is small surface protein (S). (An) exemplary coding region(s) of the one or more HBV envelope proteins (is) are shown in SEQ ID NO: 36 (L), SEQ ID NO: 37 (M) and/or SEQ ID NO: 38 (S). In HBV nucleotides 217 to 222 (TTGTTG) of SEQ ID NO: 38 (S) can be mutated to e.g. TAGTAG to prevent the expression of envelope proteins.

A candidate molecule is determined to be capable of inhibiting cccDNA of a hepadnavirus, if the (expression) level of the surrogate marker of cccDNA, tagged hepadnavirus e antigen, is decreased compared to a control.

It is to be understood that the assessed (expression) level of a tagged hepadnavirus e antigen is compared to a control, like a standard or reference value, of the (expression) level of a tagged hepadnavirus e antigen. The control (standard/reference value) may be assessed in a cell, tissue, or non-human animal as defined herein, which has not been contacted with a candidate molecule. Alternatively, the control (standard/reference value) may be assessed in a cell, tissue, or non-human animal as defined herein prior to the above contacting step. The decrease in the (expression) level of a tagged hepadnavirus e antigen upon contacting with (a) candidate molecule(s) may also be compared to the decrease of the (expression) level of a tagged hepadnavirus e antigen induced by (a) routinely used reference compound(s), like a compound known to be unable to inhibit cccDNA. A skilled person is easily in the position to determine/assess whether the (expression) level of a tagged hepadnavirus e antigen is decreased.

Vice versa, and without deferring from the gist of the present invention, a positive control can be used, for example a reference compound(s), like a compound known to be capable of inhibiting cccDNA. If the (expression) level of the surrogate marker of cccDNA, tagged hepadnavirus e antigen, is equivalent to or even increased compared to such a (positive) control, a candidate molecule is determined to be capable of inhibiting cccDNA of a hepadnavirus.

In accordance with this invention, in particular the screening or identifying methods described herein, a cell, tissue or non-human animal to be contacted with a candidate molecule comprises a nucleic acid molecule comprising a nucleic acid sequence encoding a tagged hepadnavirus e antigen as defined herein.

For example said cell, tissue or non-human animal can be capable of expressing a tagged hepadnavirus e antigen as defined herein. As explained herein, the capability of a candidate molecule to inhibit/antagonize cccDNA can, accordingly, be detected by measuring the expression level of such gene products, particular the protein expression level, of a nucleic acid sequence encoding a tagged hepadnavirus e antigen. A low(er) (protein) expression level (compared to a control (standard or reference value)) is indicative for the capacity of the candidate molecule to act as inhibitor/antagonist.

Due to the reduced transcript/expression level also the level of the translated gene product (i.e. the protein level) will be decreased. The (protein) level of the above described tagged hepadnavirus e antigen proteins typically correlates with the signal strength of a detectable signal associated with the tagged hepadnavirus e antigen proteins. Exemplary tagged hepadnavirus e antigen proteins comprise can comprise a reporter as described above (e.g. luciferase, (green/red) fluorescent protein and variants thereof, EGFP (enhanced green fluorescent protein), and the like).

Accordingly, a decrease in reporter signal upon contacting the cell/tissue/non-human animal with a candidate molecule will indicate that the candidate molecule is indeed a cccDNA inhibitor/antagonist and, thus, capable of inhibiting cccDNA. The candidate molecules which decrease the level of tagged hepadnavirus e antigen as defined herein above are selected out of the candidate molecules tested, wherein those molecules are preferably selected which strongly decrease the level of tagged hepadnavirus e antigen (reflected, for example, in a decrease in the reporter signal).

It is envisaged in the context of the present invention (in particular the screening/identifying methods disclosed herein) that also cellular extracts can be contacted (e.g. cellular extracts comprising a nucleic acid molecule comprising a nucleic acid sequence encoding a tagged hepadnavirus e antigen as described and defined herein). For example, these cellular extracts may be obtained from the (transgenic/genetically engineered) cell(s), tissue(s) and/or non-human animal(s) to be used herein, in particular to be contacted with the candidate molecule.

The use of such cellular extracts is particular advantageous since it allows the assessment of the activity of a candidate molecule in vitro. The assessing/screening methods taking advantage of such (cellular) extracts can, for example, be used in prescreening candidate molecules, wherein the molecules selected in such a prescreen are then subject to subsequent screens, for example in the cell-based methods disclosed herein, in particular in methods wherein a (transgenic) cell(s), tissue(s) and/or non-human animal(s) are contacted with a candidate molecule. In this context, it is accordingly preferred that the candidate molecule has been selected in the in vitro pre-screening method, described herein above and below.

Thus, the term "cell" as used herein encompasses (transgenic/genetically engineered) cell(s), (transgenic/genetically engineered) tissue(s) and/or non-human (transgenic/genetically engineered) animal(s) and also cellular extracts derived therefrom.

It is to be understood that in a high throughput screening routinely, many (often thousands of candidate molecules) are screened simultaneously. Accordingly, in a (first) screen candidate molecules are selected, which decrease the level of tagged hepadnavirus e antigen.

Step (a) of the screening methods of the present invention, i.e. the "contacting step" may also be accomplished by adding a (biological) sample or composition containing said candidate molecule or a plurality of candidate molecules (i.e. various different candidate molecules) to the cell to be analyzed ((a) cell(s)/tissue(s)/non-human animal comprising a nucleic acid molecule comprising a nucleic acid sequence encoding tagged hepadnavirus e antigen).

Generally, the candidate molecule(s) or a composition comprising/containing the candidate molecule(s) may for example be added to a (transfected) cell, tissue or non-human animal comprising a nucleic acid molecule comprising a nucleic acid sequence encoding tagged hepadnavirus e antigen. As defined and disclosed herein, the term "comprising a nucleic acid molecule comprising a nucleic acid sequence encoding tagged hepadnavirus e antigen" implies the use of reporters. Also reporter constructs comprising a promoter and/or enhancer region of can be used herein.

The cell(s), tissue(s) and/or non-human animals to be used or provided in the present invention, in particular in context of the screening/identifying methods, can be stably or transiently transfected with nucleic acid molecule comprising a nucleic acid sequence encoding a tagged hepadnavirus e antigen disclosed herein.

The compounds/molecules capable of inhibiting cccDNA (as reflected in a decreased level of tagged hepadnavirus e antigen), are expected to be beneficial as agents in pharmaceutical settings disclosed herein and to be used for medical purposes, in particular, in the treatment of the diseases related to hepadnaviruses, in particular chronic diseases related to hepadnaviruses, such as chronic hepatitis and in particular chronic hepatitis B.

Candidate molecules/compounds which may function as specific an "antagonist" or "inhibitor" of cccDNA of a hepadnavirus may be small binding molecules such as small (organic) compounds.

The term "small molecule" in the context of drug discovery is known in the art and relates to medical compounds having a molecular weight of less than 2,500 Daltons, preferably less than 1,000 Daltons, more preferably between 50 and 350 Daltons. (Small) binding molecules comprise natural as well as synthetic compounds. The term "compound" (or likewise "molecule") in context of this invention comprises single substances or a plurality of substances. Said compounds/molecules may be comprised in, for example, samples, e.g., cell extracts from, e.g., plants, animals or microorganisms. Furthermore, said compound(s) may be known in the art but hitherto not known to be capable of (negatively) influencing cccDNA of a hepadnavirus. The plurality of compounds may be, e.g., added to a sample in vitro, to the culture medium or injected into the cell.

Candidate agents may also comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Exemplary classes of candidate agents may include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like. Other methods of stabilization may include encapsulation, for example, in liposomes, etc.

As mentioned above, candidate agents are also found among other biomolecules including amino acids, fatty acids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

It is also envisaged in the present invention that compounds/molecules including, inter alia, peptides, proteins, nucleic acids (including cDNA expression libraries), small organic compounds, ligands, PNAs and the like can be assessed for the capacity to inibit cccDNA. Said compounds can also be functional derivatives or analogues.

Methods for the preparation of chemical derivatives and analogues are well known to those skilled in the art and are described in, for example, Beilstein, "Handbook of Organic Chemistry", Springer Edition New York, or in "Organic Synthesis", Wiley, New York. Furthermore, said derivatives and analogues can be tested for their effects, i.e. their antagonistic effects on cccDNA in according with the present invention.

Furthermore, peptidomimetics and/or computer aided design of appropriate antagonists or inhibitors of cccDNA can be used. Appropriate computer systems for the computer aided design of, e.g., proteins and peptides are described in the art, for example, in Berry (1994) Biochem. Soc. Trans. 22:1033-1036; Wodak (1987), Ann. N. Y. Acad. Sci. 501:1-13; Pabo (1986), Biochemistry 25:5987-5991. The results obtained from the above-described computer analysis can be used in combination with the method of the invention for, e.g., optimizing known compounds, substances or molecules. Appropriate compounds can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh (1996) Methods in Enzymology 267: 220-234 and Dorner (1996) Bioorg. Med. Chem. 4:709-715. Furthermore, the three-dimensional and/or crystallographic structure of antagonists of cccDNA can be used for the design of (peptidomimetic) antagonists of cccDNA (Rose (1996) Biochemistry 35:12933-12944; Rutenber (1996) Bioorg. Med. Chem. 4:1545-1558).

The identification/assessment of candidate molecules which are capable of inhibiting cccDNA may be, inter alia, performed by transfecting an appropriate host with a nucleic acid molecule comprising a nucleic acid sequence encoding a tagged hepadnavirus e antigen and contacting said host with (a) candidate molecule(s).

The cell(s)/host(s) to be used herein is(are) preferably (a) eukaryotic cell(s), in particular (a) eukaryotic cell(s) of hepatocyte origin. The eukaryotic cell(s) is(are) preferably (a) hepatoma cell(s) or (a) hepatic cell(s). The eukaryotic cell(s) may also be derived from (a) hepatoma cell(s) or (a) hepatic cell(s). A preferred cell to be used herein is eukaryotic cell HepG2 (ATCC #HB-8065). HepG2 cells are known to support functional HBV cccDNA formation and transcription. The use of other cells is envisaged herein, like hepatocyte-derived cells (e.g. Huh7). Also (a) non-hepatic cell(s)/host(s) may be used in accordance with the invention, provided that they support hepadnavirus cccDNA formation (or, in a wider sense, hapadnavirus DNA replication). For example, such (a) non-hepatic cell(s)/hosts(s) can be modified to support hepadnavirus cccDNA formation (or hepadnavirus DNA replication) if viral pregenomic RNA is introduced into the cells, or transcribed from the DNA template by an exogenous promoter. cccDNA transcription may work if liver specific transcription factors are transcomplemented in such nonhepatic cells. The nucleic acid molecule of the invention or the vector comprising same can be stably integrated in the genome of the cell(s).

The nucleic acid molecule to be used in accordance with the present invention (i.e. the nucleic acid molecule comprising a nucleic acid sequence encoding a tagged hepadnavirus e antigen) or the vector comprising same preferably consists (essentially) of DNA.

The explanations given herein above in respect of "cells" also apply to and encompass tissues/non-human animals comprising or derived from these cells. A cell to be used herein may be comprised in a sample, for example, a biological, medical or pathological sample. For example, the use of fluids that comprise cells, tissues or cell cultures is envisaged. Such a fluid may be a body fluid or also excrements and may also be a culture sample. The body fluids may comprise but are not limited to blood, serum, plasma, urine, saliva, synovial fluid, spinal fluid, cerebrospinal fluid, tears, stool and the like.

Likewise, the candidate molecule(s) may be comprised in a (biological) sample or composition. The (plurality of) candidate molecule(s) are often subject to a first screen. The samples/compositions tested positive in the first screen can be subject to subsequent screens in order to verify the previous findings and to select the most potent inhibitors/antagonists. Upon multiple screening and selection rounds those candidate molecules can be selected which show a pronounced capacity to inhibit/antagonize cccDNA as defined and disclosed herein. For example, batches (i.e. compositions/samples) containing many candidate molecules will be rescreened and batches with no or insufficient inhibitory activity of candidate molecules be discarded without re-testing.

For example, if a (biological) sample or composition with many different candidate molecules is tested and one (biological) sample or composition is tested positive, then it is either possible in a second screening to screen, preferably after purification, the individual molecule(s) of the (biological) sample or composition. It may also be possible to screen subgroups of the (biological) sample or composition of the first screen in (a) subsequent screen(s). The screening of compositions with subgroups of those candidate molecules tested in previous screening rounds will thus narrow in on (an) potential potent cccDNA inhibitor(s). This may facilitate and accelerate the screening process in particular when a large number of molecules is screened. Accordingly, the cycle number of screening rounds is reduced compared to testing each and every individual candidate molecule in (a) first (and subsequent) screen(s) (which is, of course, also possible). Thus, depending on the complexity or the number of the candidate molecules, the steps of the screening method described herein can be performed several times until the (biological) sample or composition to be screened comprises a limited number, preferably only one substance which is indicative for the capacity of screened molecule to decrease the level of tagged hepadnavirus e antigen.

Herein envisaged is the use of optical measurement techniques that allow a resolution of e.g fluorescence on the level of single cells or single cells of a tissue, for example at the subcellular level. These techniques can involve fluorescence, for example confocal microscopy, digital image recording, like a CCD camera and suitable picture analysis software. For example, step (b) is carried out after the measurement of a standard response by performing a control experiment. For example, the level of tagged hepadnavirus e antigen is determined in a cell, tissue or a non-human animal comprising tagged hepadnavirus e antigen without contacting a candidate molecule in a first screen. In a second screen, after contacting the candidate molecule, the level of tagged hepadnavirus e antigen is measured/assessed. A difference in the level indicates whether the tested candidate molecule is indeed an antagonist/inhibitor of a cccDNA.

The level of tagged hepadnavirus e antigen can be quantified by measuring, for example, the level of gene products (particularly the protein level of tagged hepadnavirus e antigen) by any of the herein described methods, in particular protein measuring/detecting/assessing techniques.

For example, the expression can be determined on the protein level by taking advantage of immunoagglutination, immunoprecipitation (e.g. immunodiffusion, immunoelectrophoresis, immune fixation), western blotting techniques (e.g. (in situ) immunohistochemistry, (in situ) immunocytochemistry, affinity chromatography, enzyme immunoassays), and the like. Amounts of purified polypeptide in solution can be determined by physical methods, e.g. photometry. Methods of quantifying a particular polypeptide in a mixture rely on specific binding, e.g. of antibodies. Specific detection and quantitation methods exploiting the specificity of antibodies comprise for example immunohistochemistry (in situ). For example, concentration/amount of the level of tagged hepadnavirus e antigen proteins in a cell, tissue or a non-human animal can be determined by enzyme linked-immunosorbent assay (ELISA).

It is envisaged herein that assessing the level of the tagged hepadnavirus e antigen according to step (b) can be performed by ELISA, CLIA or AlphaLISA.

The herein provided methods take advantage of the use of established tags (like HA-tags, or His-tag, Flag-tag, c-myc-tag, V5-tag or C9-tag that can be used in the place of an HA-tag or in addition thereto). These tags can be used in the purification and detection of tagged hepadnavirus e antigen. By using antibodies specifically binding to the tag (e.g. via ELISA assays, like chemiluminescence ELISA (CLIA) and AlphaLISA), the level of tagged hepadnavirus e antigen can be reliably and rapidly assessed and cross-reactions with core protein be avoided.

Assessing the level of the tagged hepadnavirus e antigen according to step (b) of the herein provided method can comprise the use of an antibody specifically recognizing said hepadnavirus e antigen, preferably hepatitis B virus e antigen, (like, but not limited to Anti-HBe: clone 29, Lot 20110305, Autobio Diagnostics) and one or more antibodies specifically recognizing the one or more tags (like, but not limited to, Anti-HA: cat #A01244-100, Genscript).

The following antibodies specifically recognize hepatits B virus e antigen and may be used in accordance with the present invention:

Imai, et al. Demonstration of two distinct antigenic determinants on hepatitis B e antigen by monoclonal antibodies. J Immunol. 1982 January; 128(1):69-72.

Ferns and Tedder. Monoclonal antibodies to hepatitis B antigen (HBeAg) derived from hepatitis B core antigen (HBcAg): their use in characterization and detection of HBeAg. J Gen Virol. 1984 May; 65 (Pt 5):899-908.

Mondelli et al. Differential distribution of hepatitis B core and E antigens in hepatocytes: analysis by monoclonal antibodies. Hepatology. 1986 6(2):199-204.

Stuckmann and Mushahwar. Re-examination and further characterization of a monoclonal antibody to hepatitis B e antigen (anti-HBe). J Virol Methods. 1986 July; 13(4): 351-62.

Korec et al. Monoclonal antibodies against hepatitis B e antigen: production, characterization, and use for diagnosis. J Virol Methods. 1990 May; 28(2):165-9.

Usuda et al. A monoclonal antibody against a hepatitis B e antigen epitope borne by six amino acids encoded by the precore region. J Virol Methods. 1997 November; 68(2): 207-15.

Sogut et al. Monoclonal antibodies specific for hepatitis B e antigen and hepatitis B core antigen. Hybridoma (Larchmt). 2011 October; 30(5):475-9.

Alternatively, Western Blot analysis or immunohistochemical staining can be performed. Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction.

A skilled person is capable of determining the amount of polypeptides/proteins, in particular the gene products described herein above, by taking advantage of a correlation, preferably a linear correlation, between the intensity of a detection signal and the amount of, for example, polypeptides/proteins to be determined. Accordingly, the level of tagged hepadnavirus e antigen can be quantified based on the protein level of the tagged hepadnavirus e antigen. A skilled person is aware of standard methods to be used in determining the amount/concentration of the level of tagged hepadnavirus e antigen protein expression product in a sample or may deduce corresponding methods from standard textbooks (e.g. Sambrook, 2001).

A candidate molecule(s) is (are) selected, if the level of tagged hepadnavirus e antigen (or of a corresponding reporter signal) is strongly decreased, preferably is very low or non-dectable. For example, the level of tagged hepadnavirus e antigen (or of a corresponding reporter signal) may be decreased by at least 50%, 60%, 70%, 80%, more preferably by at least 90% compared to the (control) standard value.

Methods for transfecting cells or tissues are known in the art. Accordingly, calcium phosphate treatment or electroporation may be used for transfecting cells or tissues to express said reporter constructs (see Sambrook (2001), loc. cit.). Furthermore, nucleic acid molecules expressing said reporter constructs can be reconstituted into liposomes for delivery to target cells. As a further alternative, cells may be transduced to express specific reporter construct using genetically engineered viral vectors.

In another embodiment, the non-human animal comprising said reporter construct for detecting cccDNA inhibition is a transgenic non-human animal. The non-human organism to be used in the described screening assays can be selected from the group consisting of C. elegans, yeast, drosophila, zebrafish, guinea pig, rat and mouse. The generation of such a transgenic animal is within the skill of a skilled artisan. Corresponding techniques are, inter alia, described in "Current Protocols in Neuroscience" (2001), John Wiley&Sons, Chapter 3.16.

Accordingly, the invention also relates to a method for the generation of a non-human transgenic animal comprising the step of introducing a nucleic acid molecule comprising a nucleic acid sequence encoding a tagged hepadnavirus e antigen as disclosed herein into an ES-cell or a germ cell. The non-human transgenic animal provided and described herein is particular useful in screening methods and pharmacological tests described herein above. The non-human transgenic animal described herein may be employed in drug screening assays as well as in scientific and medical studies wherein antagonists/inhibitors of cccDNA for the treatment of a disease associated with hepadnaviruses are tracked, selected and/or isolated.

The transgenic/genetically engineered cell(s), tissue(s), and/or non-human animals to be used in context of the present invention, in particular, the screening/identifying methods, comprise the herein described and defined nucleic acid molecule comprising a nucleic acid sequence encoding a tagged hepadnavirus e antigen.

The present invention relates to the use of a cell, tissue or a non-human animal for screening and/or validation of a compound suspected of being an inhibitor of cccDNA of a hepadnavirus.

The term "transgenic non-human-animal", "transgenic cell" or "transgenic tissue" as used herein refers to an non-human animal, tissue or cell, not being a human that comprises different genetic material of a corresponding wild-type animal, tissue or cell. The term "genetic material" in this context may be any kind of a nucleic acid molecule, or analogues thereof, for example a nucleic acid molecule, or analogues thereof as defined herein. The term "different" means that additional or fewer genetic material in comparison to the genome of the wild type animal or animal cell. An overview of different expression systems to be used for generating transgenic cell/animal refers for example to Methods in Enzymology 153 (1987), 385-516, in Bitter et al (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440).

The present invention relates to a nucleic acid molecule as defined herein above, i.e. a nucleic acid molecule comprising a nucleic acid sequence encoding a tagged hepadnavirus e antigen. The explanations and definitions given herein above apply mutatis mutandis here. The hepadnavirus e antigen is preferably Hepatitis B virus e antigen (HBeAg).

The tagged hepadnavirus e antigen can contain only one tag. The tag can consist of 6 to 22 amino acids A typical and herein preferred (epitope) tag consists of 8, 9, 10 or 11 amino acids. 6× His is a minimal epitope tag that can be be used herein. It is possible that an insertion of less than 6 amino acids may assemble into a new epitope together with the adjacent HBeAg amino acids, so that also such an insertion results in a tagged hepadnavirus. The tag can be a hemagglutinin (HA) tag, His-tag, Flag-tag, c-myc-tag, V5-tag or C9-tag. The Flag-tag can be a 1×Flag-tag or a 3×Flag-tag.

The tagged hepadnavirus e antigen can contain two or more tags. The two or more tags are preferably different tags. The entire length of said two or more tags can be from about 12 to about 31 amino acids. For example, the entire length of the two or more tags can be 12, 13, 14, 15, 16, 17, 18, 19, 20, 21, 22, 23, 24, 25, 26, 27, 28, 29, 30 or 31 amino acids. The two or more tag can be two or more of a hemagglutinin (HA) tag, His-tag, Flag-tag, c-myc-tag, V5-tag and/or C9-tag. The Flag-tag can be a 1×Flag-tag or a 3×Flag-tag.

Exemplary nucleic acid sequences encoding the tag(s) are a nucleic acid sequence encoding the HA tag as shown in SEQ ID NO: 1, a nucleic acid sequence encoding the His-tag as shown in SEQ ID NO: 2, a nucleic acid sequence encoding the c-myc-tag as shown in SEQ ID NO: 4, a nucleic acid sequence encoding the V5-tag as shown in SEQ ID NO: 5, and/or a nucleic acid sequence encoding the C9-tag as shown in SEQ ID NO: 6.

Exemplary nucleic acid sequences encoding a Flag-tag are a nucleic acid sequence encoding the 1×Flag-tag as shown in SEQ ID NO: 3, or a nucleic acid sequence encoding the 3×Flag-tag as shown in SEQ ID NO: 7.

Exemplary amino acid sequences of the tag(s) are an amino acid sequence of the HA tag as shown in SEQ ID NO: 8, an amino acid sequence of the His-tag as shown in SEQ ID NO: 9, an amino acid sequence of the c-myc-tag as shown in SEQ ID NO: 11, an amino acid sequence of the V5-tag as shown in SEQ ID NO: 12, and/or an amino acid sequence of the C9-tag as shown in SEQ ID NO: 13.

Exemplary amino acid sequences of the Flag-tag are an amino acid sequence of the 1×Flag-tag as shown in SEQ ID NO: 10 or an amino acid sequence of the 3×Flag-tag as shown in SEQ ID NO: 14.

An exemplary nucleic acid sequence encoding the HBeAg is shown in SEQ ID NO: 16. An exemplary amino acid sequence of the HBeAg is shown in SEQ ID NO: 18.

The nucleic acid molecule can comprise a nucleic acid sequence encoding a hepadnavirus precore protein. An exemplary nucleic acid sequence encoding a hepadnavirus precore protein is shown in SEQ ID NO: 15. An exemplary amino acid sequence of the hepadnavirus precore protein is shown in SEQ ID NO: 17.

The nucleic acid molecule can comprise a nucleic acid sequence encoding the one or more tag, wherein said sequence is (inserted) 3' downstream of the nucleic acid sequence encoding the N-terminal signal peptide and linker of the hepadnavirus precore protein.

The nucleic acid sequence encoding the one or more tag can be (inserted) 3' downstream of the nucleic acid sequence encoding the N-terminal 29 amino acids of a hepatitis B virus precore protein.

The nucleic acid molecule can comprise a hepadnavirus genome. Preferably, the hepadnavirus genome is a Hepatitis B virus (HBV) genome. The HBV genome can be the genome of HBV genotype A, B, C, D, E, F, G or H. The HBV genome can be the genome of HBV genotype D. Preferably, the HBV genome is a genome of HBV genotype D, subgenotype ayw.

The nucleic acid encoding the one or more tag can be (inserted) 5' upstream of the nucleic acid encoding a hepadnavirus core protein, preferably a HBV core protein. An exemplary nucleic acid sequence encoding a HBV core protein is shown in SEQ ID NO: 23. The core protein can be a HBV core protein. An exemplary amino acid sequence of a HBV core protein is shown in SEQ ID NO: 24.

The nucleic acid molecule comprising a sequence encoding the one or more tag can be inserted into the epsilon structure of a hepadnavirus pgRNA, preferably HBV pgRNA, or of an epsilon structure as encoded by a hepadnavirus genome, preferably a HBV genome as defined herein. An exemplary nucleic acid sequence of the epsilon structure as encoded by a HBV genome is shown in SEQ ID NO: 25. The nucleic acid molecule comprising a sequence encoding the one or more tag can be inserted into the lower stem of the epsilon structure of a hepadnavirus pgRNA, preferably HBV pgRNA, or of an epsilon structure as encoded by a hepadnavirus genome, preferably a HBV genome.

The nucleic acid molecule comprising a sequence encoding the one or more tag can be inserted between nucleotides corresponding to position C1902 and A1903 of the HBV genome.

The nucleic acid molecule can comprise 5' of the sequence encoding the one or more tag a sequence that is capable of forming base pairs with the lower stem of the epsilon structure of a hepadnavirus pgRNA, preferably HBV pgRNA, or of an epsilon structure as encoded by a hepadnavirus genome, preferably a HBV genome. The sequence that is capable of forming base pairs with the lower stem of the epsilon structure of (or encoded by) a hepadnavirus genome, preferably HBV, is primarily capable of forming base pairs with nucleotides preferably corresponding to positions T1849 to A1854, or optionally, corresponding to positions T1849 to T1855 of the HBV genome. The sequence that is capable of forming base pairs with the lower stem of the epsilon structure of a hepadnavirus genome can consist of (up to) 9 nucleotides.

An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome consists of the sequence shown in SEQ ID No. 26. An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome, encodes a polypeptide as shown in SEQ ID NO. 40.

The nucleic acid molecule can comprise 3' of the sequence encoding the one or more tag a sequence encoding a linker. The linker can consist of one or more amino acid residues. Preferably, the linker consists of only one amino acid residue, such as a glycine residue. The sequence encoding a linker can consist of the sequence GGC. The sequence encoding a linker can encode a glycine residue. The sequence encoding can be useful and appropriately selected to keep the authentic Kozak motif of core start codon.

The nucleic acid molecule can comprise a nucleic acid sequence encoding a tagged hepadnavirus e antigen that comprises a nucleic acid sequence as shown in SEQ ID NO. 41. The nucleic acid molecule can comprise a nucleic acid sequence encoding a tagged hepadnavirus e antigen comprises a nucleic acid sequence encoding an amino acid sequence as shown in SEQ ID NO. 42.

The one or more tag is preferably fused in frame in the hepadnavirus e antigen (or into the hepadnavirus e precore protein), preferably a Hepatitis B virus e antigen (HBeAg) (or into the Hepatitis B virus precore protein).

An exemplary nucleic acid sequence encoding the tagged HBeAg is shown in SEQ ID NO: 20. A preferred amino acid sequence of the tagged HBeAg is shown in SEQ ID NO: 22.

An exemplary nucleic acid sequence nucleic acid sequence encoding a tagged Hepatitis B virus precore protein is shown in SEQ ID NO: 19. An exemplary nucleic acid sequence amino acid sequence of the tagged Hepatitis B virus precore protein is shown in SEQ ID NO: 21.

Exemplary nucleic acid sequences of the HBV genome are shown in SEQ ID NO: 27, 28, 29, 30, 31, 32, 33 or 34.

The nucleic acid can be transcriptable into pregenomic (pg) hepadnavirus RNA. The hepadnavirus RNA is preferably HBV RNA.

The nucleic acid molecule comprising a nucleic acid sequence encoding the tagged hepadnavirus e antigen can be comprised in a vector, such as an expression vector. Preferably, the hepadnavirus e antigen is Hepatitis B virus e antigen (HBeAg).

The nucleic acid generally allows the translation of the tagged hepadnavirus e antigen, preferably Hepatitis B virus e antigen (HBeAg). The nucleic acid can be comprised in a vector that comprises a sequence as shown in SEQ ID NO: 39.

In certain embodiments the nucleic acid is designed to prevent the translation of the tagged hepadnavirus e antigen. For example, the nucleic acid does not contain a start codon ATG 5' upstream of the nucleic acid encoding a tagged hepadnavirus e antigen. For example, a start codon ATG 5' upstream of the nucleic acid encoding a tagged hepadnavirus e antigen can be replaced by the nucleic acids TG. The nucleic can be modified by point mutation in order to prevent the translation of a tagged hepadnavirus e antigen. The vector can comprise a sequence as shown in SEQ ID NO: 35.

The nucleic acid molecule comprising a nucleic acid sequence encoding the tagged hepadnavirus e antigen, preferably Hepatitis B virus e antigen (HBeAg), can be under control of an inducible promoter.

The inducible promoter can be a tetracycline-inducible promoter, a doxycline-inducible promoter, an antibiotic-inducible promoter, a copper-inducible promoter, an alcohol-inducible promoter, a steroid-inducible promoter, or a herbicide-inducible promoter.

The inducible promoter can preferably be a CMV promoter. The inducible promoter can be a tet-EF-1 alpha promoter.

One or more stop codons can be introduced into the coding region of one or more hepadnavirus envelope proteins, preferably one or more HBV envelope proteins.

The one or more HBV envelope protein can be one or more of L, M and/or S. The HBV envelope protein can be S.

Exemplary coding regions of (or exemplary nucleic acid sequences encoding) the one or more HBV envelope proteins is shown in SEQ ID NO: 36 (L), 37 (M) or 38 (S). The HBV nucleotides 217 to 222 (TTGTTG) of SEQ ID NO: 38 (S) can be mutated to TAGTAG to prevent the expression of envelope proteins.

The present invention relates to a protein encoded by the nucleic acid molecule as defined and provided herein above.

The protein comprises a tagged hepadnavirus e antigen, preferably a tagged Hepatitis B virus e antigen (HBeAg).

The Hepatitis B virus e antigen (HBeAg) can comprise an amino acid sequence as shown in SEQ ID NO: 18. Preferably, the tagged hepadnavirus e antigen contains only one tag.

The tag can consist of 6 to 22 amino acids. The tag can be hemagglutinin (HA) tag, His-tag, Flag-tag, c-myc-tag, V5-tag or C9-tag. The Flag-tag can be a 1×Flag-tag or a 3×Flag-tag.

The tagged hepadnavirus e antigen can contain two or more tags. Preferably the two or more tags are different tags. The entire length of said two or more tags is from about 14 to about 31 amino acids. The two or more tag can be two or more of a hemagglutinin (HA) tag, His-tag, Flag-tag, c-myc-tag, V5-tag and/or C9-tag. The Flag-tag can be a 1×Flag-tag or a 3×Flag-tag.

Exemplary nucleic acid sequences encoding a tag are a nucleic acid sequence encoding the HA tag as shown in SEQ ID NO: 1, a nucleic acid sequence encoding the His-tag as shown in SEQ ID NO: 2, a nucleic acid sequence encoding the c-myc-tag as shown in SEQ ID NO: 4, a nucleic acid sequence encoding the V5-tag as shown in SEQ ID NO: 5, and/or a nucleic acid sequence encoding the C9-tag as shown in SEQ ID NO: 6.

Exemplary nucleic acid sequences encoding a Flag-tag are a nucleic acid sequence encoding a 1×Flag-tag as shown in SEQ ID NO: 3 or a nucleic acid sequence encoding a 3×Flag-tag as shown in SEQ ID NO: 7.

Exemplary amino acid sequences of a tag are an amino acid sequence of the HA tag as shown in SEQ ID NO: 8, an amino acid sequence of the His-tag as shown in SEQ ID NO: 9, an amino acid sequence of the c-myc-tag as shown in SEQ ID NO: 11, an amino acid sequence of the V5-tag as shown in SEQ ID NO: 12; and/or an amino acid sequence of the C9-tag as shown in SEQ ID NO: 13.

Exemplary amino acid sequences of a Flag-tag are an amino acid sequence of the 1×Flag-tag as shown in SEQ ID NO: 10 or an amino acid sequence of the 3×Flag-tag as shown in SEQ ID NO: 14.

The protein can comprise a hepadnavirus precore protein. An exemplary nucleic acid sequence encoding a hepadnavirus precore protein is shown in SEQ ID NO: 15. An exemplary amino acid sequence of the hepadnavirus precore protein is shown in SEQ ID NO: 17.

The protein can comprise an amino acid sequence of the one or more tag, wherein said sequence is C-terminal of the amino acid sequence of the sequence of the signal peptide and of the linker of the hepadnavirus precore protein. The protein can comprise an amino acid sequence of the one or more tag C-terminal of the amino acid sequence of the N-terminal 29 amino acids of a hepatitis B virus precore protein.

The protein can comprise an amino acid sequence of the one or more tag, wherein said sequence is N-terminal of an amino acid sequence of a hepadnavirus core protein, preferably N-terminal of an amino acid sequence of a HBV core protein. An exemplary nucleic acid encoding a HBV core protein is shown in SEQ ID NO: 23. An exemplary amino acid sequence of a HBV core protein is shown in SEQ ID NO: 24.

The amino acid sequence of the one or more tag can be inserted into an amino acid sequence encoded by the epsilon structure of a hepadnavirus pgRNA, preferably HBV pgRNA, or of an epsilon structure as encoded by a hepadnavirus genome, preferably an HBV genome. An exemplary nucleic acid sequence of the epsilon structure as encoded by an HBV genome is shown in SEQ ID NO: 25. The amino acid sequence of the one or more tag can be inserted into an amino acid sequence encoded by the lower stem of the epsilon structure of a hepadnavirus pgRNA, preferably HBV pgRNA, or of an epsilon structure as encoded by a hepadnavirus genome, preferably an HBV genome, preferably into an amino acid sequence encoded by the lower stem of the epsilon structure of a hepadnavirus pgRNA, preferably HBV pgRNA, or of an epsilon structure as encoded by a hepadnavirus genome, preferably an HBV genome.

The amino acid sequence of the one or more tag can be inserted between amino acid residues corresponding to position G29 and position M30 of a HBV precore protein, such as the one as shown in SEQ ID NO. 17.

The protein can further comprise N-terminal to the amino acid sequence of the one or more tag an amino acid sequence of (up to) 3 amino acids, wherein said amino acid sequence of up to 3 amino acids is encoded by a nucleic acid sequence that is capable of forming base pairs with the lower stem of the epsilon structure of a hepadnavirus pgRNA, preferably HBV pgRNA, or of an epsilon structure as encoded by a hepadnavirus genome, preferably an HBV genome. The nucleic sequence that is capable of forming base pairs with the lower stem of the epsilon structure of a hepadnavirus pgRNA, preferably HBV pgRNA, or of an epsilon structure as encoded by a hepadnavirus genome, preferably an HBV genome, is primarily capable of forming base pairs with nucleotides preferably corresponding to positions T1849 to T1855 or, optionally, corresponding to positions T1849 to T1855 of the HBV genome. An exemplary nucleic acid sequence that is capable of forming base pairs with the lower stem of the epsilon structure of a hepadnavirus pgRNA, preferably HBV pgRNA, or of an epsilon structure as encoded by a hepadnavirus genome, preferably an HBV genome, consists of the sequence shown in SEQ ID No. 26. An exemplary amino acid sequence of (up to) 3 amino acids is shown in SEQ ID NO. 40.

The protein can further comprise C-terminal to the amino acid sequence of the one or more tag a linker. The linker can consist of one or more amino acid residues. Preferably, the linker consists of only one amino acid residue, such as a glycine residue.

The amino acid sequence of a tagged hepadnavirus e antigen can comprise an amino acid sequence encoded by a nucleic acid sequence as shown in SEQ ID NO. 41. The amino acid sequence of a tagged hepadnavirus e antigen can comprise an amino acid sequence as shown in SEQ ID NO. 42.

The one or more tag is preferably fused in frame into the hepadnavirus e antigen, preferably an Hepatitis B virus e antigen (HBeAg).

An exemplary nucleic acid sequence encoding the tagged HBeAg is shown in SEQ ID NO: 20. Preferably, the tagged HBeAg has an amino acid sequence as shown in SEQ ID NO: 22.

An exemplary nucleic acid sequence encoding a tagged HBV precore protein is shown in SEQ ID NO: 19. An exemplary amino acid sequence of a tagged HBV precore protein is shown in SEQ ID NO: 21.

The present invention relates to a host cell comprising the nucleic acid molecule as defined and provided herein and/or to a host cell comprising or the protein as defined and provided herein. The host cell can be a eukaryotic cell. The eukaryotic cell can be of hepatocyte origin. The eukaryotic cell can be a hepatoma cell or can be derived from a hepatoma cell. In a preferred embodiment, the eukaryotic cell is HepG2 (ATCC #HB-8065).

The present invention relates to a process for the production of the protein as defined herein above, said process comprising culturing a host as defined herein above under conditions allowing the expression of the protein and recovering the produced protein from the culture.

The present invention relates to a kit for use in the method of the present invention. Likewise, the present invention relates to the use of a kit for screening candidate molecules suspected to be capable of inhibiting covalently closed circular DNA of hepadnavirus. The explanations provided herein above in relation to the method for assessing the capacity of a candidate molecule to inhibit cccDNA of a hepadnavirus apply mutatis mutandis here.

The kit can comprise an antibody specifically recognizing a hepadnavirus antigen e as defined herein and one or more antibodies specifically recognizing one or more tags as defined herein.

The kit (to be prepared in context) of this invention or the methods and uses of the invention may further comprise or be provided with (an) instruction manual(s). For example, said instruction manual(s) may guide the skilled person (how) to assess the capacity of a candidate molecule to inhibit cccDNA and/or how to assess the level of tagged hepadnavirus e antigen in accordance with the present invention. Particularly, said instruction manual(s) may comprise guidance to use or apply the herein provided methods or uses.

The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) compound(s) required for specifically determining the (protein (expression)) level of said tagged hepadnavirus e antigen as defined herein.

The present invention relates to the use of the nucleic molecule as defined and provided herein, the protein as defined and provided herein and/or the host cell as defined and provided herein for screening candidate molecules suspected to be capable of inhibiting covalently closed circular DNA of hepadnavirus. The explanations provided herein above in relation to the method for assessing the capacity of a candidate molecule to inhibit cccDNA of a hepadnavirus apply mutatis mutandis here.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of." Thus, the terms "comprising"/"including"/"having" mean that any further component (or likewise features, integers, steps and the like) can be present.

The term "consisting of" means that no further component (or likewise features, integers, steps and the like) can be present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means that specific further components (or likewise features, integers, steps and the like) can be present, namely those not materially affecting the essential characteristics of the composition, device or method. In other words, the term "consisting essentially of" (which can be interchangeably used herein with the team "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

As used herein, the term "isolated" refers to a composition that has been removed from its in-vivo location. Preferably the isolated compositions or compounds of the present invention are substantially free from other substances (e.g., other proteins or other compounds) that are present in their in-vivo location (i.e. purified or semi-purified compositions or compounds.)

As used herein the term "about" refers to ±10%.

The present invention is further described by reference to the following non-limiting figures and examples.

Unless otherwise indicated, established methods of recombinant gene technology were used as described, for example, in Sambrook, Russell "Molecular Cloning, A Laboratory Manual", Cold Spring Harbor Laboratory, N.Y. (2001)) which is incorporated herein by reference in its entirety.

The following example illustrates the invention:

The Figures Show:

FIG. 1. Insertion of HA-tag sequence into HBV precore ORF.

The ORF of HBV precore protein (genotype D, subtype ayw, nt 1816-2454) is depicted with the 5' portion (nt 1816-1941) shown in nucleotide sequence. The sequence between nt 1941 and the stop codon of precore ORF is omitted. The start codon of precore ORF, direct repeat sequence 1 (DR1), and in-frame start codon of core ORF are boxed. The start codon of 5' end precore ORF is mutated (ATG to TG) in plasmid pTREHBV-HAe. The authentic pgRNA transcription initiation site (nt 1820) is marked with arrow. The HBV nucleotide position is according to Galibert nomenclature (5). A critical stem-loop structure (epsilon, c), which serves as essential cis-element in HBV pgRNA for subsequent DNA replication, is illustrated with predicted internal structures (lower stein, bulge, upper stem, loop). To place an in-frame fused HA-tag sequence into precore ORF without altering the base paring of epsilon, an HA-tag-containing DNA sequence (gtggacatcTACCCATACGACGTTCCAGATTACGCTggc; SEQ ID NO: 41) is inserted into an in-frame upstream position adjacent to the start codon of core ORF (see the insert box). The sequence modification results in an in-frame fusion of HA-tag plus linker sequences into precore protein, and the intact ORF of core protein is maintained at the downstream of epsilon.

FIG. 2. Expression and secretion of HA-tagged HBeAg (A) Intracellular expression of wildtype and HA-tagged precore. HepG2 cells were transfected with plasmid pcHBe or pcHA-HBe, 5 days later, whole cell lysates were subjected to western blot analysis by using anti-HBc (top panel) and anti-HA (middle panel) antibodies. β-actin served as loading control. Wildtype precore and HA-tagged precore (HA-precore) are labeled.

(B) Detection of HA-tagged HBeAg in culture fluid. HepG2 cells were mock transfected or transfected with plasmid pcHBe or pcHA-HBe, supernatant samples were collected at indicated time point and cells were harvested at day 5 post transfection. The supernatant samples were subjected to immunoprecipitation (IP) using anti-HA antibody and the HA-tagged HBeAg (HA-HBeAg) were detected by Western blot with antibody against HA. The light chain (LC) of antibody is indicated. The intracellular expression of HA-precore was revealed by HA Western blot.

Figure 3:
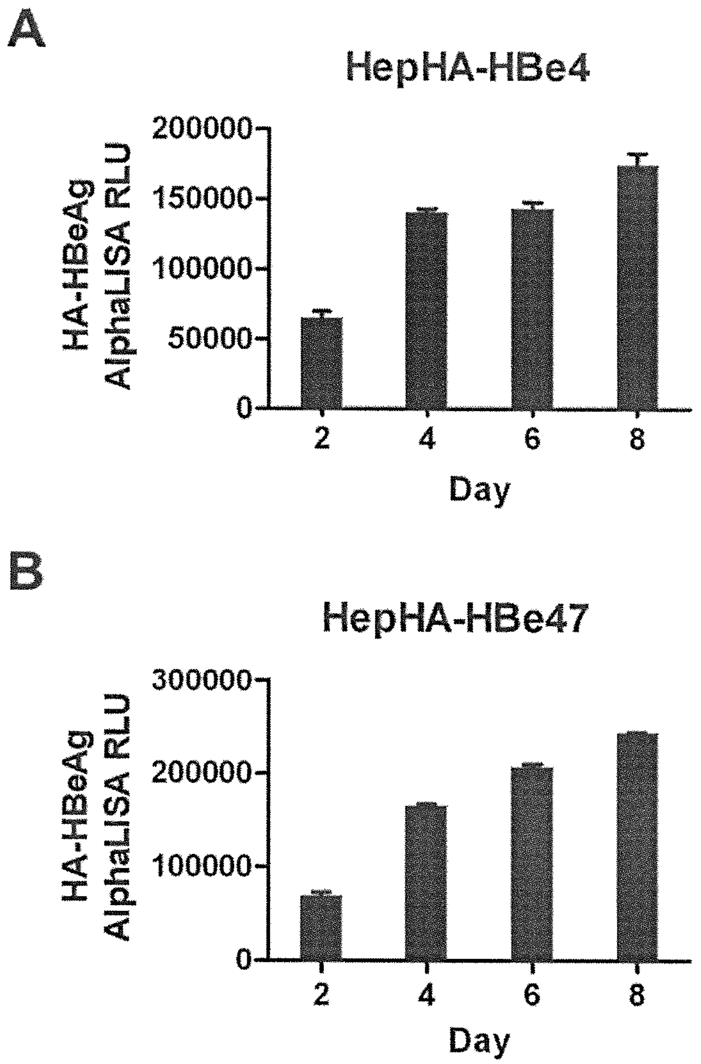

FIG. 3. Secretion of HA-HBeAg in HepHA-HBe cell lines.

The established HA-tagged HBeAg stable expression cell lines, specifically HepHA-HBe4 and HepHA-HBe47 cells, were seeded into collagen-coated 12-well plates at confluent condition. The day when cells were seeded was set as day 0, and media were replenished every other day. The supernatant samples were collected at indicated time point and HA-HBeAg was detected by AlphaLISA analysis as described in Materials and Methods. The AlphaLISA signals (relative light unit) (Y-axis) were plotted in correspondence to the time points (X-axis) in the histogram.

Figure 4:
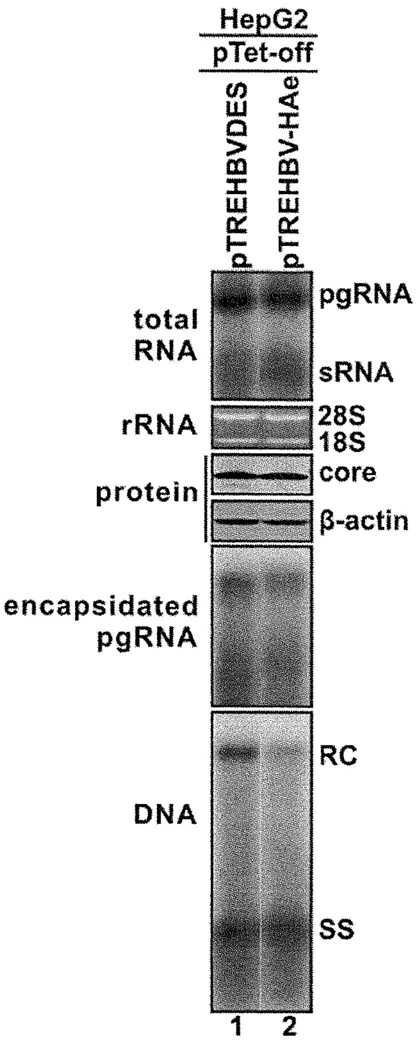

FIG. 4. Replication of HA-recombinant HBV genome in transiently transfected cells.

HepG2 cells were cotransfected with pTREHBVDES or pTREHBV-HAe and plasmid pTet-off. Cells were harvested 5 days post transfection, and plasmid-based production of HBV RNA, core protein, encapsidated pgRNA, and viral DNA replication were analyzed by Northern blot, Western blot, and Southern blot hybridization, respectively. pgRNA: pregenomic RNA; sRNA: surface RNA; RC: relaxed circular DNA; SS: single stranded DNA.

FIG. 5. Schematic illustration of the rational design of HBV cccDNA-dependent HA-tagged HBeAg expression in HepBHAe stable cell line.

In pTREHBV-HAe and pTet-off stably transfected cells, the transgene contains a 1.1 overlength HBV genome under the control of tet-CMV promoter. The start codon (ATG) of precore was mutated at the 5' end of HBV DNA, with the second one unchanged at the 3' redundancy. The HA-tag-containing fragment (shown in gray) was inserted into the precore ORF as described in the Materials and Methods. The transgene also contains two tandem stop codons in the small surface (S) ORF to prevent viral envelope protein expression. (B) Upon the removal of Tet, pgRNA is transcribed and core and polymerase are produced, resulting in pgRNA packaging and (C) reverse transcription of pgRNA to rcDNA. DNA Repair mechanisms convert (D) rcDNA to (E) the circular cccDNA template, in which the HA-precore ORF is restored, giving rise to HA-precore mRNA, and (F) pgRNA for de novo viral replication. (G) HA-precore translation from HA-precore mRNA and process into secreted HA-HBeAg, which can be detected by ELISA. preC, C, pol, L, M, S and X represent ORF start codons for precore, core, polymerase, large, middle and small s antigen, and X protein, respectively. DR represents direct repeat sequences. CTD represents C-terminal domain.

Figure 6:
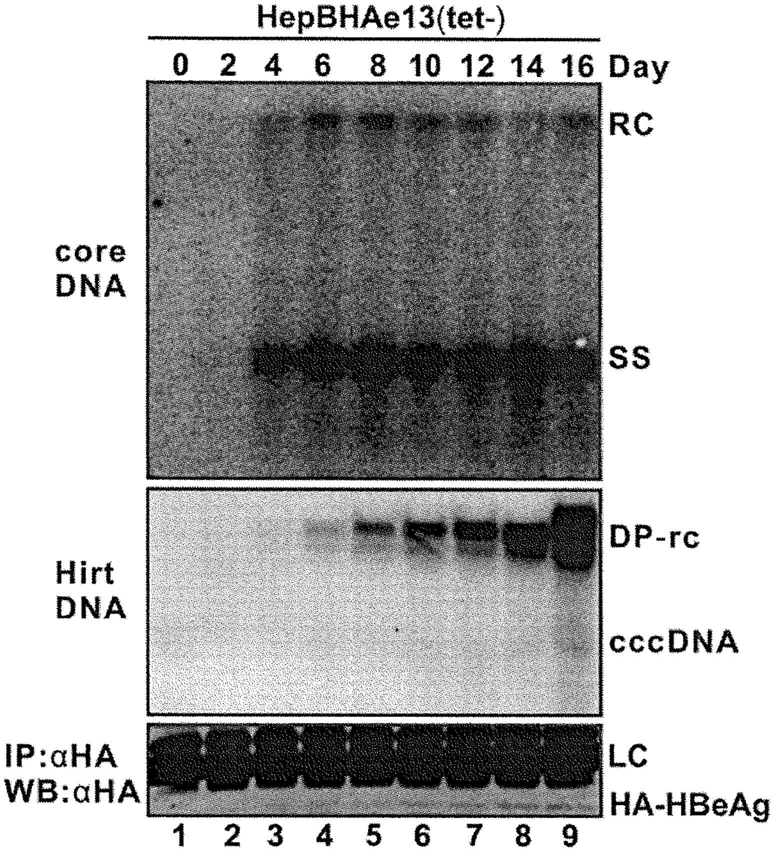

FIG. 6. Kinetics of viral DNA replication, cccDNA accumulation, and HA-tagged HBeAg production in HepBHAe13 cells.

HepBHAe13 cells were seeded in 6-well-plates in the presence of tetracycline. When cell monolayer became confluent, tetracycline was removed from the culture medium and medium was changed every other day. Cells and supernatant samples were harvested at indicated time points. Intracellular core DNA (upper panel) and cccDNA (bottom panel) were extracted and analyzed by Southern blot hybridization. DP-rc represents the deproteinized (protein-free) RC DNA. The secreted HA-tagged HBeAg was detected by HA IP-Western blot as described above.

Figure 7:
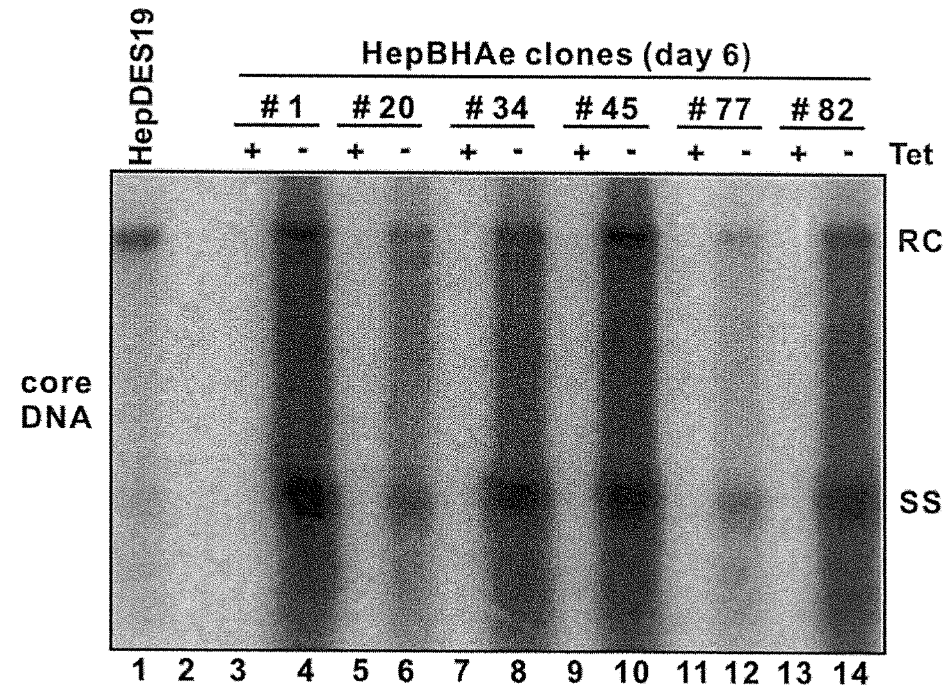

FIG. 7. Additional inducible HepBHAe cell lines that support HA-recombinant HBV DNA replication.

HepDES19 cells and the newly established HepBHAe cells with different clone numbers were seeded in 6-well-plates at the same density in the presence of tetracycline. When cells reached confluent, one set of cells were cultured in the presence of tetracycline, and another set of cells were cultured in the absence of tetracycline. 6 days later, cells were harvested and viral core DNA was analyzed by Southern blot.

Figure 8:
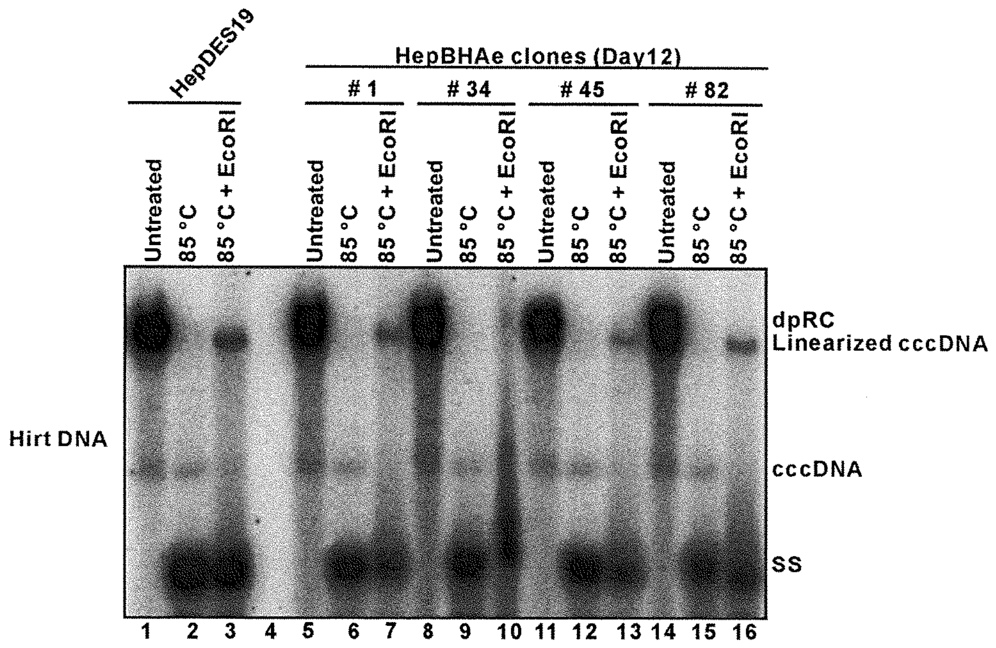

FIG. 8. The authenticity of cccDNA in HepBHAe cell lines.

cccDNA produced in HepDES19 cells and the indicated HepBHAe cells were extracted by Hirt extraction and subjected to gel electrophoresis and Southern blot hybridization (lanes 1, 5, 8, 11, 14). To further validate the authenticity of HBV cccDNA, the Hirt DNA samples were heated to 85° C. for 5 min before gel loading, a condition that denatures DP-rcDNA into SS DNA, while the cccDNA stays undenatured and its electrophoretic mobility remains unchanged (lanes 2, 6, 9, 12, 15). The heat denatured DNA samples were further digested with EcoRI, in which condition the cccDNA is linearized to a genome-length double-stranded DNA (lanes 3, 7, 10, 13, 16).

Figure 9:
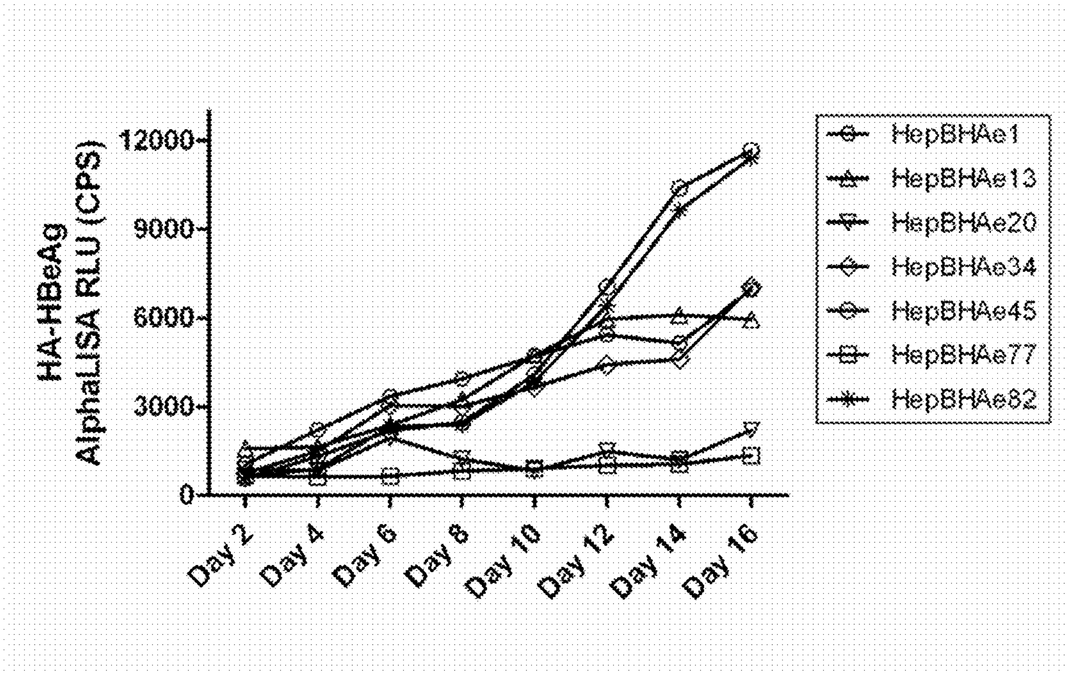

FIG. 9. AlphaLISA detection of HA-HBeAg in HepBHAe cell lines.

HepBHAe cells were seeded in plates in the presence of tetracycline. When cells became confluent, tetracycline was removed from the culture medium and medium was changed every other day. Supernatant samples were harvested at indicated time point and subjected to AlphaLISA for HA-HBeAg detection. The AlphaLISA readouts (relative light unit, RLU) were expressed as counts per second (CPS).

FIG. 10. HBV replication inhibitor (3TC) blocks HA-HBeAg expression in HepBHAe13 cells.

HepBHAe13 cells were cultured in 6-well-plate in the presence of tetracycline until confluent. One set of cells was maintained continually in the presence of tetracycline. The second set of cells was then switched to tetracycline-free medium. The third set of cells was then cultured in tetracycline-free medium containing 10 μM 3TC. The culture medium was replenished every other day, and the harvested supernatant samples at indicated time points were subjected to chemiluminescence immunoassay (CLIA) for HA-tagged HBeAg.

Figure 11:
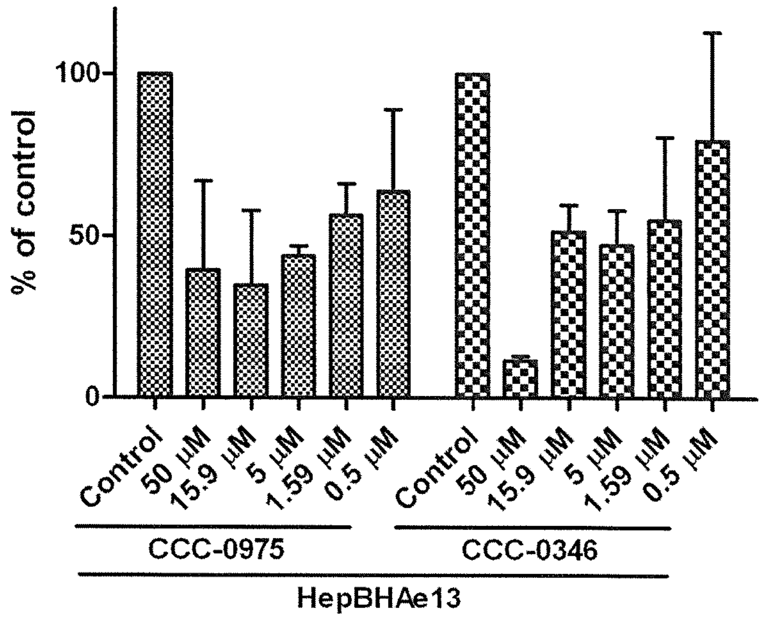

FIG. 11. HBV cccDNA formation inhibitors reduced the HA-HBeAg levels in HepBHAe13 cells. Cells were seeded into 96-well-plate and tetracycline was removed from the medium to induce viral replication when cells became confluent. Simultaneously, cells were left untreated or treated with compounds at indicated concentrations, DMSO concentration was normalized to 0.5% in treated and untreated groups. Treatment was repeated every four days. At day 12 post treatment, culture fluid was subjected to HA-HBeAg CLIA and readout was plotted as percentage (mean±SD) to control.

Figure 12:
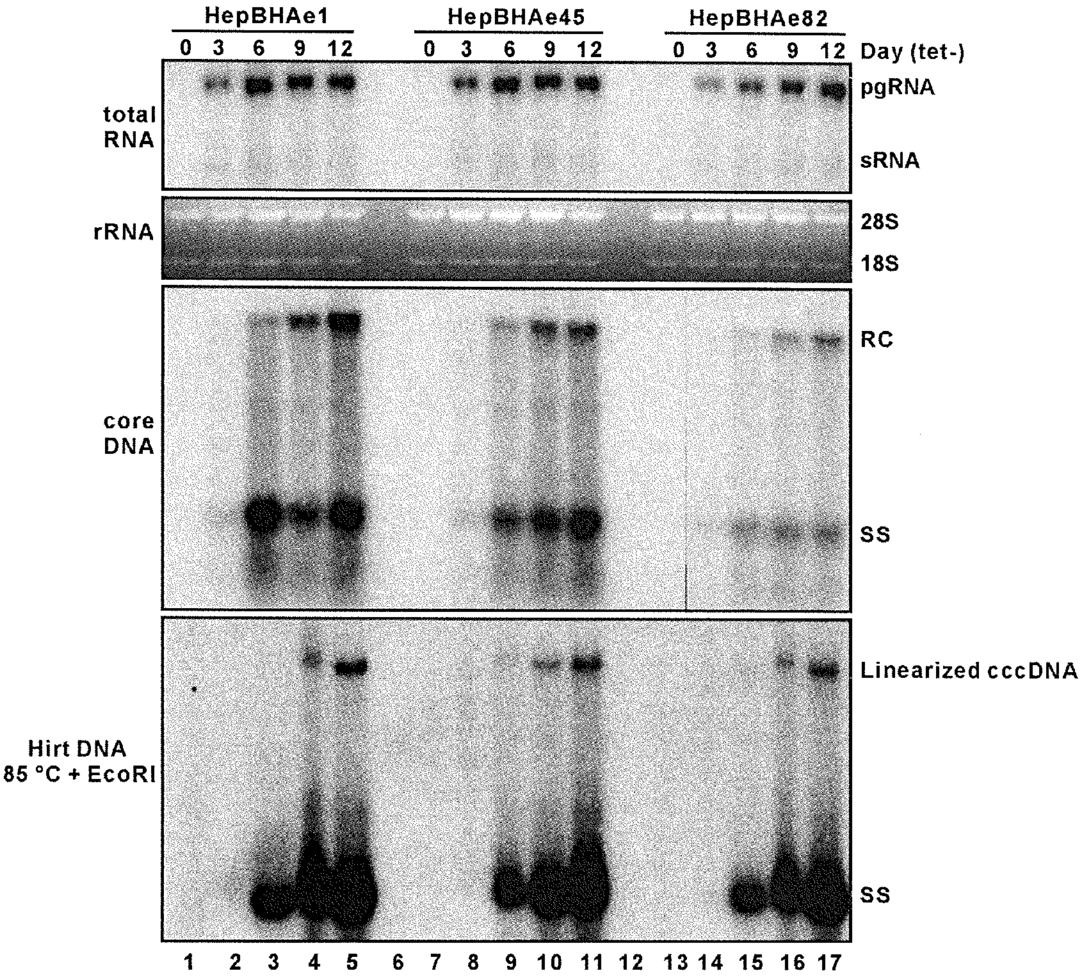

FIG. 12. Kinetics of viral RNA transcription, DNA replication and cccDNA accumulation in additional HepBHAe cell clones.

The indicated HepBHAe cells were seeded in 6-well-plates in the presence of tetracycline. When cell monolayer became confluent, tetracycline was removed from the culture medium and medium was changed every other day. Cells were harvested at indicated time points. Total viral RNA (upper panel), cytoplamic core DNA (middle panel) were extracted and analyzed by Northern and Southern blot hybridization, respectively. The extracted cccDNA was heat denatured at 85° C. for 5 min and then linearized by EcoR I, followed by Southern blot analysis (bottom panel).

Figure 13:
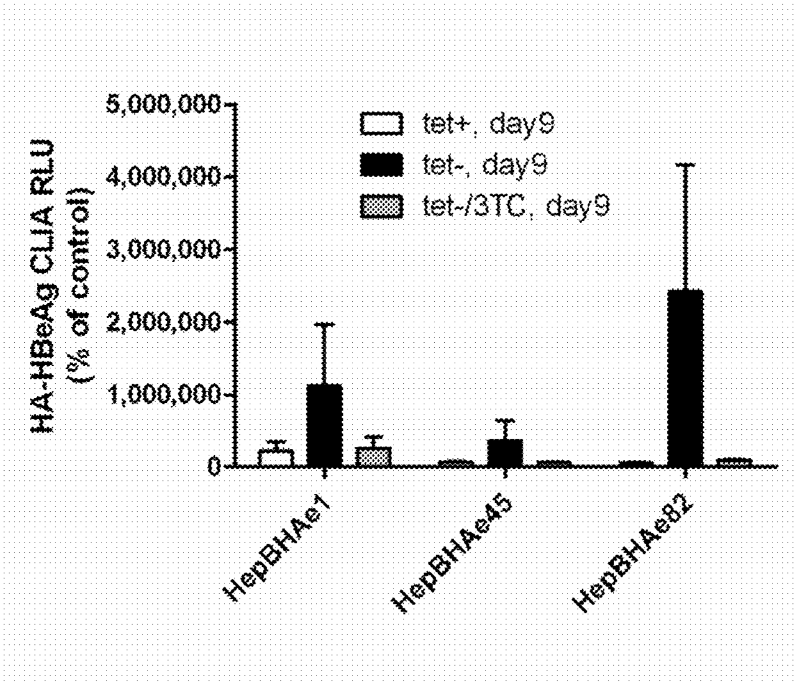

FIG. 13. cccDNA-dependent expression of HA-HBeAg in additional HepBHAe cell clones.

The selected HepBHAe cells were cultured in 96-well-plate in the presence of tetracycline until confluent. One set of cells was maintained continually in the presence of tetracycline. The second set of cells was then switched to tetracycline-free medium. The third set of cells was then cultured in tetracycline-free medium containing 10 μM 3TC. The culture medium was replenished every other day, and the harvested supernatant samples at day 9 post treatment were subjected to chemiluminescence immunoassay (CLIA) for HA-tagged HBeAg detection.

The Example illustrates the invention.

EXAMPLE 1

Cultured Cell Line That Inducibly Expresses Hepatitis B Virus Covalently Closed Circular DNA-Dependent Epitope-Tagged e Antigen, and Uses Thereof for Screening Antiviral Substances Materials and Methods Plasmids In order to construct a tetracycline-inducible HBV replicating vector which contains a Human influenza hemagglutinin (HA) fused precore open reading frame with its start codon knockout, a DNA fragment containing the TATA box motif of CMV-IE promoter and downstream HBV fragment (genotype D, subtype ayw, nt 1805-2335) with a deletion of nt 1816(A) and the insertion of HA-tag sequence in precore ORF was chemically synthesized by Genscript Inc. Within this DNA fragment, a Sad restriction enzyme site is present at the 5' end and an authentic BspEI restriction site exists at the 3' terminus. The vector pTREHBV-HAe was constructed through insertion of the synthesized DNA fragment into the SacI/BspEI restriction sites in plasmid pTREHBVDES. The complete sequence of pTREHBV-HAe is shown in SEQ ID NO. 35.

To generate the HA-fused precore expression vector, a PCR fragment containing HBV nt 1816-2335 with HA sequence insertion was amplified from pTREHBV-HAe by using primers 5'-ATTGGATCCACCATGCAACTTTTTCACCTCTGC-3' and 5'-ACAGTAGTTTCCGGAAGTGTTGATAGGATAGGGG-3'. The PCR fragment was restricted with BamHI and BspEI and inserted into the same restriction sites in precore expression vector (pcHBe) to yield plasmid pcHA-HBe. The complete sequence of pcHA-HBe is shown in SEQ ID NO. 39.

Cell Cultures

HepG2 cell (ATCC® HB-8065™), a hepatoblastoma cell line which supports HBV replication, was obtained from ATCC. HepG2-derived HepDES19 cell line that inducibly expressed HBV DNA and cccDNA has been described previously (7). Cell lines were maintained in Dulbecco's modified Eagle's medium (DMEM)-F12 medium (Cellgro) supplemented with 10% fetal bovine serum, 100 U/ml penicillin, and 100 μg/ml streptomycin.

To establish HepBHAe cell line, HepG2 cells were transfected with plasmid pTet-off (Clontech) that expresses the Tet-responsive transcriptional activator and plasmid pTREHBV-HAe, in which the transcription of modified HBV pgRNA is controlled by a CMV-IE promoter with tetracycline-responsive elements. Transfected HepG2 cells were selected with 500 μg/ml G418 in the presence of 1 μg/ml tetracycline. G418-resistant colonies were picked and expanded into cell lines. HBV replication was induced by culturing cells in tetracycline-free medium, and the levels of viral DNA replicative intemiediates were determined by Southern blot hybridization. The cell line with high levels of HBV replication were chosen and designated as HepBHAe with different clone numbers.

The HA-tagged HBeAg stable expression cell line HepHA-HBe was generated by transfection of HepG2 cells with pcHA-HBe plasmid, colonies were selected with 500 μg/ml G418 and positive colonies were identified by anti-HA western blot analysis.

HepBHAe and HepHA-HBe stable cell lines were cultured in the same way as HepG2, except for the addition of G418 at 500 μg/ml. For HepBHAe cells, tetracycline was routinely added at 1 μg/ml during maintenance to suppress HBV pgRNA transcription.

Cell Transfection

Cells (~$1.0\times10^6$) were seeded in a collagen coated 35-mm-diameter dish in antibiotics-free DMEM/F12 medium. After overnight incubation, each well was transfected with a total of 4 μg plasmids with Lipofectamine 2000 (Life Technologies) by following the manufacturer's directions. Transfected cells or supernatant samples were harvested at the indicated time points.

Viral Nucleic Acid Analysis

Total cellular RNA was extracted with TRIzol reagent (Life Technologies) by following the manufacturer's protocols. Encapsidated viral pgRNA was purified as follows, cells from one 12-well plate well were lysed in 250 μl of lysis buffer containing 10 mM Tris-HCl (pH 8.0), 1 mM EDTA, 1% NP-40, and 50 mM NaCl at 37° C. for 10 min and the nuclei were removed by centrifugation. The sample was incubated with 6 U of micrococcal nuclease and 15 μl of 100 mM $CaCl_2$ and incubated for 15 min at 37° C. to digest free nucleic acids. Encapsidated viral pgRNA was extracted by the addition of 750 μl TRIzol LS reagent (Invitrogen) according to the manufacturer's protocols. RNA samples were electrophoresed through 1.5% agarose gel containing 2.2 M formaldehyde and transferred onto Hybond-XL membrane (GE Healthcare) in 20×SSC buffer (1×SSC is 0.15 M NaCl plus 0.015 M sodium citrate).

Cytoplasmic viral core DNA was extracted as follows, cells from one 35-mm diameter dish were lysed with 0.5 ml of lysis buffer containing 10 mM Tris-HCl, pH 8.0, 10 mM EDTA, 1% NP40 and 2% sucrose at 37° C. for 10 min. Cell debris and nuclei were removed by centrifugation, and supernatant was incubated with 3 μl of 1 M $Mg(OAc)_2$ and 5 μl of 10 mg/ml DNase I (Calbiochem) for 30 min at 37° C. The supernatant was then mixed with 15 μl of 0.5 M EDTA and 130 μl of 35% polyethylene glycol (PEG) 8000 containing 1.5 M NaCl for nucleocapsids precipitation. After incubation on ice for 1 h, viral nucleocapsids were pelleted by centrifugation at 10,000 rpm for 5 min at 4° C., followed by digestion at 37° C. for 1 h in 400 μl of digestion buffer containing 0.5 mg/ml pronase (Calbiochem), 0.5% sodium dodecyl sulfate (SDS), 100 mM NaCl, 25 mM Tris-HCl (pH 7.4), and 10 mM EDTA. The digestion mixture was extracted with phenol, and DNA was precipitated with ethanol and dissolved in TE (10 mM Tris-HCl, pH 8.0, 1 mM EDTA) buffer. One-third of the core DNA sample from each plate was resolved by electrophoresis into a 1.2% agarose gel. The gel was then subjected to depurination in a buffer containing 0.2N HCl, denaturation in a solution containing 0.5 M NaOH and 1.5 M NaCl, and neutralization in a buffer containing 1 M Tris-HCl (pH 7.4) and 1.5 M NaCl. DNA was then blotted onto Hybond-XL membrane in 20×SSC buffer.

Extraction of protein-free viral DNA (cccDNA and protein-free rcDNA) was carried out by using a modified Hirt extraction procedure (4, 8). Briefly, cells from one 35-mm diameter dish were lysed in 3 ml of 10 mM Tris-HCl (pH 7.5), 10 mM EDTA, and 0.7% SDS. After 30-min incubation at room temperature, the lysate was transferred into a 15-ml tube, and this step was followed by the addition of 0.8 ml of 5 M NaCl and incubation at 4° C. overnight. The lysate was then clarified by centrifugation at 10,000 rpm for 30 min at 4° C. and extracted twice with phenol and once with phenol:chloroform:isoamyl alcohol (25:24:1). DNA was precipitated in ethanol at room temperature for overnight and dissolved in TE buffer. One-third of the protein-free DNA sample was then resolved in a 1.2% agarose gel and transferred onto Hybond-XL membrane.

For the detection of HBV RNA and DNA, membranes were probed with a [α-$^{32}$P]UTP (800 Ci/mmol; Perkin Elmer)-labeled plus- or minus-strand-specific full-length HBV riboprobe. Hybridization was carried out in 5 ml of EKONO hybridization buffer (Genotech) with prehybridization at 65° C. for 1 h and overnight hybridization at 65° C., followed by wash in 0.1×SSC and 0.1% SDS at 65° C. for 1 h. The membrane was exposed to a phosphorimager screen, and hybridization signals were detected by Typhoon FLA-7000 system (GE Healthcare).

Western Blot Analysis

Cells in 35 mm dish were washed once with PBS buffer and lysed in 500 μl of 1×Laemmli buffer. A total of 50 μl of the cell lysate was resolved on an SDS-12% polyacrylamide gel and transferred onto polyvinylidene difluoride membrane (Millipore). The membranes were blocked with Western Breeze blocking buffer (Life Technologies) and probed with antibodies against HBcAg (aa170-183), HA-tag (Sigma-Aldrich, clone M2), β-actin (Sigma-Aldrich). Bound antibodies were revealed by IRDye secondary antibodies. The immunoblot signals were visualized and quantified with the Li-COR Odyssey system.

Immunoprecipitation

Cells from one 35-mm diameter dish were lysed with 0.5 ml of lysis buffer containing 10 mM Tris-HCl, pH 8.0, 10 mM EDTA, 1% NP40, 2% sucrose and 1×protease inhibitor cocktails (G-biosciences). After centrifugation to remove the cell debris, the clarified cell lysates were incubated with 50 μl of Ezview Red Anti-HA (Sigma-Aldrich) at 4° C. for overnight with gentle rotation. 0.5 ml of medium sample from one 35-mm diameter dish (1 ml in total) was subjected to immunoprecipitation directly. The beads were washed with TBS buffer (0.15 M NaCl, 0.05 M Tris-HCl [pH 7.4]) for three times at 4° C. The pelleted beads were subjected to protein sample preparation with Laemmli buffer Immunoprecipitated HA-tagged proteins were detected by Western blot using antibodies against HA-tag (Sigma-Aldrich).

ELISA for Detection of HA-Tagged HBeAg

For chemiluminescence enzyme immunoassay (CLIA) detection of HA-tagged HBeAg, high sensitivity streptavidin coated plate (Black, cat #: 15525, Thermo Scientific) was washed by PBST (PBS plus 0.05% Tween 20) for 3 times, and then incubated with 50 μl of anti-HA-biotin (cat #: A00203, Genscript; 5 μg/ml in PBS) at RT for 30 min, followed by wash with 200 μl PBST for 3 times. After removal of the wash buffer, 50 μl of culture supernatant samples was added in the ELISA wells and incubated at RT for 30 min, followed by wash with 200 μl PBST for 3 times. Then 50 μl of horseradish peroxidase (HRP)-conjugated anti-HBe antibodies (from HBeAg CLIA kit, cat #: CL0312-2, Autobio Diagnostics) was added in the well and incubated at RT for 30 min. After wash with 200 μl PBST for 5 times, 25 μl of each substrate A and B from the CLIA kit were added and the plate was gently shaken for 10 sec. The plate was read on a luminometer.

For AlphaLISA detection of HA-tagged HBeAg, anti-HA-biotin (cat #: A00203, Genscript) was diluted to 2 μg/ml in 1×assay buffer (25 mM HEPES, 0.1M NaCl, 0.1% BSA, pH7.4) and dispensed 5 μl into each wells of Proxiplate-384 HS (cat #: 6008279, Perkin Elmer). 5 μl of culture fluid samples was then added in wells and mixed gently, followed by incubation at RT for 30 min. Subsequently, 5 μl of 0.2 μg/ml anti-HBe (clone 29, Lot 20110305, Autobio Diagnostics) was added and gently mixed, followed by incubation at RT for 30 min. Then, the assay solution was mixed with 5 μl of diluted Anti-mouse IgG AlphaLISA acceptor beads (cat #: AL105C, Perkin Elmer) (125 μg/ml) and incubated at RT for 30 min, followed by incubation with 5 μl of AlphaScreen Streptavidin donor beads (cat #: 6760002S, Perkin Elmer) (125 μg/ml) at RT for 1 h. After incubation, the plate was read on Envision 2104 Multilabel reader (Perkin Elmer).

Results

Herein provided are two types of novel cell lines for expressing HA-tagged HBeAg (HA-HBeAg) from transgene and HBV cccDNA, respectively, and methods for detecting the recombinant HBeAg by chemiluminescence immunoassay and AlphaLISA assay. The cell lines and assays are suitable for high throughput screen of compounds that reduce HBV cccDNA level and/or silence cccDNA transcription.

The small compact HBV DNA genome size and the overlapped genomic organization restrict the insertion of reporter genes without affecting viral DNA replication and subsequent cccDNA formation in transfected cells.

Precore/HBeAg can be engineered into cccDNA-dependent manner in HepDE19 cells (3). In the art it is known that HBV genome has a highly compact gene organization which exhibits overlapped ORFs and multiple cis elements. Therefore, it was believed that gene insertion/deletion or sequence replacement would very likely affect viral DNA replication. Previous works have replaced HBV sequence, such as envelope coding region in most cases, by GFP to make recombinant HBV genome, but trans-complement of viral proteins was needed to support viral replication and virion assembly (Protzer, et al, PNAS (1999), 96: 10818-23.). Moreover, those reported recombinant HBV genome can only make first round cccDNA synthesis if used to infect permissive cells, intracellular amplification of cccDNA is blocked due to the defective viral DNA replication.

Despite the above prior art knowledge, it was attempted and reasoned herein that an in-frame fused short exogenous epitope tag in precore open reading frame (ORF) could be tolerated by HBV genome and expressed from cccDNA template, thus a pair of tag-specific antibody and HBeAg antibody would significantly improve the specificity of ELISA detection.

In order to construct a tetracycline-inducible HBV replicating vector with a Human influenza hemagglutinin (HA) fused precore open reading frame, an HA-tag-containing DNA sequence (gtggacatc TACCCATACGACGTTCCAGATTACGCTggc; SED ID NO. 41) was inserted into an in-frame upstream position adjacent to the start codon of core ORF in HBV expression vector pTREHBVDES, in which the HBV pgRNA expression is governed by a tetracycline (tet) regulated CMV-IE promoter in a Tet-off manner. The flanking sequences (in lower case) of HA-tag (in upper case) were designed to maintain the base pairing of the stem loop structure (epsilon, ε) of HBV genome and the Kozak motif of core ORF start codon (FIG. 1). The obtained recombinant plasmid was designated pTREHBV-HAe (SEQ ID NO: 35). Besides the HA-tag insertion, the plasmid pTREHBV-HAe contains a point deletion in the 5' end start codon of precore ORF (ATG to TG), by which prevents the expression of precore from the HBV genome in the plasmid template. In addition, two tandem stop codons were introduced into the coding region of the amino terminus of the small (S) envelope protein (217TTGTTG222 to 217TAGTAG222; mutations are underlined) to block the production of HBV infectious particles.

To test the feasibility of epitope-tagged HBV precore protein expression and HBeAg secretion, the HA-tag-containing DNA sequence was inserted into the same viral DNA position, as described above, in precore expression plasmid pcHBe and the construct was designated pcHA-HBe (SEQ ID NO: 39). Transfection of pcHA-HBe in HepG2 cells led to the intracellular expression of HA-tagged precore protein and extracellular accumulation of HA-tagged HBeAg (FIG. 2), thus confirming that the insertion of HA tag into precore protein does not affect precore expression, post-translational processing, and HBeAg secretion. A chemiluminescence ELISA and an AlphaLISA for detecting HA-tagged HBeAg (HA-HBeAg) has also been established, as described in the Materials and Methods section.

In accordance with the above, a cell line that constitutively expresses HA-tagged HBeAg was established by stably transfecting pcHA-HBe into HepG2 cells. Two clones with the high levels of HA-tagged HBeAg expression were selected through AlphaLISA assay, and were designated HepHA-HBe4 and HepHA-HBe47, respectively (FIG. 3).

The recombinant HBV plasmid pTREHBV-HAe was able to replicate HBV DNA to a comparable level as pTREHBVDES did in the transient transfection assay (FIG. 4), suggesting the HA-tag insertion was tolerated by HBV genome replication. Then, pTREHBV-HAe was stably co-transfected with pTET-off (Clontech) into HepG2 cells to make tetracycline inducible HBV cell line. Theoretically, in such cell line, upon induction, no precore protein and its derivative HBeAg will be produced from transgene due to the silence of precore ORF start codon. The transcribed pgRNA will express viral core protein and polymerase and initiate reverse transcription to generate rcDNA, resulting in cccDNA formation via the intracellular amplification pathway. The start codon of the incomplete precore ORF at the 3' redundancy of pgRNA will be copied into viral DNA sequence, and the intact ORF of HA-tagged procore will be reconstituted during rcDNA conversion into cccDNA. Thus, the HA-precore mRNA can be transcribed only from cccDNA, making secreted HA-tagged HBeAg a surrogate marker for intranuclear cccDNA (FIG. 5).

We have obtained 5 cell lines (HepBHAe1, HepBHAe13, HepBHAe34, HepBHAe45, HepBHAe82) that support high level of HBV DNA replication in a tetracycline-dependent fashion (FIGS. 6 and 7).

In the representative line HepBHAe13 cells, time-dependent kinetics of the synthesis and accumulation of viral products, including the replicative DNA intermediates and cccDNA, were observed upon tetracycline withdrawal. In the culture fluid of HepBHAe13 cells, the HA-tagged HBeAg was also detected by Western blot at day 6 after the removal of tetracycline and the antigen level gradually increased afterward. The level of HA-tagged HBeAg (HA-HBeAg) was proportional to the intracellular level of viral core DNA and cccDNA (FIG. 6). The authenticity of cccDNA produced from HepBHAe cell lines has been confirmed by heat denature and further restriction enzyme digestion (FIG. 8). Thus, inducible cell lines supporting DNA replication and cccDNA formation of the recombinant HBV with HA-tag insertion in precore have been established.

AlphaLISA assay on the supernatant samples from cultured HepBHAe cells demonstrated the increased levels of HA-tagged HBeAg in a 16-day time course study (FIG. 9).

HepHBAe13 cells were selected for further validation. The cells were cultured under three conditions: 1) in the presence of tetracycline to suppress transgene expression; 2) in the absence of tetracycline to induce viral DNA replication; 3) in the absence of tetracycline but with 3TC treatment to block viral DNA replication and subsequent cccDNA formation. Chemiluminescence immunoassay (CLIA) showed that the HA-tagged HBeAg signal in culture medium appeared at day 6 after tetracycline withdrawn and gradually increased afterward, as a consequence of cccDNA establishment and gene expression. As predicted, no HA-HBeAg was detected in the culture fluid at any time points in the presence of tetracycline or under 3TC treatment (tet-) (FIG. 10). Furthermore, two previously identified cccDNA formation inhibitors, specifically CCC-0975 and CCC-0346 (3), exhibited dose-dependent inhibition of HA-HBeAg production from HepBHAe13 cells (FIG. 11). Therefore, the production of HA-tagged HBeAg is cccDNA-dependent in HepBHAe13 cells.

In addition, time course study of other HepBHAe cell lines, including HepBHAe1, HepBHAe45, and HepBHAe82, demonstrated a time-dependent accumulation of HBV mRNA, cytoplasmic core DNA, and nuclear cccDNA upon withdrawal of tetracycline (FIG. 12). As shown in FIG. 13, a cccDNA-dependent HA-tagged HBeAg production was validated in these three additional HepBHAe cell lines.

Taken together, herein novel inducible cell lines have been established that express HBV cccDNA-dependent HA-tagged HBeAg, which can serve as a surrogate marker for HBV cccDNA in antiviral compound screen with the HA-HBeAg detection methods described herein.

The present invention refers to the following nucleotide and amino acid sequences:

The sequences provided herein are available in the NCBI database and can be retrieved from world wide web at ncbi.nlm.nih.gov/sites/entrez?db=gene; Theses sequences also relate to annotated and modified sequences. The present invention also provides techniques and methods wherein homologous sequences, and variants of the concise sequences provided herein are used. Preferably, such "variants" are genetic variants.

SEQ ID No. 1:

Nucleotide sequence encoding a hemagglutinin (HA) tag

TACCCATACGACGTTCCAGATTACGCT

SEQ ID No. 2:

Nucleotide sequence encoding a His-tag

CATCATCATCATCATCAC

SEQ ID No. 3:

Nucleotide sequence encoding a Flag-tag

GACTACAAGGACGACGACGACAAG

SEQ ID No. 4:
Nucleotide sequence encoding c-myc-tag

ATG GCA TCA ATG CAG AAG CTG ATC TCA GAG GAG GAC
CTG

SEQ ID No. 5:
Nucleotide sequence encoding V5-tag

GGT AAG CCT ATC CCT AAC CCT CTC CTC GGT CTC GAT
TCT ACG

SEQ ID No. 6:
Nucleotide sequence encoding a C9-tag

ACTGAAACATCTCAAGTAGCTCCAGCT

SEQ ID No. 7:
Nucleotide sequence encoding a 3×Flag-tag

GACTACAAAGACCACGACGGTGACTACAAAGACCACGACATCGACTACAA
GGACGACGACGACAAG

SEQ ID No. 8:
Amino acid sequence of a HA tag

YPYDVPDYA

SEQ ID No. 9:
Amino acid sequence of a His-tag

HHHHHH

SEQ ID No. 10:
Amino acid sequence of a Flag-tag

DYKDDDDK

SEQ ID No. 11:
Amino acid sequence of a c-myc-tag

EQKLISEEDL

SEQ ID No. 12:
Amino acid sequence of a V5-tag

GKPIPNPLLGLDST

SEQ ID No. 13:
Amino acid sequence of a C9-tag

TETSQVAPA

SEQ ID No. 14:
Amino acid sequence of a 3×Flag-tag

DYKDHDGDYKDHDIDYKDDDDK

SEQ ID No. 15:

Nucleotide sequence encoding a hepatitis B virus precore protein

Precore ORF sequence:

ATGCAACTTTTTCACCTCTGCCTAATCATCTCTTGTTCATGTCCTACTGT

TCAAGCCTCCAAGCTGTGCCTTGGGTGGCTTTGGGGCATGGACATCGACC

CTTATAAAGAATTTGGAGCTACTGTGGAGTTACTCTCGTTTTTGCCTTCT

GACTTCTTTCCTTCAGTACGAGATCTTCTAGATACCGCCTCAGCTCTGTA

TCGGGAAGCCTTAGAGTCTCCTGAGCATTGTTCACCTCACCATACTGCAC

TCAGGCAAGCAATTCTTTGCTGGGGGGAACTAATGACTCTAGCTACCTGG

GTGGGTGTTAATTTGGAAGATCCAGCATCTAGAGACCTAGTAGTCAGTTA

TGTCAACACTAATATGGGCCTAAAGTTCAGGCAACTCTTGTGGTTTCACA

TTTCTTGTCTCACTTTTGGAAGAGAAACCGTTATAGAGTATTTGGTGTCT

TTCGGAGTGTGGATTCGCACTCCTCCAGCTTATAGACCACCAAATGCCCC

TATCCTATCAACACTTCCGGAAACTACTGTTGTTAGACGACGAGGCAGGT

CCCCTAGAAGAAGAACTCCCTCGCCTCGCAGACGAAGGTCTCAATCGCCG

CGTCGCAGAAGATCTCAATCTCGGGAACCTCAATGTTAG

SEQ ID No. 16:

Nucleotide sequence encoding a hepatitis B virus e antigen (HBeAg)

HBeAg DNA sequence:

TCCAAGCTGTGCCTTGGGTGGCTTTGGGGCATGGACATCGACCCTTATAA

AGAATTTGGAGCTACTGTGGAGTTACTCTCGTTTTTGCCTTCTGACTTCT

TTCCTTCAGTACGAGATCTTCTAGATACCGCCTCAGCTCTGTATCGGGAA

GCCTTAGAGTCTCCTGAGCATTGTTCACCTCACCATACTGCACTCAGGCA

AGCAATTCTTTGCTGGGGGGAACTAATGACTCTAGCTACCTGGGTGGGTG

TTAATTTGGAAGATCCAGCATCTAGAGACCTAGTAGTCAGTTATGTCAAC

ACTAATATGGGCCTAAAGTTCAGGCAACTCTTGTGGTTTCACATTTCTTG

TCTCACTTTTGGAAGAGAAACCGTTATAGAGTATTTGGTGTCTTTCGGAG

TGTGGATTCGCACTCCTCCAGCTTATAGACCACCAAATGCCCCTATCCTA

TCAACACTTCCGGAAACTACTGTTGTT

SEQ ID No. 17:

Amino acid sequence of a hepatitis B virus precore protein precore amino acid sequence:

MQLFHLCLIISCSCPTVQASKLCLGWLWGMDIDPYKEFGATVELLSFLPS

DFFPSVRDLLDTASALYREALESPEHCSPHHTALRQAILCWGELMTLATW

VGVNLEDPASRDLVVSYVNTNMGLKFRQLLWFHISCLTFGRETVIEYLVS

FGVWIRTPPAYRPPNAPILSTLPETTVVRRRGRSPRRRTPSPRRRRSQSP

RRRRSQSREPQC

SEQ ID No. 18:

Amino acid sequence of a hepatitis B virus e antigen (HBeAg)

HBeAg amino acid sequence (removes N-terminal signal peptide (19 aa) and C-terminal arginine-rich domain (34 aa) from precore):

SKLCLGWLWGMDIDPYKEFGATVELLSFLPSDFFPSVRDLLDTASALYRE

ALESPEHCSPHHTALRQAILCWGELMTLATWVGVNLEDPASRDLVVSYVN

TNMGLKFRQLLWFHISCLTFGRETVIEYLVSFGVWIRTPPAYRPPNAPIL

STLPETTVV

SEQ ID No. 19:

Nucleotide sequence encoding a HA-tagged hepatitis B virus precore protein.

HA-tagged precore DNA sequence:

ATGCAACTTTTTCACCTCTGCCTAATCATCTCTTGTTCATGTCCTACTGT

TCAAGCCTCCAAGCTGTGCCTTGGGTGGCTTTGGGGCGTGGACATCTACC

CATACGACGTTCCAGATTACGCTGGCATGGACATCGACCCTTATAAAGAA

TTTGGAGCTACTGTGGAGTTACTCTCGTTTTTGCCTTCTGACTTCTTTCC

TTCAGTACGAGATCTTCTAGATACCGCCTCAGCTCTGTATCGGGAAGCCT

TAGAGTCTCCTGAGCATTGTTCACCTCACCATACTGCACTCAGGCAAGCA

ATTCTTTGCTGGGGGGAACTAATGACTCTAGCTACCTGGGTGGGTGTTAA

TTTGGAAGATCCAGCATCTAGAGACCTAGTAGTCAGTTATGTCAACACTA

ATATGGGCCTAAAGTTCAGGCAACTCTTGTGGTTTCACATTTCTTGTCTC

ACTTTTGGAAGAGAAACCGTTATAGAGTATTTGGTGTCTTTCGGAGTGTG

GATTCGCACTCCTCCAGCTTATAGACCACCAAATGCCCCTATCCTATCAA

CACTTCCGGAAACTACTGTTGTTAGACGACGAGGCAGGTCCCCTAGAAGA

AGAACTCCCTCGCCTCGCAGACGAAGGTCTCAATCGCCGCGTCGCAGAAG

ATCTCAATCTCGGGAACCTCAATGTTAG

SEQ ID No. 20:

Nucleotide sequence encoding a HA-tagged hepatitis B virus e antigen (HBeAg)

HA-tagged HBeAg DNA sequence:

TCCAAGCTGTGCCTTGGGTGGCTTTGGGGCGTGGACATCTACCCATACGA

CGTTCCAGATTACGCTGGCATGGACATCGACCCTTATAAAGAATTTGGAG

CTACTGTGGAGTTACTCTCGTTTTTGCCTTCTGACTTCTTTCCTTCAGTA

CGAGATCTTCTAGATACCGCCTCAGCTCTGTATCGGGAAGCCTTAGAGTC

TCCTGAGCATTGTTCACCTCACCATACTGCACTCAGGCAAGCAATTCTTT

GCTGGGGGGAACTAATGACTCTAGCTACCTGGGTGGGTGTTAATTTGGAA

GATCCAGCATCTAGAGACCTAGTAGTCAGTTATGTCAACACTAATATGGG

CCTAAAGTTCAGGCAACTCTTGTGGTTTCACATTTCTTGTCTCACTTTTG

GAAGAGAAACCGTTATAGAGTATTTGGTGTCTTTCGGAGTGTGGATTCGC

ACTCCTCCAGCTTATAGACCACCAAATGCCCCTATCCTATCAACACTTCC

GGAAACTACTGTTGTT

SEQ ID No. 21:

Amino acid sequence of a HA-tagged hepatitis B virus precore protein. The HA-tag is underlined.

HA-tagged precore amino acid sequence:

MQLFHLCLIISCSCPTVQASKLCLGWLWGVDIYPYDVPDYAGMDIDPYKE
FGATVELLSFLPSDFFPSVRDLLDTASALYREALESPEHCSPHHTALRQA
ILCWGELMTLATWVGVNLEDPASRDLVVSYVNTNMGLKFRQLLWFHISCL
TFGRETVIEYLVSFGVWIRTPPAYRPPNAPILSTLPETTVVRRRGRSPRR
RTPSPRRRRSQSPRRRRSQSREPQC

SEQ ID No. 22:

Amino acid sequence of HA-tagged hepatitis B virus e antigen (HBeAg). The HA-tag is underlined.

HA-tagged HBeAg amino acid sequence:

SKLCLGWLWGVDIYPYDVPDYAGMDIDPYKEFGATVELLSFLPSDFFPSV
RDLLDTASALYREALESPEHCSPHHTALRQAILCWGELMTLATWVGVNLE
DPASRDLVVSYVNTNMGLKFRQLLWFHISCLTFGRETVIEYLVSFGVWIR
TPPAYRPPNAPILSTLPETTVV

SEQ ID No. 23:

Nucleotide sequence encoding a HBV core protein

ATGGACATCGACCCTTATAAAGAATTTGGAGCTACTGTGGAGTTACTCTC
GTTTTTGCCTTCTGACTTCTTTCCTTCAGTACGAGATCTTCTAGATACCG
CCTCAGCTCTGTATCGGGAAGCCTTAGAGTCTCCTGAGCATTGTTCACCT
CACCATACTGCACTCAGGCAAGCAATTCTTTGCTGGGGGGAACTAATGAC
TCTAGCTACCTGGGTGGGTGTTAATTTGGAAGATCCAGCATCTAGAGACC
TAGTAGTCAGTTATGTCAACACTAATATGGGCCTAAAGTTCAGGCAACTC
TTGTGGTTTCACATTTCTTGTCTCACTTTTGGAAGAGAAACCGTTATAGA
GTATTTGGTGTCTTTCGGAGTGTGGATTCGCACTCCTCCAGCTTATAGAC
CACCAAATGCCCCTATCCTATCAACACTTCCGGAAACTACTGTTGTTAGA
CGACGAGGCAGGTCCCCTAGAAGAAGAACTCCCTCGCCTCGCAGACGAAG
GTCTCAATCGCCGCGTCGCAGAAGATCTCAATCTCGGGAACCTCAATGTT
AG

SEQ ID No. 24:

Amino acid sequence of a HBV core protein

MDIDPYKEFGATVELLSFLPSDFFPSVRDLLDTASALYREALESPEHCSP
HHTALRQAILCWGELMTLATWVGVNLEDPASRDLVVSYVNTNMGLKFRQL
LWFHISCLTFGRETVIEYLVSFGVWIRTPPAYRPPNAPILSTLPETTVVR
RRGRSPRRRTPSPRRRRSQSPRRRRSQSREPQC

SEQ ID No. 25:

Nucleotide sequence of an epsilon structure as encoded by an HBV genome

TGTTCATGTCCTACTGTTCAAGCCTCCAAGCTGTGCCTTGGGTGGCTTTG
GGGCATGGACA

SEQ ID No. 26:

Nucleotide sequence capable of forming base pairs with the lower stem of the epsilon structure of a hepadnavirus genome

GTGGACATC

SEQ ID No. 27:

Nucleotide sequence of HBV genome, HBV genotype D, subtype ayw. Genbank accession #U95551(C1902 and A1903 are in bold. The ORF of precore is underlined.)

AATTCCACAACCTTTCACCAAACTCTGCAAGATCCCAGAGTGAGAGGCCT
GTATTTCCCTGCTGGTGGCTCCAGTTCAGGAGCAGTAAACCCTGTTCCGA
CTACTGCCTCTCCCTTATCGTCAATCTTCTCGAGGATTGGGGACCCTGCG
CTGAACATGGAGAACATCACATCAGGATTCCTAGGACCCCTTCTCGTGTT
ACAGGCGGGGTTTTTCTTGTTGACAAGAATCCTCACAATACCGCAAAGTC
TAGACTCGTGGTGGACTTCTCTCAATTTTCTAGGGGGAACTACCGTGTGT
CTTGGCCAAAATTCGCAGTCCCCAACCTCCAATCACTCACCAACCTCCTG
TCCTCCAACTTGTCCTGGTTATCGCTGGATGTGTCTGCGGCGTTTTATCA
TCTTCCTCTTCATCCTGCTGCTATGCCTCATCTTCTTGTTGGTTCTTCTG
GACTATCAAGGTATGTTGCCCGTTTGTCCTCTAATTCCAGGATCCTCAAC
CACCAGCACGGGACCATGCCGAACCTGCATGACTACTGCTCAAGGAACCT
CTATGTATCCCTCCTGTTGCTGTACCAAACCTTCGGACGGAAATTGCACC
TGTATTCCCATCCCATCATCCTGGGCTTTCGGAAAATTCCTATGGGAGTG
GGCCTCAGCCCGTTTCTCCTGGCTCAGTTTACTAGTGCCATTTGTTCAGT
GGTTCGTAGGGCTTTCCCCCACTGTTTGGCTTTCAGTTATATGGATGATG
TGGTATTGGGGGCCAAGTCTGTACAGCATCTTGAGTCCCTTTTTACCGCT
GTTACCAATTTTCTTTTGTCTTTGGGTATACATTTAAACCCTAACAAAAC
AAAGAGATGGGGTTACTCTCTGAATTTTATGGGTTATGTCATTGGAAGTT
ATGGGTCCTTGCCACAAGAACACATCATACAAAAAATCAAAGAATGTTTT
AGAAAACTTCCTATTAACAGGCCTATTGATTGGAAAGTATGTCAACGAAT
TGTGGGTCTTTTGGGTTTTGCTGCCCCATTTACACAATGTGGTTATCCTG
CGTTAATGCCCTTGTATGCATGTATTCAATCTAAGCAGGCTTTCACTTTC
TCGCCAACTTACAAGGCCTTTCTGTGTAAACAATACCTGAACCTTTACCC
CGTTGCCCGGCAACGGCCAGGTCTGTGCCAAGTGTTTGCTGACGCAACCC
CCACTGGCTGGGGCTTGGTCATGGGCCATCAGCGCGTGCGTGGAACCTTT
TCGGCTCCTCTGCCGATCCATACTGCGGAACTCCTAGCCGCTTGTTTTGC
TCGCAGCAGGTCTGGAGCAAACATTATCGGGACTGATAACTCTGTTGTCC
TCTCCCGCAAATATACATCGTATCCATGGCTGCTAGGCTGTGCTGCCAAC

-continued

TGGATCCTGCGCGGGACGTCCTTTGTTTACGTCCCGTCGGCGCTGAATCC

TGCGGACGACCCTTCTCGGGGTCGCTTGGGACTCTCTCGTCCCCTTCTCC

GTCTGCCGTTCCGACCGACCACGGGGCGCACCTCTCTTTACGCGGACTCC

CCGTCTGTGCCTTCTCATCTGCCGGACCGTGTGCACTTCGCTTCACCTCT

GCACGTCGCATGGAGACCACCGTGAACGCCCACCGAATGTTGCCCAAGGT

CTTACATAAGAGGACTCTTGGACTCTCTGCAATGTCAACGACCGACCTTG

AGGCATACTTCAAAGACTGTTTGTTTAAAGACTGGGAGGAGTTGGGGGAG

GAGATTAGATTAAAGGTCTTTGTACTAGGAGGCTGTAGGCATAAATTGGT

CTGCGCACCAGCACCATGCAACTTTTTCACCTCTGCCTAATCATCTCTTG

TTCATGTCCTACTGTTCAAGCCTCCAAGCTGTGCCTTGGGTGGCTTTGGG

GCATGGACATCGACCCTTATAAAGAATTTGGAGCTACTGTGGAGTTACTC

TCGTTTTTGCCTTCTGACTTCTTTCCTTCAGTACGAGATCTTCTAGATAC

CGCCTCAGCTCTGTATCGGGAAGCCTTAGAGTCTCCTGAGCATTGTTCAC

CTCACCATACTGCACTCAGGCAAGCAATTCTTTGCTGGGGGGAACTAATG

ACTCTAGCTACCTGGGTGGGTGTTAATTTGGAAGATCCAGCATCTAGAGA

CCTAGTAGTCAGTTATGTCAACACTAATATGGGCCTAAAGTTCAGGCAAC

TCTTGTGGTTTCACATTTCTTGTCTCACTTTTGGAAGAGAAACCGTTATA

GAGTATTTGGTGTCTTTCGGAGTGTGGATTCGCACTCCTCCAGCTTATAG

ACCACCAAATGCCCCTATCCTATCAACACTTCCGGAAACTACTGTTGTTA

GACGACGAGGCAGGTCCCCTAGAAGAAGAACTCCCTCGCCTCGCAGACGA

AGGTCTCAATCGCCGCGTCGCAGAAGATCTCAATCTCGGGAACCTCAATG

TTAGTATTCCTTGGACTCATAAGGTGGGGAACTTTACTGGTCTTTATTCT

TCTACTGTACCTGTCTTTAATCCTCATTGGAAAACACCATCTTTTCCTAA

TATACATTTACACCAAGACATTATCAAAAAATGTGAACAGTTTGTAGGCC

CACTTACAGTTAATGAGAAAAGAAGATTGCAATTGATTATGCCTGCTAGG

TTTTATCCAAAGGTTACCAAATATTTACCATTGGATAAGGGTATTAAACC

TTATTATCCAGAACATCTAGTTAATCATTACTTCCAAACTAGACACTATT

TACACACTCTATGGAAGGCGGGTATATTATATAAGAGAGAAACAACACAT

AGCGCCTCATTTTGTGGGTCACCATATTCTTGGGAACAAGATCTACAGCA

TGGGGCAGAATCTTTCCACCAGCAATCCTCTGGGATTCTTTCCCGACCAC

CAGTTGGATCCAGCCTTCAGAGCAAACACAGCAAATCCAGATTGGGACTT

CAATCCCAACAAGGACACCTGGCCAGACGCCAACAAGGTAGGAGCTGGAG

CATTCGGGCTGGGTTTCACCCCACCGCACGGAGGCCTTTTGGGGTGGAGC

CCTCAGGCTCAGGGCATACTACAAACTTTGCCAGCAAATCCGCCTCCTGC

CTCCACCAATCGCCAGACAGGAAGGCAGCCTACCCCGCTGTCTCCACCTT

TGAGAAACACTCATCCTCAGGCCATGCAGTGG

SEQ ID No. 28:

Nucleotide sequence of HBV genome, HBV genotype A (Genbank accession #AP007263)

AATTCCACTGCCTTCCACCAAGCTCTGCAGGATCCCAGAGTCAGGGGTCT

GTATTTTCCTGCTGGTGGCTCCAGTTCAGGAACAGTAAACCCTGCTCCGA

ATATTGCCTCTCACATCTCGTCAATCTCCGCGAGGACTGGGGACCCTGTG

GCGAACATGGAGAACATCACATCAGGATTCCTAGGACCCCTGCTCGTGTT

ACAGGCGGGGTTTTTCTTGTTGACAAGAATCCTCACAATACCGCAGAGTC

TAGACTCGTGGTGGACTTCTCTCAATTTTCTAGGGGGATCACCCGTGTGT

CTTGGCCAAAATTCGCAGTCCCCAACCTCCAATCACTCACCAACCTCCTG

TCCTCCAATTTGTCCTGGTTATCGCTGGATGTGTCTGCGGCGTTTTATCA

TATTCCTCTTCATCCTGCTGCTATGCCTCATCTTCTTATTGGTTCTTCTG

GATTATCAAGGTATGTTGCCCGTTTGTCCTCTAATTCCAGGATCAACAAC

AACCAGTACGGGACCATGCAAAACCTGCACGACTCCTGCTCAAGGCAACT

CTATGTTTCCCTCATGTTGCTGTACAAAACCTACGGATGGAAATTGCACC

TGTATTCCCATCCCATCGTCCTGGGCTTTCGCAAAATACCTATGGGAGTG

GGCCTCAGTCCGTTTCTCTTGGCTCAGTTTACTAGTGCCATTTGTTCAGT

GGTTCGTAGGGCTTTCCCCCACTGTTTGGCTTTCAGCTATATGGATGATG

TGGTATTGGGGGCCAAGTCTGTACAGCATCGTGAGTCCCTTTATACCGCT

GTTACCAATTTTCTTTTGTCTCTGGGTATACATTTAAACCCTAACAAAAC

AAAAAGATGGGGTTATTCCCTAAACTTCATGGGTTACATAATTGGAAGTT

GGGGAACTTTGCCACAGGATCATATTGTACAAAAGATCAAACACTGTTTT

AGAAAACTTCCTGTTAACAGGCCTATTGATTGGAAAGTATGTCAAAGAAT

TGTGGGTCTTTTGGGCTTTGCTGCTCCATTTACACAATGTGGATATCCTG

CCTTAATGCCTTTGTATGCATGTATACAAGCTAAACAGGCTTTCACTTTC

TCGCCAACTTACAAGGCCTTTCTAAGTAAACAGTACATGAACCTTTACCC

CGTTGCTCGGCAACGGCCTGGTCTGTGCCAAGTGTTTGCTGACGCAACCC

CCACTGGCTGGGGCTTGGCCATAGGCCATCAGCGCATGCGTGGAACCTTT

GTGGCTCCTCTGCCGATCCATACTGCGGAACTCCTAGCCGCTTGTTTTGC

TCGCAGCCGGTCTGGAGCAAAGCTCATCGGAACTGACAATTCTGTCGTCC

TCTCGCGGAAATATACATCGTTTCCATGGCTGCTAGGCTGTGCTGCCAAC

TGGATCCTTCGCGGAACGTCCTTTGTCTACGTCCCGTCGGCGCTGAATCC

CGCGGACGACCCCTCTCGGGGCCGCTTGGGACTCTCTCGTCCCCTTCTCC

GTCTGCCGTTCCAGCCGACCACGGGGCGCACCTCTCTTTACGCGGTCTCC

CCGTCTGTGCCTTCTCATCTGCCGGTCCGTGTGCACTTCGCTTCACCTCT

GCACGTTGCATGGAGACCACCGTGAACGCCCATCAGATCCTGCCCAAGGT

CTTACATAAGAGGACTCTTGGACTCCCAGCAATGTCAACGACCGACCTTG

AGGCCTACTTCAAAGACTGTGTGTTTAAGGACTGGGAGGAGCTGGGGGAG

GAGATTAGGTTAAAGGTCTTTGTATTAGGAGGCTGTAGGCATAAATTGGT

CTGCGCACCAGCACCATGCAACTTTTTCACCTCTGCCTAATCATCTCTTG

TACATGTCCCACTGTTCAAGCCTCCAAGCTGTGCCTTGGGTGGCTTTGGG

GCATGGACATTGACCCTTATAAAGAATTTGGAGCTACTGTGGAGTTACTC

TCGTTTTTGCCTTCTGACTTCTTTCCTTCCGTCAGAGATCTCCTAGACAC

CGCCTCAGCTCTGTATCGAGAAGCCTTAGAGTCTCCTGAGCATTGCTCAC

CTCACCATACTGCACTCAGGCAAGCCATTCTCTGCTGGGGGGAATTGATG

ACTCTAGCTACCTGGGTGGGTAATAATTTGGAAGATCCAGCATCCAGGGA

TCTAGTAGTCAATTATGTTAATACTAACATGGGTTTAAAGATCAGGCAAC

TATTGTGGTTTCATATATCTTGCCTTACTTTTGGAAGAGAGACTGTACTT

GAATATTTGGTCTCTTTCGGAGTGTGGATTCGCACTCCTCCAGCCTATAG

ACCACCAAATGCCCCTATCTTATCAACAATTCCGGAAACTACTGTTGTTA

GACGACGGGACCGAGGCAGGTCCCCTAGAAGAAGAACTCCCTCGCCTCGC

AGACGCAGATCTCAATCGCCGCGTCGCAGAAGATCTCAATCTCGGGAATC

TCAATGTTAGTATTCCTTGGACTCATAAGGTGGGAAACTTTACGGGGCTT

TATTCCTCTACAGTACCTATCTTTAATCCTGAATGGCAAACTCCTTCCTT

TCCTAAGATTCATTTACAAGAGGACATTATTAATAGGTGTCAACAATTTG

TGGGCCCTCTCACTGTAAATGAAAAGAGAAGATTGAAATTAATTATGCCT

GCTAGATTCTATCCTACCCACACTAAATATTTGCCCTTAGACAAAGGAAT

TAAACCTTATTATCCAGATCAGGTAGTTAATCATTACTTCCAAACCAGAC

ATTATTTACATACTCTTTGGAAGGCTGGTATTCTATATAAGAGGGAAACC

ACACGTAGCGCATCATTTTGCGGGTCACCATATTCTTGGGAACAAGAGCT

ACAGCATGGGAGGTTGGTCATCAAAACCTCGCAAAGGCATGGGGACGAAT

CTTTCTGTTCCCAACCCTCTGGGATTCTTTCCCGATCATCAGTTGGACCC

TGCATTCGGAGCCAACTCAAACAATCCAGATTGGGACTTCAACCCCATCA

AGGACCACTGGCCAACAGCCAACCAGGTAGGAGTGGGAGCATTCGGGCCA

GGGCTCACCCCTCCACACGGCGGTATTTTGGGGGGGAGCCCTCAGGCTCA

GGGCATATTGACCACAGTGTCAACAATTCCTCCTCCTGCCTCCACCAATC

GGCAGTCAGGAAGGCAGCCTACTCCCATCTCTCCACCTCTAAGAGACAGT

CATCCTCAGGCCATGCAGTGG

SEQ ID No. 29:

Nucleotide sequence of HBV genome, HBV genotype B (Genbank accession #AB602818)

AACTCCACCACTTTTCACCAAACTCTTCAAGATCCCAGAGTCCGGGCTCT

GTACTTTCCTGCTGGTGGCTCCAGTTCAGGAACAGTAAGCCCTGCTCAGA

ATACTGTCTCTGCCATATCGTCAATCTTATCGAAGACTGGGGACCCTGTG

CCGAACATGGAGAACATCGCATCAGGACTCCTAGGACCCCTGCTCGTGTT

ACAGGCGGGGTTTTTCTTGTTGACAAAAATCCTCACAATACCACAGAGTC

TAGACTCGTGGTGGACTTCTCTCAATTTTCTAGGGGGAACACCCGTGTGT

CTTGGCCAAAATTCGCAGTCCCAAATCTCCAGTCACTCACCAACCTGTTG

TCCTCCAATTTGTCCTGGTTATCGCTGGATGTGTCTGCGGCGTTTTATCA

TCTTCCTCTGCATCCTGCTGCTATGCCTCATCTTCTTGTTGGTTCTTCTG

GACTATCAAGGTATGTTGCCCGTTTGTCCTCTAATTCCAGGATCATCAAC

CACCAGCACGGGACCATGCAAGACCTGCACAACTCCTGCTCAAGGAACCT

CTATGTTTCCCTCATGTTGCTGTACAAAACCTACGGATGGAAACTGCACC

TGTATTCCCATCCCATCATCTTGGGCTTTCGCAAAATACCTATGGGAGTG

GGCCTCAGTCCGTTTCTCTTGGCTCAGTTTACTAGTGCCATTTGTTCAGT

GGTTCGTAGGGCTTTCCCCCACTGTCTGGCTTTCAGTTATATGGATGATG

TGGTATTGGGGGCCAAGTCTGTACAACATCTTGAGTCCCTTTATGCCGCT

GTTACCAATTTTCTTTTGTCTTTGGGTATACATTTAAACCCTCACAAAAC

AAAAAGATGGGGATATTCCCTTAACTTCATGGGATATGTAATTGGGAGTT

GGGGCACATTGCCACAGGAACATATTGTACAAAAAATCAAACTATGTTTT

AGGAAACTTCCTGTAAACAGGCCTATTGATTGGAAAGTATGTCAACGAAT

TGTGGGTCTTTTGGGGTTTGCTGCCCCTTTTACGCAATGTGGATATCCTG

CTTTAATGCCTTTATATGCATGTATACAAGCAAAACAGGCTTTTACTTTC

TCGCCAACTTACAAGGCCTTTCTAAGTAAACAGTATCTAGCCCTTTACCC

CGTTGCTCGGCAACGGCCTGGTCTGTGCCAAGTGTTTGCTGACGCAACCC

CCACTGGTTGGGGCTTGGCCATAGGCCATCAGCGCATGCGTGGAACCTTT

GTGTCTCCTCTGCCGATCCATACTGCGGAACTCCTAGCCGCTTGTTTTGC

TCGCAGCAGGTCTGGAGCGAAACTCATCGGGACTGACAATTCTGTCGTGC

TCTCCCGCAAGTATACATCGTTTCCATGGCTGCTAGGCTGTGCTGCCAAC

TGGATCCTGCGCGGGACGTCCTTTGTTTACGTCCCGTCGGCGCTGAATCC

CGCGGACGACCCCTCCCGGGGCCGCTTGGGGCTCTACCGCCCGCTTCTCC

GTCTGCCGTACCGACCGACCACGGGGCGCACCTCTCTTTACGCGGACTCC

CCGTCTGTGCCTTCTCGTCTGCCGGACCGTGTGCACTTCGCTTCACCTCT

GCACGTCGCATGGAAACCACCGTGAACGCCCACCGGAACCTGCCCAAGGT

CTTGCACAAGAGGACTCTTGGACTTTCAGCAATGTCAACGACCGACCTTG

AGGCATACTTCAAAGACTGTGTGTTTCATGAGTGGGAGGAGCTGGGGGAG

GAGATTAGGTTAAAGGTCTTTGTACTAGGAGGCTGTAGGCATAAATTGGT

CTGTTCACCAGCACCATGCAACTTTTTCACCTCTGCCTAGTCATCTCTTG

TTCATGTCCTACTGTTCAAGCCTCCAAGCTGTGCCTTGGGTGGCTTTGGG

ACATGGACATTGACCCTTATAAAGAATTTGGAGCTACTGTGGAGTTACTC

TCTTTTTTGCCTTCTGACTTCTTTCCGTCGGTACGAGACCTCCTAGATAC

CGCTGCTGCTCTGTATCGGGAAGCCTTAGAATCTCCTGAACATTGCTCAC

CTCACCACACAGCACTCAGGCAAGCTATTCTGTGCTGGGGGGAATTAATG

ACTCTAGCTACCTGGGTGGGTAATAATTTAGAAGATCCAGCGTCCAGGGA

TCTAGTAGTCAATTATGTTAACACTAACATGGGCCTAAAGATCAGGCAAT

TATTGTGGTTTCACATTTCCTGTCTTACTTTTGGAAGAGAAACTGTTCTT

GAATATTTGGTGTCTTTTGGAGTGTGGATTCGCACTCCTCCGGCCTACAG

ACCACCAAATGCCCCTATCTTATCAACACTTCCGGAAACTACTGTTGTTA

GACGACGAGGCAGGTCCCCTAGAAGAAGAACTCCCTCGCCTCGCAGACGA

AGGTCTCAATCACCGCGTCGCAGAAGATCTCAATCTCGGGAATCCCAATG

TTAGTATTCCTTGGACTCATAAGGTGGGAAACTTTACGGGGCTCTATTCT

-continued

TCTACAGTACCTGTCTTTAATCCTGAATGGCAAACTCCTTCTTTTCCAGA

CATTCATTTGCAGGAGGATATTGTTGATAGATGTAAGCAATTTGTGGGAC

CCCTTACAGTAAATGAAAACAGGAGACTAAAATTAATAATGCCTGCTAGA

TTTTATCCTAATGTTACCAAATATTTGCCCTTAGATAAAGGGATCAAACC

TTATTATCCAGAGCATGTAGTTAATCATTACTTCCAGACAAGACATTATT

TGCATACTCTTTGGAAGGCGGGTATCTTATATAAGAGAGAGTCAACACAT

AGCGCCTCATTTTGCGGGTCACCATATTCTTGGGAACAAGATCTACAGCA

TGGGAGGTTGGTCTTCCAAACCTCGAAAAGGCATGGGGACAAATCTTTCT

GTCCCCAATCCCCTGGGATTCTTCCCCGATCATCAGTTGGACCCTGCATT

CAAAGCCAACTCAGAAAATCCAGATTGGGACCTCAACCCACACAAGGACA

ACTGGCCGGACGCCCACAAGGTGGGAGTGGGAGCATTCGGGCCAGGGTTC

ACCCCTCCCCACGGGGGACTGTTGGGGTGGAGCCCTCAGGCTCAGGGCAT

ACTTACATCTGTGCCAGCAGCTCCTCCTCCTGCCTCCACCAATCGGCAGT

CAGGAAGGCAGCCTACTCCCTTATCTCCACCTCTAAGGGACACTCATCCT

CAGGCCATGCAGTGG

SEQ ID No. 30:

Nucleotide sequence of HBV genome, HBV genotype C (Genbank accession #AB540584)

AACTCCACAACTTTCCACCAAGCTCTGCTAGATCCCAGAGTGAGGGGCCT

ATACTTTCCTGCTGGTGGCTCCAGTTCCGGAACAGTAAACCCTGTTCCGA

CTACTGCCTCTCCCATATCGTCAATCTTCACGAGGACTGGGGACCCTGTA

CCGAACATGGAGAACACAACATCAGGATTCCTAGGACCCCTGCTCGTGTT

ACAGGCGGGGTTTTTCTTGTTGACAAGAATCCTCACAATACCGCAGAGTC

TAGACTCGTGGTGGACTTCTCTCAATTTTCTAGGGGGAGCACCCACGTGT

CCTGGCCAAAATTCGCAGTCCCCAACCTCCAATCACTCACCAACCTCTTG

TCCTCCAATTTGTCCTGGCTATCGCTGGATGTGTCTGCGGCGTTTTATCA

TATTCCTCTTCATCCTGCTGCTATGCCTCATCTTCTTGTTGGTTCTTCTG

GACTATCAAGGTATGTTGCCCGTTTGTCCTCTACTTCCAGGAACATCAAC

TACAAGCACGGGACCATGCAAGACCTGCACGATTCCTGCTCAAGGAAMCT

CTATGTTTCCCTCTTGTTGCTGTACAAAACCTTCGGACGGAAACTGCACT

TGTATTCCCATCCCATCATCCTGGGCTTTCGCAAGATTCCTATGGGAGTG

GGCCTCAGTCCGTTTCTCCTGGCTCAGTTTACTAGTGCCATTTGTTCAGT

GGTTCGTAGGGCTTTCCCCCACTGTTTGGCTTTCAGCTATATGGATGATG

TGGTATTGGGGGCCAAGTCTGTACAACATCTTGAGTCCCTTTTTACCTCT

ATTACCAATTTTCTTTTGTCTTTGGGTATACATTTGAACCCTAATAAAAC

CAAGCGTTGGGGCTACTCCCTTAACTTTATGGGATATGTAATTGGAAGTT

GGGGTACTTTACCACAGGAACATATTGTTCTAAAAATCAAACAATGTTTT

CGGAAACTGCCTGTAAATAGACCTATTGATTGGAAAGTATGTCAACGAAT

TGTGGGTCTTCTGGGCTTTGCTGCCCCTTTTACACAATGTGGGTATCCTG

CCTTGATGCCTTTGTATGCATGTATACAAGCTAAGCAGGCTTTCACTTTC

-continued

TCGCCAACTTATAAGGCCTTTCTGTGTAAACAATATCTGAACCTTTACCC

CGTTGCTCGGCAACGGTCAGGTCTCTGCCAAGTATTTGCTGACGCAACCC

CCACTGGATGGGGCTTGGCAATAGGCCATCAGCGCATGCGTGGAACCTTT

GTGGCTCCTCTGCCGATCCATACTGCGGAACTCTTAGCAGCCTGCTTTGC

TCGCAGCCGGTCTGGAGCRAATCTTATTGGAACCGACAACTCCGTTGTCC

TCTCTCGGAAATACACCTCCTTTCCATGGCTGCTAGGGTGTGCTGCAAAC

TGGATCCTGCGCGGGACGTCCTTTGTCTACGTCCCGTCGGCGCTGAATCC

AGCGGACGACCCGTCTCGGGGCCGTTTGGGACTCTACCGTCCCCTTCTTC

GTCTGCCGTTCCGGCCGACCACGGGGCGCACCTCTCTTTACGCGGTCTCC

CCGTCTGTGCCTTCTCATCTGCCGGACCGTGTGCACTTCGCTTCACCTCT

GCACGTCGCATGGAGACCACCGTGAACGCCCACCAGGTCTTGCCCAAGGT

CTTACATAAGAGGACTCTTGGACTCTCGGCAATGTCAACGACCGACCTTG

AGGCATACTTCAAAGACTGTGTGTTTAAAGACTGGGAGGAGTTGGGGGAG

GAGATTAGGTTAAAGGTCTTTGTACTAGGAGGCTGTAGGCATAAATTGGT

CTGTTCACCAGCACCATGCAACTTTTTCACCTCTGCCTAATCATCTCATG

TTCATGTCCTACTGTTCAAGCCTCCAAGCTGTGCCTTGGGTGGCTTTGGG

GCATGGACATTGACCCGTATAAAGAATTTGGAGCTTCTGTGGAGTTACTC

TCTTTTTTGCCTTCTGACTTCTTTCCTTCCATTCGAGATCTCCTCGACAC

CGCCTCTGCTCTGTATCGGGAGGCCTTAGAGTCTCCGGAACATTGTTCAC

CTCACCATACAGCACTCAGGCAAGCTATTCTGTGTTGGGGTGAGTTGATG

AATCTGGCCACCTGGGTGGGAAGTAATTTGGAAGACCCAGCATCTAGGGA

ATTAGTAGTCAGTTATGTTAATGTTAATATGGGCCTAAAGATCAGACAAC

TATTGTGGTTTCACATTTCCTGTCTTACTTTTGGAAGAGAAACTGTTCTT

GAGTATTTGGTGTCCTTTGGAGTGTGGATACGCACTCCTCCCGCTTACAG

ACCACCAAATGCCCCTATCTTATCAACACTTCCGGAAACTACTGTTGTTA

GACGACGAGGCAGGTCCCCTAGAAGAAGAACTCCCTCGCCTCGCAGACGA

AGGTCTCAATCGCCGCGTCGCAGAAGATCTCAATCTCGGGAATCTCAATG

TTAGTATCCCTTGGACTCATAAGGTGGGAAATTTTACTGGGCTTTATTCT

TCTACTGTACCTGTCTTCAATCCTGAGTGGCAAACTCCCTCCTTTCCTCA

CATTCATTTGCAGGAGGACATTATTAATAGATGTCAACAATATGTGGGCC

CTCTTACAGTTAATGAAAAAAGGAGATTAAAATTAATTATGCCTGCCAGG

TTTTATCCTAACCGTACCAAATATTTGCCCCTAGATAAAGGCATTAAACC

TTATTATCCTGAATATACAGTTAATCATTACTTCCAAACCAGGCATTATT

TACATACTCTGTGGAAGGCTGGCATTCTATATAAGAGAGAAACTACACGC

AGCGCCTCATTTTGTGGGTCACCATATTCTTGGGAACAAGAGCTACAGCA

TGGGAGGTTGGTCCTCCAAACCTCGAAAGGGCATGGGGACGAATCTTTCT

GTTCCCAATCCTCTGGGCTTCTTTCCCGATCACCAGTTGGACCCTGCATT

CGGAGCCAACTCAAACAATCCGGATTGGGACTTCAATCCCAACAAGGATC

ACTGGCCAGCAGCAAACCAGGTAGGAGCGGGAGCCTTCGGGCCAGGGTTC

ACCCCACCGCACGGCGGTCTTTTGGGGTGGAGCCCTCAGGCTCAGGGCGT

ATTGACAACAGTGCCAGCAGCGCCTCCTCCTGCCTCCACCAATCGGCAGT

CAGGCAGACAGCCTACTCCCATCTCTCCACCTCTAAGAGACAGTCATCCT

CAGGCCATGCAGTGG

SEQ ID No. 31:

Nucleotide sequence of HBV genome, HBV genotype E (Genbank accession #AP007262)

AATTCCACAACATTCCACCAAGCTCTGCAGGATCCCAGAGTAAGAGGCCT

GTATCTTCCTGCTGGTGGCTCCAGTTCCGGAACAGTGAACCCTGTTCCGA

CTACTGCCTCACTCATCTCGTCAATCTTCTCGAGGATTGGGGACCCTGCA

CCGAACATGGAAGGCATCACATCAGGATTCCTAGGACCCCTGCTCGTGTT

ACAGGCGGGGTTTTTCTTGTTGACAAAAATCCTCACAATACCGCAGAGTC

TAGACTCGTGGTGGACTTCTCTCAATTTTCTAGGGGGAGCTCCCGTGTGT

CTTGGCCAAAATTCGCAGTCCCCAATCTCCAATCACTCACCAACCTCTTG

TCCTCCAATTTGTCCTGGCTATCGCTGGATGTGTCTGCGGCGTTTTATCA

TCTTCCTCTTCATCCTGCTGCTATGCCTCATCTTCTTGTTGGTTCTTCTG

GACTATCAAGGTATGTTGCCCGTTTGTCCTCTAATTCCAGGATCATCAAC

CACCAGTACGGGACCCTGCCGAACCTGCACGACTCTTGCTCAAGGAACCT

CTATGTTTCCCTCATGTTGTTGTTTAAAACCTTCGGACGGAAATTGCACT

TGTATTCCCATCCCATCATCATGGGCTTTCGGAAAATTCCTATGGGAGTG

GGCCTCAGCCCGTTTCTCCTGGCTCAGTTTACTAGTGCCATTTGTTCAGT

GGTTCGCCGGGCTTTCCCCCACTGTCTGGCTTTCAGTTATATGGATGATG

TGGTATTGGGGGCCAAGTCTGTACAACATCTTGAGTCCCTTTATACCTCT

GTTACCAATTTTCTTTTGTCTTTGGGTATACATTTAAATCCCAACAAAAC

AAAAAGATGGGGATATTCCCTAAATTTCATGGGTTATGTAATTGGTAGTT

GGGGGTCATTACCACAAGAACACATCAGACTGAAAATCAAAGACTGTTTT

AGAAAGCTCCCTGTTAACAGGCCTATTGATTGGAAAGTATGTCAAAGAAT

TGTGGGTCTTTTGGGCTTTGCTGCCCCTTTTACACAATGTGGATATCCTG

CTTTAATGCCTCTATATGCGTGTATTCAATCTAAGCAGGCTTTCACTTTC

TCGCCAACTTACAAGGCCTTTCTGTGTAAACAATATATGAACCTTTACCC

CGTTGCCCGGCAACGGCCAGGTCTGTGCCAAGTGTTTGCTGATGCAACCC

CCACTGGCTGGGGCTTGGCCATAGGCCATCAGCGCATGCGTGGAACCTTT

GTGGCTCCTCTGCCGATCCATACTGCGGAACTCCTAGCCGCTTGTTTTGC

TCGCAGCAGGTCTGGAGCGAAACTCATAGGGACAGATAATTCTGTCGTTC

TCTCCCGGAAATATACATCATTTCCATGGCTGCTAGGCTGTGCTGCCAAC

TGGATCCTGCGAGGGACGTCCTTTGTCTACGTCCCGTCAGCGCTGAATCC

TGCGGACGACCCCTCTCGGGGCCGCTTGGGGGTCTATCGTCCCCTTCTCC

GTCTGCCGTTCCGGCCGACCACGGGGCGCACCTCTCTTTACGCGGTCTCC

CCGTCTGTGCCTTCTCATCTGCCGGACCGTGTGCACTTCGCTTCACCTCT

GCACGTCGCATGGAGACCACCGTGAACGCCCACCAGATCTTGCCCAAGGT

CTTACATAAGAGGACTCTTGGACTCTCTGCAATGTCAACGACCGACCTTG

AGGCATACTTCAAAGACTGTTTGTTTAAAGACTGGGAGGAGTTGGGGGAG

GAGACTAGATTAATGATCTTTGTACTAGGAGGCTGTAGGCATAAATTGGT

CTGCGCACCAGCACCATGCAACTTTTTCACCTCTGCCTAATCATCTCTTG

TTCATGTCCTACTGTTCAAGCCTCCAAGCTGTGCCTTGGGTGGCTTTGGG

ACATGGACATTGACCCTTATAAAGAATTTGGAGCTACTGTGGAGTTACTC

TCGTTTTTGCCTTCTGACTTCTTTCCTTCAGTAAGAGATCTTCTAGATAC

CGCCTCTGCTCTGTATCGGGATGCCTTAGAATCTCCTGAGCATTGTTCAC

CTCACCATACTGCACTCAGGCAAGCCATTCTTTGCTGGGGAGAATTAATG

ACTCTAGCTACCTGGGTGGGTGTAAATTTGGAAGATCCAGCATCCAGGGA

CCTAGTAGTCAGTTATGTCAATACTAATATGGGCCTAAAGTTCAGGCAAT

TATTGTGGTTTCACATTTCTTGTCTCACTTTTGGAAGAGAAACCGTCATA

GAGTATTTGGTGTCTTTTGGAGTGTGGATTCGCACTCCTCCAGCTTATAG

ACCACCAAATGCCCCTATCTTATCAACACTTCCGGAGAATACTGTTGTTA

GACGAAGAGGCAGGTCCCCTAGAAGAAGAACTCCCTCGCCTCGCAGACGA

AGATCTCAATCGCCGCGTCGCAGAAGATCTCAATCTCCAGCTTCCCAATG

TTAGTATTCCTTGGACTCACAAGGTGGGAAATTTTACGGGGCTTTATTCT

TCTACTATACCTGTCTTTAATCCTAACTGGAAAACTCCATCTTTTCCTGA

TATTCATTTGCACCAGGACATTATTAACAAATGTGAACAATTTGTAGGTC

CTYTAACAGTAAATGAAAAACGAAGATTAAACTTAGTCATGCCTGCTAGA

TTTTTTCCCATCTCCACGAAATATTTGCCCCTAGAGAAAGGTATAAAACC

TTATTATCCAGATAATGTAGTTAATCATTACTTCCAAACCAGACACTATT

TACATACCCTATGGAAGGCGGGCATCTTATATAAAAGAGAAACTACCCGT

AGCGCCTCATTTTGTGGGTCACCTTATTCTTGGGAACACGAGCTACATCA

TGGGGCTTTCTTGGACGGTCCCTCTCGAATGGGGGAAGAATCATTCCACC

ACCAATCCTCTGGGATTTTTTCCCGACCACCAGTTGGATCCAGCATTCAG

AGCAAACACCAGAAATCCAGATTGGGACCACAATCCCAACAAAGACCACT

GGACAGAAGCCAACAAGGTAGGAGTGGGAGCATTTGGGCCGGGGTTCACT

CCCCCACACGGAGGCCTTTTGGGGTGGAGCCCTCAGGCTCAAGGCATGCT

AAAAACATTGCCAGCAAATCCGCCTCCTGCCTCCACCAATCGGCAGTCAG

GAAGGCAGCCTACCCCAATCACTCCACCTTTGAGAGACACTCATCCTCAG

GCCATGCAGTGG

SEQ ID No. 32:

Nucleotide sequence of HBV genome, HBV genotype F (Genbank accession #HE974366)

AACTCAACCCAGTTCCATCAGGCTCTGTTGGATCCCAGGGTAAGGGCTCT

GTATCTTCCTGCTGGTGGCTCCAGTTCAGGAACACAAAACCCTGCTCCGA

CTATTGCCTCTCTCACATCCTCAATCTTCTCGACGACTGGGGGCCCTGCT

ATGAACATGGACAACATTACATCAGGACTCCTAGGACCCCTGCTCGTGTT

ACAGGCGGTGTGTTTCTTGTTGACAAAAATCCTCACAATACCACAGAGTC

TAGACTCGTGGTGGACTTCTCTCAATTTTCTAGGGGGACTACCCGGGTGT

-continued

CCTGGCCAAAATTCGCAGTCCCCAACCTCCAATCACTTACCAACCTCCTG

TCCTCCAACTTGTCCTGGCTATCGTTGGATGTGTCTGCGGCGTTTTATCA

TCTTCCTCTTCATCCTGCTGCTATGCCTCATCTTCTTGTTGGTTCTTCTG

GACTACCAGGGTATGTTGCCCGTTTGTCCTCTACTTCCAGGATCCACGAC

CACCAGCACGGGACCCTGCAAAACCTGCACAACTCTTGCACAAGGAACCT

CTATGTTTCCCTCCTGTTGCTGTTCAAAACCCTCGGACGGAAACTGCACT

TGTATTCCCATCCCATCATCCTGGGCTTTAGGAAAATACCTATGGGAGTG

GGCCTCAGCCCGTTTCTCATGGCTCAGTTTACTAGTGCAATTTGTTCAGT

GGTGCGTAGGGCTTTCCCCCACTGTCTGGCTTTTAGTTATATTGATGATC

TGGTATTGGGGGCCAAATCTGTGCAGCACCTTGAGTCCCTTTATACCGCT

GTTACCAATTTTCTGTTATCTGTGGGTATCCATTTAAATACTTCTAAAAC

TAAGAGATGGGGTTACACCCTACATTTTATGGGTTATGTCATTGGTAGTT

GGGGATCATTACCTCAAGATCATATTGTACACAAAATCAAAGAATGTTTT

CGGAAACTGCCTGTAAATCGTCCAATTGATTGGAAAGTCTGTCAACGCAT

TGTGGGTCTTTTGGGCTTTGCTGCCCCTTTCACACAATGTGGTTATCCTG

CTCTCATGCCTCTGTATGCTTGTATTACTGCTAAACAGGCTTTTGTTTTT

TCGCCAACTTACAAGGCCTTTCTCTGTAAACAATACATGAACCTTTACCC

CGTTGCCAGGCAACGGCCGGGCCTGTGCCAAGTGTTTGCTGACGCAACCC

CCACTGGTTGGGGCTTGGCCATTGGCCATCAGCGCATGCGTGGAACCTTT

GTGGCTCCTCTGCCGATCCATACTGCGGAACTCCTTGCAGCTTGTTTCGC

TCGCAGCAGGTCTGGAGCGACTCTCATCGGCACGGACAACTCTGTTGTCC

TCTCTAGGAAGTACACCTCCTTCCCATGGCTGCTCGGGTGTGCTGCAAAC

TGGATCCTGCGCGGGACGTCCTTTGTTTACGTCCCGTCGGCGCTGAATCC

CGCGGACGACCCCTCCCGGGGCCGCTTGGGGCTGTACCGCCCTCTTCTCC

GTCTGCCGTTCCAGCCGACAACGGGTCGCACCTCTCTTTACGCGGACTCC

CCGTCTGTTCCTTCTCATCTGCCGGACCGTGTGCACTTCGCTTCACCTCT

GCACGTCGCATGGAGACCACCGTGAACGCCCCTTGGAGTTTGCCAACAGT

CTTACATAAGAGGACTCTTGGACTTTCAGGAGGGTCAATGACCCGGATTG

CAGAATACATCAAAGACTGTGTATTTAAGGACTGGGAGGAGTTGGGGGAG

GAGACTAGGTTAATGATCTTTGTACTAGGAGGCTGTAGGCATAAATTGGT

CTGTTCACCAGCACCATGCAACTTTTTCACCTCTGCCTAATCATCTTTTG

TTCATGTCCTACTGTTCAAGCCTCCAAGCTGTGCCTTGGGTGGCTTTGGG

ACATGGACATTGACCCTTATAAAGAATTTGGCGCTTCTGTGGAGTTACTC

TCTTTTTTGCCTTCTGATTTCTTTCCATCGGTTCGGGACCTACTCGACAC

CGCTTCAGCCCTTTACCGGGATGCTTTAGAGTCACCTGAACATTGCACTC

CCCATCACACTGCCCTCAGGCAAGTTATTTTGTGCTGGGGTGAGTTAATG

ACTTTGGCTTCCTGGGTGGGCAATAACTTGGAAGACCCTGCTGCCAGGGA

TTTAGTAGTTAACTATGTTAACACTAACATGGGCCTAAAAATTAGACAAC

TACTGTGGTTTCACATTTCCTGCCTTACTTTTGGAAGAGATATAGTTCTT

GAGTATTTGGTGTCCTTTGGAGTGTGGATTCGCACTCCTCCTGCTTACAG

-continued

ACCACAAAATGCCCCTATCCTATCCACACTTCCGGAAACTACTGTTGTTA

GACGACGAGGCAGGTCCCCTAGAAGAAGAACTCCCTCGCCTCGCAGACGA

AGATCTCAATCGCCGCGTCGCCGAAGATCTCAATCTCCAGCTTCCCAATG

TTAGTATTCCTTGGACTCATAAGGTGGGAAATTTTACGGGGCTTTACTCT

TCTACTGTGCCTGCTTTTAATCCTGACTGGTTAACTCCTTCTTTTCCTAA

TATTCATTTACATCAAGACCTAATTTCTAAATGTGAACAATTTGTAGGCC

CACTCACTAAAAATGAATTAAGGAGGTTAAAATTGGTTATGCCAGCTAGA

TTTTATCCTAAGGTTACCAAATATTTTCCTATGGAGAAAGGAATCAAGCC

TTATTATCCTGAGCATGCAGTTAATCATTACTTTAAAACAAGACATTATT

TGCATACTTTATGGAAGGCGGAATTTTATATAAGAGAGAATCCACACGT

AGCGCATCATTTTGTGGGTCACCATATTCCTGGGAACAAGAGCTACAGCA

TGGGAGCACCTCTCTCAACGACAAGAAGAGGCATGGGACAGAATCTTTCT

GTGCCCAATCCTCTGGGATTCTTTCCAGACCATCAGCTGGATCCGCTATT

CAAAGCAAATTCCAGCAGTCCCGACTGGGACTTCAACACAAACAAGGACA

GTTGGCCAATGGCAAACAAGGTAGGAGTGGGAGCATACGGTCCAGGGTTC

ACACCCCCACACGGTGGCCTGCTGGGGTGGAGCCCTCAGGCACAAGGTAT

GTTAACAACCTTGCCAGCAGATCCGCCTCCTGCTTCCACCAATCGGCGGT

CCGGGAGAAAGCCAACCCCAGTCTCTCCACCTCTAAGAGACACTCATCCA

CAGGCAATGCAGTGG

SEQ ID No. 33:

Nucleotide sequence of HBV genome, HBV genotype G (Genbank accession #AP007264)

AACTCTACAGCATTCCACCAAGCTCTACAAAATCCCAAAGTCAGGGGCCT

GTATTTTCCTGCTGGTGGCTCCAGTTCAGGGATAGTGAACCCTGTTCCGA

CTATTGCCTCTCACATCTCGTCAATCTTCTCCAGGATTGGGGACCCTGCA

CCGAACATGGAGAACATCACATCAGGATTCCTAGGACCCCTGCTCGTGTT

ACAGGCGGGGTTTTTCTTGTTGACAAGAATCCTCACAATACCGCAGAGTC

TAGACTCGTGGTGGACTTCTCTCAATTTTCTAGGGGGAGTGCCCGTGTGT

CCTGGCCTAAATTCGCAGTCCCCAACCTCCAATCACTCACCAATCTCCTG

TCCTCCAACTTGTCCTGGCTATCGCTGGATGTGTCTGCGGCGTTTTATCA

TATTCCTCTTCATCCTGCTGCTATGCCTCATCTTCTTGTTGGTTCTTCTG

GACTATCAAGGTATGTTGCCCGTTTGTCCTCTGATTCCAGGATCCTCGAC

CACCAGTACGGGACCCTGCAAAACCTGCACGACTCCTGCTCAAGGCAACT

CTATGTATCCCTCATGTTGCTGTACAAAACCTTCGGACGGAAATTGCACC

TGTATTCCCATCCCATCATCTTGGGCTTTCGCAAAATACCTATGGGAGTG

GGCCTCAGTCCGTTTCTCTTGGCTCAGTTTACTAGTGCCATTTGTTCAGT

GGTTCGTAGGGCTTTCCCCCACTGTCTGGCTTTCAGCTATATGGATGATG

TGGTATTGGGGGCCAAATCTGTACAACATCTTGAGTCCCTTTATACCGCT

GTTACCAATTTTCTTTTGTCTTTGGGTATACATCTAAACCCTAACAAAAC

AAAAAGATGGGGTTATTCCTTAAATTTTATGGGATATGTAATTGGAAGTT

-continued

GGGGTACTTTGCCACAAGAACACATCACACAGAAAATTAAGCAATGTTTT

CGGAAACTCCCTGTTAACAGGCCAATTGATTGGAAAGTCTGTCAACGAAT

AACTGGTCTGTTGGGTTTCGCTGCTCCTTTTACCCAATGTGGTTACCCTG

CCTTAATGCCTTTATATGCATGTATACAAGCTAAGCAGGCTTTTACTTTC

TCGCCAACTTATAAGGCCTTTCTCTGTAAACAATACATGAACCTTTACCC

CGTTGCTAGGCAACGGCCCGGTCTGTGCCAAGTGTTTGCTGACGCAACCC

CCACTGGTTGGGGCTTGGCCATCGGCCATCAGCGCATGCGTGGAACCTTT

GTGGCTCCTCTGCCGATCCATACTGCGGAACTCCTAGCTGCTTGTTTTGC

TCGCAGCCGGTCTGGAGCAAAACTCATTGGGACTGACAATTCTGTCGTCC

TTTCTCGGAAATATACATCCTTTCCATGGCTGCTAGGCTGTGCTGCCAAC

TGGATCCTTCGCGGGACGTCCTTTGTTTACGTCCCGTCAGCGCTGAATCC

AGCGGACGACCCCTCCCGGGGCCGTTTGGGGCTCTGTCGCCCCCTTCTCC

GTCTGCCGTTCCTGCCGACCACGGGGCGCACCTCTCTTTACGCGGTCTCC

CCGTCTGTGCCTTCTCATCTGCCGGACCGTGTGCACTTCGCTTCACCTCT

GCACGTTACATGGAAACCGCCATGAACACCTCTCATCATCTGCCAAGGCA

GTTATATAAGAGGACTCTTGGACTGTTTGTTATGTCAACAACCGGGGTGG

AGAAATACTTCAAGGACTGTGTTTTTGCTGAGTGGGAAGAATTAGGCAAT

GAGTCCAGGTTAATGACCTTTGTATTAGGAGGCTGTAGGCATAAATTGGT

CTGCGCACCAGCACCATGTAACTTTTTCACCTCTGCCTAATCATCTCTTG

TTCATGTCCTACTGTTCAAGCCTCCAAGCTGTGCCTTGGGTGGCTTTAGG

GCATGGATAGAACAACTTTGCCATATGGCCTTTTTGGCTTAGACATTGAC

CCTTATAAAGAATTTGGAGCTACTGTGGAGTTGCTCTCGTTTTTGCCTTC

TGACTTTTTCCCGTCTGTTCGTGATCTTCTCGACACCGCTTCAGCTTTGT

ACCGGGAATCCTTAGAGTCCTCTGATCATTGTTCGCCTCACCATACAGCA

CTCAGGCAAGCAATCCTGTGCTGGGGTGAGTTGATGACTCTAGCTACCTG

GGTGGGTAATAATTTGGAAGATCCAGCATCCAGAGATTTGGTGGTCAATT

ATGTTAATACTAATATGGGTTTAAAAATCAGGCAACTATTGTGGTTTCAC

ATTTCCTGTCTTACTTTTGGGAGAGAAACCGTTCTTGAGTATTTGGTGTC

TTTTGGAGTGTGGATTCGCACTCCTCCTGCTTATAGACCACCAAATGCCC

CTATCCTATCAACACTTCCGGAGACTACTGTTGTTAGACGAAGAGGCAGG

TCCCCTCGAAGAAGAACTCCCTCGCCTCGCAGACGAAGATCTCAATCGCC

GCGTCGCAGAAGATCTGCATCTCCAGCTTCCCAATGTTAGTATTCCTTGG

ACTCACAAGGTGGGAAACTTTACGGGGCTGTATTCTTCTACTATACCTGT

CTTTAATCCTGATTGGCAAACTCCTTCTTTTCCAAATATCCATTTGCATC

AAGACATTATAACTAAATGTGAACAATTTGTGGGCCCTCTCACAGTAAAT

GAGAAACGAAGATTAAAACTAGTTATGCCTGCCAGATTTTTCCCAAACTC

TACTAAATATTTACCATTAGACAAAGGTATCAAACCGTATTATCCAGAAA

ATGTAGTTAATCATTACTTCCAGACCAGACATTATTTACATACCCTTTGG

AAGGCGGGTATTCTATATAAGAGAGAAACGTCCCGTAGCGCTTCATTTTG

TGGGTCACCATATACTTGGGAACAAGATCTACAGCATGGGGCTTTCTTGG

-continued

ACGGTCCCTCTCGAGTGGGGAAAGAACCTTTCCACCAGCAATCCTCTAGG

ATTCCTTCCCGATCACCAGTTGGACCCAGCATTCAGAGCAAATACCAACA

ATCCAGATTGGGACTTCAATCCCAAAAAGGACCCTTGGCCAGAGGCCAAC

AAAGTAGGAGTTGGAGCCTATGGACCCGGGTTCACCCCTCCACACGGAGG

CCTTTTGGGGTGGAGCCCTCAGTCTCAGGGCACACTAACAACTTTGCCAG

CAGATCCGCCTCCTGCCTCCACCAATCGTCAGTCAGGGAGGCAGCCTACT

CCCATCTCTCCACCACTAAGAGACAGTCATCCTCAGGCCATGCAGTGG

SEQ ID No. 34:

Nucleotide sequence of HBV genome, HBV genotype H (Genbank accession #AB516393)

AACTCAACACAGTTCCACCAAGCACTGTTGGATTCGAGAGTAAGGGGTCT

GTATTTTCCTGCTGGTGGCTCCAGTTCAGAAACACAGAACCCTGCTCCGA

CTATTGCCTCTCTCACATCATCAATCTTCTCGAAGACTGGGGACCCTGCT

ATGAACATGGAGAACATCACATCAGGACTCCTAGGACCCCTTCTCGTGTT

ACAGGCGGTGTGTTTCTTGTTGACAAAAATCCTCACAATACCACAGAGTC

TAGACTCGTGGTGGACTTCTCTCAATTTTCTAGGGGTACCACCCGGGTGT

CCTGGCCAAAATTCGCAGTCCCCAATCTCCAATCACTTACCAACCTCCTG

TCCTCCAACTTGTCCTGGCTATCGTTGGATGTGTCTGCGGCGTTTTATCA

TCTTCCTCTTCATCCTGCTGCTATGCCTCATCTTCTTGTTGGTTCTTCTG

GACTATCAAGGTATGTTGCCCGTGTGTCCTCTACTTCCAGGATCTACAAC

CACCAGCACGGGACCCTGCAAAACCTGCACCACTCTTGCTCAAGGAACCT

CTATGTTTCCCTCCTGCTGCTGTACCAAACCTTCGGACGGAAATTGCACC

TGTATTCCCATCCCATCATCTTGGGCTTTCGGAAAATACCTATGGGAGTG

GGCCTCAGCCCGTTTCTCTTGGCTCAGTTTACTAGTGCAATTTGCTCAGT

GGTGCGTAGGGCTTTCCCCCACTGTCTGGCTTTTAGTTATATGGATGATT

TGGTATTGGGGGCCAAATCTGTGCAGCATCTTGAGTCCCTTTATACCGCT

GTTACCAATTTTTTGTTATCTGTGGGCATCCATTTGAACACAGCTAAAAC

AAAATGGTGGGGTTATTCCTTACACTTTATGGGTTATATAATTGGGAGTT

GGGGGACCTTGCCTCAGGAACATATTGTGCATAAAATCAAAGATTGCTTT

CGCAAACTTCCCGTGAATAGACCCATTGATTGGAAGGTTTGTCAACGCAT

TGTGGGTCTTTTGGGCTTTGCAGCCCCTTTTACTCAATGTGGTTATCCTG

CTCTCATGCCCTTGTATGCCTGTATTACCGCTAAGCAGGCTTTTGTTTTC

TCGCCAACTTACAAGGCCTTTCTCTGTCAACAATACATGAACCTTTACCC

CGTTGCTCGGCAACGGCCAGGCCTTTGCCAAGTGTTTGCTGACGCAACCC

CCACTGGCTGGGGCTTGGCGATTGGCCATCAGCGCATGCGCGGAACCTTT

GTGGCTCCTCTGCCGATCCATACTGCGGAACTCCTAGCAGCCTGTTTCGC

TCGCAGCAGGTCTGGAGCGGACGTTATCGGCACTGACAACTCCGTTGTCC

TTTCTCGGAAGTACACCTCCTTCCCATGGCTGCTAGGCTGTGCTGCCAAC

TGGATCCTGCGCGGGACGTCCTTTGTCTACGTCCCGTCGGCGCTGAATCC

TGCGGACGACCCCTCTCGTGGTCGCTTGGGGCTCTGCCGCCCTCTTCTCC

-continued

```
GCCTACCGTTCCGGCCGACGACGGGTCGCACCTCTCTTTACGCGGACTCC
CCGCCTGTGCCTTCTCATCTGCCGGCCCGTGTGCACTTCGCTTCACCTCT
GCACGTCGCATGGAGACCACCGTGAACGCCCCTTGGAACTTGCCAACAAC
CTTACATAAGAGGACTCTTGGACTTTCGCCCCGGTCAACGACCTGGATTG
AGGAATACATCAAAGACTGTGTATTTAAGGACTGGGAGGAGTCGGGGGAG
GAGTTGAGGTTAAAGGTCTTTGTATTAGGAGGCTGTAGGCATAAATTGGT
CTGTTCACCAGCACCATGCAACTTTTTCACCTCTGCCTAATCATCTTTTG
TTCATGTCCCACTGTTCAAGCCTCCAAGCTGTGCCTTGGGTGGCTTTGGG
GCATGGACATTGACCCTTATAAAGAATTTGGAGCTTCTGTGGAGTTACTC
TCATTTTTGCCTTCTGACTTCTTCCCGTCTGTCCGGGACCTACTCGACAC
CGCTTCAGCCCTCTACCGAGATGCCTTAGAATCACCCGAACATTGCACCC
CCAACCACACTGCTCTCAGGCAAGCTATTTTGTGCTGGGGTGAGTTGATG
ACCTTGGCTTCCTGGGTGGGCAATAATTTAGAGGATCCTGCAGCAAGAGA
TCTAGTAGTTAATTATGTCAATACTAACATGGGTCTAAAAATTAGACAAT
TATTATGGTTTCACATTTCCTGCCTTACATTTGGAAGAGAAACTGTGCTT
GAGTATTTGGTGTCTTTTGGAGTGTGGATCCGCACTCCACCTGCTTACAG
ACCACCAAATGCCCCTATCCTATCAACACTTCCGGAGACTACTGTTGTTA
GACAACGAGGCAGGGCCCCTAGAAGAAGAACTCCCTCGCCTCGCAGACGA
AGATCTCAATCACCGCGTCGCAGAAGATCTCAATCTCCAGCTTCCCAATG
TTAGTATTCCTTGGACTCATAAGGTGGGAAACTTTACCGGTCTTTACTCC
TCTACTGTACCTGTTTTCAATCCTGACTGGTTAACTCCTTCTTTTCCTGA
CATTCACTTGCATCAAGATCTGATACAAAAATGTGAACAATTTGTAGGCC
CACTCACTACAAATGAAAGGAGACGATTGAAACTAATTATGCCAGCTAGG
TTTTATCCCAAAGTTACTAAATACTTCCCTTTGGATAAAGGTATTAAGCC
TTACTATCCAGAGAATGTGGTTAATCATTACTTTAAAACTAGACATTATT
TACATACTTTGTGGAAGGCAGGAATTCTATATAAGAGAGAATCCACACAT
AGCGCCTCATTTTGTGGGTCACCATATTCCTGGGAACAAGAGCTACAGCA
TGGGAGCACCTCTCTCAACGGCGAGAAGGGGCATGGGACAGAATCTTTCT
GTGCCCAATCCTCTGGGATTCTTTCCAGACCACCAGTTGGATVCACTATT
CAGAGCAAATTCCAGCAGTCCCGATTGGGACTTCAACACAAACAAGGACA
ATTGGCCAATGGCAAACAAGGTAGGAGTGGGAGGCTTCGGTCCAGGGTTC
ACACCCCCACACGGTGGCCTTCTGGGGTGGAGCCCTCAGGCACAGGGCAT
TCTGACAACCTCGCCACCAGATCCACCTCCTGCTTCCACCAATCGGAGGT
CAGGAAGAAAGCCAACCCCAGTCTCTCCACCTCTAAGGGACACACATCCA
CAGGCCATGCAGTGG
```

SEQ ID No. 35:
Nucleotide sequence of Vector: pTREHBV-HAe (5,980 nt)
Vector: pTRE2(Clontech)
nt 356-452: HBV nt 1805-1902 with A1816 deletion
nt 453-491: HA-tag insertion with flanking sequence
nt 462-488: HA-tag sequence
nt 492-3761: HBV nt 1903-3182/1-1990

```
   1 CTCGAGTTTA CCACTCCCTA TCAGTGATAG AGAAAAGTGA AAGTCGAGTT TACCACTCCC
  61 TATCAGTGAT AGAGAAAAGT GAAAGTCGAG TTTACCACTC CCTATCAGTG ATAGAGAAAA
 121 GTGAAAGTCG AGTTTACCAC TCCCTATCAG TGATAGAGAA AAGTGAAAGT CGAGTTTACC
 181 ACTCCCTATC AGTGATAGAG AAAAGTGAAA GTCGAGTTTA CCACTCCCTA TCAGTGATAG
 241 AGAAAAGTGA AAGTCGAGTT TACCACTCCC TATCAGTGAT AGAGAAAAGT GAAAGTCGAG
 301 CTCGGTACCC GGGTCGAGGT AGGCGTGTAC GGTGGGAGGC CTATATAAGC GTCGAGCACC
 361 AGCACCTGCA ACTTTTTCAC CTCTGCCTAA TCATCTCTTG TTCATGTCCT ACTGTTCAAG
 421 CCTCCAAGCT GTGCCTTGGG TGGCTTTGGG GCGTGGACAT CTACCCATAC GACGTTCCAG
 481 ATTACGCTGG CATGGACATC GACCCTTATA AAGAATTTGG AGCTACTGTG GAGTTACTCT
 541 CGTTTTTGCC TTCTGACTTC TTTCCTTCAG TACGAGATCT TCTAGATACC GCCTCAGCTC
 601 TGTATCGGGA AGCCTTAGAG TCTCCTGAGC ATTGTTCACC TCACCATACT GCACTCAGGC
 661 AAGCAATTCT TTGCTGGGGG GAACTAATGA CTCTAGCTAC CTGGGTGGGT GTTAATTTGG
 721 AAGATCCAGC ATCTAGAGAC CTAGTAGTCA GTTATGTCAA CACTAATATG GGCCTAAAGT
 781 TCAGGCAACT CTTGTGGTTT CACATTTCTT GTCTCACTTT TGGAAGAGAA ACCGTTATAG
 841 AGTATTTGGT GTCTTTCGGA GTGTGGATTC GCACTCCTCC AGCTTATAGA CCACCAAATG
 901 CCCCTATCCT ATCAACACTT CCGGAAACTA CTGTTGTTAG ACGACGAGGC AGGTCCCCTA
 961 GAAGAAGAAC TCCCTCGCCT CGCAGACGAA GGTCTCAATC GCCGCGTCGC AGAAGATCTC
1021 AATCTCGGGA ACCTCAATGT TAGTATTCCT TGGACTCATA AGGTGGGGAA CTTTACTGGT
1081 CTTTATTCTT CTACTGTACC TGTCTTTAAT CCTCATTGGA AAACACCATC TTTTCCTAAT
```

-continued

```
1141 ATACATTTAC ACCAAGACAT TATCAAAAAA TGTGAACAGT TTGTAGGCCC ACTTACAGTT
1201 AATGAGAAAA GAAGATTGCA ATTGATTATG CCTGCTAGGT TTTATCCAAA GGTTACCAAA
1261 TATTTACCAT TGGATAAGGG TATTAAACCT TATTATCCAG AACATCTAGT TAATCATTAC
1321 TTCCAAACTA GACACTATTT ACACACTCTA TGGAAGGCGG GTATATTATA TAAGAGAGAA
1381 ACAACACATA GCGCCTCATT TTGTGGGTCA CCATATTCTT GGGAACAAGA TCTACAGCAT
1441 GGGGCAGAAT CTTTCCACCA GCAATCCTCT GGGATTCTTT CCCGACCACC AGTTGGATCC
1501 AGCCTTCAGA GCAAACACAG CAAATCCAGA TTGGGACTTC AATCCCAACA AGGACACCTG
1561 GCCAGACGCC AACAAGGTAG GAGCTGGAGC ATTCGGGCTG GGTTTCACCC CACCGCACGG
1621 AGGCCTTTTG GGGTGGAGCC CTCAGGCTCA GGGCATACTA CAAACTTTGC CAGCAAATCC
1681 GCCTCCTGCC TCCACCAATC GCCAGACAGG AAGGCAGCCT ACCCCGCTGT CTCCACCTTT
1741 GAGAAACACT CATCCTCAGG CCATGCAGTG GAATTCCACA ACCTTTCACC AAACTCTGCA
1801 AGATCCCAGA GTGAGAGGCC TGTATTTCCC TGCTGGTGGC TCCAGTTCAG GAGCAGTAAA
1861 CCCTGTTCCG ACTACTGCCT CTCCCTTATC GTCAATCTTC TCGAGGATTG GGGACCCTGC
1921 GCTGAACATG GAGAACATCA CATCAGGATT CCTAGGACCC CTTCTCGTGT TACAGGCGGG
1981 GTTTTTCTAG TAGACAAGAA TCCTCACAAT ACCGCAAAGT CTAGACTCGT GGTGGACTTC
2041 TCTCAATTTT CTAGGGGGAA CTACCGTGTG TCTTGGCCAA AATTCGCAGT CCCCAACCTC
2101 CAATCACTCA CCAACCTCCT GTCCTCCAAC TTGTCCTGGT TATCGCTGGA TGTGTCTGCG
2161 GCGTTTTATC ATCTTCCTCT TCATCCTGCT GCTATGCCTC ATCTTCTTGT TGGTTCTTCT
2221 GGACTATCAA GGTATGTTGC CCGTTTGTCC TCTAATTCCA GGATCCTCAA CCACCAGCAC
2281 GGGACCATGC CGAACCTGCA TGACTACTGC TCAAGGAACC TCTATGTATC CCTCCTGTTG
2341 CTGTACCAAA CCTTCGGACG GAAATTGCAC CTGTATTCCC ATCCCATCAT CCTGGGCTTT
2401 CGGAAAATTC CTATGGGAGT GGGCCTCAGC CCGTTTCTCC TGGCTCAGTT TACTAGTGCC
2461 ATTTGTTCAG TGGTTCGTAG GGCTTTCCCC CACTGTTTGG CTTTCAGTTA TATGGATGAT
2521 GTGGTATTGG GGGCCAAGTC TGTACAGCAT CTTGAGTCCC TTTTTACCGC TGTTACCAAT
2581 TTTCTTTTGT CTTTGGGTAT ACATTTAAAC CCTAACAAAA CAAAGAGATG GGGTTACTCT
2641 CTGAATTTTA TGGGTTATGT CATTGGAAGT TATGGGTCCT TGCCACAAGA ACACATCATA
2701 CAAAAAATCA AAGAATGTTT TAGAAAACTT CCTATTAACA GGCCTATTGA TTGGAAAGTA
2761 TGTCAACGAA TTGTGGGTCT TTTGGGTTTT GCTGCCCCAT TTACACAATG TGGTTATCCT
2821 GCGTTAATGC CCTTGTATGC ATGTATTCAA TCTAAGCAGG CTTTCACTTT CTCGCCAACT
2881 TACAAGGCCT TTCTGTGTAA ACAATACCTG AACCTTTACC CCGTTGCCCG GCAACGGCCA
2941 GGTCTGTGCC AAGTGTTTGC TGACGCAACC CCCACTGGCT GGGGCTTGGT CATGGGCCAT
3001 CAGCGCGTGC GTGGAACCTT TTCGGCTCCT CTGCCGATCC ATACTGCGGA ACTCCTAGCC
3061 GCTTGTTTTG CTCGCAGCAG GTCTGGAGCA AACATTATCG GGACTGATAA CTCTGTTGTC
3121 CTCTCCCGCA AATATACATC GTATCCATGG CTGCTAGGCT GTGCTGCCAA CTGGATCCTG
3181 CGCGGGACGT CCTTTGTTTA CGTCCCGTCG GCGCTGAATC CTGCGGACGA CCCTTCTCGG
3241 GGTCGCTTGG GACTCTCTCG TCCCCTTCTC CGTCTGCCGT TCCGACCGAC CACGGGGCGC
3301 ACCTCTCTTT ACGCGGACTC CCCGTCTGTG CCTTCTCATC TGCCGGACCG TGTGCACTTC
3361 GCTTCACCTC TGCACGTCGC ATGGAGACCA CCGTGAACGC CCACCGAATG TTGCCCAAGG
3421 TCTTACATAA GAGGACTCTT GGACTCTCTG CAATGTCAAC GACCGACCTT GAGGCATACT
```

-continued

3481 TCAAAGACTG TTTGTTTAAA GACTGGGAGG AGTTGGGGGA GGAGATTAGA TTAAAGGTCT

3541 TTGTACTAGG AGGCTGTAGG CATAAATTGG TCTGCGCACC AGCACCATGC AACTTTTTCA

3601 CCTCTGCCTA ATCATCTCTT GTTCATGTCC TACTGTTCAA GCCTCCAAGC TGTGCCTTGG

3661 GTGGCTTTGG GGCATGGACA TCGACCCTTA TAAAGAATTT GGAGCTACTG TGGAGTTACT

3721 CTCGTTTTTG CCTTCTGACT TCTTTCCTTC AGTACGAGAT CCACTAGTTC TAGAGCGGCC

3781 CCAAACAATT GCTCAAACCG ATACAATTGT ACTTTGTCCC GAGCAAATAT AATCCTGCTG

3841 ACGGCCCATC CAGGCACAAA CCTCCTGATT GGACGGCTTT TCCATACACC CCTCTCTCGA

3901 AAGCAATATA TATTCCACAT AGGCTATGTG GAACTTAAGC TTCCTCGCTC ACTGACTCGC

3961 TGCGCTCGGT CGTTCGGCTG CGGCGAGCGG TATCAGCTCA CTCAAAGGCG GTAATACGGT

4021 TATCCACAGA ATCAGGGGAT AACGCAGGAA AGAACATGTG AGCAAAAGGC CAGCAAAAGG

4081 CCAGGAACCG TAAAAAGGCC GCGTTGCTGG CGTTTTTCCA TAGGCTCCGC CCCCCTGACG

4141 AGCATCACAA AAATCGACGC TCAAGTCAGA GGTGGCGAAA CCCGACAGGA CTATAAAGAT

4201 ACCAGGCGTT TCCCCCTGGA AGCTCCCTCG TGCGCTCTCC TGTTCCGACC CTGCCGCTTA

4261 CCGGATACCT GTCCGCCTTT CTCCCTTCGG GAAGCGTGGC GCTTTCTCAT AGCTCACGCT

4321 GTAGGTATCT CAGTTCGGTG TAGGTCGTTC GCTCCAAGCT GGGCTGTGTG CACGAACCCC

4381 CCGTTCAGCC CGACCGCTGC GCCTTATCCG GTAACTATCG TCTTGAGTCC AACCCGGTAA

4441 GACACGACTT ATCGCCACTG GCAGCAGCCA CTGGTAACAG GATTAGCAGA GCGAGGTATG

4501 TAGGCGGTGC TACAGAGTTC TTGAAGTGGT GGCCTAACTA CGGCTACACT ATAAGAACAG

4561 TATTTGGTAT CTGCGCTCTG CTGAAGCCAG TTACCTTCGG AAAAAGAGTT GGTAGCTCTT

4621 GATCCGGCAA ACAAACCACC GCTGGTAGCG GTGGTTTTTT TGTTTGCAAG CAGCAGATTA

4681 CGCGCAGAAA AAAAGGATCT CAAGAAGATC CTTTGATCTT TTCTACGGGG TCTGACGCTC

4741 AGTGGAACGA AAACTCACGT TAAGGGATTT TGGTCATGAG ATTATCAAAA AGGATCTTCA

4801 CCTAGATCCT TTTAAATTAA AAATGAAGTT TTAAATCAAT CTAAAGTATA TATGAGTAAA

4861 CTTGGTCTGA CAGTTACCAA TGCTTAATCA GTGAGGCACC TATCTCAGCG ATCTGTCTAT

4921 TTCGTTCATC CATAGTTGCC TGACTCCCCG TCGTGTAGAT AACTACGATA CGGGAGGGCT

4981 TACCATCTGG CCCCAGTGCT GCAATGATAC CGCGAGACCC ACGCTCACCG GCTCCAGATT

5041 TATCAGCAAT AAACCAGCCA GCCGGAAGGG CCGAGCGCAG AAGTGGTCCT GCAACTTTAT

5101 CCGCCTCCAT CCAGTCTATT AATTGTTGCC GGGAAGCTAG AGTAAGTAGT TCGCCAGTTA

5161 ATAGTTTGCG CAACGTTGTT GCCATTGCTA CAGGCATCGT GGTGTCACGC TCGTCGTTTG

5221 GTATGGCTTC ATTCAGCTCC GGTTCCCAAC GATCAAGGCG AGTTACATGA TCCCCCATGT

5281 TGTGCAAAAA AGCGGTTAGC TCCTTCGGTC CTCCGATCGT TGTCAGAAGT AAGTTGGCCG

5341 CAGTGTTATC ACTCATGGTT ATGGCAGCAC TGCATAATTC TCTTACTGTC ATGCCATCCG

5401 TAAGATGCTT TTCTGTGACT GGTGAGTACT CAACCAAGTC ATTCTGAGAA TAGTGTATGC

5461 GGCGACCGAG TTGCTCTTGC CCGGCGTCAA TACGGGATAA TACCGCGCCA CATAGCAGAA

5521 CTTTAAAAGT GCTCATCATT GGAAAACGTT CTTCGGGGCG AAAACTCTCA AGGATCTTAC

5581 CGCTGTTGAG ATCCAGTTCG ATGTAACCCA CTCGTGCACC CAACTGATCT TCAGCATCTT

5641 TTACTTTCAC CAGCGTTTCT GGGTGAGCAA AAACAGGAAG GCAAAATGCC GCAAAAAAGG

5701 GAATAAGGGC GACACGGAAA TGTTGAATAC TCATACTCTT CCTTTTTCAA TATTATTGAA

5761 GCATTTATCA GGGTTATTGT CTCATGAGCG GATACATATT TGAATGTATT TAGAAAAATA

5821 AACAAATAGG GGTTCCGCGC ACATTTCCCC GAAAAGTGCC ACCTGACGTC TAAGAAACCA

-continued

5881 TTATTATCAT GACATTAACC TATAAAAATA GGCGTATCAC GAGGCCCTTT CGTCTTCACT

5941 CGAATATCTG CAGGCGTATC ACGAGGCCCT TTCGTCTTCA 5980

SEQ ID No. 36:

Nucleotide sequence encoding HBV envelope protein, Large Surface protein (L)

ATGGGGCAGAATCTTTCCACCAGCAATCCTCTGGGATTCTTTCCCGACCA
CCAGTTGGATCCAGCCTTCAGAGCAAACACAGCAAATCCAGATTGGGACT
TCAATCCCAACAAGGACACCTGGCCAGACGCCAACAAGGTAGGAGCTGGA
GCATTCGGGCTGGGTTTCACCCCACCGCACGGAGGCCTTTTGGGGTGGAG
CCCTCAGGCTCAGGGCATACTACAAACTTTGCCAGCAAATCCGCCTCCTG
CCTCCACCAATCGCCAGACAGGAAGGCAGCCTACCCCGCTGTCTCCACCT
TTGAGAAACACTCATCCTCAGGCCATGCAGTGGAATTCCACAACCTTTCA
CCAAACTCTGCAAGATCCCAGAGTGAGAGGCCTGTATTTCCCTGCTGGTG
GCTCCAGTTCAGGAGCAGTAAACCCTGTTCCGACTACTGCCTCTCCCTTA
TCGTCAATCTTCTCGAGGATTGGGGACCCTGCGCTGAACATGGAGAACAT
CACATCAGGATTCCTAGGACCCCTTCTCGTGTTACAGGCGGGGTTTTTCT
TGTTGACAAGAATCCTCACAATACCGCAAAGTCTAGACTCGTGGTGGACT
TCTCTCAATTTTCTAGGGGGAACTACCGTGTGTCTTGGCCAAAATTCGCA
GTCCCCAACCTCCAATCACTCACCAACCTCCTGTCCTCCAACTTGTCCTG
GTTATCGCTGGATGTGTCTGCGGCGTTTTATCATCTTCCTCTTCATCCTG
CTGCTATGCCTCATCTTCTTGTTGGTTCTTCTGGACTATCAAGGTATGTT
GCCCGTTTGTCCTCTAATTCCAGGATCCTCAACCACCAGCACGGGACCAT
GCCGAACCTGCATGACTACTGCTCAAGGAACCTCTATGTATCCCTCCTGT
TGCTGTACCAAACCTTCGGACGGAAATTGCACCTGTATTCCCATCCCATC
ATCCTGGGCTTTCGGAAAATTCCTATGGGAGTGGGCCTCAGCCCGTTTCT
CCTGGCTCAGTTTACTAGTGCCATTTGTTCAGTGGTTCGTAGGGCTTTCC
CCCACTGTTTGGCTTTCAGTTATATGGATGATGTGGTATTGGGGGCCAAG
TCTGTACAGCATCTTGAGTCCCTTTTTACCGCTGTTACCAATTTTCTTTT
GTCTTTGGGTATACATTTAA

SEQ ID No. 37:

Nucleotide sequence encoding HBV envelope protein, Middle surface protein (M)

ATGCAGTGGAATTCCACAACCTTTCACCAAACTCTGCAAGATCCCAGAGT
GAGAGGCCTGTATTTCCCTGCTGGTGGCTCCAGTTCAGGAGCAGTAAACC
CTGTTCCGACTACTGCCTCTCCCTTATCGTCAATCTTCTCGAGGATTGGG
GACCCTGCGCTGAACATGGAGAACATCACATCAGGATTCCTAGGACCCCT
TCTCGTGTTACAGGCGGGGTTTTTCTTGTTGACAAGAATCCTCACAATAC
CGCAAAGTCTAGACTCGTGGTGGACTTCTCTCAATTTTCTAGGGGGAACT
ACCGTGTGTCTTGGCCAAAATTCGCAGTCCCCAACCTCCAATCACTCACC
AACCTCCTGTCCTCCAACTTGTCCTGGTTATCGCTGGATGTGTCTGCGGC

-continued

GTTTTATCATCTTCCTCTTCATCCTGCTGCTATGCCTCATCTTCTTGTTG
GTTCTTCTGGACTATCAAGGTATGTTGCCCGTTTGTCCTCTAATTCCAGG
ATCCTCAACCACCAGCACGGGACCATGCCGAACCTGCATGACTACTGCTC
AAGGAACCTCTATGTATCCCTCCTGTTGCTGTACCAAACCTTCGGACGGA
AATTGCACCTGTATTCCCATCCCATCATCCTGGGCTTTCGGAAAATTCCT
ATGGGAGTGGGCCTCAGCCCGTTTCTCCTGGCTCAGTTTACTAGTGCCAT
TTGTTCAGTGGTTCGTAGGGCTTTCCCCCACTGTTTGGCTTTCAGTTATA
TGGATGATGTGGTATTGGGGGCCAAGTCTGTACAGCATCTTGAGTCCCTT
TTTACCGCTGTTACCAATTTTCTTTTGTCTTTGGGTATACATTTAA

SEQ ID No. 38:

Nucleotide sequence encoding HBV envelope protein, Small surface protein (S)

ATGGAGAACATCACATCAGGATTCCTAGGACCCCTTCTCGTGTTACAGGC
GGGGTTTTTCTTGTTGACAAGAATCCTCACAATACCGCAAAGTCTAGACT
CGTGGTGGACTTCTCTCAATTTTCTAGGGGGAACTACCGTGTGTCTTGGC
CAAAATTCGCAGTCCCCAACCTCCAATCACTCACCAACCTCCTGTCCTCC
AACTTGTCCTGGTTATCGCTGGATGTGTCTGCGGCGTTTTATCATCTTCC
TCTTCATCCTGCTGCTATGCCTCATCTTCTTGTTGGTTCTTCTGGACTAT
CAAGGTATGTTGCCCGTTTGTCCTCTAATTCCAGGATCCTCAACCACCAG
CACGGGACCATGCCGAACCTGCATGACTACTGCTCAAGGAACCTCTATGT
ATCCCTCCTGTTGCTGTACCAAACCTTCGGACGGAAATTGCACCTGTATT
CCCATCCCATCATCCTGGGCTTTCGGAAAATTCCTATGGGAGTGGGCCTC
AGCCCGTTTCTCCTGGCTCAGTTTACTAGTGCCATTTGTTCAGTGGTTCG
TAGGGCTTTCCCCCACTGTTTGGCTTTCAGTTATATGGATGATGTGGTAT
TGGGGGCCAAGTCTGTACAGCATCTTGAGTCCCTTTTTACCGCTGTTACC
AATTTTCTTTTGTCTTTGGGTATACATTTAA

SEQ ID No. 39:

Nucleotide sequence of expression vector pcHA-HBe (6,682 nt)

Vector: pcDNA3.1/V5-His-TOPO (Invitrogen)

nt 929-1015: HBV nt1816-1902 nt 1016-1054: insertion nt 1025-1051: HA-tag sequence nt 1055-2112: HBV 1903-2605/1573-1926

```
   1 GACGGATCGG GAGATCTCCC GATCCCCTAT GGTCGACTCT CAGTACAATC TGCTCTGATG
  61 CCGCATAGTT AAGCCAGTAT CTGCTCCCTG CTTGTGTGTT GGAGGTCGCT GAGTAGTGCG
 121 CGAGCAAAAT TTAAGCTACA ACAAGGCAAG GCTTGACCGA CAATTGCATG AAGAATCTGC
 181 TTAGGGTTAG GCGTTTTGCG CTGCTTCGCG ATGTACGGGC CAGATATACG CGTTGACATT
 241 GATTATTGAC TAGTTATTAA TAGTAATCAA TTACGGGGTC ATTAGTTCAT AGCCCATATA
 301 TGGAGTTCCG CGTTACATAA CTTACGGTAA ATGGCCCGCC TGGCTGACCG CCCAACGACC
 361 CCCGCCCATT GACGTCAATA ATGACGTATG TTCCCATAGT AACGCCAATA GGGACTTTCC
 421 ATTGACGTCA ATGGGTGGAC TATTTACGGT AAACTGCCCA CTTGGCAGTA CATCAAGTGT
 481 ATCATATGCC AAGTACGCCC CCTATTGACG TCAATGACGG TAAATGGCCC GCCTGGCATT
 541 ATGCCCAGTA CATGACCTTA TGGGACTTTC CTACTTGGCA GTACATCTAC GTATTAGTCA
 601 TCGCTATTAC CATGGTGATG CGGTTTTGGC AGTACATCAA TGGGCGTGGA TAGCGGTTTG
 661 ACTCACGGGG ATTTCCAAGT CTCCACCCCA TTGACGTCAA TGGGAGTTTG TTTTGGCACC
 721 AAAATCAACG GGACTTTCCA AAATGTCGTA ACAACTCCGC CCCATTGACG CAAATGGGCG
 781 GTAGGCGTGT ACGGTGGGAG GTCTATATAA GCAGAGCTCT CTGGCTAACT AGAGAACCCA
 841 CTGCTTACTG GCTTATCGAA ATTAATACGA CTCACTATAG GGAGACCCAA GCTGGCTAGT
 901 TAAGCTTGGT ACCGAGCTCG GATCCACCAT GCAACTTTTT CACCTCTGCC TAATCATCTC
 961 TTGTTCATGT CCTACTGTTC AAGCCTCCAA GCTGTGCCTT GGGTGGCTTT GGGGCGTGGA
1021 CATCTACCCA TACGACGTTC CAGATTACGC TGGCATGGAC ATCGACCCTT ATAAAGAATT
1081 TGGAGCTACT GTGGAGTTAC TCTCGTTTTT GCCTTCTGAC TTCTTTCCTT CAGTACGAGA
1141 TCTTCTAGAT ACCGCCTCAG CTCTGTATCG GGAAGCCTTA GAGTCTCCTG AGCATTGTTC
1201 ACCTCACCAT ACTGCACTCA GGCAAGCAAT TCTTTGCTGG GGGGAACTAA TGACTCTAGC
1261 TACCTGGGTG GGTGTTAATT TGGAAGATCC AGCATCTAGA GACCTAGTAG TCAGTTATGT
1321 CAACACTAAT ATGGGCCTAA AGTTCAGGCA ACTCTTGTGG TTTCACATTT CTTGTCTCAC
1381 TTTTGGAAGA GAAACCGTTA TAGAGTATTT GGTGTCTTTC GGAGTGTGGA TTCGCACTCC
1441 TCCAGCTTAT AGACCACCAA ATGCCCCTAT CCTATCAACA CTTCCGGAAA CTACTGTTGT
1501 TAGACGACGA GGCAGGTCCC CTAGAAGAAG AACTCCCTCG CCTCGCAGAC GAAGGTCTCA
1561 ATCGCCGCGT CGCAGAAGAT CTCAATCTCG GGAACCTCAA TGTTAGTATT CCTTGGACTC
1621 ATAAGGTGGG GAACTTTACT GGTCTTTATT CTTCTACTGT ACCTGTCTTT AATCCTCATT
1681 GGAAAACACC ATCTTTTCCT AATATACATT TACACCAAGA CATTATCAAA AAATGTGAAC
1741 AGTTTGTAGG CCCACTTACG GACCGTGTGC ACTTCGCTTC ACCTCTGCAC GTCGCATGGA
1801 GACCACCGTG AACGCCCACC GAATGTTGCC CAAGGTCTTA CATAAGAGGA CTCTTGGACT
1861 CTCTGCAATG TCAACGACCG ACCTTGAGGC ATACTTCAAA GACTGTTTGT TTAAAGACTG
1921 GGAGGAGTTG GGGGAGGAGA TTAGATTAAA GGTCTTTGTA CTAGGAGGCT GTAGGCATAA
1981 ATTGGTCTGC GCACCAGCAC CATGCAACTT TTTCACCTCT GCCTAATCAT CTCTTGTTCA
2041 TGTCCTACTG TTCAAGCCTC CAAGCTGTGC CTTGGGTGGC TTTGGGGCAT GGACATCGAC
2101 CCTTATAAAG AAAAGGGCAA TTCTGCAGAT ATCCAGCACA GTGGCGGCCG CTCGAGTCTA
2161 GAGGGCCCGC GGTTCGAAGG TAAGCCTATC CCTAACCCTC TCCTCGGTCT CGATTCTACG
2221 CGTACCGGTC ATCATCACCA TCACCATTGA GTTTAAACCC GCTGATCAGC CTCGACTGTG
2281 CCTTCTAGTT GCCAGCCATC TGTTGTTTGC CCCTCCCCCG TGCCTTCCTT GACCCTGGAA
2341 GGTGCCACTC CCACTGTCCT TTCCTAATAA AATGAGGAAA TTGCATCGCA TTGTCTGAGT
2401 AGGTGTCATT CTATTCTGGG GGGTGGGGTG GGGCAGGACA GCAAGGGGGA GGATTGGGAA
```

-continued

2461 GACAATAGCA GGCATGCTGG GGATGCGGTG GGCTCTATGG CTTCTGAGGC GGAAAGAACC

2521 AGCTGGGGCT CTAGGGGGTA TCCCCACGCG CCCTGTAGCG GCGCATTAAG CGCGGCGGGT

2581 GTGGTGGTTA CGCGCAGCGT GACCGCTACA CTTGCCAGCG CCCTAGCGCC CGCTCCTTTC

2641 GCTTTCTTCC CTTCCTTTCT CGCCACGTTC GCCGGCTTTC CCCGTCAAGC TCTAAATCGG

2701 GGCATCCCTT TAGGGTTCCG ATTTAGTGCT TTACGGCACC TCGACCCCAA AAAACTTGAT

2761 TAGGGTGATG GTTCACGTAG TGGGCCATCG CCCTGATAGA CGGTTTTTCG CCCTTTGACG

2821 TTGGAGTCCA CGTTCTTTAA TAGTGGACTC TTGTTCCAAA CTGGAACAAC ACTCAACCCT

2881 ATCTCGGTCT ATTCTTTTGA TTTATAAGGG ATTTTGGGGA TTTCGGCCTA TTGGTTAAAA

2941 AATGAGCTGA TTTAACAAAA ATTTAACGCG AATTAATTCT GTGGAATGTG TGTCAGTTAG

3001 GGTGTGGAAA GTCCCCAGGC TCCCCAGGCA GGCAGAAGTA TGCAAAGCAT GCATCTCAAT

3061 TAGTCAGCAA CCAGGTGTGG AAAGTCCCCA GGCTCCCCAG CAGGCAGAAG TATGCAAAGC

3121 ATGCATCTCA ATTAGTCAGC AACCATAGTC CCGCCCCTAA CTCCGCCCAT CCCGCCCCTA

3181 ACTCCGCCCA GTTCCGCCCA TTCTCCGCCC CATGGCTGAC TAATTTTTTT TATTTATGCA

3241 GAGGCCGAGG CCGCCTCTGC CTCTGAGCTA TTCCAGAAGT AGTGAGGAGG CTTTTTTGGA

3301 GGCCTAGGCT TTTGCAAAAA GCTCCCGGGA GCTTGTATAT CCATTTTCGG ATCTGATCAA

3361 GAGACAGGAT GAGGATCGTT TCGCATGATT GAACAAGATG GATTGCACGC AGGTTCTCCG

3421 GCCGCTTGGG TGGAGAGGCT ATTCGGCTAT GACTGGGCAC AACAGACAAT CGGCTGCTCT

3481 GATGCCGCCG TGTTCCGGCT GTCAGCGCAG GGGCGCCCGG TTCTTTTTGT CAAGACCGAC

3541 CTGTCCGGTG CCCTGAATGA ACTGCAGGAC GAGGCAGCGC GGCTATCGTG GCTGGCCACG

3601 ACGGGCGTTC CTTGCGCAGC TGTGCTCGAC GTTGTCACTG AAGCGGGAAG GGACTGGCTG

3661 CTATTGGGCG AAGTGCCGGG GCAGGATCTC CTGTCATCTC ACCTTGCTCC TGCCGAGAAA

3721 GTATCCATCA TGGCTGATGC AATGCGGCGG CTGCATACGC TTGATCCGGC TACCTGCCCA

3781 TTCGACCACC AAGCGAAACA TCGCATCGAG CGAGCACGTA CTCGGATGGA AGCCGGTCTT

3841 GTCGATCAGG ATGATCTGGA CGAAGAGCAT CAGGGGCTCG CGCCAGCCGA ACTGTTCGCC

3901 AGGCTCAAGG CGCGCATGCC CGACGGCGAG GATCTCGTCG TGACCCATGG CGATGCCTGC

3961 TTGCCGAATA TCATGGTGGA AAATGGCCGC TTTTCTGGAT TCATCGACTG TGGCCGGCTG

4021 GGTGTGGCGG ACCGCTATCA GGACATAGCG TTGGCTACCC GTGATATTGC TGAAGAGCTT

4081 GGCGGCGAAT GGGCTGACCG CTTCCTCGTG CTTTACGGTA TCGCCGCTCC CGATTCGCAG

4141 CGCATCGCCT TCTATCGCCT TCTTGACGAG TTCTTCTGAG CGGGACTCTG GGGTTCGCGA

4201 AATGACCGAC CAAGCGACGC CCAACCTGCC ATCACGAGAT TTCGATTCCA CCGCCGCCTT

4261 CTATGAAAGG TTGGGCTTCG GAATCGTTTT CCGGGACGCC GGCTGGATGA TCCTCCAGCG

4321 CGGGGATCTC ATGCTGGAGT TCTTCGCCCA CCCCAACTTG TTTATTGCAG CTTATAATGG

4381 TTACAAATAA AGCAATAGCA TCACAAATTT CACAAATAAA GCATTTTTTT CACTGCATTC

4441 TAGTTGTGGT TTGTCCAAAC TCATCAATGT ATCTTATCAT GTCTGTATAC CGTCGACCTC

4501 TAGCTAGAGC TTGGCGTAAT CATGGTCATA GCTGTTTCCT GTGTGAAATT GTTATCCGCT

4561 CACAATTCCA CACAACATAC GAGCCGGAAG CATAAAGTGT AAAGCCTGGG GTGCCTAATG

4621 AGTGAGCTAA CTCACATTAA TTGCGTTGCG CTCACTGCCC GCTTTCCAGT CGGGAAACCT

4681 GTCGTGCCAG CTGCATTAAT GAATCGGCCA ACGCGCGGGG AGAGGCGGTT TGCGTATTGG

4741 GCGCTCTTCC GCTTCCTCGC TCACTGACTC GCTGCGCTCG GTCGTTCGGC TGCGGCGAGC

-continued

4801 GGTATCAGCT CACTCAAAGG CGGTAATACG GTTATCCACA GAATCAGGGG ATAACGCAGG

4861 AAAGAACATG TGAGCAAAAG GCCAGCAAAA GGCCAGGAAC CGTAAAAAGG CCGCGTTGCT

4921 GGCGTTTTTC CATAGGCTCC GCCCCCCTGA CGAGCATCAC AAAAATCGAC GCTCAAGTCA

4981 GAGGTGGCGA AACCCGACAG GACTATAAAG ATACCAGGCG TTTCCCCCTG GAAGCTCCCT

5041 CGTGCGCTCT CCTGTTCCGA CCCTGCCGCT TACCGGATAC CTGTCCGCCT TTCTCCCTTC

5101 GGGAAGCGTG GCGCTTTCTC AATGCTCACG CTGTAGGTAT CTCAGTTCGG TGTAGGTCGT

5161 TCGCTCCAAG CTGGGCTGTG TGCACGAACC CCCCGTTCAG CCCGACCGCT GCGCCTTATC

5221 CGGTAACTAT CGTCTTGAGT CCAACCCGGT AAGACACGAC TTATCGCCAC TGGCAGCAGC

5281 CACTGGTAAC AGGATTAGCA GAGCGAGGTA TGTAGGCGGT GCTACAGAGT TCTTGAAGTG

5341 GTGGCCTAAC TACGGCTACA CTAGAAGGAC AGTATTTGGT ATCTGCGCTC TGCTGAAGCC

5401 AGTTACCTTC GGAAAAAGAG TTGGTAGCTC TTGATCCGGC AAACAAACCA CCGCTGGTAG

5461 CGGTGGTTTT TTTGTTTGCA AGCAGCAGAT TACGCGCAGA AAAAAAGGAT CTCAAGAAGA

5521 TCCTTTGATC TTTTCTACGG GGTCTGACGC TCAGTGGAAC GAAAACTCAC GTTAAGGGAT

5581 TTTGGTCATG AGATTATCAA AAAGGATCTT CACCTAGATC CTTTTAAATT AAAAATGAAG

5641 TTTTAAATCA ATCTAAAGTA TATATGAGTA AACTTGGTCT GACAGTTACC AATGCTTAAT

5701 CAGTGAGGCA CCTATCTCAG CGATCTGTCT ATTTCGTTCA TCCATAGTTG CCTGACTCCC

5761 CGTCGTGTAG ATAACTACGA TACGGGAGGG CTTACCATCT GGCCCCAGTG CTGCAATGAT

5821 ACCGCGAGAC CCACGCTCAC CGGCTCCAGA TTTATCAGCA ATAAACCAGC CAGCCGGAAG

5881 GGCCGAGCGC AGAAGTGGTC CTGCAACTTT ATCCGCCTCC ATCCAGTCTA TTAATTGTTG

5941 CCGGGAAGCT AGAGTAAGTA GTTCGCCAGT TAATAGTTTG CGCAACGTTG TTGCCATTGC

6001 TACAGGCATC GTGGTGTCAC GCTCGTCGTT TGGTATGGCT TCATTCAGCT CCGGTTCCCA

6061 ACGATCAAGG CGAGTTACAT GATCCCCCAT GTTGTGCAAA AAAGCGGTTA GCTCCTTCGG

6121 TCCTCCGATC GTTGTCAGAA GTAAGTTGGC CGCAGTGTTA TCACTCATGG TTATGGCAGC

6181 ACTGCATAAT TCTCTTACTG TCATGCCATC CGTAAGATGC TTTTCTGTGA CTGGTGAGTA

6241 CTCAACCAAG TCATTCTGAG AATAGTGTAT GCGGCGACCG AGTTGCTCTT GCCCGGCGTC

6301 AATACGGGAT AATACCGCGC CACATAGCAG AACTTTAAAA GTGCTCATCA TTGGAAAACG

6361 TTCTTCGGGG CGAAAACTCT CAAGGATCTT ACCGCTGTTG AGATCCAGTT CGATGTAACC

6421 CACTCGTGCA CCCAACTGAT CTTCAGCATC TTTTACTTTC ACCAGCGTTT CTGGGTGAGC

6481 AAAAACAGGA AGGCAAAATG CCGCAAAAAA GGGAATAAGG GCGACACGGA AATGTTGAAT

6541 ACTCATACTC TTCCTTTTTC AATATTATTG AAGCATTTAT CAGGGTTATT GTCTCATGAG

6601 CGGATACATA TTTGAATGTA TTTAGAAAAA TAAACAAATA GGGGTTCCGC GCACATTTCC

6661 CCGAAAAGTG CCACCTGACG TC 6682

SEQ ID No. 40:

Amino acid sequence N-terminal to a tag

```
VDI
```

SEQ ID No. 41:

Nucleotide sequence encoding a HA-tag comprising 5'- and 3'-additional nucleotides. The underlined nucleotides show the sequence encoding the HA-tag.

```
GTGGACATCTACCCATACGACGTTCCAGATTACGCTGGC.
```

SEQ ID No. 42:

Amino acid sequence of a HA-tag comprising N-terminal and C-terminal additional amino acids. The underlined amino acid residues show the sequence of the HA-tag.

```
VDIYPYDVPDYAG
```

ADDITIONAL REFERENCES AS DISCUSSED HEREIN

1. Arzumanyan, A., H. M. Reis, and M. A. Feitelson. 2013. Pathogenic mechanisms in HBV- and HCV-associated hepatocellular carcinoma. Nature reviews. Cancer 13:123-135.
2. Block, T. M., H. Guo, and J. T. Guo. 2007. Molecular virology of hepatitis B virus for clinicians. Clin Liver Dis 11:685-706, vii.
3. Cai, D., C. Mills, W. Yu, R. Yan, C. E. Aldrich, J. R. Saputelli, W. S. Mason, X. Xu, J. T. Guo, T. M. Block, A. Cuconati, and H. Guo. 2012. Identification of disubstituted sulfonamide compounds as specific inhibitors of hepatitis B virus covalently closed circular DNA formation. Antimicrob Agents Chemother 56:4277-4288.
4. Cai, D., H. Nie, R. Yan, J. T. Guo, T. M. Block, and H. Guo. 2013. A southern blot assay for detection of hepatitis B virus covalently closed circular DNA from cell cultures. Methods Mol Biol 1030:151-161.
5. Galibert, F., E. Mandart, F. Fitoussi, and P. Charnay. 1979. Nucleotide sequence of the hepatitis B virus genome (subtype ayw) cloned in *E. coli*. Nature 281:646-650.
6. Gish, R. G., A. S. Lok, T. T. Chang, R. A. de Man, A. Gadano, J. Sollano, K. H. Han, Y. C. Chao, S. D. Lee, M. Harris, J. Yang, R. Colonno, and H. Brett-Smith. 2007. Entecavir therapy for up to 96 weeks in patients with HBeAg-positive chronic hepatitis B. Gastroenterology 133:1437-1444.
7. Guo, H., D. Jiang, T. Zhou, A. Cuconati, T. M. Block, and J. T. Guo. 2007. Characterization of the intracellular deproteinized relaxed circular DNA of hepatitis B virus: an intermediate of covalently closed circular DNA formation. J Virol 81:12472-12484.
8. Hirt, B. 1967. Selective extraction of polyoma DNA from infected mouse cell cultures. J Mol Biol 26:365-369.
9. Hoofnagle, J. H., E. Doo, T. J. Liang, R. Fleischer, and A. S. Lok. 2007. Management of hepatitis B: summary of a clinical research workshop. Hepatology 45:1056-1075.
10. Ito, K., K. H. Kim, A. S. Lok, and S. Tong. 2009. Characterization of genotype-specific carboxyl-terminal cleavage sites of hepatitis B virus e antigen precursor and identification of furin as the candidate enzyme. J Virol 83:3507-3517.
11. Ladner, S. K., M. J. Otto, C. S. Barker, K. Zaifert, G. H. Wang, J. T. Guo, C. Seeger, and R. W. King. 1997. Inducible expression of human hepatitis B virus (HBV) in stably transfected hepatoblastoma cells: a novel system for screening potential inhibitors of HBV replication. Antimicrob Agents Chemother 41:1715-1720.
12. Liang, T. J. 2009. Hepatitis B: the virus and disease. Hepatology 49:S13-21.
13. Liu, N., L. Ji, M. L. Maguire, and D. D. Loeb. 2004. cis-Acting sequences that contribute to the synthesis of relaxed-circular DNA of human hepatitis B virus. J Virol 78:642-649.
14. McMahon, B. J. 2014. Chronic hepatitis B virus infection. The Medical clinics of North America 98:39-54.
15. Nassal, M. 2008. Hepatitis B viruses: reverse transcription a different way. Virus Res 134:235-249.
16. Pawlotsky, J. M., G. Dusheiko, A. Hatzakis, D. Lau, G. Lau, T. J. Liang, S. Locarnini, P. Martin, D. D. Richman, and F. Zoulim. 2008. Virologic monitoring of hepatitis B virus therapy in clinical trials and practice: recommendations for a standardized approach. Gastroenterology 134: 405-415.
17. Protzer, U., M. Nassal, P. W. Chiang, M. Kirschfink, and H. Schaller. 1999. Interferon gene transfer by a hepatitis B virus vector efficiently suppresses wild-type virus infection. Proc Natl Acad Sci USA 96:10818-10823.
18. Quasdorff, M., and U. Protzer. 2010. Control of hepatitis B virus at the level of transcription. J Viral Hepat 17:527-536.
19. Seeger, C., and W. S. Mason. 2000. Hepatitis B virus biology. Microbiol Mol Biol Rev 64:51-68.
20. Sells, M. A., M. Chen, and G. Acs. 1987. Production of hepatitis B virus particles in hepG2 cells transfected with cloned hepatitis B virus DNA. Proc. Natl. Acad. Sci. USA 84:1005-1009.
21. Wang, J., A. S. Lee, and J. H. Ou. 1991. Proteolytic conversion of hepatitis B virus e antigen precursor to end product occurs in a postendoplasmic reticulum compartment. J Virol 65:5080-5083.
22. Wang, Z., L. Wu, X. Cheng, S. Liu, B. Li, H. Li, F. Kang, J. Wang, H. Xia, C. Ping, M. Nassal, and D. Sun. 2013. Replication-competent infectious hepatitis B virus vectors carrying substantially sized transgenes by redesigned viral polymerase translation. PLoS One 8:e60306.
23. Zhou, T., H. Guo, J. T. Guo, A. Cuconati, A. Mehta, and T. M. Block. 2006. Hepatitis B virus e antigen production is dependent upon covalently closed circular (ccc) DNA in HepAD3 8 cell cultures and may serve as a cccDNA surrogate in antiviral screening assays. Antiviral Res 72:116-124.
24. Zoulim, F., and S. Locarnini. 2009. Hepatitis B virus resistance to nucleos(t)ide analogues. Gastroenterology 137:1593-1608 e1591-1592.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

In accordance with the above and as also laid down in the appended claims, the present invention relates in particular to the following items:

1. A method for assessing the capacity of a candidate molecule to inhibit covalently closed circular (ccc) DNA of a hepadnavirus comprising the steps of (a) contacting a cell comprising a nucleic acid molecule comprising a nucleic acid sequence encoding a tagged hepadnavirus e antigen with said candidate molecule;
(b) assessing the level of the tagged hepadnavirus e antigen; and
(c) selecting a candidate molecule when the level of tagged hepadnavirus e antigen is decreased compared to a control.

2. The method of item 1, wherein said hepadnavirus is Hepatitis B virus (HBV) and wherein said hepadnavirus e antigen is Hepatitis B virus e antigen (HBeAg).
3. The method of item 1 or 2, wherein said tagged hepadnavirus e antigen contains only one tag.
4. The method of item 3, wherein said tag consists of 6 to 22 amino acids.
5. The method of item 3 or 4, wherein said tag is selected from the group consisting of a hemagglutinin (HA) tag, His-tag, Flag-tag, c-myc-tag, V5-tag and C9-tag.
6. The method of item 5, wherein said Flag-tag is 1×Flag-tag or 3×Flag-tag.
7. The method of item 1 or 2, wherein said tagged hepadnavirus e antigen contains two or more tags.
8. The method of item 7, wherein said two or more tags are different tags.
9. The method of item 7 or 8, wherein said tag consists of 6 to 22 amino acids.
10. The method of any one of itemss 7 to 9, wherein said two or more tags are two or more of a hemagglutinin (HA)-tag, His-tag, Flag-tag, c-myc-tag, V5-tag and/or C9-tag.
11. The method of item 10, wherein said Flag-tag is 1×Flag-tag or 3×Flag-tag.
12. The method of item 5 or 10,
wherein the nucleic acid sequence encoding the HA tag is shown in SEQ ID NO: 1;
wherein the nucleic acid sequence encoding the His-tag is shown in SEQ ID NO: 2;
wherein the nucleic acid sequence encoding the c-myc-tag is shown in SEQ ID NO: 4;
wherein the nucleic acid sequence encoding the V5-tag is shown in SEQ ID NO: 5;
and/or wherein the nucleic acid sequence encoding the C9-tag is shown in SEQ ID NO: 6.
13. The method of item 6 or 11, wherein the nucleic acid sequence encoding the 1×Flag-tag is shown in SEQ ID NO: 3; or wherein the nucleic acid sequence encoding the 3×Flag-tag is shown in SEQ ID NO: 7.
14. The method of item 5 or 10,
wherein the amino acid sequence of the HA tag is shown in SEQ ID NO: 8;
wherein the amino acid sequence of the His-tag is shown in SEQ ID NO: 9; wherein the
amino acid sequence of the c-myc-tag is shown in SEQ ID NO: 11;
wherein the amino acid sequence of the V5-tag is shown in SEQ ID NO: 12; and/or
wherein the amino acid sequence of the C9-tag is shown in SEQ ID NO: 13.
15. The method of item 6 or 11,
wherein the amino acid sequence of the 1×Flag-tag is shown in SEQ ID NO: 10; or
wherein the amino acid sequence of the 3×Flag-tag is shown in SEQ ID NO: 14.
16. The method of any one of items 2 to 15, wherein the nucleic acid sequence encoding the HBeAg is shown in SEQ ID NO: 16.
17. The method of any one of items 2 to 15, wherein the amino acid sequence of the HBeAg is shown in SEQ ID NO: 18.
18. The method of any one of items 1 to 17, wherein the nucleic acid molecule comprises a nucleic acid sequence encoding a hepadnavirus precore protein.
19. The method of item 18, wherein the nucleic acid sequence encoding a hepadnavirus precore protein is shown in SEQ ID NO: 15.
20. The method of item 18, wherein the amino acid sequence of the hepadnavirus precore protein is shown in SEQ ID NO: 17.
21. The method of any one of items 1 to 17, wherein the nucleic acid molecule comprises a nucleic acid sequence encoding the one or more tag, wherein said sequence is 3' downstream of the nucleic acid sequence encoding the N-terminal signal peptide and linker of the hepadnavirus precore protein.
22. The method of item 21, wherein said nucleic acid sequence encoding the one or more tag is 3' downstream of the nucleic acid sequence encoding the N-terminal 29 amino acids of a hepatitis B virus precore protein.
23. The method of any one of items 1 to 22, wherein the nucleic acid molecule comprises a hepadnavirus genome.
24. The method of item 23, wherein said hepadnavirus genome is a Hepatitis B virus (HBV) genome.
25. The method of item 24, wherein said HBV genome is the genome of HBV genotype A, B, C, D, E, F, G or H.
26. The method of item 24, wherein said HBV genome is the genome of HBV genotype D.
27. The method of item 26, wherein said genome of HBV genotype D is a genome of HBV subgenotype ayw.
28. The method of any one of items 1 to 27, wherein the nucleic acid encoding the one or more tag is 5' upstream of a nucleic acid encoding a hepadnavirus core protein.
29. The method of item 28, wherein the hepadnavirus core protein is a HBV core protein.
30. The method of item 29, wherein the nucleic acid encoding the HBV core protein is shown in SEQ ID NO: 23.
31. The method of item 29, wherein the amino acid sequence of the HBV core protein is shown in SEQ ID NO: 24.
32. The method of any one of items 1 to 31, wherein the nucleic acid molecule comprising a sequence encoding the one or more tag is inserted into the epsilon structure as encoded by a hepadnavirus genome.
33. The method of item 32, wherein the hepadnavirus genome is a HBV genome.
34. The method of item 33, wherein the nucleic acid sequence of the epsilon structure as encoded by a HBV genome is shown in SEQ ID NO: 25.
35. The method of any one of items 1 to 34, wherein the nucleic acid molecule comprising a sequence encoding the one or more tag is inserted into the lower stem of the epsilon structure as encoded by a hepadnavirus genome.
36. The method of item 35, wherein the hepadnavirus genome is a HBV genome.
37. The method of any one of items 1 to 36, wherein the nucleic acid molecule comprising a sequence encoding the one or more tag is inserted between nucleotides corresponding to position C1902 and position A1903 of the HBV genome.
38. The method of any one of items 1 to 37, wherein the nucleic acid molecule comprises 5' of the sequence encoding the one or more tag a sequence that is capable of forming base pairs with the lower stem of the epsilon structure as encoded by a hepadnavirus genome.

39. The method of item 38, wherein the sequence that is capable of forming base pairs with the lower stem of the epsilon structure as encoded by a hepadnavirus genome is capable of forming base pairs with nucleotides corresponding to positions T1849 to A1854 of the HBV genome.
40. The method of item 38 or 39, wherein the sequence that is capable of forming base pairs with the lower stem of the epsilon structure as encoded by a hepadnavirus genome consists of up to 9 nucleotides.
41. The method of item 40, wherein the sequence that is capable of forming base pairs with the lower stem of the epsilon structure as encoded by a hepadnavirus genome consists of the sequence shown in SEQ ID No. 26; or wherein the sequence that is capable of forming base pairs with the lower stem of the epsilon structure as encoded by a hepadnavirus genome encodes a polypeptide as shown in SEQ ID NO. 40.
42. The method of any one of items 1 to 41, wherein the nucleic acid molecule comprises 3' of the sequence encoding the one or more tag a sequence encoding a linker.
43. The method of item 42, wherein said linker consists of one or more amino acid residues.
44. The method of item 42, wherein said linker consists of only one amino acid residues.
45. The method of item 44, wherein said amino acid is a glycine residue.
46. The method of any one of items 42 to 44, wherein said sequence encoding a linker consists of the sequence GGC; or wherein said sequence encodes a glycine residue.
47. The method of any one of items 1 to 46, wherein the nucleic acid molecule comprising
  a nucleic acid sequence encoding a tagged hepadnavirus e antigen comprises a nucleic acid sequence as shown in SEQ ID NO. 41; or
  wherein the nucleic acid molecule comprising a nucleic acid sequence encoding atagged hepadnavirus e antigen comprises a nucleic acid sequence encoding an amino acid sequence as shown in SEQ ID NO. 42.
48. The method of any one of items 1 to 47, wherein said one or more tag is fused in frame into the hepadnavirus e antigen.
49. The method of item 48, wherein the hepadnavirus e antigen is Hepatitis B virus e antigen (HBeAg).
50. The method of any one of items 2 to 49, wherein the nucleic acid sequence encoding the tagged HBeAg is shown in SEQ ID NO: 20.
51. The method of any one of items 2 to 50, wherein the amino acid sequence of the tagged HBeAg is shown in SEQ ID NO: 22.
52. The method of any one of items 2 to 51, wherein the nucleic acid sequence encoding a tagged HBV precore protein is shown in SEQ ID NO: 19.
53. The method of any one of items 2 to 52, wherein the amino acid sequence of the tagged HBV precore protein is shown in SEQ ID NO: 21.
54. The method of any one of items 24 to 53, wherein the nucleic acid sequence of the HBV genome is shown in any one of SEQ ID NO: 27, 28, 29, 30, 31, 32, 33 or 34.
55. The method of any one of items 23 to 54, wherein the nucleic acid is transcriptable into pregenomic (pg) hepadnavirus RNA, in particular pregenomic (pg) HBV RNA.
56. The method of any one of items 1 to 55, wherein said nucleic acid prevents the translation of the tagged hepadnavirus e antigen.
57. The method of item 56, wherein said nucleic acid does not contain a start codon ATG 5' upstream of the nucleic acid encoding a tagged hepadnavirus e antigen.
58. The method of item 56 or 57, wherein a start codon ATG 5' upstream of the nucleic acid encoding a tagged hepadnavirus e antigen has been replaced by the nucleic acids TG.
59. The method of any one of items 56 to 58, wherein said nucleic has been modified by point mutation in order to prevent the translation of a tagged hepadnavirus e antigen.
60. The method of any one of items 1 to 59, wherein the nucleic acid molecule comprising a nucleic acid sequence encoding the tagged hepadnavirus e antigen is comprised in a vector.
61. The method of item 60, wherein the vector comprises a sequence as shown in SEQ ID NO: 35.
62. The method of any one of items 1 to 61, wherein the nucleic acid molecule comprising a nucleic acid sequence encoding the tagged hepadnavirus e antigen is under control of an inducible promoter.
63. The method of any one of items 56 to 62, wherein the hepadnavirus e antigen is Hepatitis B virus e antigen (HBeAg).
64. The method of item 62 or 63, wherein the inducible promoter is a tetracycline-inducible promoter, a doxycline-inducible promoter, an antibiotic-inducible promoter, a copper-inducible promoter, an alcohol-inducible promoter, a steroid-inducible promoter, or a herbicide-inducible promoter.
65. The method of any one of items 62 to 64, wherein the inducible promoter is a CMV promoter or a tet-EF-1 alpha promoter.
66. The method of any one of items 23 to 65, wherein one or more stop codons are introduced into the coding region of one or more hepadnavirus envelope proteins.
67. The method of item 66, wherein said one or more hepadnavirus envelope proteins is/are one or more HBV envelope proteins.
68. The method of item 67, wherein the one or more HBV envelope protein is one or more of large surface protein (L), middle surface protein (M) and small surface protein (S).
69. The method of item 67, wherein the HBV envelope protein is small surface protein (S).
70. The method of any one of items 67 to 69, wherein the coding region of the one or more HBV envelope proteins is shown in SEQ ID NO: 36 (L), SEQ ID NO: 37 (M) and/or SEQ ID NO: 38 (S).
71. The method of item 70, wherein the HBV nucleotides 217 to 222 (TTGTTG) of SEQ ID NO: 38 (S) are mutated to TAGTAG to prevent the expression of envelope proteins.
72. The method of any one of items 1 to 71, wherein the cell is a eukaryotic cell.
73. The method of item 72, wherein the eukaryotic cell is of hepatocyte origin.
74. The method of item 72 or 73, wherein the eukaryotic cell is a hepatoma cell or is derived from a hepatoma cell.
75. The method of any one of items 72 to 74, wherein the eukaryotic cell is HepG2 (ATCC #HB-8065).
76. The method of any one of items 1 to 75, wherein the nucleic acid molecule or the vector comprising same is stably integrated in the genome of the cell.
77. The method of any one of items 1 to 76, wherein said step (a) further comprises a step (aa) which comprises culturing a cell comprising a nucleic acid molecule comprising a nucleic acid sequence encoding a tagged hepadnavirus e antigen in conditions allowing
(i) the synthesis of hepadnavirus pregenomic (pg) RNA;
(ii) the reverse transcription of said synthesized pgRNA into a minus strand DNA;
(iii) the synthesis of a second plus strand DNA so that said minus strand DNA and said plus strand DNA form a double stranded relaxed circular DNA;
(iv) formation of cccDNA from said relaxed circular double stranded DNA;
(v) optionally restoration of conditions allowing the translation of the tagged hepadnavirus e antigen;
(vi) transcription of an mRNA encoding a tagged hepadnavirus e antigen;
(vii) translation of a tagged hepadnavirus e antigen.

78. The method of item 77, wherein the restoration of conditions allowing the translation of the tagged hepadnavirus e antigen is the restoration of the start codon.
79. The method of any one of items 1 to 78, wherein said method is for assessing the capacity of a candidate molecule to inhibit the formation of ccc DNA of a hepadnavirus.
80. The method of item 79, wherein the cell is contacted with the candidate molecule before cccDNA has formed.
81. The method of any one of items 1 to 78, wherein said method is for assessing the capacity of a candidate molecule to decrease the amount or number of ccc DNA of a hepadnavirus.
82. The method of any one of items 1 to 78, wherein said method is for assessing the capacity of a candidate molecule to decrease the transcription of ccc DNA of a hepadnavirus.
83. The method of item 81 or 82, wherein the cell is contacted with the candidate molecule after cccDNA has formed.
84. The method of any one of items 1 to 83, wherein assessing the level of the tagged hepadnavirus e antigen according to step (b) is performed by ELISA, CLIA or AlphaLISA.
85. The method of any one of items 1 to 84, wherein assessing the level of the tagged hepadnavirus e antigen according to step (b) comprises the use of an antibody specifically recognizing said hepadnavirus e antigen and one or more antibodies specifically recognizing the one or more tags.
86. The method of any one of items 77 to 85, wherein said hepadnavirus is Hepatitis B virus (HBV) and wherein said hepadnavirus e antigen is Hepatitis B virus e antigen (HBeAg).
87. A nucleic acid molecule comprising a nucleic acid sequence encoding a tagged hepadnavirus e antigen.
88. The nucleic acid molecule of item 87, wherein said hepadnavirus e antigen is Hepatitis B virus e antigen (HBeAg).
89. The nucleic acid molecule of item 87 or 88, wherein said tagged hepadnavirus e antigen contains only one tag.
90. The nucleic acid molecule of item 89, wherein said tag consists of 6 to 22 amino acids.
91. The nucleic acid molecule of item 89 or 90, wherein said tag is selected from the group consisting of a hemagglutinin (HA) tag, His-tag, Flag-tag, c-myc-tag, V5-tag and C9-tag.
92. The nucleic acid molecule of item 91, wherein said Flag-tag is a 1×Flag-tag or a 3×Flag-tag.
93. The nucleic acid molecule of item 87 or 88, wherein said tagged hepadnavirus e antigen contains two or more tags.
94. The nucleic acid molecule of item 93, wherein said two or more tags are different tags.
95. The nucleic acid molecule of item 93 or 94, wherein the entire length of said two or more tags is of from 14 to 31 amino acids.
96. The nucleic acid molecule of any one of items 93 to 95, wherein said two or more tag are two or more of a hemagglutinin (HA) tag, His-tag, Flag-tag, c-myc-tag, V5-tag and/or C9-tag.
97. The nucleic acid molecule of item 96, wherein said Flag-tag is a 1×Flag-tag or a 3×Flag-tag.
98. The nucleic acid molecule of any one of items 91 or 96,
wherein the nucleic acid sequence encoding the HA tag is shown in SEQ ID NO: 1;
wherein the nucleic acid sequence encoding the His-tag is shown in SEQ ID NO: 2;
wherein the nucleic acid sequence encoding the c-myc-tag is shown in SEQ ID NO: 4;
wherein the nucleic acid sequence encoding the V5-tag is shown in SEQ ID NO: 5;
and/or wherein the nucleic acid sequence encoding the C9-tag is shown in SEQ ID NO: 6.
99. The nucleic acid molecule of item 92 or 97,
wherein the nucleic acid sequence encoding the 1×Flag-tag is shown in SEQ ID NO: 3; or
wherein the nucleic acid sequence encoding the 3×Flag-tag is shown in SEQ ID NO: 7.
100. The nucleic acid molecule of item 91 or 96,
wherein the amino acid sequence of the HA tag is shown in SEQ ID NO: 8;
wherein the amino acid sequence of the His-tag is shown in SEQ ID NO: 9;
wherein the amino acid sequence of the c-myc-tag is shown in SEQ ID NO: 11;
wherein the amino acid sequence of the V5-tag is shown in SEQ ID NO: 12; and/or
wherein the amino acid sequence of the C9-tag is shown in SEQ ID NO: 13.
101. The nucleic acid molecule of item 92 or 97,
wherein the amino acid sequence of the 1×Flag-tag is shown in SEQ ID NO: 10; or
wherein the amino acid sequence of the 3×Flag-tag is shown in SEQ ID NO: 14.
102. The nucleic acid molecule of any one of items 88 to 101, wherein the nucleic acid sequence encoding the HBeAg is shown in SEQ ID NO: 16.
103. The nucleic acid molecule of any one of items 88 to 101, wherein the amino acid sequence of the HBeAg is shown in SEQ ID NO: 18.
104. The nucleic acid molecule of any one of items 87 to 103, wherein the nucleic acid molecule comprises a nucleic acid sequence encoding a hepadnavirus precore protein.
105. The nucleic acid molecule of item 104, wherein the nucleic acid sequence encoding a hepadnavirus precore protein is shown in SEQ ID NO: 15.
106. The nucleic acid molecule of item 104, wherein the amino acid sequence of the hepadnavirus precore protein is shown in SEQ ID NO: 17.
107. The nucleic acid molecule of any one of items 87 to 106, wherein the nucleic acid molecule comprises a nucleic acid sequence encoding the one or more tag, wherein said sequence is 3' downstream of the nucleic acid sequence encoding the N-terminal signal peptide and linker (the “precore” region) of the hepadnavirus precore protein.

108. The method of item 107, wherein said nucleic acid sequence encoding the one or more tag is 3' downstream of the nucleic acid sequence encoding the N-terminal 29 amino acids of a hepatitis B virus precore protein.
109. The nucleic acid molecule of any one of items 87 to 108, wherein the nucleic acid molecule comprises a hepadnavirus genome.
110. The nucleic acid molecule of item 109, wherein said hepadnavirus genome is a Hepatitis B virus (HBV) genome.
111. The nucleic acid molecule of item 110, wherein said HBV genome is the genome of HBV genotype A, B, C, D, E, F, G or H.
112. The nucleic acid molecule of item 110, wherein said HBV genome is the genome of HBV genotype D.
113. The nucleic acid molecule of item 112, wherein said genome of HBV genotype D is a genome of HBV subgenotype ayw.
114. The nucleic acid molecule of any one of items 87 to 113, wherein the nucleic acid encoding the one or more tag is 5' upstream of the nucleic acid encoding a hepadnavirus core protein.
115. The nucleic acid molecule of item 114, wherein the nucleic acid sequence encodes a HBV core protein.
116. The nucleic acid molecule of item 115, wherein the nucleic acid sequence encoding a HBV core protein is shown in SEQ ID NO: 23.
117. The nucleic acid molecule of item 114, wherein the core protein is a HBV core protein.
118. The nucleic acid molecule of item 116, wherein the amino acid sequence of the HBV core protein is shown in SEQ ID NO: 24.
119. The nucleic acid molecule of any one of items 87 to 118, wherein the nucleic acid molecule comprising a sequence encoding the one or more tag is inserted into the epsilon structure as encoded by a hepadnavirus genome.
120. The nucleic acid molecule of item 119, wherein said hepadnavirus genome is a HBV genome.
121. The nucleic acid molecule of item 120, wherein the nucleic acid sequence of the epsilon structure as encoded by a HBV genome is shown in SEQ ID NO: 25.
122. The nucleic acid molecule of any one of items 87 to 121, wherein the nucleic acid molecule comprising a sequence encoding the one or more tag is inserted into the lower stem of the epsilon structure as encoded by a hepadnavirus genome.
123. The nucleic acid molecule of item 122, wherein said hepadnavirus genome is a HBV genome.
124. The nucleic acid molecule of any one of items 87 to 123, wherein the nucleic acid molecule comprising a sequence encoding the one or more tag is inserted between nucleotides corresponding to position C1902 and A1903 of the HBV genome.
125. The nucleic acid molecule of any one of items 87 to 124, wherein the nucleic acid molecule comprises 5' of the sequence encoding the one or more tag a sequence that is capable of forming base pairs with the lower stem of the epsilon structure as encoded by a hepadnavirus genome.
126. The nucleic acid molecule of item 125, wherein the sequence that is capable of forming base pairs with the lower stem of the epsilon structure as encoded by a hepadnavirus genome is capable of form base pairs with nucleotides corresponding to positions T1849 to A1854 of the HBV genome.
127. The nucleic acid molecule of item 125 or 126, wherein the sequence that is capable of forming base pairs with the lower stem of the epsilon structure as encoded by a hepadnavirus genome consists of up to 9 nucleotides.
128. The nucleic acid molecule of item 127, wherein the sequence that is capable of forming base pairs with the lower stem of the epsilon structure as encoded by a hepadnavirus genome consists of the sequence shown in SEQ ID No. 26; or wherein the sequence that is capable of forming base pairs with the lower stem of the epsilon structure as encoded by a hepadnavirus genome encodes a polypeptide as shown in SEQ ID NO. 40.
129. The nucleic acid molecule of any one of items 87 to 128, wherein the nucleic acid molecule comprises 3' of the sequence encoding the one or more tag a sequence encoding a linker.
130. The nucleic acid molecule of item 129, wherein said linker consists of one or more amino acid residues.
131. The nucleic acid molecule of item 129, wherein said linker consists of only one amino acid residues.
132. The nucleic acid molecule of item 131, wherein said amino acid is a glycine residue.
133. The nucleic acid molecule of any one of items 129 to 131, wherein said sequence encoding a linker consists of the sequence GGC; or wherein said sequence encodes a glycine residue.
134. The nucleic acid molecule of any one of items 87 to 133, wherein the nucleic acid molecule comprising a nucleic acid sequence encoding a tagged hepadnavirus e antigen comprises a nucleic acid sequence as shown in SEQ ID NO. 41; or
wherein the nucleic acid molecule comprising a nucleic acid sequence encoding a tagged hepadnavirus e antigen comprises a nucleic acid sequence encoding an amino acid sequence as shown in SEQ ID NO. 42
135. The nucleic acid molecule of any one of items 87 to 134, wherein said one or more tag is fused in frame in the hepadnavirus e antigen.
136. The nucleic acid molecule of item 135, wherein said hepadnavirus e antigen is Hepatitis B virus e antigen (HBeAg).
137. The nucleic acid molecule of any one of items 88 to 136, wherein the nucleic acid sequence encoding the tagged HBeAg is shown in SEQ ID NO: 20.
138. The nucleic acid molecule of any one of items 88 to 137, wherein the amino acid sequence of the tagged HBeAg is shown in SEQ ID NO: 22.
139. The nucleic acid molecule of any one of items 88 to 138, wherein the nucleic acid sequence encoding the tagged HBV precore protein is shown in SEQ ID NO: 19.
140. The nucleic acid molecule of any one of items 88 to 139, wherein the amino acid sequence of the tagged HBV precore protein is shown in SEQ ID NO: 21.
141. The nucleic acid molecule of any one of items 110 to 140, wherein the nucleic acid sequence of the HBV genome is shown in any one of SEQ ID NO: 27, 28, 29, 30, 31, 32, 33 or 34.
142. The nucleic acid molecule of any one of items 109 to 141, wherein the nucleic acid is transcriptable into pregenomic (pg) hepadnavirus RNA.
143. The nucleic acid molecule of item 142, wherein said hepadnavirus RNA is HBV RNA.
144. The nucleic acid molecule of any one of items 87 to 143, wherein the nucleic acid molecule comprising a nucleic acid sequence encoding the tagged hepadnavirus e antigen is comprised in a vector.
145. The nucleic acid molecule of item 144, wherein said hepadnavirus e antigen is Hepatitis B virus e antigen (HBeAg)

146. The nucleic acid molecule of any one of items 87 to 145, wherein said nucleic acid allows the translation of the tagged hepadnavirus e antigen.
147. The nucleic acid molecule of item 146, wherein said hepadnavirus e antigen is Hepatitis B virus e antigen (HBeAg).
148. The nucleic acid molecule of item 147, wherein the nucleic acid is comprised in a vector that comprises a sequence as shown in SEQ ID NO: 39.
149. The nucleic acid molecule of any one of items 87 to 148, wherein said nucleic acid prevents the translation of the tagged hepadnavirus e antigen.
150. The nucleic acid molecule of item 149, wherein said nucleic acid does not contain a start codon ATG 5' upstream of the nucleic acid encoding a tagged hepadnavirus e antigen.
151. The nucleic acid molecule of item 147 or 150, wherein a start codon ATG 5' upstream of the nucleic acid encoding a tagged hepadnavirus e antigen has been replaced by the nucleic acids TG.
152. The nucleic acid molecule of any one of items 147 to 151, wherein said nucleic has been modified by point mutation in order to prevent the translation of a tagged hepadnavirus e antigen.
153. The nucleic acid molecule of any one of items 144, 145 and 149 to 152, wherein the vector comprises a sequence as shown in SEQ ID NO: 35.
154. The nucleic acid molecule of any one of items 87 to 153, wherein the nucleic acid molecule comprising a nucleic acid sequence encoding the tagged hepadnavirus e antigen is under control of an inducible promoter.
155. The nucleic acid molecule of any one of items 149 to 154, wherein the hepadnavirus e antigen is Hepatitis B virus e antigen (HBeAg).
156. The nucleic acid molecule of item 154 or 155, wherein the inducible promoter is a tetracycline-inducible promoter, a doxycline-inducible promoter, an antibiotic-inducible promoter, a copper-inducible promoter, an alcohol-inducible promoter, a steroid-inducible promoter, or a herbicide-inducible promoter.
157. The nucleic acid molecule of any one of items 154 to 156, wherein the inducible promoter is a CMV promoter or a tet-EF-1 alpha promoter.
158. The nucleic acid molecule of any one of items 110 to 157, wherein one or more stop codons are introduced into the coding region of one or more hepadnavirus envelope proteins.
159. The nucleic acid molecule of item 158, wherein said one or more hepadnavirus envelope proteins is/are one or more HBV envelope proteins.
160. The nucleic acid molecule of item 159, wherein the one or more HBV envelope protein is one or more of L, M and/or S.
161. The nucleic acid molecule of item 159, wherein the HBV envelope protein is S.
162. The nucleic acid molecule of any one of items 159 to 161, wherein the coding region of the one or more HBV envelope proteins is shown in SEQ ID NO: 36 (L), 37 (M) or 38 (S).
163. The nucleic acid molecule of item 162, wherein the HBV nucleotides 217 to 222 (TTGTTG) of SEQ ID NO: 38 (S) are mutated to TAGTAG to prevent the expression of envelope proteins.
164. A protein encoded by the nucleic acid molecule as defined in any one of items 87 to 163.
165. A protein comprising a tagged hepadnavirus e antigen.
166. The protein of item 165, wherein said hepadnavirus e antigen is Hepatitis B virus e antigen (HBeAg).
167. The protein of item 166, wherein the Hepatitis B virus e antigen (HBeAg) comprises an amino acid sequence as shown in SEQ ID NO: 18.
168. The protein of any one of items 165 to 167, wherein said tagged hepadnavirus e antigen contains only one tag.
169. The protein of item 168, wherein said tag consists of 6 to 22 amino acids.
170. The protein of any one of items 165 to 169, wherein said tag is selected from the group consisting of a hemagglutinin (HA) tag, His-tag, Flag-tag, c-myc-tag, V5-tag and C9-tag.
171. The protein of item 170, wherein said Flag-tag is a 1×Flag-tag or a 3×Flag-tag.
172. The protein of any one of items 165 to 167, wherein said tagged hepadnavirus e antigen contains two or more tags.
173. The protein of item 172, wherein said two or more tags are different tags.
174. The protein of item 172 or 173, wherein the entire length of said two or more tags is of from 14 to 31 amino acids.
175. The protein of any one of items 172 to 174, wherein said two or more tag are two or more of a hemagglutinin (HA) tag, His-tag, Flag-tag, c-myc-tag, V5-tag and/or C9-tag.
176. The protein of item 175, wherein said Flag-tag is a 1×Flag-tag or a 3×Flag-tag.
177. The protein of item 170 or 175,
wherein the nucleic acid sequence encoding the HA tag is shown in SEQ ID NO: 1;
wherein the nucleic acid sequence encoding the His-tag is shown in SEQ ID NO: 2;
wherein the nucleic acid sequence encoding the c-myc-tag is shown in SEQ ID NO: 4;
wherein the nucleic acid sequence encoding the V5-tag is shown in SEQ ID NO: 5;
and/or wherein the nucleic acid sequence encoding the C9-tag is shown in SEQ ID NO: 6.
178. The protein of item 171 or 176,
wherein the nucleic acid sequence encoding the 1×Flag-tag is shown in SEQ ID NO: 3; or
wherein the nucleic acid sequence encoding the 3×Flag-tag is shown in SEQ ID NO: 7.
179. The protein of item 170 or 175,
wherein the amino acid sequence of the HA tag is shown in SEQ ID NO: 8;
wherein the amino acid sequence of the His-tag is shown in SEQ ID NO: 9;
wherein the amino acid sequence of the c-myc-tag is shown in SEQ ID NO: 11;
wherein the amino acid sequence of the V5-tag is shown in SEQ ID NO: 12; and/or
wherein the amino acid sequence of the C9-tag is shown in SEQ ID NO: 13.
180. The protein of item 171 or 176,
wherein the amino acid sequence of the 1×Flag-tag is shown in SEQ ID NO: 10; or
wherein the amino acid sequence of the 3×Flag-tag is shown in SEQ ID NO: 14.
181. The protein of any one of items 165 to 180, comprising a hepadnavirus precore protein.
182. The protein of item 181, wherein the nucleic acid sequence encoding a hepadnavirus precore protein is shown in SEQ ID NO: 15.

183. The protein of item 181, wherein the amino acid sequence of the hepadnavirus precore protein is shown in SEQ ID NO: 17.

184. The protein of any one of items 165 to 183, wherein the protein comprises an amino acid sequence of the one or more tag, wherein said sequence is C-terminal of the amino acid sequence of the sequence of the signal peptide and of the linker of the hepadnavirus precore protein.

185. The protein of item 184, wherein said protein comprising an amino acid sequence of the one or more tag is C-terminal of the amino acid sequence of the N-terminal 29 amino acids of a hepatitis B virus precore protein.

186. The protein of any one of items 165 to 183, wherein protein comprises an amino acid sequence of the one or more tag, wherein said sequence is N-terminal of an amino acid sequence of a hepadnavirus core protein.

187. The protein of item 186, wherein the hepadnavirus core protein is a HBV core protein.

188. The protein of item 187, wherein the nucleic acid encoding the HBV core protein is shown in SEQ ID NO: 23.

189. The protein of item 187, wherein the amino acid sequence of the HBV core protein is shown in SEQ ID NO: 24.

190. The protein of any one of items 165 to 189, wherein the amino acid sequence of the one or more tag is inserted into an amino acid sequence encoded by the epsilon structure as encoded by a hepadnavirus genome.

191. The protein of item 190, wherein the hepadnavirus genome is a HBV genome.

192. The protein of item 191, wherein the nucleic acid sequence of the epsilon structure as encoded by a HBV genome is shown in SEQ ID NO: 25.

193. The protein of any one of items 165 to 192, wherein the amino acid sequence of the one or more tag is inserted into an amino acid sequence encoded by the lower stem of the epsilon structure as encoded by a hepadnavirus genome.

194. The protein of item 193, wherein the hepadnavirus genome is a HBV genome.

195. The protein of any one of items 165 to 194, wherein the amino acid sequence of the one or more tag is inserted between amino acid residues corresponding to position G29 and position M30 of a HBV precore protein (such as the one as shown in SEQ ID NO. 17).

196. The protein of any one of items 165 to 195, further comprising N-terminal to the amino acid sequence of the one or more tag an amino acid sequence of up to 3 amino acids, wherein said amino acid sequence of up to 3 amino acids is encoded by a nucleic acid sequence that is capable of forming base pairs with the lower stem of the epsilon structure as encoded by a hepadnavirus genome.

197. The protein of item 196, wherein the nucleic sequence that is capable of forming base pairs with the lower stem of the epsilon structure as encoded by a hepadnavirus genome is capable of form base pairs with nucleotides corresponding to positions T1849 to A1854 of the HBV genome.

198. The protein of item 198, wherein the nucleic acid sequence that is capable of forming base pairs with the lower stem of the epsilon structure as encode by a hepadnavirus genome consists of the sequence shown in SEQ ID No. 26.

199. The protein of any one of items 196 to 198, wherein said amino acid sequence of up to 3 amino acids is shown in SEQ ID NO. 40.

200. The protein of any one of items 165 to 199, further comprising C-terminal to the amino acid sequence of the one or more tag a linker.

201. The protein of item 200, wherein said linker consists of one or more amino acid residues.

202. The protein of item 201, wherein said linker consists of only one amino acid residue.

203. The protein of item 202, wherein said amino acid is a glycine residue.

204. The protein of any one of items 1 to 46, wherein the amino acid sequence of a tagged hepadnavirus e antigen comprises an amino acid sequence encoded by a nucleic acid sequence as shown in SEQ ID NO. 41; or wherein the amino acid sequence of a tagged hepadnavirus e antigen comprises an amino acid sequence as shown in SEQ ID NO. 42

205. The protein of any one of items 165 to 204, wherein said one or more tag is fused in frame into the hepadnavirus e antigen.

206. The protein of item 205, wherein the hepadnavirus e antigen is Hepatitis B virus e antigen (HBeAg).

207. The protein of any one of items 166 to 206, wherein the nucleic acid sequence encoding the tagged HBeAg is shown in SEQ ID NO: 20.

208. The protein of any one of items 166 to 207, wherein the amino acid sequence of the tagged HBeAg is shown in SEQ ID NO: 22.

209. The protein of any one of items 166 to 208, wherein the nucleic acid sequence encoding a tagged HBV precore protein is shown in SEQ ID NO: 19.

210. The protein of any one of items 166 to 209, wherein the amino acid sequence of a tagged HBV precore protein is shown in SEQ ID NO: 21.

211. A host cell comprising the nucleic acid molecule of any one of items 87 to 163 or the protein of any one of items 164 to 210.

212. The host cell of item 211, wherein the cell is a eukaryotic cell.

213. The host cell of item 212, wherein the eukaryotic cell is of hepatocyte origin.

214. The host cell of item 212 or 213, wherein the eukaryotic cell is a hepatoma cell or is derived from a hepatoma cell.

215. The host cell of any one of items 212 to 214, wherein the eukaryotic cell is HepG2 (ATCC #HB-8065).

216. A process for the production of the protein as defined in any one of items 164 to 210, said process comprising culturing a host of any one of items 210 to 215 under conditions allowing the expression of the protein and recovering the produced protein from the culture.

217. Kit for use in the method of any one of items 1 to 86.

218. Kit comprising an antibody specifically recognizing a hepadnavirus antigen e as defined in any one of items 165 to 167 and one or more antibodies specifically recognizing one or more tags as defined in any one of items 168 to 180.

219. Use of the nucleic molecule of any one of items 87 to 163, the protein of any one of items 164 to 210 and/or the host cell of any one of items 211 to 215 for screening candidate molecules suspected to be capable of inhibiting covalently closed circular DNA of hepadnavirus.

The invention claimed is:

1. A method for assessing the capacity of a candidate molecule to inhibit covalently closed circular (ccc) DNA of a hepadnavirus comprising the steps of (a) contacting a cell comprising a nucleic acid molecule comprising a nucleic acid sequence encoding a tagged hepadnavirus e antigen with said candidate molecule; wherein the nucleic acid molecule comprises a sequence encoding one or more tags, wherein the sequence is inserted into the epsilon structure as encoded by a hepadnavirus genome, wherein said nucleic acid molecule comprising a sequence encoding the one or more tag is inserted between nucleotides corresponding to position C1902 and position A1903 of the HBV genome, wherein said nucleic acid molecule comprises 5' of the sequence encoding the one or more tag a sequence that is capable of forming base pairs with the lower stem of the epsilon structure as encoded by a hepadnavirus genome and wherein the sequence that is capable of forming base pairs with said lower stem of the epsilon structure as encoded by a hepadnavirus genome is capable of forming base pairs with nucleotides corresponding to positions T1849 to A1854 of the HBV genome;

(b) assessing the level of the tagged hepadnavirus e antigen; and (c) selecting a candidate molecule when the level of tagged hepadnavirus e antigen is decreased compared to a control.

2. The method of claim 1, wherein said hepadnavirus is Hepatitis B virus (HBV) and wherein said hepadnavirus e antigen is Hepatitis B virus e antigen (HBeAg).

3. The method of claim 1, wherein said tagged hepadnavirus e antigen contains only one tag; or wherein said tagged hepadnavirus e antigen contains two or more tags.

4. The method of claim 3, wherein said tag is selected from the group consisting of hemagglutinin (HA)-tag, His-tag, Flag-tag (like 1×Flag-tag or 3×Flag-tag), c-myc-tag, V5-tag and/or C9-tag.

5. The method of claim 4, wherein the nucleic acid sequence encoding the HA tag is shown in SEQ ID NO: 1;

wherein the nucleic acid sequence encoding the His-tag is shown in SEQ ID NO: 2;

wherein the nucleic acid sequence encoding the 1×Flag-tag is shown in SEQ ID NO: 3;

wherein the nucleic acid sequence encoding the 3×Flag-tag is shown in SEQ ID NO: 7;

wherein the nucleic acid sequence encoding the c-myc-tag is shown in SEQ ID NO: 4;

wherein the nucleic acid sequence encoding the V5-tag is shown in SEQ ID NO: 5; and/or wherein the nucleic acid sequence encoding the C9-tag is shown in SEQ ID NO: 6; or wherein the amino acid sequence of the HA tag is shown in SEQ ID NO: 8;

wherein the amino acid sequence of the His-tag is shown in SEQ ID NO: 9;

wherein the amino acid sequence of the 1×Flag-tag is shown in SEQ ID NO: 10;

wherein the amino acid sequence of the 3×Flag-tag is shown in SEQ ID NO: 14;

wherein the amino acid sequence of the c-myc-tag is shown in SEQ ID NO: 11;

wherein the amino acid sequence of the V5-tag is shown in SEQ ID NO: 2; and/or wherein the amino acid sequence of the C9-tag is shown in SEQ ID NO: 13.

6. The method of claim 1, wherein the nucleic acid molecule comprises a nucleic acid sequence encoding a hepadnavirus precore protein.

7. The method of claim 6, wherein the nucleic acid sequence encoding a hepadnavirus precore protein is the nucleic acid sequence of a hepatitis B virus precore protein as shown in SEQ ID NO: 15; or wherein the amino acid sequence of the hepadnavirus precore protein the amino acid sequence of a hepatitis B virus precore protein as shown in SEQ ID NO: 17.

8. The method of claim 6, wherein said nucleic acid sequence encoding the one or more tag is 3' downstream of the nucleic acid sequence encoding the N-terminal 29 amino acids of a hepatitis B virus precore protein.

9. The method of claim 1, wherein the nucleic acid molecule comprises a hepadnavirus genome, such as a Hepatitis B virus (HBV) genome as shown in any one of SEQ ID NO: 27, 28, 29, 30, 31, 32, 33 or 34.

10. The method of claim 9, wherein said HBV genome is a genome of HBV subgenotype ayw.

11. The method of claim 1, wherein the epsilon structure as encoded by a hepadnavirus genome is the epsilon structure as encoded by an HBV genome as shown in SEQ ID NO: 25.

12. The method of claim 1, wherein the sequence that is capable of forming base pairs with the lower stem of the epsilon structure as encoded by a hepadnavirus genome consists of the sequence shown in SEQ ID NO: 26; or wherein the sequence that is capable of forming base pairs with the lower stem of the epsilon structure as encoded by a hepadnavirus genome encodes a polypeptide as shown in SEQ ID NO: 40.

13. The method of claim 1, wherein the nucleic acid molecule comprising a nucleic acid sequence encoding a tagged hepadnavirus e antigen comprises a nucleic acid sequence as shown in SEQ ID NO: 41; or wherein the nucleic acid molecule comprising a nucleic acid sequence encoding a tagged hepadnavirus e antigen comprises a nucleic acid sequence encoding an amino acid sequence as shown in SEQ ID NO: 42.

14. The method of claim 2, wherein the nucleic acid sequence encoding the tagged HBeAg is shown in SEQ ID NO: 20; or wherein the amino acid sequence of the tagged HBeAg is shown in SEQ ID NO: 22.

15. The method of claim 1, wherein said step (a) further comprises a step (aa) which comprises culturing a cell comprising a nucleic acid molecule comprising a nucleic acid sequence encoding a tagged hepadnavirus e antigen in conditions allowing (i) the synthesis of hepadnavirus pregenomic (pg) RNA;

(ii) the reverse transcription of said synthesized pgRNA into a minus strand DNA;

(iii) the synthesis of a second plus strand DNA so that said minus strand DNA and said plus strand DNA form a double stranded relaxed circular DNA;

(iv) formation of cccDNA from said relaxed circular double stranded DNA;

(v) optionally restoration of conditions allowing the translation of the tagged hepadnavirus e antigen;

(vi) transcription of an mRNA encoding a tagged hepadnavirus e antigen;

(vii) translation of a tagged hepadnavirus e antigen, wherein the restoration of conditions allowing the translation of the tagged hepadnavirus e antigen is the restoration of the start codon.

16. The method of claim 1, wherein assessing the level of the tagged hepadnavirus e antigen according to step (b) is performed by ELISA, CLIA, or AlphaLISA.

17. The method of claim 1, wherein assessing the level of the tagged hepadnavirus e antigen according to step (b) comprises the use of an antibody specifically recognizing said hepadnavirus e antigen and one or more antibodies specifically recognizing the one or more tags.

18. The method of claim 2, wherein said tagged hepadnavirus e antigen contains only one tag; or wherein said tagged hepadnavirus e antigen contains two or more tags.

19. The method of claim 7, wherein said nucleic acid sequence encoding the one or more tag is 3' downstream of the nucleic acid sequence encoding the N-terminal 29 amino acids of a hepatitis B virus precore protein.

20. The method of claim 6, wherein the nucleic acid sequence encoding the tagged HBV precore protein is shown in SEQ ID NO: 19; or wherein the amino acid sequence of the tagged HBV precore protein is shown in SEQ ID NO: 21.

* * * * *

UNITED STATES PATENT AND TRADEMARK OFFICE
CERTIFICATE OF CORRECTION

PATENT NO. : 10,072,047 B2
APPLICATION NO. : 15/309680
DATED : September 11, 2018
INVENTOR(S) : Haitao Guo et al.

It is certified that error appears in the above-identified patent and that said Letters Patent is hereby corrected as shown below:

In the Specification

Column 3, Line 31, replace "Examplary" with --Exemplary--;
      Line 37, replace "examplary" with --exemplary--.

Column 4, Line 60, replace "hepadnarrius" with --hepadnavirus--.

Column 6, Line 25, replace "hapadnavirus" with --hepadnavirus--.

Column 7, Line 15, replace "becounter-screened" with --be counter-screened--.

Column 8, Line 25, replace "hepadnvirus" with --hepadnavirus--.

Column 9, Line 56, replace "etc)," with --etc.),--;
      Line 59, replace "measurements etc." with --measurements, etc.--.

Column 10, Line 67, replace "tages" with --tags--.

Column 11, Line 29, replace "e.g" with --e.g.--.

Column 13, Line 16, replace "a a hepadnavirus" with --a hepadnavirus--.

Column 14, Line 2, replace "hapadnavirus" with --hepadnavirus--.

Column 15, Line 12, replace "hepatits" with --hepatitis--;
      Line 28, replace "(DHBV),since" with --(DHBV), since--;
      Lines 29-30, replace "it thus not even" with --it is, thus, not even--;
      Line 56, replace "are" with --is--.

Column 17, Line 19, replace "condon" with --codon--.

Signed and Sealed this
Eighth Day of December, 2020

Andrei Iancu
*Director of the United States Patent and Trademark Office*

Column 19, Line 11, replace "system" with --systems--.

Column 22, Line 31, replace "inibit" with --inhibit--.

Column 23, Line 15, replace "hapadnavirus" with --hepadnavirus--;
  Line 43, replace "are" with --is (are)--.

Column 24, Line 13, replace "e.g" with --e.g.--.

Column 25, Line 3, replace "hepatits" with --hepatitis--;
  Line 54, replace "non-dectable" with --non-detectable--.

Column 26, Line 36, replace "an" with --a--;
  Line 61, replace "acids A" with --acids. A--;
  Line 63, replace "be be" with --be--.

Column 27, Line 9, replace "tag" with --tags--.

Column 29, Line 39, replace "a" with --an--.

Column 31, Line 40, replace "an" with --a--.

Column 33, Line 21, replace "(2001))" with --(2001)--;
  Line 37, replace "epsilon, c" with --epsilon, ε--.

Column 36, Line 28, replace "Sad" with --Sac I--;
  Line 64, replace "intemiediates" with --intermediates--.

Column 38, Line 44, replace "buffer Immuno-" with --buffer. Immuno---.

Column 41, replace "afterward, as" with --afterward as--.

Column 77, Line 26, replace "residues" with --residue--;
  Line 38, replace "atagged" with --a tagged--.

Column 82, Line 6, replace "consists" with --consisting--;
  Line 33, replace "42" with --42.--;
  Line 67, replace "Ag)" with --Ag).--.

Column 86, Line 18, replace "42" with --42.--.

Column 139, Line 63, replace "tag a sequence" with --tags a sequence--.

In the Claims

Column 141, Line 24, replace "SEQ ID NO: 2" with --SEQ ID NO: 12--;

Lines 34-36, replace "wherein the amino acid sequence of the hepadnavirus precore protein the amino acid sequence of a hepatitis B virus precore protein as shown in SEQ ID NO: 17." with --wherein the amino acid sequence of the hepadnavirus precore protein is the amino acid sequence of hepatitis B virus precore protein as shown in SEQ ID NO: 17--.